(12) United States Patent
Allison et al.

(10) Patent No.: US 8,242,275 B2
(45) Date of Patent: Aug. 14, 2012

(54) BICYCLIC PYRAZOLE COMPOUNDS AS ANTIBACTERIAL AGENTS

(75) Inventors: Brett D. Allison, Del Mar, CA (US); Laurent Gomez, San Diego, CA (US); Cheryl A. Grice, Carlsbad, CA (US); Michael D. Hack, San Diego, CA (US); Brian J. Morrow, Lebanon, NJ (US); S. Timothy Motley, Carlsbad, CA (US); Alejandro Santillan, Jr., San Diego, CA (US); Karen J. Shaw, Poway, CA (US); Kimberly L. Schwarz, San Diego, CA (US); Liu Y. Tang, San Diego, CA (US); Hariharan Venkatesan, San Diego, CA (US); John J. M. Wiener, La Jolla, CA (US)

(73) Assignee: Janssen Pharmaceutica NV, Beerse (BE)

( * ) Notice: Subject to any disclaimer, the term of this patent is extended or adjusted under 35 U.S.C. 154(b) by 207 days.

(21) Appl. No.: 12/833,621

(22) Filed: Jul. 9, 2010

(65) Prior Publication Data
US 2010/0280240 A1    Nov. 4, 2010

Related U.S. Application Data

(62) Division of application No. 11/393,558, filed on Mar. 30, 2006, now Pat. No. 7,842,810.

(60) Provisional application No. 60/667,198, filed on Mar. 31, 2005.

(51) Int. Cl.
*C07D 471/02* (2006.01)
(52) U.S. Cl. ...................................................... 546/122
(58) Field of Classification Search .................... 546/122
See application file for complete search history.

(56) References Cited

U.S. PATENT DOCUMENTS

| | | | |
|---|---|---|---|
| 6,403,610 B1 | 6/2002 | Malleron et al. | |
| 2004/0058919 A1 | 3/2004 | Bacque et al. | |
| 2004/0087619 A1 | 5/2004 | Bacque et al. | |
| 2006/0040949 A1 | 2/2006 | Surivet et al. | |
| 2006/0205719 A1 | 9/2006 | Hubschwerlen et al. | |

FOREIGN PATENT DOCUMENTS

| | | |
|---|---|---|
| WO | WO 00/21952 A1 | 4/2000 |
| WO | WO 01/07433 A2 | 2/2001 |
| WO | WO 02/08224 A1 | 1/2002 |
| WO | WO 02/24684 A1 | 3/2002 |
| WO | WO 02/50040 A1 | 6/2002 |
| WO | WO 02/50061 A1 | 6/2002 |
| WO | WO 02/056882 A1 | 7/2002 |
| WO | WO 03/064421 A1 | 8/2003 |
| WO | WO 03/064431 A2 | 8/2003 |
| WO | WO 2004/024712 A1 | 3/2004 |
| WO | WO 2004/035569 A2 | 4/2004 |
| WO | WO 2004/041210 A2 | 5/2004 |
| WO | WO 2004050659 * | 6/2004 |
| WO | WO 2004/058144 A2 | 7/2004 |
| WO | WO 2004/087145 A2 | 10/2004 |
| WO | WO 2004/089947 A2 | 10/2004 |

OTHER PUBLICATIONS

Amábile-Cuevas, C.F. New Antibiotics and New Resistance. Amer. Scientist 2003, 91, 138-149.
Berge, S.M. et al. Pharmaceutical Salts. J. Pharm. Sci. 1977, 66, 1-19.
Correa, A. et al. Novel Alternative for the N-N Bond Formation through a PIFA-Mediated Oxidative Cyclization and Its Application to the Synthesis of Indazo-3-ones. J. Org. Chem. 2006, 71, 3501-3505.
Gaut PL. et al. "Intravenous/oral Ciprofloxacin Therapy Versus Intravenous Ceftazidime Therapy for Selected Bacterial Infections" American Journal of Medicine, 1989, 87(5A),169S-175S.
Gomez L. et al. "Novel pyrazole derivatives as potent inhibitors of type II topoisomerases. Part 1: synthesis and preliminary SAR analysis" Bioorganic & Medicinal Chemistry Letters, 2007, 17(10), 2723-7.
Nagakura, M. et al. "Synthesis and Antiinflammatory Actions of 4,5,6,7-Tetrahydro Indazole-5-carboxylic Acids" Journal of Medicinal Chemistry, 1979, 22(1), 48-52.
Nicolaus et al. "Symbiotic Approach to Drug Design" Decision Making in Drug Research, 1983, pp. 173-186.
Sanders, Jr., W.E. et al. Inducible Beta-lactamases: Clinical and Epidemiologic Implications for the Use of Newer Cephalosporins. Reviews of Infectious Diseases 1988, 10(4), 830-838.
Wiener J. et al. "Tetrahydroindazole inhibitors of bacterial type II topoisomerases. Part 2: SAR development and potency against multidrug-resistant strains" Bioorganic & Medicinal Chemistry Letters, 2007, 17(10), 2718-22.
European Extended Search Report dated Feb. 3, 2010 for European Appln. No. 06748931.0.

* cited by examiner

*Primary Examiner* — Janet Andres
*Assistant Examiner* — John Mabry
(74) *Attorney, Agent, or Firm* — Thomas J. Dodd

(57) ABSTRACT

Antibacterial compounds, compositions containing them, and methods of use for the inhibition of bacterial activity and the treatment, prevention or inhibition of bacterial infection.

28 Claims, No Drawings

BICYCLIC PYRAZOLE COMPOUNDS AS ANTIBACTERIAL AGENTS

This application is a divisional of U.S. patent application Ser. No. 11/393,558 filed on Mar. 30, 2006, now U.S. Pat. No. 7,842,810 which in turn claims the benefit of U.S. provisional patent application Ser. No. 60/667,198, filed on Mar. 31, 2005, each of which is incorporated herein by reference in its entirety.

FIELD OF THE INVENTION

This invention relates to heterocyclic compounds, more particularly pyrazole compounds, compositions containing them, and methods of using them as antibacterial agents.

BACKGROUND OF THE INVENTION

The chemical and medical literature describes compounds that are antimicrobial, i.e., capable of destroying or suppressing the growth or reproduction of microorganisms, such as bacteria. For example, such antibacterial agents are described in *Antibiotics, Chemotherapeutics, and Antibacterial Agents for Disease Control* (M. Greyson, ed., 1982), *The Molecular Basis of Antibiotic Action*, 2d ed. (E. Gale, et al., 1981), *Recent Research Developments in Antimicrobial Agents & Chemotherapy* (S. G. Pandalai, ed., 2001), *Quinolone Antimicrobial Agents* (J. S. Wolfson, D. C. Hooper, eds., 1989), and *Antibiotics and Chemotherapy*, 7th edn. (F. O'Grady, H. P. Lambert, R. G. Finch, D. Greenwood, M. Dedicoat, 1997).

The mechanisms of action of these antibacterial agents vary. However, they may function in one or more ways including: by inhibiting cell wall synthesis or repair; by altering cell wall or membrane permeability; by inhibiting or altering protein synthesis; by inhibiting the synthesis of nucleic acids or by inhibition of folate metabolism. For example, beta-lactam antibacterial agents act through inhibiting essential penicillin binding proteins (PBPs) in bacteria, which are essential for cell wall synthesis. As another example, quinolones act, at least in part by inhibiting synthesis of DNA, thus preventing the cell from replicating.

The pharmacological characteristics of antimicrobial agents, and their suitability for any given clinical use, vary. For example, the classes of antimicrobial agents (and members within a class) may vary in 1) their relative efficacy against different types of microorganisms, 2) their frequency and rate of development of microbial resistance and 3) their pharmacological characteristics, such as their bioavailability and biodistribution. Accordingly, selection of an appropriate antimicrobial agent in a given clinical situation requires analysis of many factors, including the type of organism involved, the desired method of administration, the location of the infection to be treated and other considerations.

However, many such attempts to produce improved antimicrobial agents yield equivocal results. Indeed, few antimicrobial agents have been produced that are truly clinically acceptable in terms of their spectrum of antimicrobial activity, avoidance of microbial resistance, pharmacology, and toxicology. Thus, there is a continuing need for antimicrobial agents that are effective against resistant microbes. This need has been highlighted in the relevant literature. See, for example, C. F. Amábile-Cuevas, "New Antibiotics and New Resistance", *American Scientist*, vol. 91, 138-149 (March-April 2003) (noting that for nearly twenty years, until the late 1990s, "not a single truly new antibiotic was introduced into clinical use", while "resistance keeps evolving, and drugs are rapidly losing their efficacy, resulting in increased treatment costs, loss of labor time and, of course worst of all, lost lives.").

Examples of bacterial infections resistant to antibiotic therapy have been reported in the past; they are now a significant threat to public health. For example, methicillin-resistant *Staphylococcus aureus* (MRSA) is a type of bacterium that is resistant to certain antibiotics. These antibiotics include methicillin, amoxicillin, and ciprofloxacin. Staphylococcus infections, such as those with MRSA, have a plurality of origins. They occur most frequently among persons in hospitals and healthcare facilities, such as nursing homes and dialysis centers, who have weakened immune systems. These infections, however, are not limited to exposure to the environment in healthcare facilities or medical procedures such as dialysis, surgery, and catheters, but they are also acquired by the population at large, hence the term community-associated MRSA. The development of microbial resistance (perhaps as a result of the extensive use of antibacterial agents) is of increasing concern in medical science. "Resistance" can be defined as the existence of organisms, within a population of a given microbial species, that are considerably less susceptible to the action of a given antimicrobial agent. This resistance is of particular concern in environments such as hospitals and nursing homes, where relatively high rates of infection and extensive use of antibacterial agents are common. See, e.g., W. Sanders, Jr., et al., "Inducible Beta-lactamases: Clinical and Epidemiologic Implications for the Use of Newer Cephalosporins", *Review of Infectious Diseases*, p. 830 (1988).

Pathogenic bacteria are known to acquire resistance via several distinct mechanisms including inactivation of the antibiotic by bacterial enzymes (e.g., β-lactamases hydrolyzing penicillin and cephalosporins), whether these enzymes are encoded by genes native to the organism or encoded by genes acquired through transfer from an external source (e.g., methicillin-resistance in *Staphylococcus aureus*); removal of the antibiotic using efflux pumps; modification of the target of the antibiotic via mutation and genetic recombination (e.g., penicillin-resistance in Neiserria gonorrhoeae). There are certain Gram-positive pathogens, such as vancomycin-resistant *Enterococcus faecium*, which are resistant to virtually all commercially available antibiotics.

Hence existing antibacterial agents have limited capacity in overcoming the threat of resistance. Thus it would be advantageous to provide new antibacterial agents that can be used against resistant microbes.

The present invention includes pyrazole compounds and derivatives thereof; the use of said pyrazole compounds as inhibitors of bacterial growth; their use for the treatment of bacterial infection; and the preparation of pharmaceutical compositions for the treatment of bacterial infection. Compounds according to the present invention and derivatives thereof can also be used as reference compounds in assays to assess antibacterial characteristics in light of one or more factors concerning bacterial activity, such as bacterial growth inhibition, toxicity, bioavailability, and protein binding capability.

SUMMARY OF THE INVENTION

There are provided by the present invention compounds that have the following general formula (I):

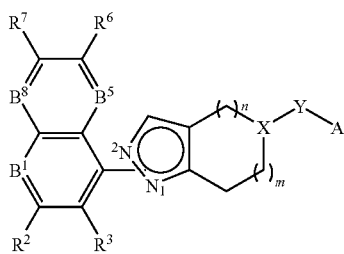

(I)

where said formula (I) has a B-containing bicyclic ring system

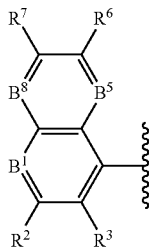

and a fused pyrazole moiety

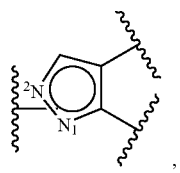

, wherein
each of $B^1$, $B^5$, and $B^8$ is independently $CR^a$ or N, wherein not all three $B^1$, $B^5$, and $B^8$ are N;
each of $R^a$, $R^2$, $R^3$, $R^6$ and $R^7$ is independently selected from the group consisting of —H, —$C_{1-4}$alkyl, —$C_{2-4}$alkenyl, —$C_{2-4}$alkynyl, —$C_{3-6}$cycloalkyl, —$OR^b$, —$NR^cR^d$, —$O(CH_2)_{2-3}NR^cR^d$, —$SR^b$, —$S(O)R^b$, —$SO_2R^b$, cyano, —$CF_3$, halo, —$NO_2$, —$OCF_3$, —$C(O)R^b$, —$OC(O)R^b$, —$C(O)NR^cR^d$, and —$CO_2R^b$; wherein each of $R^c$ and $R^d$ is independently selected from the group consisting of —H, —$C_{1-4}$alkyl, —$C_{3-6}$cycloalkyl, and —$C_{1-2}$alkyl($C_{3-6}$cycloalkyl)-; and wherein each alkyl or cycloalkyl moiety in any of $R^a$, $R^2$, $R^3$, $R^6$, $R^7$, $R^b$, $R^c$, and $R^d$ is optionally and independently substituted with one, two or three substituents selected from —$C_{1-3}$alkyl, halo, hydroxy, amino, and —$C_{1-3}$alkoxy;
the B-containing bicyclic ring system is attached at the 1- or 2-position of the fused pyrazole moiety;
m is 0 or 1;
n is 1 or 2, wherein m+n is 2 or 3;
X is CH or N;
provided that when X is N, then Y is —C(O)—, —$CH_2C(O)$—, or —$(CH_2)_{2-3}O$— optionally substituted with —$C_{1-3}$alkyl;
and when X is CH, then Y is —$N(R^e)Z$—;

Z is selected from the group consisting of: $C_{1-3}$alkylene optionally substituted with —$C_{1-3}$alkyl; $C_3$alkenylene optionally substituted with —$C_{1-3}$alkyl; —C(O) $C_2$alkenyl- optionally substituted with —$C_{1-3}$alkyl; —$(CH_2)_{0-1}C(O)$—; —$CH_2C(O)N(R^f)(CH_2)_{0-1}$—; —$(CH_2)_{2-3}O$—; and —$C(O)C(R^{g1})(R^{g2})$—;
where $R^e$ is —H, —$C_{1-4}$alkyl, benzyl, —$C(O)C_{1-6}$alkyl, —C(O)phenyl, —C(O)benzyl, —$C_{1-6}$alkyl$CO_2C_{1-6}$alkyl, or —$C_{1-6}$alkyl$CO_2H$;
$R^f$ is —H or —$C_{1-4}$alkyl; and
each of $R^{g1}$ and $R^{g2}$ is independently —H or methyl, or $R^{g1}$ and $g^{g2}$ are taken together with their carbon of attachment to form a $C_{3-7}$cycloalkyl, or the group $C(R^{g1})(R^{g2})$ is the group C=O;
A is an aryl or heteroaryl ring selected from the group consisting of:
a) unsubstituted phenyl, unsubstituted pyridyl, substituted phenyl, and substituted pyridyl, wherein said substituted phenyl is moiety (M1) or moiety (M2)

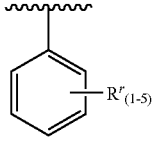

(M1)

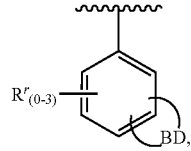

(M2)

and said substituted pyridyl is moiety (M3) or moiety (M4)

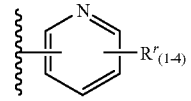

(M3)

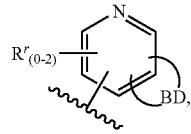

(M4)

wherein $R^r_{(p-q)}$ stands for a number of $R^r$ substituents that is at least p and does not exceed q, and

is a disubstituent at two adjacent carbon members, said disubstituent being selected from the group consisting of —O—C14AL-O—, —$N(R^h)(CH_2)_{2-3}S$—, —$N(R^h)C(O)(CH_2)_{1-2}S$—, —$N(R^h)C(O)C(CH_3)_2S$—, —$N(R^h)(CH_2)_{2-3}O$—, —$N(R^h)C(O)(CH_2)_{1-2}O$—, —$N(R^h)(CH_2)_{2-3}NH$—, and —$N(R^h)C(O)(CH_2)_{1-2}NH$—, wherein said C14AL is a $C_{1-4}$alkylene optionally mono- or di-substituted with F,
where each —$R^r$ is independently selected from the group consisting of —OH, —$C_{1-6}$alkyl, —$OC_{1-6}$ alkyl, —$C_{2-6}$alkenyl, —$OC_{3-6}$alkenyl, —$C_{2-6}$alkynyl, —$OC_{3-6}$alkynyl, —CN, —$NO_2$, —$N(R^y)R^z$, —$C(O)N(R^y)R^z$, —$N(R^t)C(O)R^t$, —$N(R^t)SO_2C_{1-6}$alkyl, —$C(O)C_{1-6}$alkyl, —$SC_{1-6}$alkyl, —$SO_2C_{1-6}$alkyl, —$SO_2N(R^y)R^z$, halo, —$CF_3$, —$OCF_3$, —$CO_2H$ and —$CO_2C_{1-6}$alkyl; wherein $R^t$ is —H or —$C_{1-6}$alkyl;

$R^y$ and $R^z$ are independently selected from —H and —$C_{1-6}$alkyl, or $R^y$ and $R^z$ are taken together with their nitrogen of attachment to form pyrrolidinyl or piperidinyl; and $R^h$ is selected from the group consisting of —H, —$C_{1-6}$alkyl, —$C_{1-6}$alkyl$CO_2H$, —$C_{1-6}$alkyl$CO_2C_{1-6}$alkyl, and benzyl;

b) a five-membered monocyclic heteroaromatic group having a carbon member which is the point of attachment, having one hetero-member that is >O, >S, >NH, or >N($C_{1-4}$alkyl), having up to one additional hetero-member that is —N═, said five-membered monocyclic heteroaromatic group being optionally mono- or di-substituted with $R^r$ and optionally benzofused or pyridofused, where the benzofused or pyridofused moiety is optionally mono-, di-, or tri-substituted with $R^r$; and c) a six-membered monocyclic heteroaromatic group having a carbon member which is the point of attachment, having two hetero-members each being —N═, said six-membered monocyclic heteroaromatic group being optionally mono- or di-substituted with $R^r$ and optionally benzofused or pyridofused, where the benzofused or pyridofused moiety is optionally mono- or di-substituted with $R^r$;

and isomers, racemates, tautomers, hydrates, solvates, and pharmaceutically acceptable salts, esters, and amides thereof.

The "(p-q)" notation used with moieties (M1)-(M4) indicates that moiety (M1) has from one to five independently selected substituents $R^r$. Moiety (M3) has from one to four independently selected substituents $R^r$. Independently selected substituents $R^r$ in moiety (M2) range in number from zero to three, and independently selected substituents $R^r$ in moiety (M4) range in number from zero to two.

It has been found that the compounds of this invention, and compositions containing these compounds have antibacterial activities against a range of pathogenic microorganisms with advantages of activity against resistant bacterial strains.

Accordingly, the present invention is also directed to a method of treating a subject having a condition caused by or contributed to by bacterial infection, which comprises administering to said subject a therapeutically effective amount of at least one compound of Formula (I), and/or derivative thereof.

The present invention is further directed to a method of preventing a subject from suffering from a condition caused by or contributed to by bacterial infection, which comprises administering to the subject a prophylactically effective amount of at least one compound of Formula (I), and/or derivative thereof.

Embodiments of compounds of formula (I) are antibacterial agents. Embodiments of this invention comprise mixtures of compounds of formula (I).

Isomeric forms of the compounds of formula (I), and of their pharmaceutically acceptable salts, amides and esters, are encompassed within the present invention, and reference herein to one of such isomeric forms is meant to refer to at least one of such isomeric forms. One of ordinary skill in the art will recognize that compounds according to this invention may exist, for example, in a single isomeric form whereas other compounds may exist in the form of a regioisomeric mixture. Compounds according to this invention may also exist, for example, in a single atropisomeric form or as a mixture of atropisomers. Atropisomers are stereoisomers resulting from hindered rotation about single bonds where the rotational barrier is high enough to allow for conformer isolation. See, for example, E. L. Eliel and S. H. Wilen, *Stereochemistry of Organic Compounds*, Ch. 14, Wiley & Sons, New york (1994), and M. Ōki, Top. Stereochem. Vol. 14, 1-81 (1984).

Whether stated explicitly or not in any part of the written description and claims, it is understood that each substituent and member assignment in the context of this invention is made independently of any other member and substituent assignment, unless stated otherwise. By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2 S^2_{example}$ is one of $S_3$ and $S_4$" is accordingly used herein for the sake of brevity, but not by way of limitation. The foregoing first example on substituent terminology, which is stated in generic terms, is meant to illustrate the various substituent R assignments described herein. The foregoing convention given herein for substituents extends, when applicable, to members such as X and Z, and to any index if applicable.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent R assignments described herein. The foregoing convention given herein for substituents extends, when applicable, to members such as X and Z, and to any index if applicable.

The nomenclature "$C_{i-j}$" with j>i, when applied herein to a class of substituents, is meant to refer to embodiments of this invention for which each and every one of the number of carbon members, from i to j, including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≦N≦m, with m>n.

When any variable referring to a substituent, compound member, or index occurs more than once, the full range of assignments is meant to apply to each occurrence, independently of the specific assignment(s) to any other occurrence of such variable. For each occurrence of a variable, it is understood that such an assignment is made independently from other member and substituent assignments.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

The present invention also features methods for inhibiting bacterial activity with such compounds, pharmaceutical compositions containing such compounds, and methods of using such compositions in the treatment or prevention of conditions that are mediated by bacterial activity, such as infection.

Pharmaceutical compositions according to the present invention include at least one of the compounds of the present invention. If more than one of such compounds is included in a composition, the therapeutically effective amount may be a jointly effective amount. As such inhibitors of bacterial activity, compounds and compositions according to the present invention are useful in the prevention, inhibition, or treatment of bacterial infection.

The invention also features a pharmaceutical composition for treating or preventing bacterial infection in a subject, comprising a therapeutically effective amount of at least one antibacterial agent selected from compounds of formula (I), enantiomers, diastereomers, racemates, tautomers, hydrates, solvates thereof, pharmaceutically acceptable salts, amides and esters thereof. In addition, the invention features a pharmaceutical composition for inhibiting bacterial activity or infection in a subject, comprising a therapeutically effective amount of at least one antibacterial agent selected from compounds of formula (I), enantiomers, diastereomers, racemates, tautomers, hydrates, solvates thereof, pharmaceutically acceptable salts, amides and esters thereof. The invention additionally features an antibacterial or anti-infective composition, comprising a therapeutically effective amount of at least one antibacterial compound selected from compounds of formula (I), enantiomers, diastereomers, racemates, tautomers, hydrates, solvates thereof, pharmaceutically acceptable salts, amides and esters thereof.

The invention also features methods for treating or preventing a bacteria-mediated condition or bacterial infection in a subject, comprising administering to the subject a pharmaceutical composition that comprises a therapeutically effective amount of at least one antibacterial agent selected from compounds of formula (I), enantiomers, diastereomers, racemates, tautomers, hydrates, solvates thereof, pharmaceutically acceptable salts, amides and esters thereof. Furthermore, the invention features methods for inhibiting bacterial activity in a subject, comprising administering to the subject a pharmaceutical composition that comprises a therapeutically effective amount of at least one antibacterial agent selected from compounds of formula (I), enantiomers, diastereomers, racemates, tautomers, hydrates, solvates thereof, pharmaceutically acceptable salts, amides and esters thereof.

This invention features methods for the treatment, prevention and/or inhibition of conditions that are associated with and/or cause bacterial infection. Subjects on which such methods are implemented are not limited by the nature of the host.

Additional features and advantages of the invention will become apparent from the detailed description below, including examples, and the appended claims.

DETAILED DESCRIPTION OF THE INVENTION

The present invention is directed to compounds of formula (I), as herein defined, enantiomers, diastereomers, racemates, tautomers, hydrates, solvates thereof, pharmaceutically acceptable salts, amides and esters thereof, pharmaceutical compositions that contain at least one of such compounds, methods of using, including treatment and/or prevention of conditions such as those that are mediated by bacterial activity, and methods of making such pharmaceutical compositions.

The following terms are defined below, and by their usage throughout the disclosure.

"Alkyl" includes straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. Alkyl does not include cycloalkyl.

"Alkenyl" includes straight chain and branched hydrocarbon radicals as above with at least one carbon-carbon double bond ($sp^2$). Unless indicated otherwise by the prefix that indicates the number of carbon members, alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on.

"Alkynyl" includes straight chain and branched hydrocarbon radicals as above with at least one carbon-carbon triple bond (sp). Unless indicated otherwise by the prefix that indicates the number of carbon members, alkynyls include ethynyl, propynyls, butynyls, and pentynyls. Hydrocarbon radicals having a mixture of double bonds and triple bonds, such as 2-penten-4-ynyl, are grouped as alkynyls herein.

"Alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and $SO_2$.

Unless indicated otherwise by the prefix that indicates the number of carbon members, "cycloalkyl" includes cyclopropyl, cyclobutyl, cyclopentyl, cyclohexyl, cycloheptyl, cyclooctyl, and so on.

Unless indicated otherwise by the prefix that indicates the number of members in the cyclic structure, "heterocyclyl", "heterocyclic" or "heterocycle" is a 3- to 8-member aromatic, saturated, or partially saturated single or fused ring system that comprises carbon atoms wherein the heteroatoms are selected from N, O, and S. Examples of heterocyclyls include thiazoylyl, furyl, pyranyl, isobenzofuranyl, pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolyl, furazanyl, pyrrolidinyl, pyrrolinyl, imidazolidinyl, imidazolinyl, pyrazolidinyl, pyrazolinyl, piperidyl, piperazinyl, indolinyl, and morpholinyl. For example, preferred heterocyclyls or heterocyclic radicals include morpholinyl, piperazinyl, pyrrolidinyl, pyridyl, cyclohexylimino, cycloheptylimino, and more preferably, piperidyl.

"Aryl" includes phenyl, naphthyl, biphenylyl, tetrahydronaphthyl, and so on, any of which may be optionally substituted. Aryl also includes arylalkyl groups such as benzyl, phenethyl, and phenylpropyl. Aryl includes a ring system containing an optionally substituted 6-membered carbocyclic aromatic ring, said system may be bicyclic, bridged, and/or fused. The system may include rings that are aromatic, or partially or completely saturated. Examples of ring systems include indenyl, pentalenyl, 1-4-dihydronaphthyl, indanyl, benzimidazolyl, benzothiophenyl, indolyl, benzofuranyl, isoquinolinyl, and so on. Unless indicated otherwise, the terms "heteroaryl" or "heteroaromatic" refer to those heterocycles that are aromatic in nature. Examples illustrating heteroaryl are thienyl, furanyl, pyrrolyl, imidazolyl, oxazolyl, thiazolyl, benzothienyl, benzofuranyl, benzimidazolyl, benzoxazolyl, benzothiazolyl, pyridyl, and pyrimidinyl.

"Halo" includes fluoro, chloro, bromo, and iodo, and is preferably fluoro or chloro.

The term "carbonyl" refers to a >C=O moiety, such that when this term is characterized as being part of a chain or cyclic structure, the carbon member in the carbonyl group is taken as being one of the carbon members of such chain or cyclic structure.

As in standard chemical nomenclature, the group phenyl is herein referred to as "phenyl" or as "Ph".

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum mass of the same entity that could be obtained under the particular stoichiometric conditions. Concentrations that are given as percentages refer to mass ratios, unless indicated differently.

It is understood that substitutions and combinations of substitutions recited herein, whether stated explicitly or not, refer to substitutions that are consistent with the valency of the member being substituted. Terms such as "valence allowed site," "valence allowed member," and morphological variations thereof are used in this sense. For example, "valence allowed" when applied to a carbon member refers to the tetravalency of C; it refers to the trivalency of N when applied to a nitrogen member; and it refers to the bonding of a nitrogen member that is conventionally characterized with a positive electric charge or that is in a quaternary form. The present invention also encompasses compounds as described herein and equivalents thereof with at least one valence allowed nitrogen member, including but not limited to a quaternary nitrogen member and a nitrogen oxide, each of which may be prepared according to known methods (see J. March, Advanced Organic Chemistry, 4th ed., 1991, pp. 411-412, 1200-1201; R. C. Larock, Comprehensive Organic Transformations, 1989, pp. 397-400, 421-425; and references cited therein).

Particular preferred compounds of the invention comprise a compound of formula (I), or an enantiomer, diastereomer, racemate, tautomer, hydrate, solvate thereof, or a pharmaceutically acceptable salt, amide or ester thereof, wherein $B^1$, $B^5$, $B^8$, $R^a$, $R^2$, $R^3$, $R^6$, $R^7$, m, n, X, Y, and A have any of the meanings defined hereinabove and equivalents thereof, or at least one of the following assignments and equivalents thereof. Such assignments may be used where appropriate with any of the definitions, claims or embodiments defined herein:

each of $B^1$, $B^5$, and $B^8$ is CH;
$B^1$ is N, $B^5$ is N, and $B^8$ is CH;
$B^1$ is N, $B^5$ is CH, and $B^8$ is CH;
$B^1$ is CH, $B^5$ is N, and $B^8$ is CH;
$R^a$, $R^2$, $R^3$, $R^6$, and $R^7$ are each independently selected from —H, —$C_{1-3}$alkyl, —$OC_{1-3}$alkyl, halo, or —$CF_3$;
$R^a$ is —H or —$CF_3$;
$R^2$ is —H, —$CH_3$, or —$CF_3$;
$R^6$ is —H, —$OC_{1-3}$alkyl, or halo;
$R^6$ is —$OC_{1-3}$alkyl;
$R^6$ is —H, —$OCH_3$, or —F;
$R^6$ is —$OCH_3$;
$R^7$ is —H or —Cl;
N2-attached regioisomer;
m=n=1;
n is 2 and m is 1;
X is N;
X is CH;
X is CH, and Y is —N(benzyl)$CH_2$—, —N($CH_2CO_2$tBu)$CH_2$—, —N($CH_2CO_2$H)$CH_2$—, —$NHCH_2$—, —NH($CH_2$)$_3$—, —$NHCH_2CHCH$—, —$NHCH_2C$(Me)CH—, —NHC(O)—, —NHC(O)CHCH—, —$NHCH_2C$(O)NH—, —$NHCH_2C$(O)$NHCH_2$—, —$NHCH_2C$(O)—, —NHC(O)C(O)—, —NH($CH_2$)$_2$O—, or —NHC(O)C($R^{g1}$)($R^{g2}$)—;
X is CH, and Z is one of $C_{1-3}$alkylene, $C_{1-3}$alkenylene, —C(O)$C_2$alkenyl-, —($CH_2$)$_{0-1}$C(O)—, —$CH_2$C(O)N($R^f$)($CH_2$)$_{0-1}$—, —($CH_2$)$_{2-3}$O—, and —C(O)C($R^{g1}R^{g2}$)—;
X is CH, $R^e$ is H and Z is C=O;
$R^6$ is —$OC_{1-3}$alkyl, X is CH, $B^8$ is CH, $B^1$ is N and $B^5$ is CH, m=n=1, N2-attached regioisomer, and A is an aryl or heteroaryl ring selected from the group consisting of a), b) and c) as defined for compound of formula (I); $R^6$ is —$OC_{1-3}$alkyl, X is CH, $B^8$ is CH, $B^1$ is N and $B^5$ is N, m=n=1, N2-attached regioisomer, and A is an aryl or heteroaryl ring selected from the group consisting of a), b) and c) as defined for compound of formula (I);

A is phenyl, 4-methylphenyl, 3-chlorophenyl, 4-chlorophenyl, 3,4-dichlorophenyl, 4-fluorophenyl, 3,4-difluorophenyl, 3,5-difluorophenyl, 2-nitrophenyl, 5-fluoro-2-trifluoromethylphenyl, 4-dimethylaminophenyl, 4-diethylaminophenyl, 4-piperidin-1-ylphenyl, 4-pyrrolidin-1-ylphenyl, 2-fluoro-4,5-dimethoxyphenyl, 2-chloro-5-nitrophenyl, 2-fluoro-3-cyano-4-dimethylaminophenyl, pyridin-3-yl, 2-chloro-pyridin-3-yl, or pyridin-2-yl;

A is 4-methyl-3-nitrophenyl, 2-fluoro-4-nitrophenyl, 2,4-difluorophenyl, 3-trifluoromethylphenyl, 5-acetylamino-2-bromophenyl, or 2,4-dichloro-5-fluorophenyl;

A is 2,3-dihydro-benzo[1,4]dioxin-6-yl, 7-fluoro-2,3-dihydro-benzo[1,4]dioxin-6-yl, 3,4-dihydro-2H-benzo[b][1,4]dioxepin-6-yl, 3-oxo-3,4-dihydro-2H-benzo[1,4]thiazin-6-yl, 7-fluoro-3-oxo-3,4-dihydro-2H-benzo[1,4]thiazin-6-yl, 7-chloro-3-oxo-3,4-dihydro-2H-benzo[1,4]thiazin-6-yl, 3,4-dihydro-2H-benzo[1,4]thiazin-6-yl, benzo[1,3]dioxol-5-yl, 2,2-difluoro-benzo[1,3]dioxol-5-yl, 3-oxo-4H-pyrido[3,2-b][1,4]oxazin-6-yl, 3-oxo-4H-benzo[1,4]oxazin-6-yl, 4-methyl-3-oxo-3,4-dihydro-2H-benzo[1,4]thiazin-6-yl, or 4-methyl-3-oxo-3,4-dihydro-2H-benzo[1,4]oxazin-7-yl;

A is 8-fluoro-2,3-dihydro-benzo[1,4]dioxin-6-yl, 7-chloro-2,3-dihydro-benzo[1,4]dioxin-6-yl, 6-chloro-benzo[1,3]dioxol-5-yl, 7-fluoro-3,4-dihydro-2H-benzo[1,4]thiazin-6-yl, 5,7-difluoro-3-oxo-3,4-dihydro-2H-benzo[1,4]thiazin-6-yl, 3-oxo-7-trifluoromethyl-3,4-dihydro-2H-benzo[1,4]thiazin-6-yl, 7-bromo-3-oxo-3,4-dihydro-2H-benzo[1,4]thiazin-6-yl, 3-oxo-3,4-dihydro-2H-benzo[1,4]oxazin-6-yl, 2,2-dimethyl-3-oxo-3,4-dihydro-2H-benzo[1,4]thiazin-6-yl, 7-methoxy-3-oxo-3,4-dihydro-2H-benzo[1,4]thiazin-6-yl, 7-methyl-3-oxo-3,4-dihydro-2H-benzo[1,4]thiazin-6-yl, 7-ethoxycarbonyl-3-oxo-3,4-dihydro-2H-benzo[1,4]thiazin-6-yl, or 7-carboxy-3-oxo-3,4-dihydro-2H-benzo[1,4]thiazin-6-yl; and A is 4,6-difluoro-1H-indol-2-yl, 1H-benzimidazol-2-yl, 1H-indol-2-yl, benzo[b]thiophen-2-yl, 4-fluoro-benzo[b]thiophen-2-yl, benzofuran-2-yl, thiophen-2-yl, quinoxalin-2-yl, 5-bromo-thiophen-2-yl, 5-acetyl-thiophen-2-yl, 5,6-difluoro-1H-indol-2-yl, 5-methyl-1H-indol-2-yl, 5-bromo-1H-indol-2-yl chloro-1H-indol-2-yl.

Compounds of formula (I) comprise compounds that satisfy any one of the combinations of definitions given herein and equivalents thereof.

It is understood that some compounds referred to herein are chiral and/or have geometric isomeric centers, for example E- and Z-isomers. The present invention encompasses all such optical isomers, including diastereoisomers and racemic mixtures, atropisomers, and geometric isomers that possess the activity that characterizes the compounds of this invention. In addition, certain compounds referred to herein can exist in solvated as well as unsolvated forms. It is understood that this invention encompasses all such solvated and unsolvated forms that possess the activity that characterizes the compounds of this invention. Compounds according to the present invention that have been modified to be detectable by some analytic technique are also within the scope of this invention. An example of such compounds is an isotopically labeled compound, such as an $^{18}F$ isotopically labeled compound that may be used as a probe in detection and/or imaging techniques, such as positron emission tomography (PET) and single-photon emission computed tomography (SPECT). Another example of such compounds is an isotopically labeled compound, such as a deuterium and/or tritium labeled compound that may be used in reaction kinetic studies.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound that may not be specifically disclosed, but that converts to the specified compound in vivo after administration to the patient. Conventional procedures for the selection and preparation of suitable prodrug derivatives are described, for example, in "Design of Prodrugs", H. Bundgaard, ed., Elsevier, 1985.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent, such as water; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

Embodiments of this invention are made according to the synthetic methods outlined in Schemes A-C, have demonstrated antibacterial activity, and are selected from:

| Ex. | Compound Name |
|---|---|
| 1 | 2,3-Dihydro-benzo[1,4]dioxine-6-carboxylic acid [2-(6-methoxy-[1,5]naphthyridin-4-yl)-4,5,6,7-tetrahydro-2H-indazol-5-yl]-amide; |
| 2 | 7-Fluoro-2,3-dihydro-benzo[1,4]dioxine-6-carboxylic acid [2-(6-methoxy-[1,5]naphthyridin-4-yl)-4,5,6,7-tetrahydro-2H-indazol-5-yl]-amide; |
| 3 | 3,4-Dihydro-2H-benzo[b][1,4]dioxepine-7-carboxylic acid [2-(6-methoxy-[1,5]naphthyridin-4-yl)-4,5,6,7-tetrahydro-2H-indazol-5-yl]-amide; |
| 4 | 3-Oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide; |
| 5 | 7-Fluoro-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide; |
| 6 | 7-Chloro-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide; |
| 7 | 4,6-Difluoro-1H-indole-2-carboxylic acid [2-(6-methoxy-[1,5]naphthyridin-4-yl)-4,5,6,7-tetrahydro-2H-indazol-5-yl]-amide; |
| 8 | 1H-Benzoimidazole-2-carboxylic acid [2-(6-methoxy-[1,5]naphthyridin-4-yl)-4,5,6,7-tetrahydro-2H-indazol-5-yl]-amide; |
| 9 | 2-(1H-Indol-2-yl)-N-[2-(6-methoxy-[1,5]naphthyridin-4-yl)-4,5,6,7-tetrahydro-2H-indazol-5-yl]-2-oxo-acetamide; |

| Ex. | Compound Name |
|---|---|
| 10 | N-[2-(6-Methoxy-[1,5]naphthyridin-4-yl)-4,5,6,7-tetrahydro-2H-indazol-5-yl]-3-phenyl-acrylamide; |
| 11 | 3-(3,5-Difluoro-phenyl)-N-[2-(6-methoxy-[1,5]naphthyridin-4-yl)-4,5,6,7-tetrahydro-2H-indazol-5-yl]-acrylamide; |
| 12 | 3-(3-Chloro-phenyl)-N-[2-(6-methoxy-[1,5]naphthyridin-4-yl)-4,5,6,7-tetrahydro-2H-indazol-5-yl]-acrylamide; |
| 13 | 3-(4-Fluoro-phenyl)-N-[2-(6-methoxy-[1,5]naphthyridin-4-yl)-4,5,6,7-tetrahydro-2H-indazol-5-yl]-acrylamide; |
| 14 | N-[2-(6-Methoxy-[1,5]naphthyridin-4-yl)-4,5,6,7-tetrahydro-2H-indazol-5-yl]-3-(3-nitro-phenyl)-acrylamide; |
| 15 | 6-[2-(6-Methoxy-[1,5]naphthyridin-4-yl)-4,5,7,8-tetrahydro-2H-1,2,6-triaza-azulene-6-carbonyl]-4H-benzo[1,4]thiazin-3-one; |
| 16 | 2,3-Dihydro-benzo[1,4]dioxine-6-carboxylic acid [2-(6-methoxy-quinolin-4-yl)-4,5,6,7-tetrahydro-2H-indazol-5-yl]-amide; |
| 17 | 3-Oxo-3,4-dihydro-2H-benzo[1,4]thiazine-6-carboxylic acid [2-(6-methoxy-quinolin-4-yl)-4,5,6,7-tetrahydro-2H-indazol-5-yl]-amide; |
| 18 | 7-Fluoro-3-oxo-3,4-dihydro-2H-benzo[1,4]thiazine-6-carboxylic acid [2-(6-methoxy-quinolin-4-yl)-4,5,6,7-tetrahydro-2H-indazol-5-yl]-amide; |
| 19 | 7-Fluoro-3-oxo-3,4-dihydro-2H-benzo[1,4]thiazine-6-carboxylic acid [1-(6-methoxy-quinolin-4-yl)-4,5,6,7-tetrahydro-1H-indazol-5-yl]-amide; |
| 20 | 7-Chloro-3-oxo-3,4-dihydro-2H-benzo[1,4]thiazine-6-carboxylic acid [2-(6-methoxy-quinolin-4-yl)-4,5,6,7-tetrahydro-2H-indazol-5-yl]-amide; |
| 21 | 1H-Indole-2-carboxylic acid [2-(6-methoxy-quinolin-4-yl)-4,5,6,7-tetrahydro-2H-indazol-5-yl]-amide; |
| 22 | 4,6-Difluoro-1H-indole-2-carboxylic acid [2-(6-methoxy-quinolin-4-yl)-4,5,6,7-tetrahydro-2H-indazol-5-yl]-amide; |
| 23 | Benzo[b]thiophene-2-carboxylic acid [2-(6-methoxy-quinolin-4-yl)-4,5,6,7-tetrahydro-2H-indazol-5-yl]-amide; |
| 24 | 4-Fluoro-benzo[b]thiophene-2-carboxylic acid [2-(6-methoxy-quinolin-4-yl)-4,5,6,7-tetrahydro-2H-indazol-5-yl]-amide; |
| 25 | Benzofuran-2-carboxylic acid [2-(6-methoxy-quinolin-4-yl)-4,5,6,7-tetrahydro-2H-indazol-5-yl]-amide; |
| 26 | 2-(1H-Indol-2-yl)-N-[2-(6-methoxy-quinolin-4-yl)-4,5,6,7-tetrahydro-2H-indazol-5-yl]-2-oxo-acetamide; |
| 27 | 3-Oxo-3,4-dihydro-2H-benzo[1,4]thiazine-6-carboxylic acid [2-(6-methoxy-quinolin-4-yl)-4,5,6,7-tetrahydro-2H-indazol-6-yl]-amide; |
| 28 | 7-Fluoro-3-oxo-3,4-dihydro-2H-benzo[1,4]thiazine-6-carboxylic acid [2-(6-methoxy-quinolin-4-yl)-4,5,6,7-tetrahydro-2H-indazol-6-yl]-amide; |
| 29 | N-[2-(6-Methoxy-quinolin-4-yl)-4,5,6,7-tetrahydro-2H-indazol-5-yl]-3-phenyl-acrylamide; |
| 30 | N-[2-(6-Methoxy-quinolin-4-yl)-4,5,6,7-tetrahydro-2H-indazol-5-yl]-3-thiophen-2-yl-acrylamide; |
| 31 | 3-Oxo-3,4-dihydro-2H-benzo[1,4]thiazine-6-carboxylic acid (2-quinolin-8-yl-4,5,6,7-tetrahydro-2H-indazol-5-yl)-amide; |
| 32 | 7-Fluoro-3-oxo-3,4-dihydro-2H-benzo[1,4]thiazine-6-carboxylic acid (2-quinolin-8-yl-4,5,6,7-tetrahydro-2H-indazol-5-yl)-amide; |
| 33 | 7-Fluoro-3-oxo-3,4-dihydro-2H-benzo[1,4]thiazine-6-carboxylic acid (2-naphthalen-1-yl-4,5,6,7-tetrahydro-2H-indazol-5-yl)-amide; |
| 34 | 3-Oxo-3,4-dihydro-2H-benzo[1,4]thiazine-6-carboxylic acid (2-naphthalen-1-yl-4,5,6,7-tetrahydro-2H-indazol-5-yl)-amide; |
| 35 | 6-Dimethylamino-2-fluoro-3-{[2-(6-methoxy-[1,5]naphthyridin-4-yl)-4,5,6,7-tetrahydro-2H-indazol-5-ylamino]-methyl}-benzonitrile; |
| 36 | (3,4-Dihydro-2H-benzo[1,4]thiazin-6-ylmethyl)-[2-(6-methoxy-[1,5]naphthyridin-4-yl)-4,5,6,7-tetrahydro-2H-indazol-5-yl]-amine; |
| 37 | Benzo[1,3]dioxol-5-ylmethyl-[2-(6-methoxy-[1,5]naphthyridin-4-yl)-4,5,6,7-tetrahydro-2H-indazol-5-yl]-amine; |
| 38 | (2,2-Difluoro-benzo[1,3]dioxol-5-ylmethyl)-[2-(6-methoxy-[1,5]naphthyridin-4-yl)-4,5,6,7-tetrahydro-2H-indazol-5-yl]-amine; |
| 39 | (4-Dimethylamino-benzyl)-[2-(6-methoxy-[1,5]naphthyridin-4-yl)-4,5,6,7-tetrahydro-2H-indazol-5-yl]-amine; |
| 40 | 7-Fluoro-6-{[2-(6-methoxy-[1,5]naphthyridin-4-yl)-4,5,6,7-tetrahydro-2H-indazol-5-ylamino]-methyl}-4H-benzo[1,4]thiazin-3-one; |
| 41 | 6-{[2-(6-Methoxy-[1,5]naphthyridin-4-yl)-4,5,6,7-tetrahydro-2H-indazol-5-ylamino]-methyl}-4H-benzo[1,4]thiazin-3-one; |
| 42 | (2,3-Dihydro-benzo[1,4]dioxin-6-ylmethyl)-[2-(6-methoxy-[1,5]naphthyridin-4-yl)-4,5,6,7-tetrahydro-2H-indazol-5-yl]-amine; |
| 43 | (7-Fluoro-2,3-dihydro-benzo[1,4]dioxin-6-ylmethyl)-[2-(6-methoxy-[1,5]naphthyridin-4-yl)-4,5,6,7-tetrahydro-2H-indazol-5-yl]-amine; |
| 44 | 6-{[2-(6-Methoxy-[1,5]naphthyridin-4-yl)-4,5,6,7-tetrahydro-2H-indazol-5-ylamino]-methyl}-4H-pyrido[3,2-b][1,4]oxazin-3-one; |
| 45 | [2-(6-Methoxy-[1,5]naphthyridin-4-yl)-4,5,6,7-tetrahydro-2H-indazol-5-yl]-(3-phenyl-propyl)-amine; |
| 46 | [2-(6-Methoxy-[1,5]naphthyridin-4-yl)-4,5,6,7-tetrahydro-2H-indazol-5-yl]-(3-phenyl-allyl)-amine; |
| 47 | [2-(6-Methoxy-[1,5]naphthyridin-4-yl)-4,5,6,7-tetrahydro-2H-indazol-5-yl]-(3-pyridin-3-yl-allyl)-amine; |
| 48 | [3-(3,4-Dichloro-phenyl)-propyl]-2-(6-methoxy-[1,5]naphthyridin-4-yl)-4,5,6,7-tetrahydro-2H-indazol-5-yl]-amine; |

-continued

| Ex. | Compound Name |
|---|---|
| 49 | [2-(6-Methoxy-[1,5]naphthyridin-4-yl)-4,5,6,7-tetrahydro-2H-indazol-5-yl]-(3-p-tolyl-propyl)-amine; |
| 50 | (2,3-Dihydro-benzo[1,4]dioxin-6-ylmethyl)-[2-(6-methoxy-quinolin-4-yl)-4,5,6,7-tetrahydro-2H-indazol-5-yl]-amine; |
| 51 | (7-Fluoro-2,3-dihydro-benzo[1,4]dioxin-6-ylmethyl)-[2-(6-methoxy-quinolin-4-yl)-4,5,6,7-tetrahydro-2H-indazol-5-yl]-amine; |
| 52 | 6-{[2-(6-Methoxy-quinolin-4-yl)-4,5,6,7-tetrahydro-2H-indazol-5-ylamino]-methyl}-4H-benzo[1,4]thiazin-3-one; |
| 53 | 7-Fluoro-6-{[2-(6-methoxy-quinolin-4-yl)-4,5,6,7-tetrahydro-2H-indazol-5-ylamino]-methyl}-4H-benzo[1,4]thiazin-3-one; |
| 54 | 6-{[2-(6-Methoxy-quinolin-4-yl)-4,5,6,7-tetrahydro-2H-indazol-5-ylamino]-methyl}-4H-pyrido[3,2-b][1,4]oxazin-3-one; |
| 55 | [2-(6-Methoxy-quinolin-4-yl)-4,5,6,7-tetrahydro-2H-indazol-5-yl]-(3-phenyl-allyl)-amine; |
| 56 | [2-(6-Methoxy-quinolin-4-yl)-4,5,6,7-tetrahydro-2H-indazol-5-yl]-(2-methyl-3-phenyl-allyl)-amine; |
| 57 | [3-(4-Fluoro-phenyl)-allyl]-[2-(6-methoxy-quinolin-4-yl)-4,5,6,7-tetrahydro-2H-indazol-5-yl]-amine; |
| 58 | N-(3,5-Difluoro-phenyl)-2-[2-(6-methoxy-[1,5]naphthyridin-4-yl)-4,5,6,7-tetrahydro-2H-indazol-5-ylamino]-acetamide; |
| 59 | 2-[2-(6-Methoxy-[1,5]naphthyridin-4-yl)-4,5,6,7-tetrahydro-2H-indazol-5-ylamino]-N-phenyl-acetamide; |
| 60 | 2-[2-(6-Methoxy-[1,5]naphthyridin-4-yl)-4,5,6,7-tetrahydro-2H-indazol-5-ylamino]-N-p-tolyl-acetamide; |
| 61 | N-(3,5-Difluoro-phenyl)-2-[2-(6-methoxy-quinolin-4-yl)-4,5,6,7-tetrahydro-2H-indazol-5-ylamino]-acetamide; |
| 62 | N-(3,4-Dichloro-phenyl)-2-[2-(6-methoxy-quinolin-4-yl)-4,5,6,7-tetrahydro-2H-indazol-5-ylamino]-acetamide |
| 63 | 6-{2-[2-(6-Methoxy-quinolin-4-yl)-4,5,6,7-tetrahydro-2H-indazol-5-ylamino]-acetyl}-4H-benzo[1,4]oxazin-3-one; |
| 64 | 6-{2-[2-(6-Methoxy-quinolin-4-yl)-2,4,6,7-tetrahydro-pyrazolo[4,3-c]pyridin-5-yl]acetyl}-4H-benzo[1,4]oxazin-3-one; |
| 65 | [2-(6-Methoxy-[1,5]naphthyridin-4-yl)-4,5,6,7-tetrahydro-2H-indazol-5-yl]-(2-phenoxy-ethyl)-amine; |
| 66 | 6-({Benzyl-[2-(6-methoxy-[1,5]naphthyridin-4-yl)-4,5,6,7-tetrahydro-2H-indazol-5-yl]-amino}-methyl)-4H-benzo[1,4]thiazin-3-one; |
| 67 | [[2-(6-Methoxy-[1,5]naphthyridin-4-yl)-4,5,6,7-tetrahydro-2H-indazol-5-yl]-(3-oxo-3,4-dihydro-2H-benzo[1,4]thiazin-6-ylmethyl)-amino]-acetic acid tert-butyl ester; |
| 68 | [[2-(6-Methoxy-[1,5]naphthyridin-4-yl)-4,5,6,7-tetrahydro-2H-indazol-5-yl]-(3-oxo-3,4-dihydro-2H-benzo[1,4]thiazin-6-ylmethyl)-amino]-acetic acid; |
| 69 | 4-Methyl-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide; |
| 70 | Quinoxaline-2-carboxylic acid [2-(6-methoxy-[1,5]naphthyridin-4-yl)-4,5,6,7-tetrahydro-2H-indazol-5-yl]-amide; |
| 71 | 1H-Benzoimidazole-2-carboxylic acid [2-(6-methoxy-quinolin-4-yl)-4,5,6,7-tetrahydro-2H-indazol-5-yl]-amide; |
| 72 | 5-Bromo-thiophene-2-carboxylic acid [2-(6-methoxy-quinolin-4-yl)-4,5,6,7-tetrahydro-2H-indazol-5-yl]-amide; |
| 73 | 5-Acetyl-thiophene-2-carboxylic acid [2-(6-methoxy-quinolin-4-yl)-4,5,6,7-tetrahydro-2H-indazol-5-yl]-amide; |
| 74 | 5,6-Difluoro-1H-indole-2-carboxylic acid [2-(6-methoxy-quinolin-4-yl)-4,5,6,7-tetrahydro-2H-indazol-5-yl]-amide; |
| 75 | 5-Methyl-1H-indole-2-carboxylic acid [2-(6-methoxy-quinolin-4-yl)-4,5,6,7-tetrahydro-2H-indazol-5-yl]-amide; |
| 76 | 5-Bromo-1H-indole-2-carboxylic acid [2-(6-methoxy-quinolin-4-yl)-4,5,6,7-tetrahydro-2H-indazol-5-yl]-amide; |
| 77 | 5-Chloro-1H-indole-2-carboxylic acid [2-(6-methoxy-quinolin-4-yl)-4,5,6,7-tetrahydro-2H-indazol-5-yl]-amide; |
| 78 | 2-Chloro-N-[2-(6-methoxy-quinolin-4-yl)-4,5,6,7-tetrahydro-2H-indazol-5-yl]-nicotinamide; |
| 79 | 4-Methyl-3,4-dihydro-2H-benzo[1,4]oxazine-7-carboxylic acid [2-(6-methoxy-quinolin-4-yl)-4,5,6,7-tetrahydro-2H-indazol-5-yl]-amide; |
| 80 | 1-(4-Chloro-phenyl)-cyclopentanecarboxylic acid [2-(6-methoxy-quinolin-4-yl)-4,5,6,7-tetrahydro-2H-indazol-5-yl]-amide; |
| 81 | 3-Oxo-3,4-dihydro-2H-benzo[1,4]thiazine-6-carboxylic acid [2-(7-chloro-quinolin-4-yl)-4,5,6,7-tetrahydro-2H-indazol-5-yl]-amide; |
| 82 | 3-Oxo-3,4-dihydro-2H-benzo[1,4]thiazine-6-carboxylic acid [2-(6-fluoro-2-methyl-quinolin-4-yl)-4,5,6,7-tetrahydro-2H-indazol-5-yl]-amide; |
| 83 | 2-[2-(6-Methoxy-[1,5]naphthyridin-4-yl)-4,5,6,7-tetrahydro-2H-indazol-5-ylamino]-N-(3-oxo-3,4-dihydro-2H-benzo[1,4]thiazin-6-yl)-acetamide; |
| 84 | N-Benzyl-2-[2-(6-methoxy-[1,5]naphthyridin-4-yl)-4,5,6,7-tetrahydro-2H-indazol-5-ylamino]-acetamide; |
| 85 | (4-Diethylamino-benzyl)-[2-(6-methoxy-[1,5]naphthyridin-4-yl)-4,5,6,7-tetrahydro-2H-indazol-5-yl]-amine; |
| 86 | [2-(6-Methoxy-[1,5]naphthyridin-4-yl)-4,5,6,7-tetrahydro-2H-indazol-5-yl]-(4-piperidin-1-yl-benzyl)-amine; |

-continued

| Ex. | Compound Name |
|---|---|
| 87 | [2-(6-Methoxy-[1,5]naphthyridin-4-yl)-4,5,6,7-tetrahydro-2H-indazol-5-yl]-(4-pyrrolidin-1-yl-benzyl)-amine; |
| 88 | (2-Fluoro-4,5-dimethoxy-benzyl)-[2-(6-methoxy-[1,5]naphthyridin-4-yl)-4,5,6,7-tetrahydro-2H-indazol-5-yl]-amine; |
| 89 | [2-(6-Methoxy-[1,5]naphthyridin-4-yl)-4,5,6,7-tetrahydro-2H-indazol-5-yl]-[3-(2-nitro-phenyl)-allyl]-amine; |
| 90 | 3-(4-Chloro-phenyl)-N-[2-(6-methoxy-[1,5]naphthyridin-4-yl)-4,5,6,7-tetrahydro-2H-indazol-5-yl]-acrylamide; |
| 91 | [3-(5-Fluoro-2-trifluoromethyl-phenyl)-allyl]-[2-(6-methoxy-[1,5]naphthyridin-4-yl)-4,5,6,7-tetrahydro-2H-indazol-5-yl]-amine; |
| 92 | 3-(3,4-Dichloro-phenyl)-N-[2-(6-methoxy-[1,5]naphthyridin-4-yl)-4,5,6,7-tetrahydro-2H-indazol-5-yl]-acrylamide; |
| 93 | 3-(3,4-Difluoro-phenyl)-N-[2-(6-methoxy-[1,5]naphthyridin-4-yl)-4,5,6,7-tetrahydro-2H-indazol-5-yl]-acrylamide; |
| 94 | 3-(2-Chloro-5-nitro-phenyl)-N-[2-(6-methoxy-[1,5]naphthyridin-4-yl)-4,5,6,7-tetrahydro-2H-indazol-5-yl]-acrylamide; |
| 95 | N-[2-(6-Methoxy-[1,5]naphthyridin-4-yl)-4,5,6,7-tetrahydro-2H-indazol-5-yl]-3-pyridin-2-yl-acrylamide; |
| 96 | 3-Oxo-3,4-dihydro-2H-benzo[1,4]thiazine-6-carboxylic acid [1-(2,8-bis-trifluoromethyl-quinolin-4-yl)-4,5,6,7-tetrahydro-1H-indazol-5-yl]-amide; |
| 97 | 3-Oxo-3,4-dihydro-2H-benzo[1,4]thiazine-6-carboxylic acid [1-(2-trifluoromethyl-quinolin-4-yl)-4,5,6,7-tetrahydro-1H-indazol-5-yl]-amide; |
| 98 | 7-Bromo-3-oxo-3,4-dihydro-2H-benzo[1,4]thiazine-6-carboxylic acid [1-(6-methoxy-quinolin-4-yl)-4,5,6,7-tetrahydro-1H-indazol-5-yl]-amide; |
| 99 | 3-Oxo-7-trifluoromethyl-3,4-dihydro-2H-benzo[1,4]thiazine-6-carboxylic acid [1-(6-methoxy-quinolin-4-yl)-4,5,6,7-tetrahydro-1H-indazol-5-yl]-amide; |
| 100 | (8-Fluoro-2,3-dihydro-benzo[1,4]dioxin-6-ylmethyl)-[2-(6-methoxy-quinolin-4-yl)-4,5,6,7-tetrahydro-2H-indazol-5-yl]-amine; |
| 101 | (8-Fluoro-2,3-dihydro-benzo[1,4]dioxin-6-ylmethyl)-[2-(6-methoxy-[1,5]naphthyridin-4-yl)-4,5,6,7-tetrahydro-2H-indazol-5-yl]-amine; |
| 102 | 3,4-Dihydro-2H-benzo[1,4]thiazin-6-ylmethyl)-[2-(6-methoxy-quinolin-4-yl)-4,5,6,7-tetrahydro-2H-indazol-5-yl]-amine; |
| 103 | (7-Chloro-2,3-dihydro-benzo[1,4]dioxin-6-ylmethyl)-[2-(6-methoxy-quinolin-4-yl)-4,5,6,7-tetrahydro-2H-indazol-5-yl]-amine; |
| 104 | (7-Chloro-2,3-dihydro-benzo[1,4]dioxin-6-ylmethyl)-[2-(6-methoxy-[1,5]naphthyridin-4-yl)-4,5,6,7-tetrahydro-2H-indazol-5-yl]-amine; |
| 105 | N-((6-chlorobenzo[d][1,3]dioxol-5-yl)methyl)-2-(6-methoxy-1,5-naphthyridin-4-yl)-4,5,6,7-tetrahydro-2H-indazol-5-amine; |
| 106 | (7-Fluoro-3,4-dihydro-2H-benzo[1,4]thiazin-6-ylmethyl)-[2-(6-methoxy-quinolin-yl)-4,5,6,7-tetrahydro-2H-indazol-5-yl]-amine; |
| 107 | (7-Fluoro-3,4-dihydro-2H-benzo[1,4]thiazin-6-ylmethyl)-[2-(6-methoxy-[1,5]naphthyridin-4-yl)-4,5,6,7-tetrahydro-2H-indazol-5-yl]-amine; |
| 108 | 5,7-Difluoro-3-oxo-3,4-dihydro-2H-benzo[1,4]thiazine-6-carboxylic acid [2-(6-methoxy-quinolin-4-yl)-4,5,6,7-tetrahydro-2H-indazol-5-yl]-amide; |
| 109 | 5,7-Difluoro-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide; |
| 110 | N-[2-(6-Methoxy-[1,5]naphthyridin-4-yl)-4,5,6,7-tetrahydro-2H-indazol-5-yl]-4-methyl-3-nitro-benzamide; |
| 111 | N-[2-(6-Methoxy-quinolin-4-yl)-4,5,6,7-tetrahydro-2H-indazol-5-yl]-4-methyl-3-nitro-benzamide; |
| 112 | 3-Oxo-7-trifluoromethyl-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide; |
| 113 | 7-Bromo-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide; |
| 114 | 7-Bromo-3-oxo-3,4-dihydro-2H-benzo[1,4]thiazine-6-carboxylic acid [2-(6-methoxy-quinolin-4-yl)-4,5,6,7-tetrahydro-2H-indazol-5-yl]-amide; |
| 115 | 3-Oxo-7-trifluoromethyl-3,4-dihydro-2H-benzo[1,4]thiazine-6-carboxylic acid [2-(6-methoxy-quinolin-4-yl)-4,5,6,7-tetrahydro-2H-indazol-5-yl]-amide; |
| 116 | 3-Oxo-3,4-dihydro-2H-benzo[1,4]oxazine-6-carboxylic acid [2-(6-methoxy-quinolin-4-yl)-4,5,6,7-tetrahydro-2H-indazol-5-yl]-amide; |
| 117 | 3-Oxo-3,4-dihydro-2H-benzo[1,4]oxazine-6-carboxylic acid [2-(6-methoxy-[1,5]naphthyridin-4-yl)-4,5,6,7-tetrahydro-2H-indazol-5-yl]-amide; |
| 118 | 2-Fluoro-N-[2-(6-methoxy-quinolin-4-yl)-4,5,6,7-tetrahydro-2H-indazol-5-yl]-4-nitro-benzamide; |
| 119 | 4-Methoxy-N-[2-(6-methoxy-[1,5]naphthyridin-4-yl)-4,5,6,7-tetrahydro-2H-indazol-5-yl]-3-nitro-benzamide; |
| 120 | 3-(2,4-Difluoro-phenyl)-N-[2-(6-methoxy-[1,5]naphthyridin-4-yl)-4,5,6,7-tetrahydro-2H-indazol-5-yl]-acrylamide; |
| 121 | [2-(3,5-Difluoro-phenoxy)-ethyl]-{2-[1-(6-methoxy-quinolin-4-yl)-1H-pyrazol-4-yl]-1-methyl-ethyl}-amine; |
| 122 | 2-[2-(6-Methoxy-[1,5]naphthyridin-4-yl)-4,5,6,7-tetrahydro-2H-indazol-5-ylamino]-N-(3-trifluoromethyl-phenyl)-acetamide; |
| 123 | N-(3-Chloro-phenyl)-2-[2-[2-(6-methoxy-[1,5]naphthyridin-4-yl)-4,5,6,7-tetrahydro-2H-indazol-5-ylamino]-acetamide; |

-continued

| Ex. | Compound Name |
|---|---|
| 124 | 5-Acetylamino-2-bromo-N-[2-(6-methoxy-[1,5]naphthyridin-4-yl)-4,5,6,7-tetrahydro-2H-indazol-5-yl]-benzamide; |
| 125 | 2,4-Dichloro-5-fluoro-N-[2-(6-methoxy-[1,5]naphthyridin-4-yl)-4,5,6,7-tetrahydro-2H-indazol-5-yl]-benzamide; |
| 126 | 6-Dimethylamino-2-fluoro-3-{[2-(6-methoxy-quinolin-4-yl)-4,5,6,7-tetrahydro-2H-indazol-5-ylamino]-methyl}-benzonitrile; |
| 127 | 8-Fluoro-2,3-dihydro-benzo[1,4]dioxine-6-carboxylic acid [2-(6-methoxy-[1,5]naphthyridin-4-yl)-4,5,6,7-tetrahydro-2H-indazol-5-yl]-amide; |
| 128 | 8-Fluoro-2,3-dihydro-benzo[1,4]dioxine-6-carboxylic acid [2-(6-methoxy-quinolin-4-yl)-4,5,6,7-tetrahydro-2H-indazol-5-yl]-amide; |
| 129 | 2,2-Dimethyl-3-oxo-3,4-dihydro-2H-benzo[1,4]thiazine-6-carboxylic acid [2-(6-methoxy-quinolin-4-yl)-4,5,6,7-tetrahydro-2H-indazol-5-yl]-amide; |
| 130 | 7-Methoxy-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide; |
| 131 | 7-Methyl-3-oxo-3,4-dihydro-2H-benzo[1,4]thiazine-6-carboxylic acid [2-(6-methoxy-quinolin-4-yl)-4,5,6,7-tetrahydro-2H-indazol-5-yl]-amide; |
| 132 | 7-Methyl-3-oxo-3,4-dihydro-2H-benzo[1,4]thiazine-6-carboxylic acid [1-(6-methoxy-quinolin-4-yl)-4,5,6,7-tetrahydro-1H-indazol-5-yl]-amide; |
| 133 | 7-Methyl-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide; |
| 134 | [2-(3,5-Difluoro-phenoxy)-ethyl]-[2-(6-methoxy-[1,5]naphthyridin-4-yl)-4,5,6,7-tetrahydro-2H-indazol-5-yl]-amine; |
| 135 | 6-[2-(6-Methoxy-quinolin-4-yl)-4,5,6,7-tetrahydro-2H-indazol-5-ylcarbamoyl]-3-oxo-3,4-dihydro-2H-benzo[1,4]thiazine-7-carboxylic acid ethyl ester; |
| 136 | 6-[2-(6-Methoxy-quinolin-4-yl)-4,5,6,7-tetrahydro-2H-indazol-5-ylcarbamoyl]-3-oxo-3,4-dihydro-2H-benzo[1,4]thiazine-7-carboxylic acid, potassium salt; |
| 137 | 6-[2-(6-Methoxy-[1,5]naphthyridin-4-yl)-4,5,6,7-tetrahydro-2H-indazol-5-ylcarbamoyl]-3-oxo-3,4-dihydro-2H-benzo[1,4]thiazine-7-carboxylic acid ethyl ester; |
| 138 | 6-[2-(6-Methoxy-[1,5]naphthyridin-4-yl)-4,5,6,7-tetrahydro-2H-indazol-5-ylcarbamoyl]-3-oxo-3,4-dihydro-2H-benzo[1,4]thiazine-7-carboxylic acid and |
| 139 | 6-{[1-(2-Trifluoromethyl-quinolin-4-yl)-4,5,6,7-tetrahydro-1H-indazol-5-ylamino]-methyl}-4H-benzo[1,4]thiazin-3-one. |

Compounds according to the present invention may be made according to processes within the skill of the art and/or according to processes of this invention, such as those described in the schemes and examples that follow and by matrix or combinatorial methods. To obtain the various compounds herein, starting materials may be employed that carry the ultimately desired substituents though the reaction scheme with or without protection as appropriate. Starting materials may be obtained from commercial sources or synthesized by methods known to one skilled in the art. Alternatively, it may be necessary to employ, in the place of the ultimately desired substituent, a suitable group, which may be carried through the reaction scheme and replaced as appropriate with the desired substituent. Those of ordinary skill in the art will be able to modify and adapt the guidance provided herein to make compounds according to the present invention.

Embodiments of processes illustrated herein include, when chemically meaningful, one or more steps such as hydrolysis, halogenation, protection, and deprotection. These steps can be implemented in light of the teachings provided herein and the ordinary skill in the art.

During any of the processes for preparation of the compounds of the present invention, it may be necessary and/or desirable to protect sensitive or reactive groups on any of the molecules concerned. In addition, compounds of this invention may be modified by using protecting groups; such compounds, precursors, or prodrugs are also within the scope of the invention. This modification may be achieved by means of conventional protecting groups, such as those described in "Protective Groups in Organic Chemistry", J. F. W. McOmie, ed., Plenum Press, 1973; and T. W. Greene & P. G. M. Wuts, "Protective Groups in Organic Synthesis", $3^{rd}$ ed., John Wiley & Sons, 1999. The protecting groups may be removed at a convenient subsequent stage using methods known in the art.

| Table of Acronyms | |
|---|---|
| Term | Acronym |
| Tetrahydrofuran | THF |
| N,N-Dimethylformamide | DMF |
| N,N-Dimethylacetamide | DMA |
| Dimethyl sulfoxide | DMSO |
| tert-Butylcarbamoyl | Boc |
| Bovine serum albumin | BSA |
| High-pressure liquid chromatography | HPLC |
| Thin layer chromatography | TLC |
| N,N-diisopropylethylamine | DIEA |
| Triethylamine | TEA |
| 1,8-Diazabicyclo[5.4.0]undec-7-ene | DBU |
| 1-(3-Dimethylaminopropyl)-3-ethylcarbodiimide hydrochloride | EDC |
| 1-Hydroxybenzotriazole | HOBT |
| Methicillin-resistant *Staphylococcus aureus* | MRSA |

Scheme A

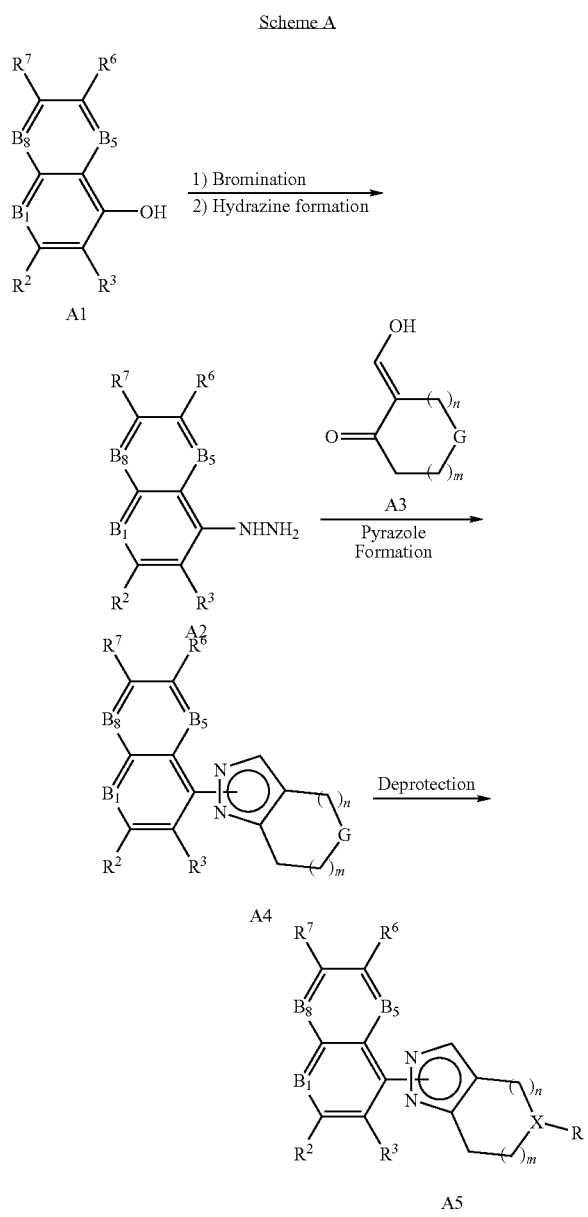

Referring to Scheme A, bicyclic alcohols A1 may be commercially available, or may be prepared as described in the Examples below. Conversion of alcohols A1 to the corresponding bromides (not shown) may be accomplished using various brominating reagents, such as $PBr_3$, $PBr_5$, or HBr, neat or in a suitable solvent such as DMF. Preferably, $PBr_3$ in DMF is used. Hyrazines A2 may be prepared from the bromides by treatment with hydrazine, in a polar solvent such as 1-methyl-2-pyrrolidinone, EtOH, or 2-methoxyethanol, at temperatures between room temperature and the boiling point of the solvent. Preferred solvents include 1-methyl-2-pyrrolidinone and EtOH. Elevated temperatures may serve to increase the rate of the desired reaction and reduce the incidence of side reactions.

Hydrazines A2 may then be condensed with ketones A3, where G is >NPro or >C(H)—NHPro, to form compounds A4. The variable "Pro" refers to a suitable nitrogen protecting group, including tert-butylcarbamoyl (Boc), benzyl, or substituted benzyl. The condensation reaction may be performed in the presence of an acid such as p-toluenesulfonic acid, acetic acid, or HCl, in a suitable solvent such as THF, EtOH, or $CH_3OH$. Alternatively, the reaction can take place without acid, in a protic solvent such as EtOH or $CH_3OH$. Preferably, reactions are performed using p-toluenesulfonic acid in THF.

The protecting group in compounds of formula A4 may be removed using methods known to one skilled in the art to form amines of formula A5. For example, where a Boc group is employed, it may be removed using HCl, TFA, or p-toluenesulfonic acid, in a solvent such as $CH_3OH$, dioxane, or $CH_2Cl_2$. Preferably, a Boc group is removed with HCl in dioxane. Where a benzyl group is used, it may be removed by catalytic hydrogenation conditions including a catalyst such as Pd black or Pd/C, a hydrogen source such as cyclohexadiene, ammonium formate, or gaseous $H_2$, and in a solvent such as $CH_3OH$, EtOH, or EtOAc. Alternatively, the benzyl group may be removed using a Lewis acid such as $AlCl_3$, in a solvent such as benzene. Preferably, hydrogenation is performed using Pd/C and ammonium formate in a solvent such as EtOH.

Scheme B

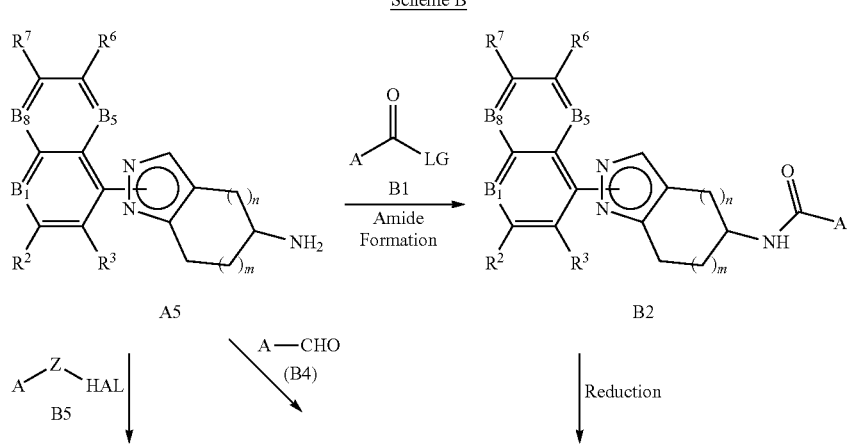

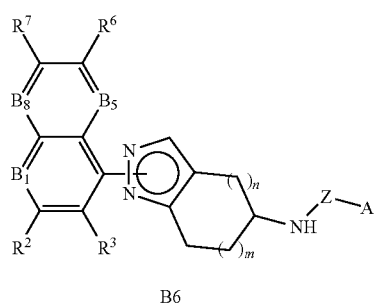

B6

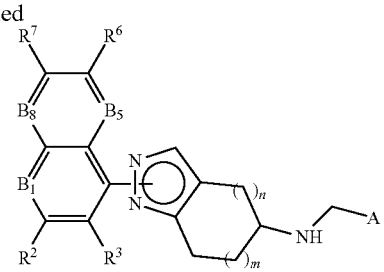

B3

Referring to Scheme B, the reactions are shown starting with compounds of formula A5 where X is CH and R is NH$_2$, but it is understood that they may also be performed on compounds of formula A5 where X is N and R is H to form compounds of formula (I).

Amines of formula A5 may be converted to amides of formula B2 by reaction with acyl derivatives of formula B1 where LG is OH through standard amide coupling methods such as HOBT/EDC, in a solvent such as DMF. Alternatively, acylation may take place through reaction with a compound of formula B1 where LG is chloride, in the presence of a suitable tertiary amine base such as Et$_3$N, in a solvent such as CH$_2$Cl$_2$. The carbonyl group in amides AS may be reduced to the methylene using an appropriate reducing agent such as BH$_3$ to form amines B3. Alternatively, amines B3 may be prepared directly from amines A5 through reductive amination with an aldehyde of formula B4. Reductive amination may be performed with or without the addition of an activating agent such as molecular sieves, AcOH, or Ti(OiPr)$_4$, followed by a reducing agent such as NaBH$_3$CN, NaB(OAc)$_3$H, or NaBH$_4$, in a solvent such as CH$_3$OH, DMF, dichloroethane, or THF. Preferred conditions include NaB(OAc)$_3$H, in the presence of catalytic acetic acid, in a solvent such as dichloroethane; NaBH$_4$ in a solvent such as CH$_3$OH; or NaBH$_4$ and Ti(OiPr)$_4$ in a solvent such as CH$_3$OH.

Amines A5 may also be alkylated with suitable halides B5 (where HAL is Cl, Br, OTs, or I) to form amines B6 where Z is C$_{1-3}$alkylene, C$_3$alkenylene, or CH$_2$C(O) where the CH$_2$ in this group CH$_2$C(O) is attached to the HAL group. Alkylation may be accomplished in the presence of a base such as K$_2$CO$_3$, Et$_3$N, NaHCO$_3$, DIEA, with or without catalytic NaI, in a solvent such as DMF, acetone, CH$_3$CN, EtOH, or THF, at temperatures between room temperature and the boiling temperature of the solvent used. Preferably, alkylation employs Et$_3$N, or K$_2$CO$_3$ with catalytic NaI, in a solvent such as DMF, at about 50° C.

Compounds of formulae B2, B3, and B6 represent compounds of formula (I) where R$^e$ is —H.

Scheme C

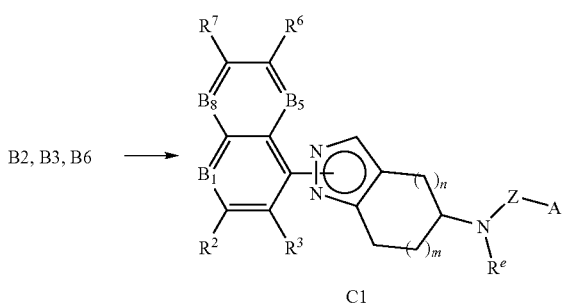

C1

Referring to Scheme C, compounds of formula B2, B3, or B6 may be alkylated, reductively aminated, or acylated using methods known to one skilled in the art to install the R$^e$ substituent and form compounds of formula C1. Compounds of formula C1 represent compounds of formula (I) where R$^e$ is not —H.

Where the processes for the preparation of the compounds according to the invention give rise to mixture of stereoisomers, these isomers may be separated by conventional techniques such as resolution, for example by formation of diastereomeric salts, kinetic resolution including variants thereof, such as dynamic resolution, preferential crystallization, biotransformation, enzymatic transformation, and preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric amines, esters, or amides, followed by chromatographic separation and removal of the chiral auxiliary. Alternatively, the compounds may be separated using a chiral HPLC column. Regioisomeric mixtures may also be separated into their constituent regioisomers by conventional techniques. Similarly, compounds of the present invention may exist in atropisomeric forms, and such forms may be separated using conventional methods.

For therapeutic use, salts of the compounds of the present invention are those that are pharmaceutically acceptable. However, salts of acids and bases that are non-pharmaceutically acceptable may also find use, for example, in the preparation or purification of a pharmaceutically acceptable compound. All salts, whether pharmaceutically acceptable or not are included within the ambit of the present invention.

Pharmaceutically acceptable salts, esters, and amides of compounds according to the present invention refer to those salt, ester, and amide forms of the compounds of the present invention which would be apparent to the pharmaceutical chemist, i.e., those which are non-toxic and which would favorably affect the pharmacokinetic properties of said compounds of the present invention. Those compounds having favorable pharmacokinetic properties would be apparent to the pharmaceutical chemist, i.e., those which are non-toxic and which possess such pharmacokinetic properties to provide sufficient palatability, absorption, distribution, metabolism and excretion. Other factors, more practical in nature, which are also important in the selection, are cost of raw materials, ease of crystallization, yield, stability, hygroscopicity and flowability of the resulting bulk drug.

Examples of acids that may be used in the preparation of pharmaceutically acceptable salts include the following: acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid and undecylenic acid.

Compounds of the present invention containing acidic protons may be converted into their therapeutically active non-toxic metal or amine addition salt forms by treatment with appropriate organic and inorganic bases. Appropriate base salt forms comprise, for example, the ammonium salts; the alkali and earth alkaline metal salts (e.g. lithium, sodium, potassium, magnesium, calcium salts, which may be prepared by treatment with, for example, magnesium hydroxide, calcium hydroxide, potassium hydroxide, zinc hydroxide, or sodium hydroxide); and amine salts made with organic bases (e.g. primary, secondary and tertiary aliphatic and aromatic amines such as L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glutamine, 2-amino-2-(hydroxymethyl)-1,3-propanediol, and tromethamine). See, e.g., S. M. Berge, et al., "Pharmaceutical Salts", J. Pharm. Sci., 1977, 66:1-19, which is incorporated herein by reference.

"Salt" also comprises the hydrates and solvent addition forms that compounds of the present invention are able to form. Examples of such forms are hydrates, alcoholates, and generally solvates.

Examples of suitable esters include $C_{1-7}$alkyl, $C_{5-7}$cycloalkyl, phenyl, substituted phenyl, and phenyl$C_{1-6}$alkyl-esters. Preferred esters include methyl esters. Furthermore, examples of suitable esters include such esters where one or more carboxyl substituents is replaced with p-methoxybenzyloxy-carbonyl, 2,4,6-trimethylbenzyloxycarbonyl, 9-anthryloxycarbonyl, $CH_3SCH_2COO$—, tetrahydrofur-2-yloxycarbonyl, tetrahydropyran-2-yloxy-carbonyl, fur-2-yloxycarbonyl, benzoylmethoxycarbonyl, p-nitrobenzyloxy-carbonyl, 4-pyridylmethoxycarbonyl, 2,2,2-trichloroethoxycarbonyl, 2,2,2-tribromoethoxycarbonyl, t-butyloxycarbonyl, t-amyloxycarbonyl, diphenylmethoxycarbonyl, triphenylmethoxycarbonyl, adamantyloxycarbonyl, 2-benzyloxyphenyloxycarbonyl, 4-methylthiophenyloxycarbonyl, or tetrahydropyran-2-yloxycarbonyl.

Whether referred to herein explicitly or not, each of the terms "pharmaceutically acceptable salts," "pharmaceutically acceptable esters," and "pharmaceutically acceptable amides" include those salts, esters and amides, respectively that do not change the intrinsic properties of the active ingredient. See, for example, Remington, The Science and Practice of Pharmacy, 704 ($20^{th}$ ed., 2000).

"Subject" or "patient" refers to eukaryotic organisms and it includes mammals such as human beings and animals (e.g., dogs, cats, horses, rats, rabbits, mice, non-human primates) in need of observation, experiment, treatment or prevention in connection with the relevant disease or condition. Preferably, the patient or subject is a human being.

"Composition" includes a product comprising the specified ingredients in the specified amounts, including in the effective amounts, as well as any product that results directly or indirectly from combinations of the specified ingredients in the specified amounts.

Administration of at least one compound of formula (I) and/or derivative thereof refers to the administration of such compound in a suitable administration form, whether as such compound itself or as part of a suitable pharmaceutical composition.

"Therapeutically effective amount" or "effective amount" and grammatically related terms mean that amount of active compound or pharmaceutical agent that elicits the biological or medicinal response in an in vitro system, a tissue system, an animal or human being, that is being sought by a researcher, veterinarian, medical doctor, or other clinician, where the medicinal response includes, but is not limited to, alleviation of the symptoms of the disease or disorder being treated. Analogously, terms such as "inhibitory amount", "anti-microbial amount", "anti-infective amount", "antibacterial amount", "prophylactically effective amount", and grammatically related terms refer to the amount of active compound or pharmaceutical agent that elicits the response being referred to, such as inhibition and antibacterial effect, in the system being studied, whether an in vitro system, an animal or a human being that is sought by a researcher, veterinarian, medical doctor, or other clinician, where the medicinal response includes, but is not limited to, alleviation of the symptoms of the disease or disorder being treated. The laboratory practice of assays and the criteria for ascertaining in light of such assays the effects referred to herein are well-known and they are part of the standard practice in this field, and therefore are not provided explicitly herein. Similarly, specific selections of embodiments of this invention according to their effects determined by such assays can be done as a matter of routine experimentation by using such assays and the teachings provided herein. Effects of embodiments of this invention are manifested against bacteria in a plurality of eukaryotic organisms. Accordingly, the specific host in which the antibacterial effect is manifested is not a limitation of the present invention. In addition to medicine, fields of use of embodiments of this invention include veterinarian applications encompassing areas such as aquaculture.

Embodiments of this invention include methods for inhibiting bacterial activity. Inhibition effects include, but are not limited to, inhibition of at least one of DNA gyrase, topoisomerase IV, MRSA, ciprofloxacin-resistant (CipR) MRSA, and combinations thereof.

As used herein, "treating" a disorder, and grammatically related terms, mean eliminating or otherwise ameliorating the cause and/or effects thereof. Terms such as to "inhibit", and grammatically related terms, the onset of a disorder or event, and to "prevent" a disorder or condition, and grammatically related terms, mean preventing, delaying or reducing the likelihood of such onset.

The terms "unit dose" and their grammatical equivalent forms are used herein to refer to physically discrete units suitable as unitary dosages for human patients and other animals, each unit containing a predetermined effective, pharmacologic amount of the active ingredient calculated to produce the desired pharmacological effect. The specifications for the novel unit dosage forms of this invention are determined by, and are directly dependent on, the characteristics of the active ingredient, and on the limitations inherent in the art of compounding such an active ingredient for therapeutic use in humans and other animals.

Compounds of the present invention may be used in pharmaceutical compositions to treat patients (humans and other mammals) with disorders involving bacterial activity. In particular, compounds of the present invention may be used in pharmaceutical compositions to treat bacterial infection.

The present invention features pharmaceutical compositions containing such compounds and methods of using such compositions in the treatment or prevention of conditions that are mediated by bacterial activity. Accordingly, the present invention also contemplates a pharmaceutical composition that comprises at least one compound according to this invention, preferably in a pharmaceutically acceptable carrier. The at least one compound according to this invention is present in such composition in an amount sufficient to inhibit bacterial activity. More particularly, the at least one compound according to this invention is present in such composition in an anti-bacterial amount.

Accordingly, a pharmaceutical composition that comprises an anti-bacterial amount of at least one compound according to the present invention in a pharmaceutically acceptable carrier is also contemplated herein. The composition comprises a unit dosage of the at least one compound according to this invention. In preferred practice, the at least one compound according to the present invention that is comprised in the pharmaceutical composition is capable of inhibiting bacterial activity in the amount at which that compound is present in the pharmaceutical composition, when that pharmaceutical composition is introduced as a unit dose into an appropriate patient or subject.

The pharmaceutical compositions can be prepared using conventional pharmaceutical excipients and compounding techniques. Examples of suitable unit dosage forms are tablets, capsules, pills, powder packets, granules, wafers, and the like, segregated multiples of any unit dosage form, as well as liquid solutions, and suspensions. Oral dosage forms may be elixirs, syrups, capsules, tablets, and the like. Examples of solid carriers include those materials usually employed in the manufacture of pills or tablets, such as lactose, starch, glucose, methylcellulose, magnesium stearate, dicalcium phosphate, mannitol, and the like, thickeners such as tragacanth and methylcellulose USP, finely divided $SiO_2$, polyvinylpyrrolidone, magnesium stearate, and the like. Typical liquid oral excipients include ethanol, glycerol, water, and the like. All excipients may be mixed as needed with inert diluents (for example, sodium and calcium carbonates, sodium and calcium phosphates, and lactose), disintegrants (for example, cornstarch and alginic acid), diluents, granulating agents, lubricants (for example, magnesium stearate, stearic acid, and talc), binders (for example, starch and gelatin), thickeners (for example, paraffin, waxes, and petrolatum), flavoring agents, coloring agents, preservatives, and the like by conventional techniques known to those of ordinary skill in the art of preparing dosage forms. Coatings can be present and include, for example, glyceryl monostearate and/or glyceryl distearate. Capsules for oral use include hard gelatin capsules in which the active ingredient is mixed with a solid diluent, and soft gelatin capsules, in which the active ingredient is mixed with water or oil, such as peanut oil, liquid paraffin, or olive oil.

Parenteral dosage forms may be prepared using water or another sterile carrier. For intramuscular, intraperitoneal, subcutaneous, and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions may include suspending agents such as cellulose derivatives, sodium alginate, polyvinyl-pyrrolidone, and gum tragacanth, and a wetting agent, such as lecithin. Suitable preservatives for aqueous suspensions include ethyl and n-propyl p-hydroxybenzoate. Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and (j) propellants.

To aid solubility, suitable ingredients, such as cyclodextrins, may be included in the compositions. Appropriate cyclodextrins (CD) are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, for example randomly methylated β-CD; hydroxy $C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-β-CD, 2-hydroxypropyl-β-CD and (2-carboxymethoxy)propyl-β-CD, and in particular 2-hydroxypropyl-β-CD (2—HP-β-CD). The term mixed ether denotes cyclodextrin derivatives wherein at least two cyclodextrin hydroxy groups are etherified with different groups such as, for example, hydroxy-propyl and hydroxy-ethyl.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

Physiologically acceptable carriers are well known in the art. Examples of liquid carriers are solutions in which compounds according to the present invention form solutions, emulsions, and dispersions. Compatible antioxidants, such as methlyparaben and propylparaben, can be present in solid and liquid compositions, as can sweeteners.

Pharmaceutical compositions according to the present invention may include suitable emulsifiers typically used in emulsion compositions. Such emulsifiers are described in standard publications such as H. P. Fiedler, 1989, Lexikon der Hilfsstoffe für Pharmazie, Kosmetic and agrenzende Gebiete, Cantor ed., Aulendorf, Germany, and in Handbook of Pharmaceutical Excipients, 1986, American Pharmaceutical Association, Washington, D.C., and the Pharmaceutical Society of Great Britain, London, UK, which are incorporated herein by reference. Examples of emulsifiers are given in U.S.

Pat. No. 6,352,998, cols. 4-5. Gelling agents may also be added to compositions according to this invention. Polyacrylic acid derivatives, such as carbomers, are examples of gelling agents, and more particularly, various types of carbopol, which are typically used in amounts from about 0.2% to about 2%. Suspensions may be prepared as a cream, an ointment, including a water-free ointment, a water-in-oil emulsion, an oil-in-water emulsion, an emulsion gel, or a gel.

It is anticipated that the compounds of the invention can be administered by oral or parenteral routes, including intravenous, intramuscular, intraperitoneal, subcutaneous, rectal, and topical administration, and inhalation. For oral administration, the compounds of the invention will generally be provided in the form of tablets, capsules, or as a solution or suspension. Other methods of administration include controlled release formulations, such as subcutaneous implants and dermal patches.

Compounds according to the present invention and mixtures thereof provide embodiments of active substance in pharmaceutical compositions that can be made with excipients and ingredients and with ordinary skill in the art. Lists of excipients and ingredients for pharmaceutical compositions are available in standard references. For example, a standard text such as The Science and Practice of Pharmacy, A. R. Gennaro, ed., provides 20 chapters in part 5, pp. 669-1050, on pharmaceutical manufacturing, including lists of ingredients to manufacture pharmaceutical compositions such as solutions (including aromatic waters, aqueous acids, douches, enemas, gargles, mouthwashes, juices, nasal solutions, otic solutions, irrigation solutions, syrups, honeys, mucilages, jellies, collodions, elixirs, glycerins, inhalants, liniments, oleopreparations, spirits, and drops), emulsions (including multiple emulsions and microemulsions), suspensions, (including gels, lotions, tablet-formulated suspensions, magmas and milks, mixtures, and official suspensions), extracts, parenteral preparations, intravenous preparations, ophthalmic preparations, topical preparations, oral solid dosage forms, coatings, controlled-release drug delivery systems, aerosols, packaging materials, antioxidants, preservatives, coloring agents, flavoring agents, diluting agents, vehicles, emulsifying agents, suspending agents, ointment bases, pharmaceutical solvents, and miscellaneous pharmaceutical necessities, including the techniques and devices for manufacturing such preparations.

Effective doses of the compounds of the present invention may be ascertained by conventional methods. The specific dosage level required for any particular patient will depend on a number of factors, including severity of the condition, type of symptoms needing treatment, the route of administration, the weight, age, and general condition of the patient, and the administration of other medicaments.

In general, it is anticipated that the daily dose (whether administered as a single dose or as divided doses) will be in the range from about 0.01 mg to about 1000 mg per day, more usually from about 1 mg to about 500 mg per day, and most usually form about 10 mg to about 200 mg per day. Expressed as dosage per unit body weight, a typical dose will be expected to be between about 0.0001 mg/kg and about 15 mg/kg, especially between about 0.01 mg/kg and about 7 mg/kg, and most especially between about 0.15 mg/kg and 2.5 mg/kg.

Anticipated oral dose ranges include from about 0.01 to 500 mg/kg, daily, more preferably from about 0.05 to about 100 mg/kg, taken in 1-4 separate doses. Some compounds of the invention may be orally dosed in the range of about 0.05 to about 50 mg/kg daily, while others may be dosed at 0.05 to about 20 mg/kg daily. Infusion doses can range from about 1.0 to about $1.0 \times 10^4$ µg/(kg min) of inhibitor, admixed with a pharmaceutical carrier over a period ranging from several minutes to several days. For topical administration, compounds of the present invention may be mixed with a pharmaceutical carrier at a concentration from about 0.1 to about 10% of drug to vehicle. Capsules, tablets or other formulations (such as liquids and film-coated tablets) may be of between 0.5 and 200 mg, such as 1, 3, 5, 10, 15, 25, 35, 50 mg, 60 mg, and 100 mg and can be administered according to the disclosed methods. Daily dosages are envisaged to be, for example, between 10 mg and 5000 mg for an adult human being of normal weight.

A method for treating a bacterial condition or infection in a patient exhibiting or susceptible to a bacterial condition or infection is also contemplated. The methods comprise administering to that patient an effective amount of a pharmaceutical composition that includes a unit dose of an active ingredient that is at least one of the compounds according to this invention dispersed in a pharmaceutically acceptable carrier.

EXAMPLES

In order to illustrate the invention, the following examples are provided. These examples do not limit the invention. They are meant to illustrate embodiments of the invention. Those skilled in the art may find additional embodiments in light of the teachings and examples provided herein, additional embodiments that are deemed to be within the scope of this invention.

General Experimental Details:

NMR spectra were obtained on a Bruker model DPX400 (400 MHz), DPX500 (500 MHz), or DPX600 (600 MHz) spectrometer. The format of the $^1$H NMR data below is: chemical shift in ppm down field of the tetramethylsilane reference (multiplicity, coupling constant J in Hz, integration).

Mass spectra were obtained on a Agilent series 1100 MSD using electropsray ionization (ESI) in either positive or negative mode as indicated.

Analytical HPLC retention times are reported in minutes, using the following methods and conditions: Instrument: Agilent HP-1100; Solvent: Acetonitrile/$H_2O$ (20 mM $NH_4OH$); Temperature: 30° C.; Wavelength: Dual detection at 220 nm and 254 nm; Method: Xterra RP 18 column (3.5 µm, 4.6×100 mm) at 1 mL/min with a 10-min linear gradient ramp from 1% $H_2O$ to 99% $H_2O$.

Preparative HPLC was performed under acidic or basic conditions: Acidic conditions: Instrument: Gilson; Solvent: Acetonitrile/$H_2O$ (0.1% TFA); Temperature: 30° C.; Wavelength: Dual detection at 220 nm and 254 nm; Method: Xterra RP 18 column (5 µm, 30×75 mm) at 20 mL/min with a gradient ramp from 1% $H_2O$ to 99% $H_2O$.

Basic conditions: Instrument, Temperature, and Wavelength as above;

Solvent: Acetonitrile/$H_2O$ (20 mM $NH_4OH$); Method: Phenomenex Synergi Max (21.2×150 mm) at 20 mL/min with a gradient ramp from 1% $H_2O$ to 99% $H_2O$.

Flash column chromatography was accomplished using the ISCO Foxy 200 system and one of the following commercially available, pre-packed columns: Biotage 40 L ($SiO_2$; 120 g), Biotage 65M ($SiO_2$; 300 g) or ISCO Redisep ($SiO_2$; 4, 12, 40, 120, or 330 g).

Supercritical fluid chromatography (SFC): Instrument: Thar Technologies SFC-50; Solvent: 15% $CH_3OH$ (0.02% $Et_3N$)/$CO_2$; Temperature: 30° C.; Pressure: 100 bar; Method: YMC-pack, DIOL-120 NP column (s-5 µm, 12 nm, 150×20 mm) at 38 mL/min.

Where solutions are said to be "concentrated," they are generally concentrated under reduced pressure using a rotary evaporator.

Example A

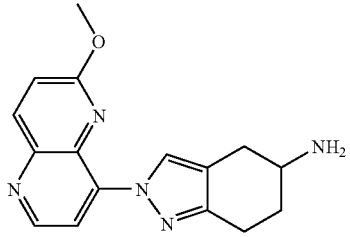

2-(6-Methoxy-[1,5]naphthyridin-4-yl)-4,5,6,7-tetrahydro-2H-indazol-5-ylamine

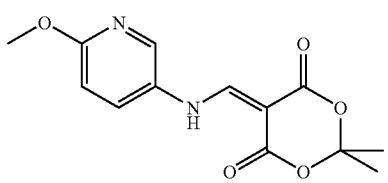

A. 5-[(6-Methoxy-pyridin-3-ylamino)-methylene]-2,2-dimethyl-[1,3]dioxane-4,6-dione. To a solution of 5-amino-2-methoxypyridine (37.2 g, 0.300 mol) in EtOH (225 mL) was added 2,2-dimethyl-1,3-dioxane-4,6-dione (Meldrum's acid) (51 g, 350 mmol) and triethyl orthoformate (44.5 g, 0.300 mol). The mixture was heated to reflux and stirred for 3 h. The resulting suspension was cooled to RT, filtered, washed with EtOH (200 mL) and dried in vacuo to provide 75 g (90%) of the title compound as a tan solid. $^1$H NMR (500 MHz, DMSO-$d_6$): 11.26 (d, J=14.6, 1H), 8.45 (d, J=14.6, 1H), 8.38 (d, J=2.9, 1H), 7.97 (dd, J=8.9, 2.9, 1H), 6.88 (d, J=8.9, 1H), 3.86 (s, 3H), 1.67 (s, 6H).

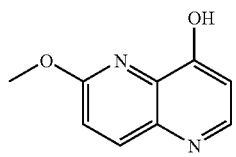

B. 6-Methoxy-[1,5]naphthyridin-4-ol. Dowtherm A (26.5: 73.5 diphenyl/diphenyl oxide) (140 mL) was added to a three-neck flask fitted with an air-condenser, thermocouple and a funnel and the solvent was heated to 260° C. To the Dowtherm A was added 5-[(6-methoxy-pyridin-3-ylamino)-methylene]-2,2-dimethyl-[1,3]dioxane-4,6-dione (34.8 g, 125 mmol) over a period of 10 min, keeping the temperature above 250° C. The funnel was rinsed with Dowtherm A (20 mL). The reaction mixture was heated for a further 4 min and then removed from the heat source. The resulting suspension was cooled to RT and treated with Et$_2$O (200 mL). The solid was filtered, washed with Et$_2$O (300 mL), hexanes (500 mL) and dried in vacuo to provide 18.8 g (85%) of the title compound as a tan solid. $^1$H NMR (500 MHz, DMSO-$d_6$): 11.88 (br s, 1H), 8.13 (br s, 2H), 7.17 (s, 1H), 6.22 (br s, 1H), 3.93 (s, 3H).

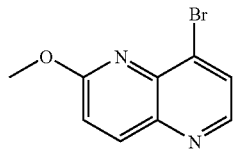

C. 8-Bromo-2-methoxy-[1,5]naphthyridine. To a suspension of 6-methoxy-[1,5]naphthyridin-4-ol (8.8 g, 0.050 mol) in DMF (167 mL) was added PBr$_3$ (4.7 mL, 0.050 mol) at 45° C. The suspension became homogeneous and then a suspension formed over 20 min. The mixture was cooled to RT and the solid was filtered and washed with Et$_2$O (100 mL). Further solids precipitated from the filtrate and were collected. Water (50 mL) was added to the solid and the suspension was basified with 1 N NaOH (200 mL). The aqueous layer was extracted with CH$_2$Cl$_2$ (3×250 mL), washed with brine (150 mL), dried (MgSO$_4$) and concentrated. The resulting residue was purified on SiO$_2$ (0-60% EtOAc/hexanes) to provide 8.9 g (75%) of the title compound as a white solid. MS (ESI): exact mass calculated for C$_9$H$_7$BrN$_2$O, 237.97; m/z found, 239.2 [M+H]$^+$. $^1$H NMR (400 MHz, DMSO-$d_6$): 8.57 (d, J=4.7, 1H), 8.27 (d, J=9.0, 1H), 8.05 (d, J=4.7, 1H), 7.30 (d, J=9.0, 1H), 4.04 (s, 3H).

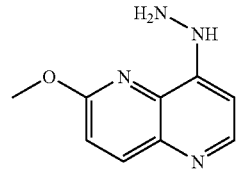

D. (6-Methoxy-[1,5]naphthyridin-4-yl)-hydrazine. To a solution of 8-bromo-2-methoxy-[1,5]naphthyridine (5.1 g, 21 mmol) in EtOH (64 mL) was added hydrazine (1.3 mL, 42 mmol). This solution was heated to 78° C. and stirred for 6 days, by which time the solution had become heterogeneous. The suspension was cooled to RT and concentrated. The resulting solid was dissolved in CH$_2$Cl$_2$ (100 mL) and washed with 10% aq. NaOH (100 mL). The aqueous phase was back-extracted with CH$_2$Cl$_2$ (2×100 mL). The combined organic extracts were dried (Na$_2$SO$_4$), filtered, and concentrated to afford 3.4 g (83%) of a brown solid. MS (ESI): exact mass calculated for C$_9$H$_{10}$N$_4$O, 190.09; m/z found, 191.3 [M+H]$^+$. $^1$H NMR (400 MHz, CDCl$_3$): 8.51 (d, J=5.2, 1H), 8.11 (d, J=9.1, 1H), 7.08 (d, J=9.1, 1H), 6.92 (d, J=5.2, 1H), 4.03 (s, 3H), 3.73 (d, J=2.8, 2H).

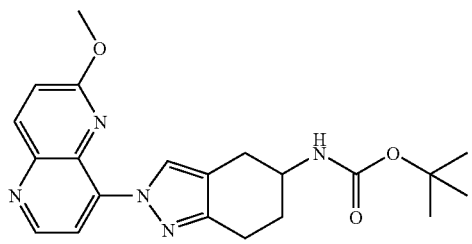

E. [2-(6-Methoxy-[1,5]naphthyridin-4-yl)-4,5,6,7-tetrahydro-2H-indazol-5-yl]-carbamic acid tert-butyl ester. To a solution of (4-oxo-cyclohexyl)-carbamic acid tert-butyl ester (5.00 g, 23.2 mmol) in THF (116 mL) was added tert-butoxy bis(dimethylamino)methane (9.6 mL, 46 mmol). The solution was heated to 65° C. and stirred for 24 h. The solution was cooled to RT, 10% aq. HCl (100 mL) was added, and the mixture was stirred for 3.5 h. The mixture was extracted with CH$_2$Cl$_2$ (2×200 mL). The combined organic extracts were washed with 10% aq. HCl (150 mL), dried (Na$_2$SO$_4$), filtered, and concentrated to afford 5.4 g of a brown oil, (3-hydroxymethylene-4-oxo-cyclohexyl)-carbamic acid tert-butyl ester, which was used without further purification, in the following step and later examples. To this oil (3.4 g, 14 mmol) was added (6-methoxy-[1,5]naphthyridin-4-yl)-hydrazine (3.23 g, 16.7 mmol), followed by THF (44.4 mL). The solution was stirred at RT for 4 h. p-Toluenesulfonic acid (7.9 g, 42 mmol) was added, and the deep red solution was stirred at RT for 13 h. The solution was poured into saturated (satd.) aq. NaHCO$_3$ (100 mL) and extracted with CH$_2$Cl$_2$ (4×150 mL). The organic extracts were dried (Na$_2$SO$_4$), filtered, and concentrated to a crude oil, which was purified on SiO$_2$ (0-100% EtOAc/hexanes) to provide 2.75 g (50%) of a brown oil. MS (ESI): exact mass calculated for C$_{21}$H$_{25}$N$_5$O$_3$, 395.20; m/z found, 396.5 [M+H]$^+$. $^1$H NMR (500 MHz, CDCl$_3$): 9.11 (s, 1H), 8.78 (d, J=5.1, 1H), 8.27 (d, J=9.1, 1H), 8.16 (d, J=5.1, 1H), 7.19 (d, J=9.1, 1H), 4.67-4.66 (m, 1H), 4.10 (s, 3H), 4.07-4.03 (m, 1H), 3.13-3.09 (m, 1H), 2.96-2.92 (m, 2H), 2.58-2.54 (m, 1H), 2.15-2.10 (m, 1H), 1.99-1.90 (m, 1H), 1.55 (s, 9H).

F. To a solution of [2-(6-methoxy-[1,5]naphthyridin-4-yl)-4,5,6,7-tetrahydro-2H-indazol-5-yl]-carbamic acid tert-butyl ester (317 mg, 0.800 mmol) in CH$_2$Cl$_2$ (3.6 mL) was added 4 M HCl in dioxane (3.40 mL, 13.7 mmol), and the solution was stirred at RT for 3.5 h. The solution was concentrated to afford a crude solid, which was dissolved in CH$_3$OH (10 mL). Anionic exchange resin (550 Å OH, 100 mg) was added and the mixture was stirred for 20 min. The mixture was filtered, and the resin was washed with CH$_3$OH (30 mL). The filtrate was concentrated to afford 234 mg (99% crude) of the title compound as a brown oil. MS (ESI): exact mass calculated for C$_{16}$H$_{17}$N$_5$O, 295.14; m/z found, 296.3 [M+H]$^+$. $^1$H NMR (400 MHz, CDCl$_3$): 9.08 (s, 1H), 8.76 (d, J=5.1, 1H), 8.26 (d, J=9.1, 1H), 8.15 (d, J=5.1, 1H), 7.18 (d, J=9.1, 1H), 4.10 (s, 3H), 3.29-3.27 (m, 1H), 3.01-2.96 (m, 2H), 2.87-2.80 (m, 1H), 2.48-2.39 (m, 1H), 2.11-2.05 (m, 1H), 1.82-1.64 (m, 3H).

Example B

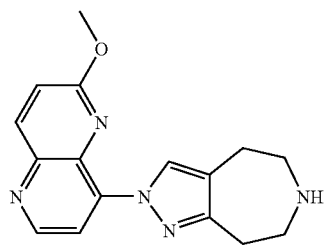

2-(6-Methoxy-[1,5]naphthyridin-4-yl)-2,4,5,6,7,8-hexahydro-1,2,6-triaza-azulene

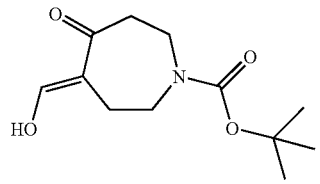

A. 4-Hydroxymethylene-5-oxo-azepane-1-carboxylic acid tert-butyl ester. To a solution of 4-oxo-azepane-1-carboxylic acid tert-butyl ester (1.0 g, 4.7 mmol) in THF (16 mL) was added tert-butoxybis(dimethylamino)methane (2.0 mL, 9.4 mmol) and the reaction was heated at 65° C. for 12 h. Upon cooling to RT, the reaction was diluted with 1 N HCl (10 mL) and stirred for 3 h at the same temperature. The reaction was diluted with Et$_2$O (30 mL). The organic layer was separated and the aqueous layer was extracted with Et$_2$O (2×20 mL). The combined organic layers were washed with 1 N NaOH (40 mL), brine (20 mL), dried (MgSO$_4$), filtered, and concentrated to afford 1.1 g (100% crude) of the title compound as a pale yellow oil which constituted of an inseparable mixture of isomers. $^1$H NMR (500 MHz, CDCl$_3$): 14.88 (br s, 0.2H), 14.40 (d, J=9.2, 0.8H), 7.81-7.62 (m, 1H), 3.90-3.88 (m, 2H), 3.57-3.47 (m, 2H), 2.67-2.65 (m, 2H), 1.80-1.75 (m, 2H), 1.46-1.35 (m, 9H).

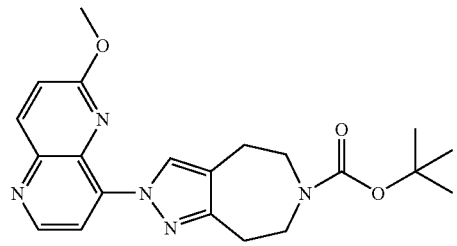

B. 2-(6-Methoxy-[1,5]naphthyridin-4-yl)-4,5,7,8-tetrahydro-2H-1,2,6-triaza-azulene-6-carboxylic acid tert-butyl ester. To a solution of 4-hydroxymethylene-5-oxo-azepane-1-carboxylic acid tert-butyl ester (500 mg, 2.0 mmol) in THF (7 mL) was added (6-methoxy-[1,5]naphthyridin-4-yl)-hydrazine (480 mg, 2.4 mmol). The reaction was stirred at RT for 4 h. Then p-toluenesulfonic acid (600 mg, 6.0 mmol) was added and the reaction was stirred at RT for an additional 12 h. The reaction was diluted with CH$_2$Cl$_2$ (30 mL) and 1 N NaOH (40 mL). The organic layer was separated and the aqueous layer was extracted with CH$_2$Cl$_2$ (2×20 mL). The combined organic layers were washed with 1 N NaOH (50 mL), brine (30 mL), dried (MgSO$_4$), filtered and concentrated. The residue was purified on SiO$_2$ (60% EtOAc/hexanes) to afford 510 mg (65%) of the title compound as a pale yellow oil. $^1$H NMR (7:3 mixture of isomers; 500 MHz, CDCl$_3$): 9.25-9.22 (m, 0.7H), 9.14 (s, 0.3H), 8.75 (d, J=5.0, 1H), 8.27-8.12 (m, 2H), 7.19-7.15 (m, 1H), 4.43-4.39 (m, 1H), 4.12 (s, 3H), 3.71-3.57 (m, 2H), 3.05-2.99 (m, 2H), 2.81-2.79 (m, 0.7H), 1.90-1.87 (m, 1.3H), 1.69-1.65 (m, 1H), 1.50 (s, 3H), 1.40 (s, 6H).

C. This compound was prepared according to the method described in Example A, Step F. The title compound was a pale yellow foam (mixture of isomers). MS (ESI): exact mass calculated for $C_{16}H_{17}N_5O$, 295.14; m/z found, 296.30 [M+H]$^+$.

Example C

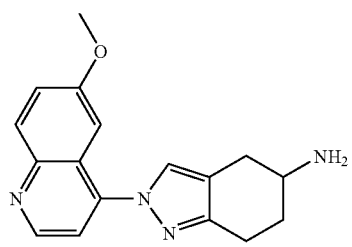

2-(6-Methoxy-quinolin-4-yl)-4,5,6,7-tetrahydro-2H-indazol-5-ylamine

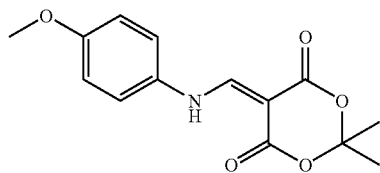

A. 5-[(4-Methoxy-phenylamino)-methylene]-2,2-dimethyl-[1,3]dioxane-4,6-dione. This compound was prepared according to the methods described in Example A, Step A. $^1$H NMR (400 MHz, CDCl$_3$): 11.26 (d, J=14.3, 1H), 8.57 (d, J=14.3, 1H), 7.24-7.20 (m, 2H), 7.00-6.96 (m, 2H), 3.87 (s, 3H), 1.78 (s, 6H).

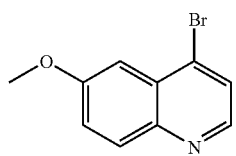

B. 4-Bromo-6-methoxy-quinoline. The title compound was prepared as described in Example A, Steps B and C to give a crude solid. In Step C, the reaction mixture was heated to 80° C. instead of 45° C. Recrystallization gave 2.02 g (36%) of a white solid. $^1$H NMR (400 MHz, CDCl$_3$): 8.53 (d, J=4.7, 1H), 8.00-7.98 (m, 1H), 7.66 (d, J=4.7, 1H), 7.41-7.39 (m, 2H), 3.98 (s, 3H).

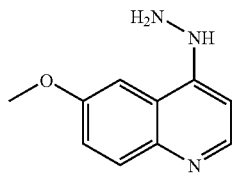

C. (6-Methoxy-quinolin-4-yl)-hydrazine. To a solution of 4-bromo-6-methoxy-quinoline (5.4 g, 28 mmol) in 1-methyl-2-pyrrolidinone (27 mL) was added hydrazine (1.52 mL, 33.6 mmol). The reaction was heated at 150° C. for 12 h. The reaction was then cooled to RT and added dropwise to an ethereal solution (700 mL) at RT. The white precipitate was collected by filtration, washed with Et$_2$O (80 mL), and dried under reduced pressure. The resulting solid was dissolved in CH$_2$Cl$_2$ (100 mL) and washed with 1 N NaOH (100 mL). The aqueous layer was back-extracted with CH$_2$Cl$_2$ (2×100 mL). The combined organic layers were washed with 1 N NaOH (50 mL), brine (30 mL), dried (MgSO$_4$), filtered and concentrated to afford 4.3 g (82% crude) of a brown solid. HPLC: R$_f$=4.22 min. MS (ESI): exact mass calculated for $C_{10}H_{11}N_3O$, 189.1; m/z found, 190.4 [M+H]$^+$. $^1$H NMR (500 MHz, CDCl$_3$): 8.26 (d, J=6.5, 1H), 7.75 (d, J=9.2, 1H), 7.52 (d, J=2.5, 1H), 7.46 (dd, J=9.2, 2.6, 1H), 7.19 (d, J=6.5, 1H), 3.95 (s, 3H).

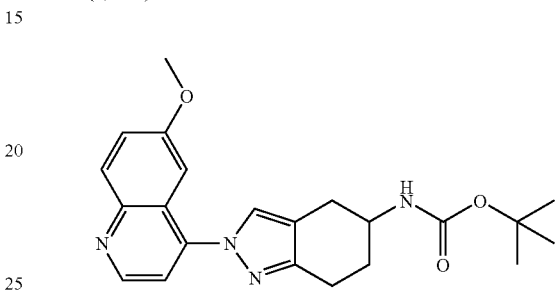

D. [2-(6-Methoxy-quinolin-4-yl)-4,5,6,7-tetrahydro-2H-indazol-5-yl]-carbamic acid tert-butyl ester. The reaction was performed according to the methods described in Example A, Step E. The crude residue was purified on SiO$_2$ (20% (2.5% (CH$_3$OH/EtOAc)/CH$_2$Cl$_2$) to afford 510 mg (65%) of the title compound as a pale yellow oil. MS (ESI): exact mass calculated for $C_{22}H_{26}N_4O_2$, 394.20; m/z found, 395.39 [M+H]$^+$. $^1$H NMR (3:2 mixture of isomers; 500 MHz, CDCl$_3$): 8.84 (d, J=4.6, 0.4H), 8.79 (d, J=4.7, 0.6H), 8.08-8.06 (m, 1H), 7.64-7.62 (m, 1H), 7.44-7.41 (m, 1H), 7.34 (d, J=4.7, 0.6H), 7.30 (d, J=4.6, 0.4H), 7.01 (s, 1H), 4.75-4.65 (m, 1H), 4.13-4.01 (m, 1H), 3.91 (s, 2H), 3.83 (s, 1H), 3.82 (t, J=7.0, 1H), 2.84-2.80 (m, 1H), 2.70-2.60 (m, 2H), 2.37 (t, J=7.0, 1H), 2.04-1.89 (m, 1H), 1.62 (s, 3.6H), 1.48 (s, 5.4H).

E. The target compound was prepared according to the methods described in Example A, Step F, to obtain a pale yellow foam. MS (ESI): exact mass calculated for $C_{17}H_{18}N_4O$, 294.15; m/z found, 295.31 [M+H]$^+$. $^1$H NMR (3:2 mixture of isomers; 500 MHz, CDCl$_3$): 8.82-8.81 (m, 0.4H), 8.76-8.75 (m, 0.6H), 8.06-8.05 (m, 1H), 7.68-7.65 (m, 1H), 7.42 (d, J=9.1, 1H), 7.34 (d, J=7.3, 1H), 7.30 (d, J=5.7, 0.6H), 7.08-7.07 (m, 0.4H), 3.90 (s, 2H), 3.83 (s, 1H), 3.38 (t, J=7.0, 1H), 3.35-3.28 (m, 1H), 3.01-2.81 (m, 1H), 2.6 (br s, 1H), 2.48-2.35 (m, 2H), 2.11-1.97 (m, 2H), 1.80-1.70 (m, 1H).

Example D

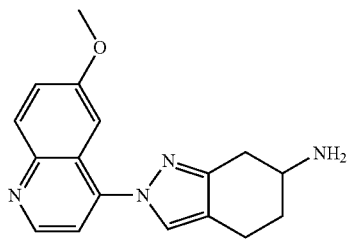

2-(6-Methoxy-quinolin-4-yl)-4,5,6,7-tetrahydro-2H-indazol-6-ylamine

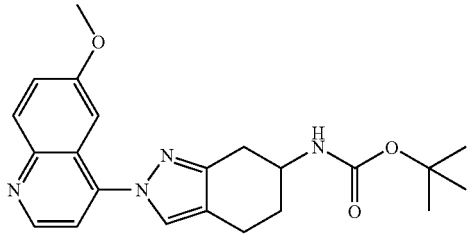

A. [2-(6-Methoxy-quinolin-4-yl)-4,5,6,7-tetrahydro-2H-indazol-6-yl]-carbamic acid tert-butyl ester. This compound was prepared according to methods described for Example A, Step E. MS (ESI): exact mass calculated for $C_{22}H_{26}N_4O_3$, 394.20; m/z found, 395.8 $[M+H]^+$. $^1H$ NMR (2:1 mixture of isomers; 500 MHz, $CDCl_3$): 8.77-8.76 (m, 1H), 8.05-8.03 (m, 1H), 7.86 (br s, 0.5H), 7.64 (br s, 0.5H), 7.62 (br s, 1H), 7.41-7.38 (m, 1H), 7.32-7.29 (m, 1H), 4.87 (br s, 1H), 4.72 (br s, 0.5H), 4.12-4.00 (m, 1H), 3.88 (s, 3H), 3.20 (dd, J=1H), 2.02-1.95 (m, 1.5H), 1.94-1.74 (m, 1.5H), 1.73-1.61 (m, 0.6H), 1.60-1.54 (m, 0.2H), 1.45 (s, 9.5H), 1.25-1.21 (m, 0.6H).

B. The target compound was prepared according to the methods described in Example A, Step F. The crude product was used without further purification.

Example E

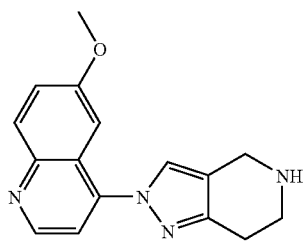

6-Methoxy-4-(4,5,6,7-tetrahydro-pyrazolo[4,3-c]pyridin-2-yl)-quinoline

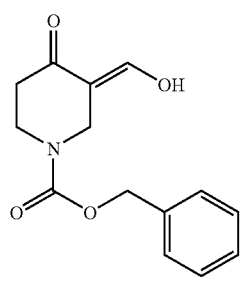

A. 3-Hydroxymethylene-4-oxo-piperidine-1-carboxylic acid benzyl ester. The reaction was performed according to the methods described in Example B, Step A, to obtain a pale yellow oil (mixture of isomers) that was used in the next step without further purification. $^1H$ NMR (500 MHz, $CDCl_3$): 8.48 (br s, 0.7H), 7.35-7.25 (m, 5H), 5.15 (s, 1.5H), 5.11 (s, 0.5H), 4.34 (s, 1.5H), 4.17 (s, 0.5H), 3.74-3.72 (m, 0.5H), 3.67-3.64 (m, 1.5H), 2.49-2.44 (m, 1.5), 1.85-1.83 (m, 0.5H).

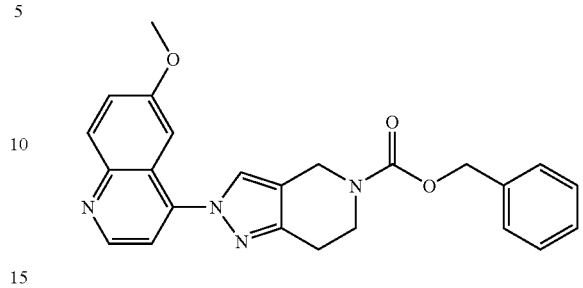

B. 2-(6-Methoxy-quinolin-4-yl)-2,4,6,7-tetrahydro-pyrazolo[4,3-c]pyridine-5-carboxylic acid benzyl ester. This reaction was performed according to the methods described in Example B, Step B. The crude residue was purified on $SiO_2$ (20% (2.5% $CH_3OH/EtoAc$)/$CH_2Cl_2$) to afford 700 mg (85%) of the title compound as a pale yellow oil. $^1H$ NMR (3:2 mixture of isomers; 500 MHz, $CDCl_3$): 8.84-8.82 (m, 0.6H), 8.79-8.77 (m, 0.4H), 8.08-8.06 (m, 1H), 7.74-7.62 (m, 2H), 7.42-7.33 (m, 5H), 7.26-7.25 (m, 0.6H), 7.12 (s, 0.4H), 5.19 (s, 2H), 4.72 (s, 0.8H), 4.62 (s, 1.2H), 3.88 (s, 2H), 3.82-3.78 (m, 3H), 3.36 (td, J=6.9, 3.3, 0.6H), 2.96 (s, 0.4H), 2.67 (s, 1H), 2.34 (t, J=7.9, 0.6H).

C. To a solution of 2-(6-methoxy-quinolin-4-yl)-2,4,6,7-tetrahydro-pyrazolo[4,3-c]pyridine-5-carboxylic acid benzyl ester (300 mg, 0.7 mmol) in EtOH (3 mL) was added $HCO_2NH_4$ (70 mg, 1 mmol) and 10% Pd/C (300 mg). The mixture was stirred at RT for 16 h. The crude mixture was filtered through diatomaceous earth, washing with EtOH (10 mL), and the filtrate was concentrated to afford 203 mg (100% crude) of the title compound as a pale yellow foam. MS (ESI): exact mass calculated for $C_{16}H_{16}N_4O$, 280.13; m/z found, 281.32 $[M+H]^+$. $^1H$ NMR (3:2 mixture of isomers; 500 MHz, $CDCl_3$): 8.80-8.79 (m, 0.6H), 8.78-8.76 (m, 0.4H), 8.08-8.05 (m, 1H), 7.73-7.62 (m, 2H), 7.24-7.18 (m, 0.6H), 7.11 (s, 0.4H), 5.00 (s, 2H), 4.68 (s, 0.8H), 4.52 (s, 1.2H), 3.61-3.58 (m, 3H), 3.01 (td, J=6.9, 3.3, 0.6H), 2.54 (s, 0.4H), 2.38 (s, 1H), 2.02 (t, J=7.9, 1H).

Example F

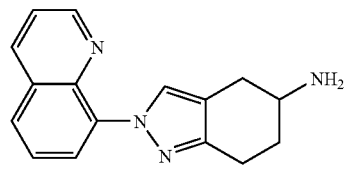

2-Quinolin-8-yl-4,5,6,7-tetrahydro-2H-indazol-5-ylamine

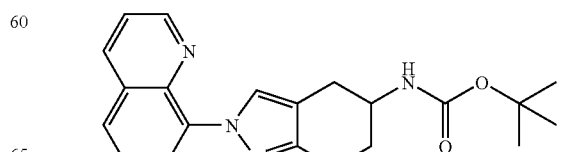

A. (2-Quinolin-8-yl-4,5,6,7-tetrahydro-2H-indazol-5-yl)-carbamic acid tert-butyl ester. The reaction was performed according to the methods described in Example A, Step E. The crude residue was purified on SiO$_2$ (40% EtOAc/hexanes) to afford 320 mg (42%) of the title compound as a pale yellow oil. $^1$H NMR (500 MHz, CDCl$_3$): 8.96 (dd, J=4.1, 1.7, 1H), 8.45 (s, 1H), 8.23 (dd, J=8.3, 1.7, 1H), 8.13 (dd, J=7.5, 1.2, 1H), 7.75 (dd, J=8.3, 1.2, 1H), 7.62 (t, J=7.5, 1H), 7.46 (dd, J=4.1, 4.1, 1H), 4.71 (br s, 1H), 4.08 (br s, 1H), 3.08 (dd, J=15.0, 5.0, 1H), 2.91 (t, J=2.4, 2H), 2.63-2.57 (m, 1H), 2.12-2.08 (m, 1H), 2.00-1.94 (m, 1H), 1.46 (s, 9H).

B. This compound was prepared according to the methods described in Example A, Step F. The crude product was used without further purification. MS (ESI): exact mass calculated for C$_{16}$H$_{16}$N$_4$, 264.16; m/z found, 265.30 [M+H]$^+$.

Example G

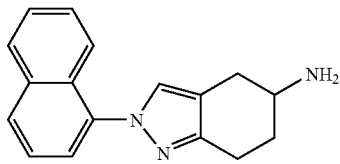

2-Naphthalen-1-yl-4,5,6,7-tetrahydro-2H-indazol-5-ylamine

This compound was prepared according to methods described for Example A, Steps E and F. The crude product was used without further purification. MS (ESI): exact mass calculated for C$_{17}$H$_{17}$N$_3$, 263.14; m/z found, 264.3 [M+H]$^+$. $^1$H NMR (9:1 mixture of isomers; 500 MHz, CDCl$_3$): 7.93-7.89 (m, 3.5H), 7.55-7.46 (m, 7H), 3.30-3.27 (m, 1H), 3.00-2.95 (m, 2H), 2.88-2.85 (m, 1H), 2.46-2.41 (m, 2H), 2.09-2.06 (m, 1H), 1.95-1.87 (m, 0.6H), 1.81-1.77 (m, 1H).

Example H

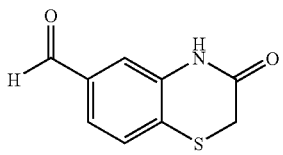

3-Oxo-3,4-dihydro-2H-benzo[1,4]thiazine-6-carbaldehyde

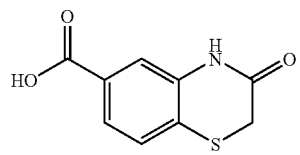

A. 3-Oxo-3,4-dihydro-2H-benzo[1,4]thiazine-6-carboxylic acid. To a solution of 3-oxo-3,4-dihydro-2H-benzo[1,4]thiazine-6-carboxylic acid methyl ester (1.5 g, 6.7 mmol) in a THF/H$_2$O mixture (1:1, 63 mL) was added 4 N LiOH (8.0 mL, 32 mmol) and the resulting solution was stirred at RT for 24 h. The solution was partially concentrated and diluted with H$_2$O (50 mL). The solution was acidified using concentrated HCl and a solid precipitated. The solid was collected via filtration, washed with H$_2$O and dried in vacuo to provide 0.79 g (60%) of the title compound as a white solid. MS (ESI): exact mass calculated for C$_9$H$_7$NO$_3$S, 209.01; m/z found, 210.2 [M+H]$^+$. $^1$H NMR (500 MHz, CD$_3$OD): 7.65-7.61 (m, 2H), 7.40 (d, J=8.1, 1H), 3.48 (s, 2H).

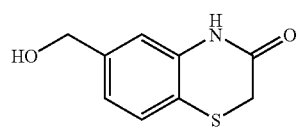

B. 6-Hydroxymethyl-4H-benzo[1,4]thiazin-3-one. To a 0° C. suspension of 3-oxo-3,4-dihydro-2H-benzo[1,4]thiazine-6-carboxylic acid (400 mg, 2 mmol) in THF (19 mL) was added Et$_3$N (0.32 mL, 2 mmol) and the resulting solution was treated with iso-butylchloroformate (0.3 mL, 2 mmol). The resulting suspension was stirred at 0° C. for 2 h, filtered and the solid was washed with THF. The filtrate was cooled to 0° C., treated with NaBH$_4$ (150 mg, 4.3 mmol) and slowly treated with H$_2$O (10 mL). The resulting suspension was warmed to RT and stirred for 18 h. The suspension was neutralized using 1 N HCl and diluted with H$_2$O (100 mL). The organic layer was extracted with EtOAc (3×200 mL). The combined organic layers were dried (MgSO$_4$), filtered and concentrated. The resulting residue was purified on SiO$_2$ (0-10% CH$_3$OH/CH$_2$Cl$_2$) to provide 330 mg (89%) of the title compound as a white solid. MS (ESI): exact mass calculated for C$_9$H$_9$NO$_2$S, 195.04; m/z found, 196.1 [M+H]$^+$. $^1$H NMR (500 MHz, CD$_3$OD): 7.26 (d, J=7.9, 1H), 7.01-6.98 (m, 2H), 4.55 (s, 2H), 3.40 (s, 2H).

C. To a solution of 6-hydroxymethyl-4H-benzo[1,4]thiazin-3-one (360 mg, 1.8 mmol) in THF/CHCl$_3$ (2:1, 18 mL) was added MnO$_2$ (1.6 g, 18 mmol) and the resulting suspension was heated to 70° C. and stirred for 4 h. The suspension was filtered through diatomaceous earth and the filtrate was concentrated. The resulting solid was triturated with EtOAc/hexanes (1:1) and a minimal amount of CH$_3$OH to provide 200 mg (56%) of the title compound as a tan solid. MS (ESI): exact mass calculated for C$_9$H$_7$NO$_2$S, 193.02; m/z found, 194.1 [M+H]$^+$. $^1$H NMR (500 MHz, CDCl$_3$): 9.94 (s, 1H), 8.78 (br s, 1H), 7.54-7.49 (m, 2H), 7.37 (d, J=1.5, 1H), 3.52 (s, 2H).

Example I

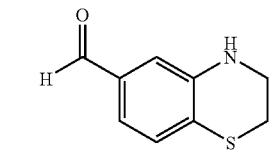

3,4-Dihydro-2H-benzo[1,4]thiazine-6-carbaldehyde

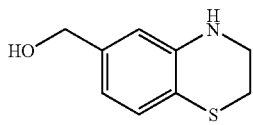

A. (3,4-Dihydro-2H-benzo[1,4]thiazin-6-yl)-methanol. To a solution of 3-oxo-3,4-dihydro-2H-benzo[1,4]thiazine-6-carboxylic acid methyl ester (750 mg, 3.4 mmol) in Et$_2$O (32 mL) was added LiAlH$_4$ (240 mg, 6.3 mmol) and the resulting suspension was stirred at RT for 24 h. The reaction mixture was cooled to 0° C. and treated with H$_2$O (0.5 mL), 15% aq. NaOH (0.5 mL), and H$_2$O (1.5 mL). The resulting suspension was filtered. The filtrate was concentrated to provide 340 mg (58%) of the title compound as an amber oil. MS (ESI): exact mass calculated for C$_9$H$_{11}$NOS, 181.06; m/z found, 182.1 [M+H]$^+$. $^1$H NMR (500 MHz, CDCl$_3$): 6.96 (d, J=7.9, 1H), 6.60 (dd, J=7.9, 1.6, 1H), 6.49 (d, J=7.9, 1H), 4.52 (s, 2H), 3.65-3.62 (m, 2H), 3.06-3.04 (m, 2H).

B. This compound was prepared according to the methods described in Example H, Step C. MS (ESI): exact mass calculated for C$_9$H$_9$NOS, 179.04; m/z found, 180.1 [M+H]$^+$. $^1$H NMR (500 MHz, CDCl$_3$): 9.79 (s, 1H), 7.14-7.08 (m, 2H), 6.95 (d, J=1.6, 1H), 3.67-3.64 (m, 2H), 3.12-3.10 (m, 2H).

Example J

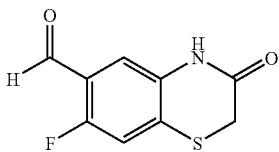

7-Fluoro-3-oxo-3,4-dihydro-2H-benzo[1,4]thiazine-6-carbaldehyde

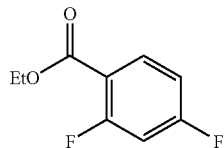

A. 2,4-Difluoro-benzoic acid ethyl ester. Into a solution of 2,4-difluorobenzoic acid (36.0 g, 228 mmol) in EtOH (250 mL) was bubbled HCl$_{(g)}$ for 15 min. The solution was heated to 80° C. and stirred for 24 h. The solution was partially concentrated and diluted with H$_2$O (300 mL). The aqueous layer was extracted with EtOAc (3×300 mL). The combined organic layers were dried (MgSO$_4$), filtered and concentrated to provide 27.2 g (76%) of the title compound as a clear oil. MS (ESI): exact mass calculated for C$_9$H$_8$F$_2$O$_2$, 186.05; m/z not found. $^1$H NMR (400 MHz, CDCl$_3$): 8.01-7.95 (m, 1H), 6.95-6.85 (m, 2H), 4.39 (q, J=7.1, 2H), 1.39 (t, J=7.1, 3H).

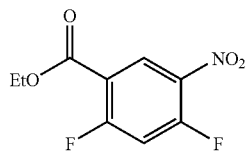

B. 2,4-Difluoro-5-nitro-benzoic acid ethyl ester. To 2,4-difluoro-benzoic acid ethyl ester (6.4 g, 34 mmol) at 0° C. was added HNO$_3$/H$_2$SO$_4$ (1:1, 10 mL). The resulting solution was allowed to warm to RT and was stirred for 18 h. The reaction mixture was partitioned between H$_2$O and CH$_2$Cl$_2$ (400 mL). The organic layer was washed with brine (200 mL), dried (MgSO$_4$), filtered and concentrated to provide 7.0 g (88%) of the title compound as a white solid. MS (ESI): exact mass calculated for C$_9$H$_7$F$_2$NO$_4$, 231.03; m/z not found. $^1$H NMR (400 MHz, CDCl$_3$): 8.78 (dd, J=8.3, 7.3, 1H), 7.14 (t, J=9.9, 1H), 4.44 (q, J=7.2, 2H), 1.42 (t, J=7.2, 3H).

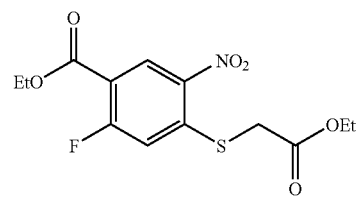

C. 4-Ethoxycarbonylmethylsulfanyl-2-fluoro-5-nitro-benzoic acid ethyl ester. To a solution of 2,4-difluoro-5-nitro-benzoic acid ethyl ester (7.0 g, 0.030 mol) in CH$_2$Cl$_2$ (125 mL) was added Et$_3$N (5.0 mL, 36 mmol) at 0° C. Following the addition of ethyl 2-mercaptoacetate (3.30 mL, 30.3 mmol), the solution was warmed to RT and stirred for 18 h. The reaction mixture was partitioned between H$_2$O and CH$_2$Cl$_2$ (400 mL). The organic layer was washed with 0.05 M HCl (200 mL), brine (200 mL), dried (MgSO$_4$), filtered and concentrated to provide 9.6 g (96%) of the title compound as a tan solid. MS (ESI): exact mass calculated for C$_{13}$H$_{14}$FNO$_6$S, 331.05; m/z not found. $^1$H NMR (500 MHz, CDCl$_3$): 8.88 (d, J=6.9, 1H), 7.14 (d, J=11.4, 1H), 4.41 (q, J=7.2, 2H), 4.29 (q, J=7.2, 2H), 3.75 (s, 2H), 1.40 (t, J=7.2, 3H), 1.29 (t, J=7.2, 3H).

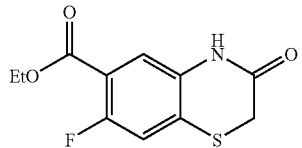

D. 7-Fluoro-3-oxo-3,4-dihydro-2H-benzo[1,4]thiazine-6-carboxylic acid ethyl ester. To a solution of 4-ethoxycarbonylmethylsulfanyl-2-fluoro-5-nitro-benzoic acid ethyl ester (2.7 g, 8.2 mmol) in acetic acid (50 mL) was added iron (4.8 g, 86 mmol) and the suspension was heated to 80° C. and stirred for 2 h. The reaction mixture was filtered and the filtrate was partitioned between H$_2$O and EtOAc (1×200 mL; 2×100 mL). The combined organic layers were washed with brine (300 mL), dried (MgSO$_4$), filtered and concentrated to provide 1.7 g (82%) of the title compound as a tan solid. MS (ESI): exact mass calculated for C$_{11}$H$_{10}$FNO$_3$S, 255.04; m/z found, 256.3 [M+H]$^+$. $^1$H NMR (400 MHz, CDCl$_3$): 8.75 (br s, 1H), 7.46 (d, J=6.1, 1H), 7.12 (d, J=10.4, 1H), 4.40 (q, J=7.1, 2H), 3.48 (s, 2H), 1.38 (t, J=7.1, 3H).

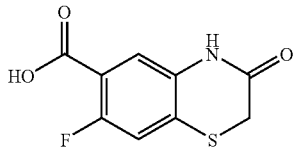

E. 7-Fluoro-3-oxo-3,4-dihydro-2H-benzo[1,4]thiazine-6-carboxylic acid. This compound was prepared according to the methods described in Example H, Step A. MS (ESI): exact mass calculated for $C_9H_6FNO_3S$, 227.01; m/z found, 228.3 [M+H]$^+$. $^1$H NMR (400 MHz, DMSO-d$_6$): 13.25 (br s, 1H), 10.72 (s, 1H), 7.46 (d, J=6.7, 1H), 7.38 (d, J=10.6, 1H), 3.55 (s, 2H).

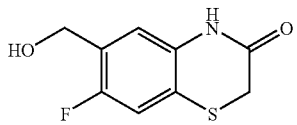

F. 7-Fluoro-6-hydroxymethyl-4H-benzo[1,4]thiazin-3-one. This compound was prepared according to the methods described in Example H, Step B. MS (ESI): exact mass calculated for $C_9H_8FNO_2S$, 213.03; m/z not found. $^1$H NMR (500 MHz, CDCl$_3$/CD$_3$OD, 9:1): 6.94 (d, J=7.8, 1H), 6.92 (d, J=5.1, 1H), 4.61 (s, 2H), 3.33 (s, 2H).

G. This compound was prepared according to the methods described in Example H, Step C. MS (ESI): exact mass calculated for $C_9H_6FNO_2S$, 211.01; m/z found, 212.5 [M+H]$^+$. $^1$H NMR (500 MHz, DMSO-d$_6$): 10.78 (br s, 1H), 10.09 (br s, 1H), 7.49 (d, J=10.5, 1H), 7.32 (d, J=6.3, 1H), 3.56 (s, 2H).

Example K

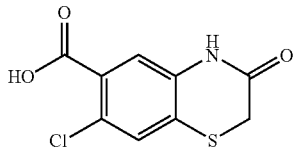

7-Chloro-3-oxo-3,4-dihydro-2H-benzo[1,4]thiazine-6-carboxylic acid

The title compound was prepared according to the procedures described in Example J, Steps A through E, starting with 2-chloro-4-fluoro-benzoic acid.

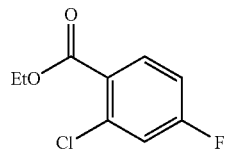

A. 2-Chloro-4-fluoro-benzoic acid ethyl ester. MS (ESI): exact mass calculated for $C_9H_8ClFO_2$, 202.02; m/z not found.

$^1$H NMR (400 MHz, CDCl$_3$): 7.89 (dd, J=8.8, 6.2, 1H), 7.19 (dd, J=8.5, 2.5, 1H), 7.05-7.00 (m, 1H), 4.39 (q, J=7.1, 2H), 1.40 (t, J=7.1, 3H).

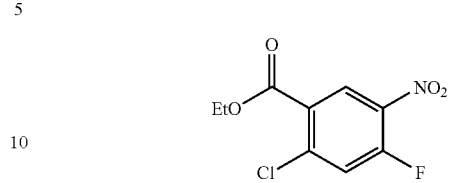

B. 2-Chloro-4-fluoro-5-nitro-benzoic acid ethyl ester. MS (ESI): exact mass calculated for $C_9H_7ClFNO_4$, 247.00; m/z not found. $^1$H NMR (500 MHz, CDCl$_3$): 8.48 (d, J=8.0, 1H), 7.35 (d, J=10.3, 1H), 4.31 (q, J=7.1, 2H), 1.31 (t, J=7.1, 3H).

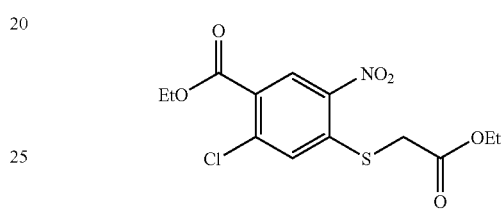

C. 2-Chloro-4-ethoxycarbonylmethylsulfanyl-5-nitro-benzoic acid ethyl ester. MS (ESI): exact mass calculated for $C_{13}H_{14}ClNO_6S$, 347.02; m/z not found. $^1$H NMR (500 MHz, CDCl$_3$): 8.78 (s, 1H), 7.57 (s, 1H), 4.42 (q, J=7.1, 2H), 4.25 (q, J=7.1, 2H), 3.77 (s, 2H), 1.41 (t, J=7.1, 3H), 1.30 (t, J=7.1, 3H).

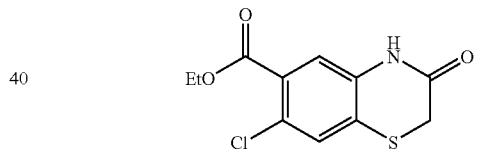

D. 7-Chloro-3-oxo-3,4-dihydro-2H-benzo[1,4]thiazine-6-carboxylic acid ethyl ester. MS (ESI): exact mass calculated for $C_{11}H_{10}ClNO_3S$, 271.01; m/z not found. $^1$H NMR (400 MHz, CDCl$_3$): 9.14 (s, 1H), 7.41 (s, 2H), 4.40 (q, J=6.9, 2H), 3.47 (s, 2H), 1.40 (t, J=6.9, 3H).

E. 7-Chloro-3-oxo-3,4-dihydro-2H-benzo[1,4]thiazine-6-carboxylic acid. MS (ESI): exact mass calculated for $C_9H_6ClNO_3S$, 242.98; m/z not found. $^1$H NMR (400 MHz, CDCl$_3$): 10.67 (s, 1H), 7.38 (s, 1H), 7.23 (s, 1H), 3.49 (s, 2H).

Example L

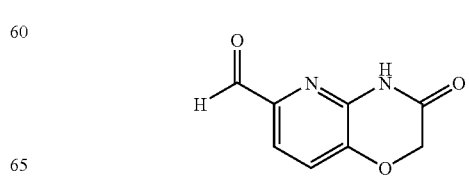

3-Oxo-3,4-dihydro-2H-pyrido[3,2-b][1,4]oxazine-6-carbaldehyde

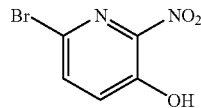

A. 6-Bromo-2-nitro-pyridin-3-ol. To a solution of 3-hydroxy-2-nitropyridine (20 g, 140 mmol) in CH$_3$OH (400 mL) was added a solution of 25% NaOCH$_3$ in CH$_3$OH (33.0 mL, 153 mmol). After stirring at RT for 30 min, the reaction mixture was cooled to 0° C. and Br$_2$ (7.2 mL, 140 mmol) added slowly. The mixture was stirred for 30 min, and then was quenched with glacial acetic acid (2.5 mL). The solvent was removed under reduced pressure. A portion of the crude material was purified on SiO$_2$ (50% EtOAc/hexanes) to provide the title compound as a white solid. MS (ESI): exact mass calculated for C$_5$H$_3$BrN$_2$O$_3$, 217.93; m/z not found. $^1$H NMR (400 MHz, CDCl$_3$): 10.24 (s, 1H), 7.74 (d, J=8.6, 1H), 7.54 (d, J=8.6, 1H).

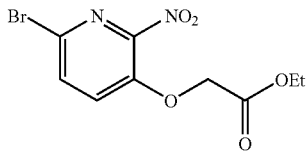

B. (6-Bromo-2-nitro-pyridin-3-yloxy)-acetic acid ethyl ester. To a suspension of 6-bromo-2-nitro-pyridin-3-ol (3.07 g, 14.0 mmol) in acetone (20 mL) was added K$_2$CO$_3$ (3.93 g, 28.0 mmol) and ethyl bromoacetate (1.55 mL, 14.0 mmol). The mixture was heated to reflux and stirred for 20 h. The resulting suspension was cooled to RT, diluted with Et$_2$O (100 mL) and filtered. The filtrate was concentrated to afford 3.14 g (74%) of the title compound, which was used without further purification. MS (ESI): exact mass calculated for C$_9$H$_9$BrN$_2$O$_5$, 303.97; m/z found, 305.2 [M+H]$^+$. $^1$H NMR (400 MHz, CDCl$_3$): 7.67 (d, J=8.6, 1H), 7.35 (d, J=8.7, 1H), 4.78 (s, 2H), 4.27 (q, J=7.1, 2H), 1.30 (t, J=8.5, 3H).

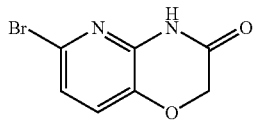

C. 6-Bromo-4H-pyrido[3,2-b][1,4]oxazin-3-one. To a solution of (6-bromo-2-nitro-pyridin-3-yloxy)-acetic acid ethyl ester (3.14 g, 10.3 mmol) in glacial acetic acid (12.4 mL) was added iron powder (1.67 g, 29.9 mmol). The suspension was heated to 90° C. and stirred for 6 h, after which it was cooled to RT and diluted with EtOAc (50 mL). The mixture was filtered through a pad of SiO$_2$ and the filtrate was concentrated. Recrystallization from CH$_3$OH provided 1.32 g (57%) of the title compound as a solid. MS (ESI): exact mass calculated for C$_7$H$_5$BrN$_2$O$_2$, 227.95; m/z found, 228.2 [M+H]$^+$. $^1$H NMR (400 MHz, CDCl$_3$): 7.98 (d, J=5.3, 1H), 7.16-7.09 (m, 1H), 6.98 (dd, J=8.0, 4.9, 1H), 4.68 (d, J=1.4, 2H).

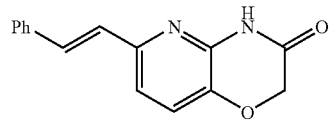

D. 6-Styryl-4H-pyrido[3,2-b][1,4]oxazin-3-one. To a solution of 6-bromo-4H-pyrido[3,2-b][1,4]oxazin-3-one (3.2 g, 14 mmol) in 1,4-dioxane (80 mL) was added trans-2-phenylvinylboronic acid (2.1 g, 14 mmol). After the reaction mixture was degassed with nitrogen, tetrakis(triphenylphosphine)palladium(0) (0.129 g, 0.112 mmol) and a solution of K$_2$CO$_3$ (3.7 g, 27 mmol) in H$_2$O (10.7 mL) were added. The reaction was heated at reflux for 17 h, then cooled to RT, and diluted with EtOAc (300 mL). The organic layer was separated, washed with H$_2$O (300 mL), brine (300 mL), dried (Na$_2$SO$_4$), and concentrated. The solid residue was purified on SiO$_2$ (5-10% EtOAc/CHCl$_3$) to provide 1.5 g (43%) of the title compound as a solid. MS (ESI): exact mass calculated for C$_{15}$H$_{12}$N$_2$O$_2$, 252.09; m/z found, 253.2 [M+H]$^+$. $^1$H NMR (400 MHz, CDCl$_3$): 7.53-7.00 (m, 9H), 4.66 (d, J=6.9, 2H).

E. To a solution of 6-styryl-4H-pyrido[3,2-b][1,4]oxazin-3-one (757 mg, 3.00 mmol) in CH$_2$Cl$_2$ (128 mL) was bubbled ozone at –78° C. with stirring until a pale blue color appeared. The excess ozone was removed by bubbling oxygen through the reaction mixture for 15 min. Me$_2$S (1.0 mL, 14 mmol) was added, and the reaction was stirred at –78° C. for 3 h and then at RT for 24 h. The solvent was concentrated and the residue was triturated with Et$_2$O (100 mL). The solid collected from filtration of the suspension was washed with additional Et$_2$O and dried in vacuo to provide 340 mg (63% crude) of a solid, which was used without further purification. MS (ESI): exact mass calculated for C$_8$H$_6$N$_2$O$_3$, 178.04; m/z found, 179.2 [M+H]$^+$.

Example M

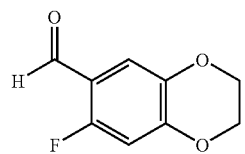

7-Fluoro-2,3-dihydro-benzo[1,4]dioxine-6-carbaldehyde

To a solution of 6-fluoroveratraldehyde (1.2 g, 6.2 mmol) in CH$_2$Cl$_2$ (62 mL) was added BBr$_3$ (6.2 mL, 62 mmol) and the solution was stirred at RT for 4 h. The solution was then cooled to 0° C., diluted with EtOAc (120 mL) and slowly treated with H$_2$O (60 mL). The organic layer was washed with brine (2×100 mL), dried, filtered and concentrated to provide the desired catechol intermediate as a dark brown solid (1.0 g, 6.4 mmol). This solid was immediately treated with 1,2-dibromoethane (0.60 mL, 7.1 mmol) and heated to 100° C. The suspension was treated with NaOH (0.50 g, 13 mmol) in H$_2$O (30 mL) dropwise over 1 h and stirred at 100° C. for 2 days. The suspension was then filtered. The collected solid was re-suspended in CHCl$_3$ and filtered. The filtrate was concentrated to provide 0.22 g (19%) of the title compound as a tan solid. MS (ESI): exact mass calculated for C$_9$H$_7$FO$_3$, 182.04; m/z not found. ¹H NMR (500 MHz, CDCl₃): 10.21 (s, 1H), 7.35 (d, J=6.7, 1H), 6.66 (d, J=10.9, 1H), 4.33 (m, 2H), 4.25 (m, 2H).

Example N

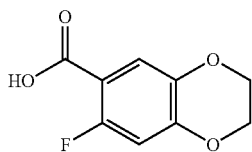

7-Fluoro-2,3-dihydro-benzo[1,4]dioxine-6-carboxylic acid

To a solution of KMnO₄ (0.35 g, 2.2 mmol) in H₂O (11 mL) at 80° C. was added 7-fluoro-2,3-dihydro-benzo[1,4]dioxine-6-carbaldehyde (0.20 g, 1.1 mmol). The resulting suspension was stirred at 100° C. for 24 h. The reaction mixture was filtered and the solids were washed with H₂O (30 mL). The filtrate was acidified with concentrated HCl, which led to the formation of a white precipitate, which was collected, washed with H₂O and dried in vacuo to provide 0.12 g (57%) of the title compound as a white solid. MS (ESI): exact mass calculated for C₆H₇FO₄, 198.03; m/z not found. ¹H NMR (400 MHz, DMSO-d₆): 12.95 (s, 1H), 7.29 (d, J=7.2, 1H), 6.87 (d, J=11.6, 1H), 4.34-4.31 (m, 2H), 4.27-4.24 (m, 2H).

Example O

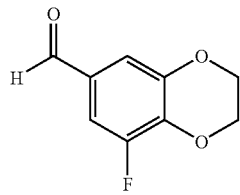

8-Fluoro-2,3-dihydro-benzo[1,4]dioxine-6-carbaldehyde

This compound was prepared according to methods described for Example M. ¹H NMR (500 MHz, CDCl₃): 9.78 (d, J=2.0, 1H), 7.22-7.26 (m, 2H), 4.38-4.41 (m, 2H), 4.33-4.35 (m, 2H).

Example P

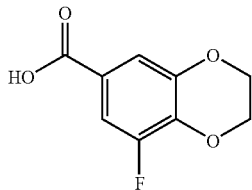

8-Fluoro-2,3-dihydro-benzo[1,4]dioxine-6-carboxylic acid

This compound was prepared according to methods described for Example N. ¹H NMR (500 MHz, DMSO-d₆): 12.98 (s, 1H), 7.27 (d, J=11.0, 1H), 7.22 (m, 1H), 4.31-4.36 (m, 4H).

Example Q

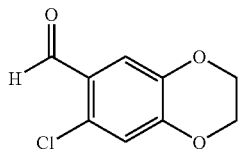

7-Chloro-2,3-dihydro-benzo[1,4]dioxine-6-carbaldehyde

This compound was prepared according to methods described for Example M. ¹H NMR (500 MHz, CDCl₃): 10.21 (s, 1H), 7.45 (s, 1H), 6.94 (s, 1H), 4.31-4.33 (m, 2H), 4.26-4.28 (m, 2H).

Example R

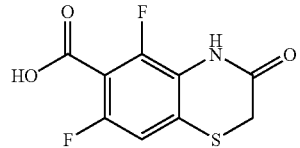

5,7-Difluoro-3-oxo-3,4-dihydro-2H-benzo[1,4]thiazine-6-carboxylic acid

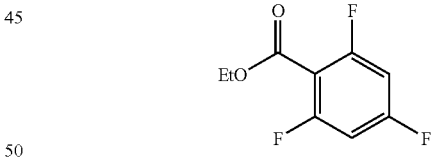

A. Ethyl 2,4,6-trifluorobenzoate. A suspension of 2,4,6-trifluorobenzoic acid (4.93 g, 28.0 mmol) in thionyl chloride (15 mL) was heated at reflux for 1 h. After cooling, the thionyl chloride was removed in vacuo, and final traces of thionyl chloride were azeotropically removed with CH₂Cl₂ leaving the acid chloride as a pale yellow liquid. To a solution of EtOH (3.3 mL, 56 mmol) and pyridine (4.5 mL, 56 mmol) in CH₂Cl₂ (20 mL) at RT was added a solution of the acid chloride in CH₂Cl₂ (5 mL) via pipet. The mixture was allowed to stir for 2 h at RT and then was poured into 1 N HCl and extracted with CH₂Cl₂. The organic layer was washed with 1 N HCl (1×) and satd. aq. NaHCO₃ (2×). The organic layer was dried (Na₂SO₄) and concentrated to provide 3.93 g (69%) of the title compound as a pale yellow liquid. ¹H NMR (400 MHz, CDCl₃): 6.72 (m, 1H), 4.41 (q, J=7.2, 2H), 1.39 (t, J=7.2, 3H).

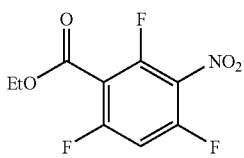

B. Ethyl 3-nitro-2,4,6-trifluorobenzoate. To a suspension of ethyl 2,4,6-trifluorobenzoate (3.93 g, 19.2 mmol) in conc. H$_2$SO$_4$ at 0° C. was added conc. HNO$_3$ (70% HNO$_3$) dropwise via pipet. After the addition was complete, the reaction was allowed to warm to RT and stir for 4 h. The biphasic mixture was poured into H$_2$O and extracted with CH$_2$Cl$_2$ (3×). The combined organic layers were dried (Na$_2$SO$_4$) and concentrated to provide 4.71 g (98%) of the title compound as a yellow solid. $^1$H NMR (400 MHz, CDCl$_3$): 6.96 (ddd, J=9.2, 9.2, 2.2, 1H), 4.45 (q, J=7.2, 2H), 1.40 (t, J=7.2, 3H).

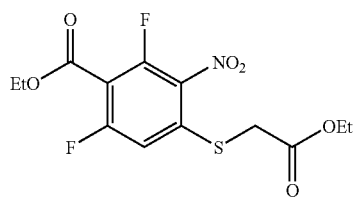

C. 4-Ethoxycarbonylmethylsulfanyl-2,6-difluoro-3-nitrobenzoic acid ethyl ester. This compound was prepared according to methods described for Example J, Step C. MS (ESI): exact mass calculated for C$_{13}$H$_{13}$F$_2$NO$_6$S, 349.0; m/z found, 350 [M+H]$^+$, 372 [M+Na]$^+$. $^1$H NMR (400 MHz, CDCl$_3$): 7.17 (dd, J=10.0, 1.9, 1H), 4.44 (q, J=7.1, 2H), 4.24 (q, J=7.2, 2H), 3.73 (s, 2H), 1.39 (t, J=7.1, 3H), 1.29 (t, J=7.1, 3H).

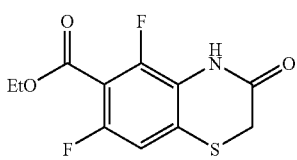

D. 5,7-Difluoro-3-oxo-3,4-dihydro-2H-benzo[1,4]thiazine-6-carboxylic acid ethyl ester. This compound was prepared according to methods described for Example J, Step D. MS (ESI): exact mass calculated for C$_{11}$H$_9$F$_2$NO$_3$S, 273.0; m/z found, 274 [M+H]$^+$. $^1$H NMR (400 MHz, CDCl$_3$): 7.89 (br s, 1H), 6.95 (d, J=8.8, 1H), 4.42 (q, J=7.0, 2H), 3.49 (s, 2H), 1.39 (t, J=7.0, 3H).

E. This compound was prepared according to methods described for Example H, Step A. The crude product was used without further purification. MS (ESI): exact mass calculated for C$_9$H$_5$F$_2$NO$_3$S, 245.0; m/z found, 246 [M+H]$^+$. $^1$H NMR (400 MHz, CD$_3$OD): 7.10 (dd, J=9.3, 1.8, 1H), 3.52 (s, 2H).

Example S

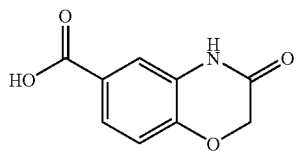

3-Oxo-3,4-dihydro-2H-benzo[1,4]oxazine-6-carboxylic acid

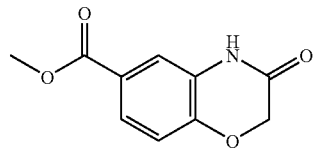

A. 3-Oxo-3,4-dihydro-2H-benzo[1,4]oxazine-6-carboxylic acid methyl ester. To a suspension of 4-hydroxy-3-nitrobenzoic acid methyl ester (10.0 g, 50.7 mmol) in acetone (72 mL) was added K$_2$CO$_3$ (14.0 g, 101 mmol) followed by ethyl bromoacetate (5.60 mL, 50.7 mmol). The mixture was heated to 55° C. and stirred for 18 h. The mixture was allowed to cool to RT, diluted with Et$_2$O (75 mL) and filtered. The filtrate was concentrated to provide 14.9 g of a solid which was dissolved in glacial acetic acid (63 mL). To this solution was added Fe powder (8.50 g, 151 mmol). The mixture was heated to 117° C. and stirred for 5.5 h, at which time it was cooled to RT and diluted with EtOAc (70 mL). The mixture was filtered through a pad of SiO$_2$, eluting with EtOAc. The filtrate was concentrated to give a solid, which was recrystallized from MeOH to provide 9.2 g (84%) of the title compound as a tan solid. MS (ESI): exact mass calculated for C$_{10}$H$_9$NO$_4$, 207.05; m/z found, 208.2 [M+H]$^+$. $^1$H NMR (500 MHz, CDCl$_3$): 8.06 (br s, 1H), 7.69 (dd, J=8.4, 7.7, 1H), 7.51 (d, J=1.9, 1H), 7.00 (d, J=8.4, 1H), 4.69 (s, 2H), 3.90 (s, 3H).

B. To a solution of 3-oxo-3,4-dihydro-2H-benzo[1,4]oxazine-6-carboxylic acid methyl ester (3.13 g, 15.1 mmol) in THF/H$_2$O (3:1; 76 mL) was added a LiOH (4 M in H$_2$O; 19.0 mL, 75.5 mmol), and the solution was stirred at RT for 24 h. The solution was concentrated, diluted with H$_2$O (50 mL), and acidified to pH<1 with conc. HCl. The resulting precipitate was collected by filtration afforded 7.6 g of the title compound contaminated with excess HCl and H$_2$O. MS (ESI): exact mass calculated for C$_6$H$_7$NO$_4$, 193.04; m/z found, 194.2 [M+H]$^+$. $^1$H NMR (500 MHz, DMSO-d$_6$): 10.85 (br s, 1H), 7.50-7.47 (m, 2H), 6.99 (d, J=8.3, 1H), 4.63 (s, 2H).

Example T

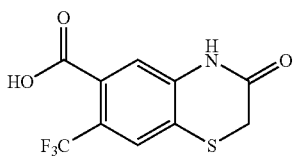

3-Oxo-7-trifluoromethyl-3,4-dihydro-2H-benzo[1,4]thiazine-6-carboxylic acid

This compound was prepared according to methods described for Example H, Step A. The crude product was used without further purification. MS (ESI): exact mass calculated for C$_{10}$H$_6$F$_3$NO$_3$S, 277.0; m/z found, 278.0 [M+H]$^+$. $^1$H NMR (400 MHz, CDCl$_3$): 7.91 (br s, 1H), 7.59 (s, 1H), 7.20 (s, 1H), 3.45 (s, 2H).

Example U

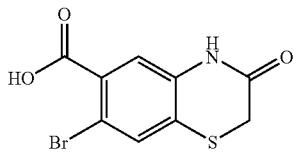

7-Bromo-3-oxo-3,4-dihydro-2H-benzo[1,4]thiazine-6-carboxylic acid

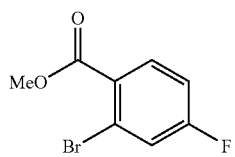

A. 2-Bromo-4-fluoro-benzoic acid methyl ester. To a solution of 2-bromo-4-fluoro-benzoic acid (10.95 g, 50 mmol) in toluene/MeOH (3:1; 200 mL) was added trimethylsilyldiazomethane (2 M in hexanes; 36 mL, 71.7 mmol) at RT for 3 h. The mixture was diluted with EtOAc (300 mL) and washed sequentially with satd. aq. NaHCO$_3$ (50 mL) and brine (50 mL), dried (MgSO$_4$), and concentrated to provide 11.5 g (99%) of the crude material which was used in the next step without further purification. $^1$H NMR (500 MHz, CDCl$_3$): 7.86 (dd, J=8.8, 6.0, 1H), 7.39 (dd, J=8.3, 2.5, 2H), 7.08-7.05 (m, 1H), 3.91 (s, 3H).

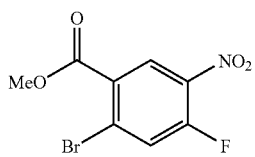

B. 2-Bromo-4-fluoro-5-nitro-benzoic acid methyl ester. To conc. fuming H$_2$SO$_4$ (8 mL) at 0° C. was added conc. fuming HNO$_3$ (8 mL) and the mixture allowed to stand for 5 min. To a solution of 2-bromo-4-fluoro-benzoic acid methyl ester (9.32 g, 40 mmol) at 0° C., the mixture of acids was added dropwise over 30 min. The mixture was allowed to warm to RT and was stirred for 18 h. The mixture was poured into ice water, diluted with EtOAc, and treated with 6 N NaOH. The aqueous layer was extracted with EtOAc (3×300 mL). The combined organic layers were washed with brine (200 mL), dried (MgSO$_4$), and concentrated. The crude material was purified on SiO$_2$ (0-25% EtOAc/hexanes) to provide 4.9 g (43%) of the title compound. $^1$H NMR (500 MHz, CDCl$_3$): 8.61 (d, J=8.0, 1H), 7.66 (d, J=10.0, 1H), 3.91 (s, 3H).

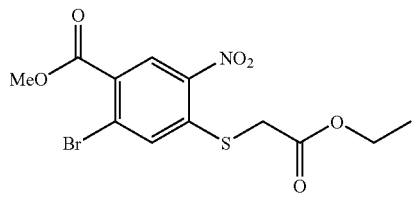

C. 2-Bromo-4-ethoxycarbonylmethylsulfanyl-5-nitro-benzoic acid methyl ester. To a 0° C. solution of 2-bromo-4-fluoro-5-nitro-benzoic acid methyl ester (4.8 g, 17.3 mmol) in CH$_2$Cl$_2$ (87 mL) was added Et$_3$N, followed by mercaptoacetic acid ethyl ester, and the resulting mixture was stirred at RT for 4 h. The mixture was diluted with EtOAc (250 mL), washed with brine (50 mL), dried (MgSO$_4$), and concentrated. The crude material was purified on SiO$_2$ (0-35% EtOAc/hexanes) to provide 5 g (77%) of the title compound. $^1$H NMR (500 MHz, CDCl$_3$): 8.75 (s, 1H), 7.79 (s, 1H), 4.24 (q, J=7.2, 2H), 3.96 (s, 3H), 3.78 (s, 2H), 1.30 (t, J=7.2, 3H).

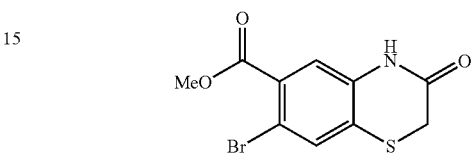

D. 7-Bromo-3-oxo-3,4-dihydro-2H-benzo[1,4]thiazine-6-carboxylic acid methyl ester. This compound was prepared according to methods described for Example J, Step D, to provide 2.26 g (94%) as the crude material which was used without further purification. MS (ESI): exact mass calculated for C$_{10}$H$_8$BrNO$_3$S, 300.94; m/z found, 302.1 [M+H]$^+$. $^1$H NMR (500 MHz, CDCl$_3$): 9.15 (s, 1H), 7.62 (s, 1H), 7.37 (s, 1H), 3.91 (s, 3H), 3.46 (s, 2H).

E. This compound was prepared according to methods described for Example H, Step A, to provide 0.17 g (60%) of the title compound. MS (ESI): exact mass calculated for C$_9$H$_6$BrNO$_3$S, 286.93; m/z found, 285.8 [M–H]$^+$. $^1$H NMR (500 MHz, DMSO-d$_6$): 13.35 (br s, 1H), 10.73 (s, 1H), 7.66 (s, 1H), 7.36 (s, 1H), 3.51 (s, 2H).

Example 1

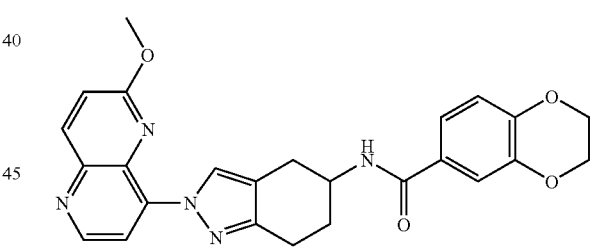

2,3-Dihydro-benzo[1,4]dioxine-6-carboxylic acid [2-(6-methoxy-[1,5]naphthyridin-4-yl)-4,5,6,7-tetrahydro-2H-indazol-5-yl]-amide To a solution of 2,3-dihydro-benzo[1,4]dioxine-6-carboxylic acid (44 mg, 0.24 mmol) and 2-(6-methoxy[1,5]naphthyridin-4-yl)-4,5,6,7-tetrahydro-2H-indazol-5-ylamine (48 mg, 0.16 mmol) in DMF (1 mL) was added HOBT (1-hydroxybenzotriazole; 33 mg, 0.24 mmol) and EDC; 47 mg, 0.24 mmol). The reaction mixture was stirred for 1.5 h at RT. The reaction mixture was diluted with CH$_3$OH and purified directly by basic reverse phase HPLC to provide 22 mg (30%) of the title compound. MS (ESI): exact mass calculated for C$_{25}$H$_{23}$N$_5$O$_4$, 457.18; m/z found, 458.3 [M+H]$^+$. $^1$H NMR (500 MHz, CDCl$_3$): 9.14 (s, 1H), 8.76 (d, J=5.1, 1H), 8.25 (d, J=9.1, 1H), 8.16 (d, J=5.1, 1H), 7.31-7.28 (m, 1H), 7.26-7.23 (m, 1H), 7.17 (d, J=9.1, 1H), 6.86 (d, J=8.4, 1H), 6.13 (d, J=7.7, 1H), 4.54-4.51 (m, 1H), 4.27-4.24

(m, 4H), 4.07 (s, 3H), 3.19 (dd, J=15.5, 5.1, 1H), 2.99-2.96 (m, 2H), 2.66 (dd, J=15.5, 7.7, 1H), 2.21-2.16 (m, 1H), 2.10-2.03 (m, 1H).

The compounds in Examples 2-32 were prepared according to the methods described for Example 1, with adjustments where noted.

Example 2

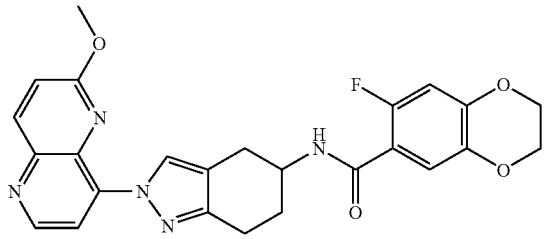

7-Fluoro-2,3-dihydro-benzo[1,4]dioxine-6-carboxylic acid [2-(6-methoxy-[1,5]naphthyridin-4-yl)-4,5,6,7-tetrahydro-2H-indazol-5-yl]-amide Once the reaction was complete, the reaction mixture was diluted with EtOAc (20 mL) and 1 N NaOH (10 mL). The aqueous layer was extracted with EtOAc (3×20 mL). The combined organic layers were washed with brine, dried (MgSO$_4$) and concentrated. The crude was purified on SiO$_2$ (0-100% EtOAc/hexanes) to provide 64 mg (69%) of the title compound. MS (ESI): exact mass calculated for $C_{25}H_{22}FN_5O_4$, 475.17; m/z found, 476.3 [M+H]$^+$. $^1$H NMR (500 MHz, CDCl$_3$): 9.15 (s, 1H), 8.78 (d, J=5.1, 1H), 8.26 (d, J=9.1, 1H), 8.17 (d, J=5.0, 1H), 7.62 (d, J=7.6, 1H), 7.19 (d, J=9.1, 1H), 6.77 (dd, J=14.2, 7.4, 1H), 6.61 (d, J=12.5, 1H), 4.57-4.52 (m, 1H), 4.30-4.28 (m, 2H), 4.25-4.24 (m, 2H), 4.09 (s, 3H), 3.21 (dd, J=15.4, 5.1, 1H), 3.00 (t, J=6.6, 2H), 2.69 (dd, J=15.5, 8.0, 1H), 2.26-2.20 (m, 1H), 2.09-2.02 (m, 1H).

Example 3

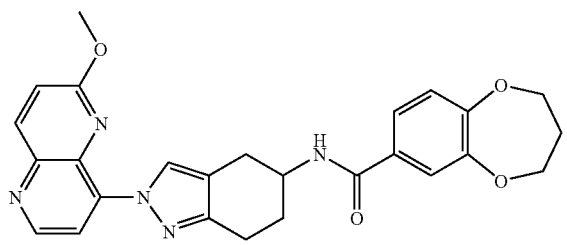

3,4-Dihydro-2H-benzo[b][1,4]dioxepine-7-carboxylic acid [2-(6-methoxy-[1,5]naphthyridin-4-yl)-4,5,6,7-tetrahydro-2H-indazol-5-yl]-amide MS (ESI): exact mass calculated for $C_{26}H_{25}N_5O_4$, 471.19; m/z found, 472.3 [M+H]$^+$. $^1$H NMR (500 MHz, CDCl$_3$): 9.15 (s, 1H), 8.77 (d, J=5.1, 1H), 8.25 (d, J=9.1, 1H), 8.17 (d, J=5.1, 1H), 7.37-7.32 (m, 2H), 7.18 (d, J=9.1, 1H), 6.96 (d, J=8.3, 1H), 6.12 (d, J=7.8, 1H), 4.55-4.52 (m, 1H), 4.27-4.21 (m, 4H), 4.08 (s, 3H), 3.19 (dd, J=15.5, 5.0, 1H), 2.99-2.97 (m, 2H), 2.67 (dd, J=15.5, 7.5, 1H), 2.22-2.17 (m, 3H), 2.09-2.05 (m, 1H).

Example 4

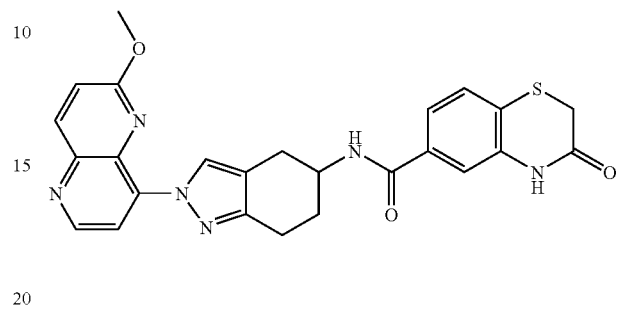

3-Oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide HPLC: R$_t$=6.29 min. MS (ESI): exact mass calculated for $C_{25}H_{22}N_6O_3S$, 486.15; m/z found, 487.4 [M+H]$^+$. $^1$H NMR (500 MHz, CDCl$_3$): 10.13 (s, 1H), 9.72 (d, J=5.1, 1H), 9.22 (d, J=9.1, 1H), 9.12 (d, J=5.1, 1H), 8.96 (br s, 1H), 8.34 (d, J=1.7, 1H), 8.30 (d, J=8.1, 1H), 8.22 (dd, J=8.1, 1.7, 1H), 8.19 (d, J=9.1, 1H), 7.13 (d, J=7.1, 1H), 5.56-5.52 (m, 1H), 5.03 (s, 3H), 4.41 (s, 2H), 4.17 (dd, J=15.5, 4.9, 1H), 3.99-3.91 (m, 2H), 3.68-3.63 (m, 1H), 3.18-3.12 (m, 2H).

Example 5

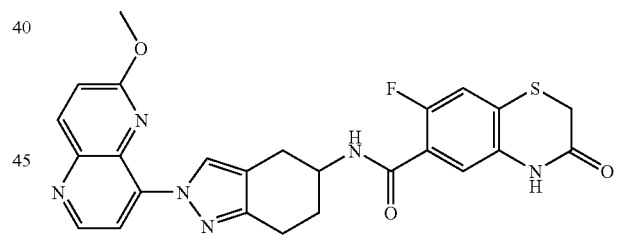

7-Fluoro-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide Once the reaction was complete, 1 N NaOH (10 mL) was added to the reaction mixture and a precipitate formed. The solids were filtered, washed with 1 N HCl, 1 N NaOH, and H$_2$O. Drying in vacuo gave 42 mg (76%) of the title compound. MS (ESI): exact mass calculated for $C_{25}H_{21}FN_6O_3S$, 504.14; m/z found, 505.3 [M+H]$^+$. $^1$H NMR (500 MHz, DMSO-d$_6$): 10.66 (br s, 1H), 9.12 (br s, 1H), 8.76 (d, J=5.1, 1H), 8.38 (d, J=6.6, 1H), 8.31 (d, J=9.1, 1H), 8.08 (d, J=5.1, 1H), 7.37-7.33 (m, 2H), 7.17 (d, J=6.6, 1H), 4.20-4.15 (m, 1H), 4.04 (s, 3H), 3.49 (s, 2H), 3.03 (dd, J=15.4, 5.1, 1H), 2.92-2.86 (m, 1H), 2.83-2.78 (m, 1H), 2.60 (dd, J=15.4, 9.4, 1H), 2.07-2.03 (m, 1H), 1.92-1.85 (m, 1H).

Example 6

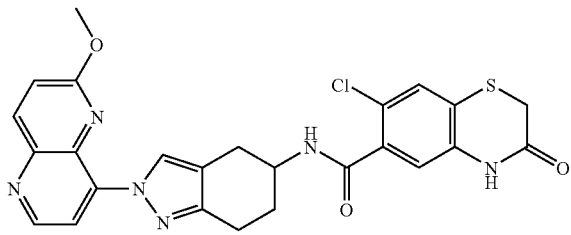

7-Chloro-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide The crude material was purified on $SiO_2$ (0-10% $CH_3OH$/ $CH_2Cl_2$, then 50-100% EtOAc/hexanes). MS (ESI): exact mass calculated for $C_{25}H_{21}ClN_6O_3S$, 520.11; m/z found, 521.3 $[M+H]^+$. $^1H$ NMR (500 MHz, DMSO-$d_6$): 10.72 (br s, 1H), 9.14 (s, 1H), 8.77 (d, J=5.0, 1H), 8.60 (d, J=7.7, 1H), 8.32 (d, J=9.1, 1H), 8.09 (d, J=5.0, 1H), 7.48 (s, 1H), 7.35 (d, J=9.1, 1H), 6.96 (s, 1H), 4.18-4.13 (m, 1H), 4.06 (s, 3H), 3.48 (s, 2H), 3.04 (dd, J=16.0, 5.0, 1H), 2.93-2.88 (m, 1H), 2.84-2.77 (m, 1H), 2.62-2.60 (m, 1H), 2.06-2.05 (m, 1H), 1.91-1.83 (m, 1H).

Example 7

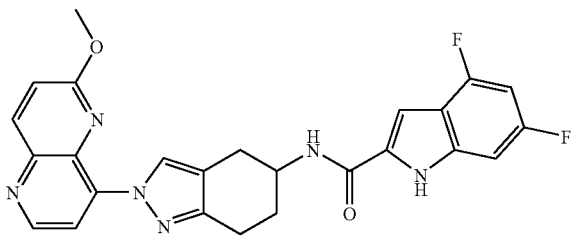

4,6-Difluoro-1H-indole-2-carboxylic acid [2-(6-methoxyl-[1,5]naphthyridin-4-yl)-4,5,6,7-tetrahydro-2H-indazol-5-yl]-amide MS (ESI): exact mass calculated for $C_{25}H_{20}F_2N_6O_2$, 474.16; m/z found, 475.3 $[M+H]^+$. $^1H$ NMR (600 MHz, $CDCl_3$): 9.43 (s, 1H), 9.19 (s, 1H), 8.80 (d, J=5.0, 1H), 8.28 (d, J=9.1, 1H), 8.19 (d, J=5.1, 1H), 7.21 (d, J=9.1, 1H), 6.94 (d, J=8.8, 1H), 6.89 (s, 1H), 6.65 (dt, J=9.9, 1.8, 1H), 6.25 (d, J=7.7, 1H), 4.63-4.57 (m, 1H), 4.10 (s, 3H), 3.25 (dd, J=15.4, 5.1, 1H), 3.03 (dd, J=6.5, 6.5, 2H), 2.74 (dd, J=15.3, 7.6, 1H), 2.29-2.22 (m, 1H), 2.16-2.10 (m, 1H).

Example 8

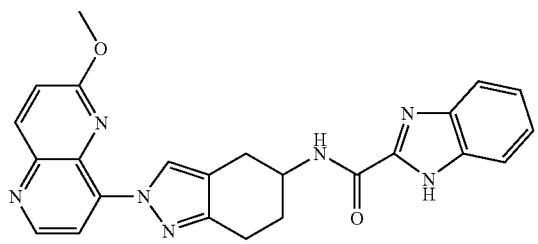

1H-Benzoimidazole-2-carboxylic acid [2-(6-methoxy-[1,5]naphthyridin-4-yl)-4,5,6,7-tetrahydro-2H-indazol-5-yl]-amide MS (ESI): exact mass calculated for $C_{24}H_{21}N_7O_2$, 439.18; m/z found, 440.4 $[M+H]^+$. $^1H$ NMR (500 MHz, $CDCl_3$ with a drop of $CD_3OD$): 9.16 (s, 1H), 8.75 (d, J=5.1, 1H), 8.26 (d, J=9.1, 1H), 8.15 (d, J=5.1, 1H), 7.68-7.63 (m, 2H), 7.36 (br s, 2H), 7.26 (d, J=9.1, 1H), 4.50 (br s, 1H), 4.13 (t, 3H), 3.25 (dd, J=15.5, 5.2, 1H), 3.18-3.08 (m, 2H), 3.04-2.98 (m, 1H), 2.84 (dd, J=15.5, 8.7, 1H), 2.36-2.31 (m, 1H), 2.19-2.11 (m, 1H).

Example 9

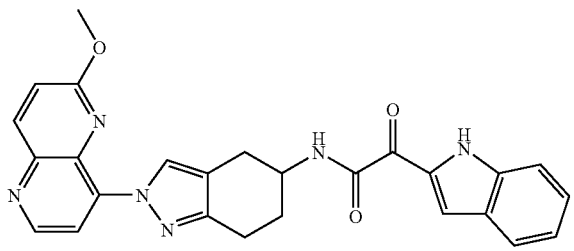

2-(1H-Indol-2-yl)-N-[2-(6-methoxy-[1,5]naphthyridin-4-yl)-4,5,6,7-tetrahydro-2H-indazol-5-yl]-2-oxo-acetamide MS (ESI): exact mass calculated for $C_{26}H_{22}N_6O_3$, 466.18; m/z found, 467.3 $[M+H]^+$. $^1H$ NMR (600 MHz, $CDCl_3$): 9.16 (s, 1H), 9.14 (d, J=3.1, 1H), 8.88 (s, 1H), 8.80 (d, J=5.0, 1H), 8.42 (d, J=7.9, 1H), 8.28 (d, J=9.1, 1H), 8.18 (d, J=5.0, 1H), 7.68 (d, J=8.0, 1H), 7.47 (d, J=7.5, 1H), 7.37-7.33 (m, 2H), 7.20 (d, J=9.1, 1H), 4.43-4.38 (m, 1H), 4.11 (s, 3H), 3.20 (dd, J=15.4, 5.2, 1H), 3.07-2.97 (m, 2H), 2.73 (dd, J=15.4, 8.2, 1H), 2.27-2.21 (m, 1H), 2.12-2.05 (m, 1H).

Example 10

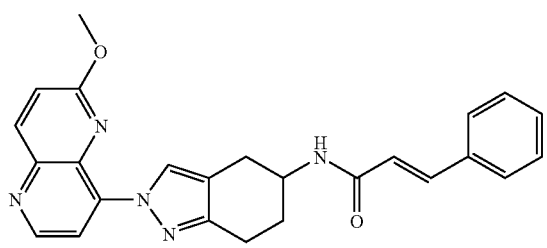

N-[2-(6-Methoxy-[1,5]naphthyridin-4-yl)-4,5,6,7-tetrahydro-2H-indazol-5-yl]-3-phenyl-acrylamide The crude material was purified on $SiO_2$ (0-10% $CH_3OH$/ EtOAc) to provide 37 mg (45%) of the title compound as a white solid. MS (ESI): exact mass calculated for $C_{25}H_{23}N_5O_2$, 425.19; m/z found, 426.8 $[M+H]^+$. $^1H$ NMR (400 MHz, $CDCl_3$): 9.07 (br s, 1H), 8.68 (d, J=5.2, 1H), 8.20 (d, J=9.1, 1H), 8.07 (d, J=5.2, 1H), 7.59-7.49 (m, 3H), 7.35-7.30 (m, 3H), 7.22 (d, J=9.1, 1H), 6.59 (d, J=15.7, 1H), 4.32-4.29 (m, 1H), 4.08 (s, 3H), 3.11 (dd, J=15.3, 5.2, 1H), 3.01-2.91 (m, 2H), 2.63 (dd, J=15.5, 9.1, 1H), 2.20-2.17 (m, 1H), 1.97-1.95 (m, 1H).

Example 11

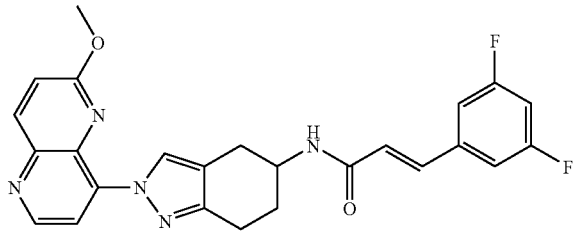

3-(3,5-Difluoro-phenyl)-N-[2-(6-methoxy-[1,5]naphthyridin-4-yl)-4,5,6,7-tetrahydro-2H-indazol-5-yl]-acrylamide The reaction mixture was stirred overnight instead of 1.5 h. MS (ESI): exact mass calculated for $C_{25}H_{21}F_2N_5O_2$, 461.17; m/z found, 462.3 [M+H]$^+$. $^1$H NMR (500 MHz, CDCl$_3$): 9.10 (s, 1H), 8.74 (d, J=5.1, 1H), 8.25 (d, J=9.1, 1H), 8.14 (d, J=5.1, 1H), 7.55 (d, J=15.5, 1H), 7.18 (d, J=9.1, 1H), 7.00-6.95 (m, 2H), 6.79-6.75 (m, 1H), 6.42 (d, J=15.5, 1H), 6.02 (d, J=7.9, 1H), 4.55-4.51 (m, 1H), 4.06 (s, 3H), 3.14 (dd, J=15.3, 4.7, 1H), 3.00-2.92 (m, 2H), 2.66 (dd, J=15.6, 6.8, 1H), 2.16-2.03 (m, 2H).

Example 12

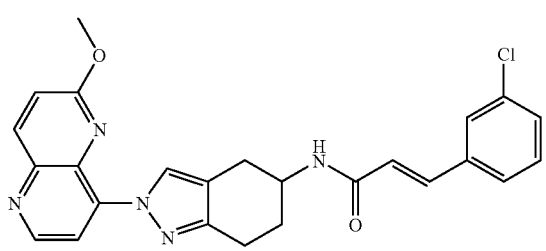

3-(3-Chloro-phenyl)-N-[2-(6-methoxy-[1,5]naphthyridin-4-yl)-4,5,6,7-tetrahydro-2H-indazol-5-yl]-acrylamide The reaction mixture was stirred overnight instead of 1.5 h. MS (ESI): exact mass calculated for $C_{25}H_{22}ClN_5O_2$, 459.15; m/z found, 460.3 [M+H]$^+$. $^1$H NMR (500 MHz, CDCl$_3$ with a drop of CD$_3$OD): 9.09 (s, 1H), 8.73 (d, J=5.1, 1H), 8.25 (d, J=9.1, 1H), 8.12 (d, J=5.1, 1H), 7.55 (d, J=9.3, 1H), 7.50 (br s, 1H), 7.39-7.37 (m, 1H), 7.33-7.28 (m, 2H), 7.22 (d, J=9.1, 1H), 6.53 (d, J=15.7, 1H), 4.46-4.41 (m, 1H), 4.09 (s, 3H), 3.15 (dd, J=15.4, 5.2, 1H), 3.03-2.93 (m, 2H), 2.66 (dd, J=15.6, 8.0, 1H), 2.22-2.16 (m, 1H), 2.07-2.01 (m, 1H).

Example 13

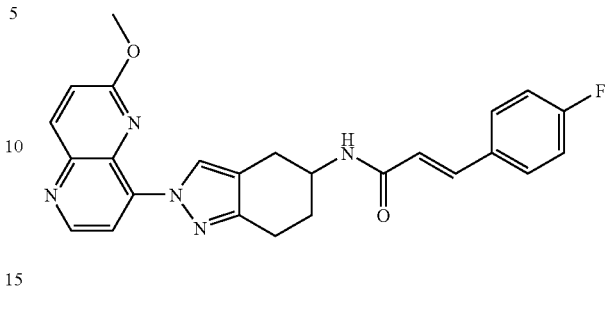

3-(4-Fluoro-phenyl)-N-[2-(6-methoxy-[1,5]naphthyridin-4-yl)-4,5,6,7-tetrahydro-2H-indazol-5-yl]-acrylamide The reaction mixture was stirred overnight instead of 1.5 h. MS (ESI): exact mass calculated for $C_{25}H_{22}FN_5O_2$, 443.18; m/z found, 444.3 [M+H]$^+$. $^1$H NMR (600 MHz, CDCl$_3$ with a drop of CD$_3$OD): 9.12 (s, 1H), 8.74 (d, J=5.4, 1H), 8.26 (d, J=9.0, 1H), 8.13 (d, J=5.4, 1H), 7.58 (d, J=15.6, 1H), 7.54-7.51 (m, 2H), 7.25 (d, J=9.0, 1H), 7.07 (t, J=8.4, 2H), 6.46 (d, J=15.6, 1H), 4.43-4.41 (m, 1H), 4.11 (s, 3H), 3.16 (dd, J=15.0, 4.8, 1H), 3.01-2.97 (m, 2H), 2.67 (dd, J=15.6, 8.4, 1H), 2.19-2.18 (m, 1H), 2.03-2.02 (m, 1H).

Example 14

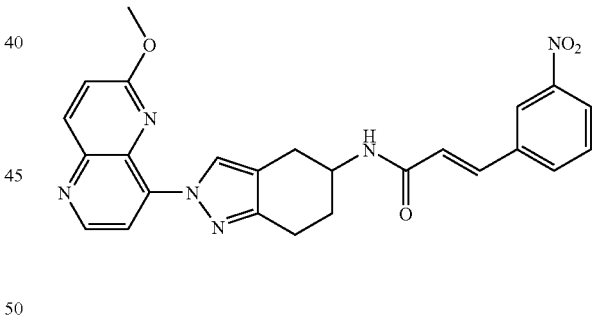

N-[2-(6-Methoxy-[1,5]naphthyridin-4-yl)-4,5,6,7-tetrahydro-2H-indazol-5-yl]-3-(3-nitro-phenyl)-acrylamide The reaction mixture was stirred overnight instead of 1.5 h. MS (ESI): exact mass calculated for $C_{25}H_{22}N_6O_4$, 470.17; m/z found, 471.3 [M+H]$^+$. $^1$H NMR (500 MHz, CDCl$_3$ with a drop of CD$_3$OD): 9.11 (s, 1H), 8.73 (d, J=4.9, 1H), 8.39 (br s, 1H), 8.25 (d, J=9.1, 1H), 8.19 (d, J=8.2, 1H), 8.12 (d, J=5.1, 1H), 7.83 (d, J=3.9, 1H), 7.66 (d, J=15.7, 1H), 7.58 (t, J=8.0, 1H), 7.24 (d, J=9.1, 1H), 6.71 (d, J=15.8, 1H), 4.43-4.40 (m, 1H), 4.10 (s, 3H), 3.17 (dd, J=15.7, 5.1, 1H), 3.05-2.94 (m, 2H), 2.24-2.21 (m, 1H), 2.07-1.99 (m, 1H).

Example 15

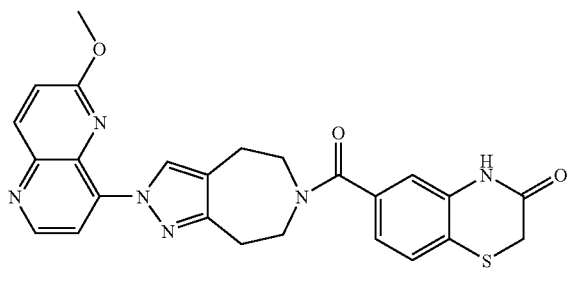

6-[2-(6-Methoxy-[1,5]naphthyridin-4-yl)-4,5,7,8-tetrahydro-2H-1,2,6-triaza-azulene-6-carbonyl]-4H-benzo[1,4]thiazin-3-one HPLC: $R_t$=5.85 min. MS (ESI): exact mass calculated for $C_{25}H_{22}N_6O_3S$, 486.15; m/z found, 487.4 [M+H]$^+$. $^1$H NMR (500 MHz, CDCl$_3$): 9.25-9.15 (m, 1H), 8.79-8.75 (m, 1H), 8.28 (d, J=9.0, 1H), 8.22-8.12 (m, 1H), 7.99-7.90 (m, 1H), 7.48-7.39 (m, 1H), 7.20 (d, J=9.1, 1H), 7.08 (dd, J=7.9, 1.6, 1H), 6.92 (d, J=1.6, 1H), 4.12-4.06 (m, 3H), 3.99-3.82 (m, 2H), 3.69-3.60 (m, 2H), 3.47 (s, 2H), 3.25-3.21 (m, 1H), 2.99-2.90 (m, 2H), 2.78-2.70 (m, 1H).

Example 16

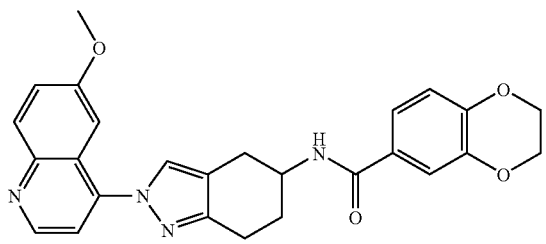

2,3-Dihydro-benzo[1,4]dioxine-6-carboxylic acid [2-(6-methoxy-quinolin-4-yl)-4,5,6,7-tetrahydro-2H-indazol-5-yl]-amide MS (ESI): exact mass calculated for $C_{26}H_{24}N_4O_4$, 456.18; m/z found, 457.5 [M+H]$^+$. $^1$H NMR (400 MHz, CDCl$_3$): 8.80 (d, J=4.7, 1H), 8.08 (d, J=9.2, 1H), 7.68 (s, 1H), 7.65 (d, J=2.8, 1H), 7.43 (dd, J=9.2, 2.8, 1H), 7.36 (d, J=4.7, 1H), 7.33-7.27 (m, 2H), 6.91 (d, J=8.4, 1H), 6.11 (d, J=7.8, 1H), 4.58-4.55 (m, 1H), 4.33-4.27 (m, 4H), 3.91 (s, 3H), 3.21 (dd, J=15.5, 5.1, 1H), 3.03-3.00 (m, 2H), 2.67 (dd, J=15.5, 7.9, 1H), 2.27-2.20 (m, 1H), 2.12-2.03 (m, 1H).

Example 17

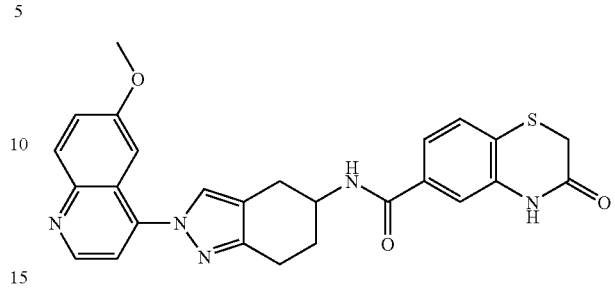

3-Oxo-3,4-dihydro-2H-benzo[1,4]thiazine-6-carboxylic acid [2-(6-methoxy-quinolin-4-yl)-4,5,6,7-tetrahydro-2H-indazol-5-yl]-amide MS (ESI): exact mass calculated for $C_{26}H_{23}N_5O_3S$, 485.15; m/z found, 486.8 [M+H]$^+$. $^1$H NMR (500 MHz, CDCl$_3$): 9.01 (d, J=5.6, 1H), 8.39 (d, J=9.4, 1H), 8.13 (d, J=2.5, 1H), 7.88 (s, 1H), 7.84 (s, 1H), 7.62-7.60 (m, 2H), 7.38-7.29 (m, 3H), 6.17 (d, J=7.6, 1H), 4.55-4.53 (m, 1H), 3.97 (s, 3H), 3.46 (s, 2H), 3.27 (dd, J=15.7, 5.7, 1H), 3.06-3.03 (m, 2H), 2.72-2.67 (m, 1H), 2.30-2.27 (m, 1H), 2.10-2.05 (m, 1H).

Example 18

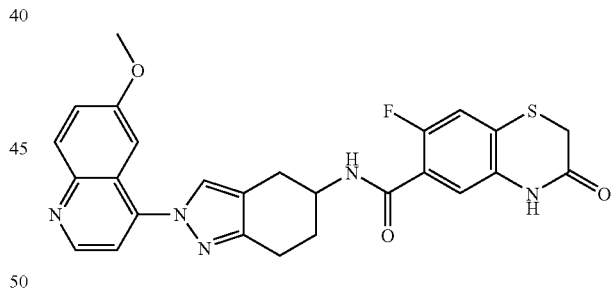

7-Fluoro-3-oxo-3,4-dihydro-2H-benzo[1,4]thiazine-6-carboxylic acid [2-(6-methoxy-quinolin-4-yl)-4,5,6,7-tetrahydro-2H-indazol-5-yl]-amide MS (ESI): exact mass calculated for $C_{26}H_{22}FN_5O_3S$, 503.14; m/z found, 504.5 [M+H]$^+$. $^1$H NMR (400 MHz, CDCl$_3$): 9.59 (s, 1H), 8.80 (d, J=4.7, 1H), 8.08 (d, J=9.2, 1H), 8.01 (d, J=7.0, 1H), 7.70 (s, 1H), 7.65 (d, J=2.8, 1H), 7.43 (dd, J=9.2, 2.8, 1H), 7.37 (d, J=4.7, 1H), 7.09 (d, J=11.5, 1H), 7.00 (dd, J=14.7, 7.8, 1H), 4.80-4.76 (m, 1H), 3.91 (s, 3H), 3.46 (s, 2H), 3.26 (dd, J=15.7, 5.0, 1H), 3.12-2.96 (m, 2H), 2.76 (dd, J=15.7, 7.3, 1H), 2.30-2.25 (m, 1H), 2.18-2.09 (m, 1H).

Example 19

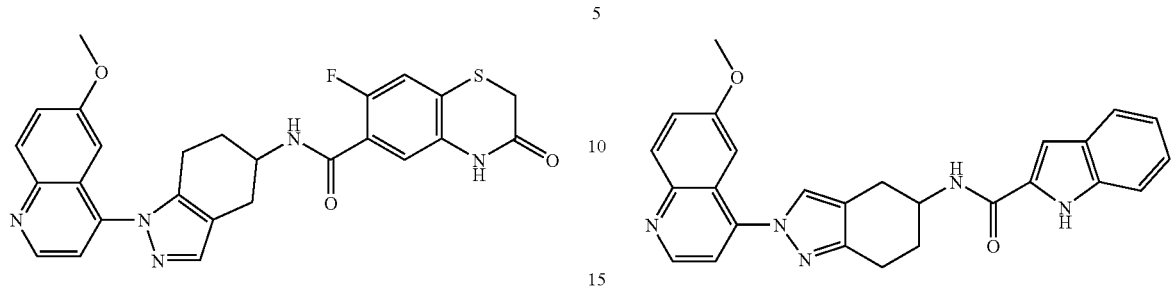

7-Fluoro-3-oxo-3,4-dihydro-2H-benzo[1,4]thiazine-6-carboxylic acid [1-(6-methoxy-quinolin-4-yl)-4,5,6,7-tetrahydro-1H-indazol-5-yl]-amide This compound was a side product from the reaction that provided Example 18. MS (ESI): exact mass calculated for $C_{26}H_{22}FN_5O_3S$, 503.14; m/z found, 504.5 [M+H]$^+$. $^1$H NMR (400 MHz, CDCl$_3$): 8.85 (d, J=4.6, 1H), 8.82 (s, 1H), 8.09 (d, J=9.2, 1H), 7.86 (d, J=6.9, 1H), 7.67 (s, 1H), 7.43 (dd, J=9.2, 2.8, 1H), 7.31 (d, J=4.6, 1H), 7.11 (d, J=11.5, 1H), 7.07 (d, J=2.8, 1H), 6.90 (dd, J=14.6, 7.9, 1H), 4.74-4.70 (m, 1H), 3.84 (s, 3H), 3.46 (s, 2H), 3.18 (dd, J=15.6, 5.1, 1H), 2.85-2.77 (m, 1H), 2.73-2.57 (m, 2H), 2.19-2.16 (m 1H), 2.06-1.99 (m, 1H).

Example 20

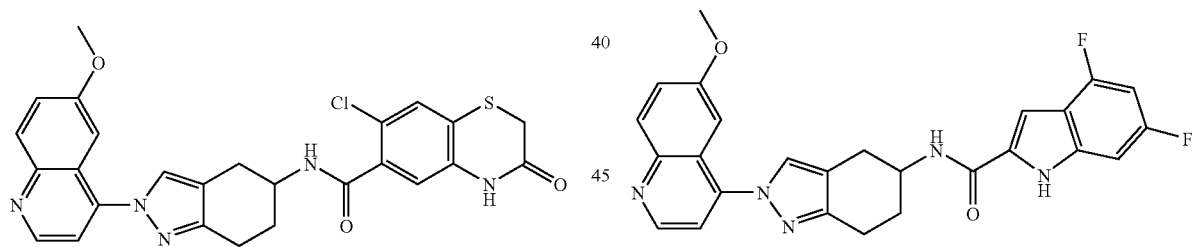

7-Chloro-3-oxo-3,4-dihydro-2H-benzo[1,4]thiazine-6-carboxylic acid [2-(6-methoxy-quinolin-4-yl)-4,5,6,7-tetrahydro-2H-indazol-5-yl]-amide The crude material was purified on SiO$_2$ (0-10% CH$_3$OH/CH$_2$Cl$_2$, then 50-100% EtOAc/hexanes). MS (ESI): exact mass calculated for $C_{26}H_{22}ClN_5O_3S$, 519.11; m/z found, 520.3 [M+H]$^+$. $^1$H NMR (500 MHz, DMSO-d$_6$): 8.79 (d, J=4.7, 1H), 8.07 (d, J=9.2, 1H), 7.80 (s, 1H), 7.68 (s, 1H), 7.62 (d, J=2.8, 1H), 7.43 (dd, J=9.2, 2.8, 1H), 7.36 (s, 1H), 7.34-7.33 (m, 2H), 6.59 (d, J=7.9, 1H), 4.63-4.60 (m, 1H), 3.90 (s, 3H), 3.44 (s, 2H), 3.20 (dd, J=15.6, 4.8, 1H), 3.04-3.01 (m, 2H), 2.75 (dd, J=15.7, 7.1, 1H), 2.27-2.22 (m, 1H), 2.17-2.13 (m, 1H).

Example 21

1H-Indole-2-carboxylic acid [2-(6-methoxy-quinolin-4-yl)-4,5,6,7-tetrahydro-2H-indazol-5-yl]-amide MS (ESI): exact mass calculated for $C_{25}H_{23}N_5O_2$, 437.19; m/z found, 438.4 [M+H]$^+$. $^1$H NMR (500 MHz, CDCl$_3$): 9.37 (s, 1H), 8.80 (d, J=4.7, 1H), 8.08 (d, J=9.2, 1H), 7.68-7.63 (m, 3H), 7.45-7.41 (m, 2H), 7.35 (d, J=4.7, 1H), 7.29 (dd, J=7.1, 1.0, 1H), 7.14 (dd, J=7.2, 0.9, 1H), 6.87 (d, J=1.3, 1H), 6.31 (d, J=7.9, 1H), 4.64-4.61 (m, 1H), 3.91 (s, 3H), 3.24 (dd, J=15.5, 5.2, 1H), 3.05 (dd, J=6.7, 6.7, 2H), 2.72 (dd, J=15.6, 8.1, 1H), 2.31-2.25 (m, 1H), 2.15-2.07 (m, 1H).

Example 22

4,6-Difluoro-1H-indole-2-carboxylic acid [2-(6-methoxy-quinolin-4-yl)-4,5,6,7-tetrahydro-2H-indazol-5-yl]-amide MS (ESI): exact mass calculated for $C_{26}H_{21}F_2N_5O_2$, 473.17; m/z found, 474.3 [M+H]$^+$. $^1$H NMR (600 MHz, CDCl$_3$): 9.77 (s, 1H), 8.81 (d, J=4.7, 1H), 8.09 (d, J=9.2, 1H), 7.70 (s, 1H), 7.66 (d, J=2.7, 1H), 7.44 (dd, J=9.2, 2.8, 1H), 7.37 (d, J=4.7, 1H), 6.96 (d, J=8.7, 1H), 6.93 (d, J=2.0, 1H), 6.66 (dt, J=10.0, 1.9, 1H), 6.31 (d, J=8.0, 1H), 4.63-4.58 (m, 1H), 3.92 (s, 3H), 3.26 (dd, J=15.5, 5.1, 1H), 3.06 (dd, J=6.6, 6.6, 2H), 2.74 (dd, J=15.5, 8.1, 1H), 2.32-2.28 (m, 1H), 2.16-2.10 (m, 1H).

Example 23

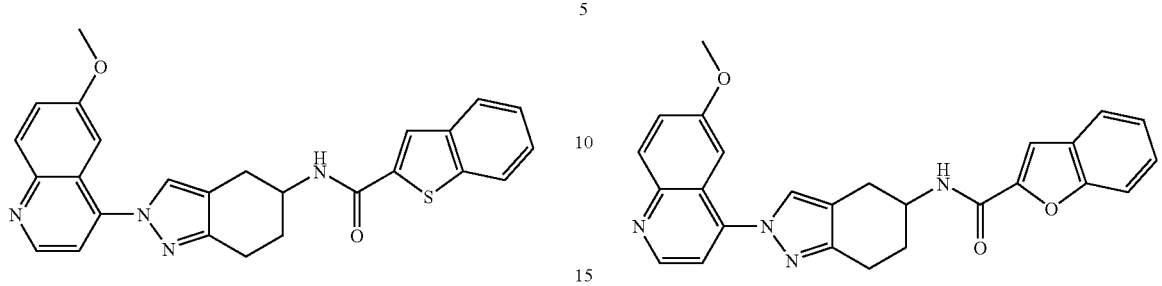

Benzo[b]thiophene-2-carboxylic acid [2-(6-methoxy-quinolin-4-yl)-4,5,6,7-tetrahydro-2H-indazol-5-yl]-amide MS (ESI): exact mass calculated for $C_{26}H_{22}N_4O_2S$, 454.15; m/z found, 455.3 [M+H]$^+$. $^1$H NMR (600 MHz, CDCl$_3$): 8.80 (d, J=4.7, 1H), 8.08 (d, J=9.2, 1H), 7.85 (dd, J=16.8, 7.9, 1H), 7.80 (s, 2H), 7.69 (s, 1H), 7.66 (dd, J=2.7, 2.7, 1H), 7.44-7.41 (m, 3H), 7.36 (d, J=4.7, 1H), 6.29 (d, J=7.7, 1H), 4.62-4.56 (m, 1H), 3.91 (s, 3H), 3.25 (dd, J=15.4, 5.1, 1H), 3.04 (dd, J=6.3, 6.3, 2H), 2.73 (dd, J=15.5, 8.1, 1H), 2.31-2.27 (m, 1H), 2.15-2.09 (m, 1H).

Example 24

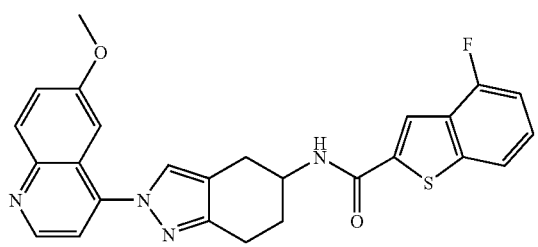

4-Fluoro-benzo[b]thiophene-2-carboxylic acid [2-(6-methoxy-quinolin-4-yl)-4,5,6,7-tetrahydro-2H-indazol-5-yl]-amide The reaction mixture was stirred overnight instead of 1.5 h. MS (ESI): exact mass calculated for $C_{26}H_{21}FN_4O_2S$, 472.14; m/z found, 473.3 [M+H]$^+$. $^1$H NMR (600 MHz, CDCl$_3$): 8.80 (d, J=4.7, 1H), 8.08 (d, J=9.2, 1H), 7.85 (s, 1H), 7.69 (s, 1H), 7.66 (d, J=2.7, 1H), 7.63 (d, J=7.6, 1H), 7.43 (dd, J=9.2, 2.8, 1H), 7.41-7.37 (m, 1H), 7.36 (d, J=4.7, 1H), 7.07 (dd, J=8.1, 1.7, 1H), 6.37 (d, J=7.7, 1H), 4.61-4.56 (m, 1H), 3.91 (s, 3H), 3.26 (dd, J=15.5, 5.1, 1H), 3.04 (dd, J=6.3, 6.3, 2H), 2.74 (dd, J=15.5, 8.2, 1H), 2.31-2.28 (m, 1H), 2.16-2.09 (m, 1H).

Example 25

Benzofuran-2-carboxylic acid [2-(6-methoxy-quinolin-4-yl)-4,5,6,7-tetrahydro-2H-indazol-5-yl]-amide MS (ESI): exact mass calculated for $C_{26}H_{22}N_4O_3$, 438.17; m/z found, 439.3 [M+H]$^+$. $^1$H NMR (600 MHz, CDCl$_3$): 8.81 (d, J=4.7, 1H), 8.09 (d, J=9.2, 1H), 7.71 (s, 1H), 7.69 (d, J=7.7, 1H), 7.67 (d, J=2.7, 1H), 7.52-7.51 (m, 2H), 7.45-7.42 (m 2H), 7.38 (d, J=4.7, 1H), 7.31 (dd, J=7.8, 7.8, 1H), 6.76 (d, J=8.0, 1H), 4.63-4.58 (m, 1H), 3.92 (s, 3H), 3.25 (dd, J=15.5, 5.2, 1H), 3.09-3.03 (m, 2H), 2.76 (dd, J=15.5, 8.3, 1H), 2.33-2.28 (m, 1H), 2.16-2.10 (m, 1H).

Example 26

2-(1H-Indol-2-yl)-N-[2-(6-methoxy-quinolin-4-yl)-4,5,6,7-tetrahydro-2H-indazol-5-yl]-2-oxo-acetamide MS (ESI): exact mass calculated for $C_{27}H_{23}N_5O_3$, 465.18; m/z found, 466.3 [M+H]$^+$. $^1$H NMR (600 MHz, CDCl$_3$): 9.21 (s, 1H), 9.14 (d, J=3.0, 1H), 8.81 (d, J=4.7, 1H), 8.42 (d, J=7.3, 1H), 8.08 (d, J=9.2, 1H), 7.72-7.70 (m, 2H), 7.65 (d, J=2.7, 1H), 7.46-7.43 (m, 2H), 7.38-7.32 (m, 3H), 4.47-4.41 (m, 1H), 3.93 (s, 3H), 3.19 (dd, J=15.5, 5.1, 1H), 3.06-3.00 (m, 2H), 2.74 (dd, J=15.5, 7.9, 1H), 2.28-2.22 (m, 1H), 2.14-2.08 (m, 1H).

Example 27

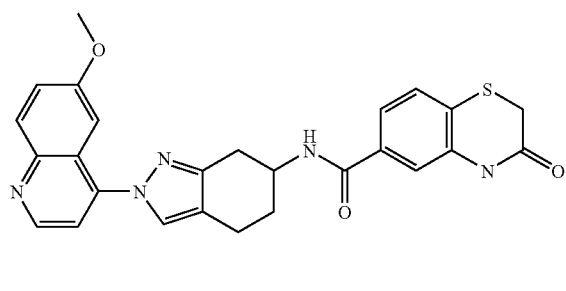

3-Oxo-3,4-dihydro-2H-benzo[1,4]thiazine-6-carboxylic acid [2-(6-methoxy-quinolin-4-yl)-4,5,6,7-tetrahydro-2H-indazol-6-yl]-amide The crude material was purified by supercritical fluid chromatography to provide the title compound. MS (ESI): exact mass calculated for $C_{26}H_{23}N_5O_3S$, 485.15; m/z found, 486.3 [M+H]$^+$. $^1$H NMR (500 MHz, CDCl$_3$): 8.79 (d, J=4.7, 1H), 8.73 (br s, 1H), 8.07 (d, J=9.3, 1H), 7.67 (s, 1H), 7.65 (d, J=2.8, 1H), 7.53 (s, 1H), 7.42 (dd, J=2.8, 9.3, 1H), 7.36-7.30 (m, 3H), 6.33 (d, J=7.9, 1H), 4.68-4.65 (m, 1H), 3.89 (s, 3H), 3.35 (dd, J=5.3, 16.1, 1H), 3.44 (s, 2H), 2.91-2.80 (m, 3H), 2.24-2.20 (m, 1H), 2.02-1.93 (m, 1H).

Example 28

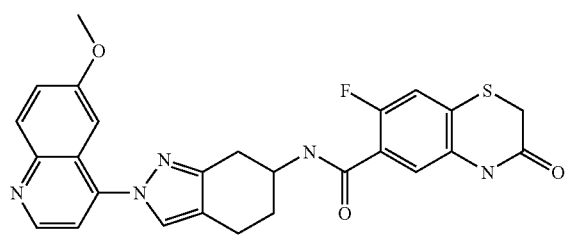

7-Fluoro-3-oxo-3,4-dihydro-2H-benzo[1,4]thiazine-6-carboxylic acid [2-(6-methoxy-quinolin-4-yl)-4,5,6,7-tetrahydro-2H-indazol-6-yl]-amide The crude material was purified by supercritical fluid chromatography to provide the title compound. MS (ESI): exact mass calculated for $C_{26}H_{22}FN_5O_3S$, 503.14; m/z found, 504.8 [M+H]$^+$. $^1$H NMR (600 MHz, CDCl$_3$): 8.95 (s, 1H), 8.80 (d, J=4.7, 1H), 8.08 (d, J=9.2, 1H), 7.89 (d, J=6.8, 1H), 7.69 (s, 1H), 7.67 (d, J=2.8, 1H), 7.43 (dd, J=9.2, 2.8, 1H), 7.35 (d, J=4.7, 1H), 7.11 (d, J=11.4, 1H), 6.94 (dd, J=14.7, 7.9, 1H), 4.82-4.79 (m, 1H), 3.91 (s, 3H), 3.46 (s, 2H), 3.36 (dd, J=16.1, 5.3, 1H), 2.96-2.92 (m, 1H), 2.91-2.83 (m, 2H), 2.26-2.23 (m, 1H), 2.04-1.97 (m, 1H).

Example 29

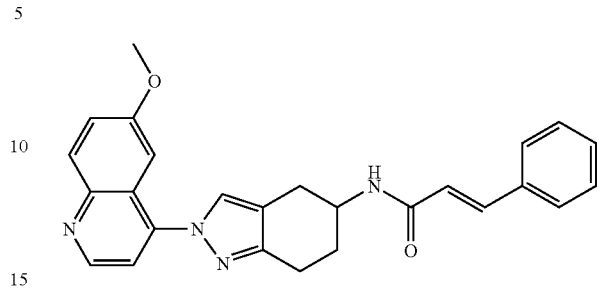

N-[2-(6-Methoxy-quinolin-4-yl)-4,5,6,7-tetrahydro-2H-indazol-5-yl]-3-phenyl-acrylamide MS (ESI): exact mass calculated for $C_{26}H_{24}N_4O_2$, 424.19; m/z found, 425.8 [M+H]$^+$. $^1$H NMR (400 MHz, CDCl$_3$): 8.79 (d, J=4.7, 1H), 8.08 (d, J=9.2, 1H), 7.70-7.66 (m, 3H), 7.52-7.49 (m, 2H), 7.43 (dd, J=9.2, 2.8, 1H), 7.38-7.33 (m, 4H), 6.44 (d, J=15.6, 1H), 5.91 (d, J=7.9, 1H), 4.57-4.52 (m, 1H), 3.91 (s, 3H), 3.18 (dd, J=15.6, 5.1, 1H), 3.02-2.99 (m, 2H), 2.66 (dd, J=15.6, 7.6, 1H), 2.24-2.17 (m, 1H), 2.12-2.02 (m, 1H).

Example 30

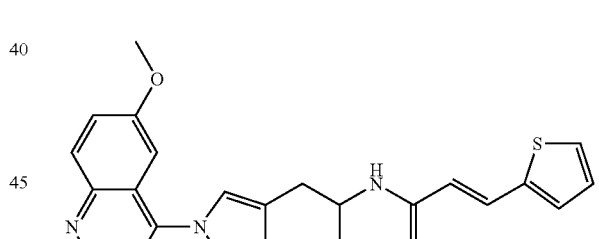

N-[2-(6-Methoxy-quinolin-4-yl)-4,5,6,7-tetrahydro-2H-indazol-5-yl]-3-thiophen-2-yl-acrylamide MS (ESI): exact mass calculated for $C_{24}H_{22}N_4O_2S$, 430.15; m/z found, 431.3 [M+H]$^+$. $^1$H NMR (600 MHz, CDCl$_3$): 8.80 (d, J=4.7, 1H), 8.08 (d, J=9.2, 1H), 7.80 (d, J=15.2, 1H), 7.68-7.66 (m, 2H), 7.43 (dd, J=9.2, 2.8, 1H), 7.35 (d, J=4.7, 1H), 7.32 (d, J=5.1, 1H), 7.23 (d, J=3.6, 1H), 7.05-7.04 (m, 1H), 6.22 (d, J=15.2, 1H), 5.72 (d, J=7.9, 1H), 4.56-4.50 (m, 1H), 3.92 (s, 3H), 3.17 (dd, J=15.5, 5.2, 1H), 3.03-2.96 (m, 2H), 2.67-2.62 (m, 1H), 2.23-2.17 (m, 1H), 2.09-2.03 (m, 1H).

Example 31

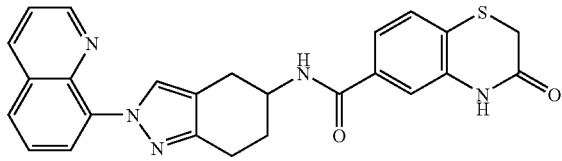

3-Oxo-3,4-dihydro-2H-benzo[1,4]thiazine-6-carboxylic acid (2-quinolin-8-yl-4,5,6,7-tetrahydro-2H-indazol-5-yl)-amide HPLC: $R_t$=8.00 min. MS (ESI): exact mass calculated for $C_{25}H_{21}N_5O_2S$, 455.14; m/z found, 456.4 [M+H]$^+$. $^1$H NMR (500 MHz, CDCl$_3$): 8.96 (dd, J=4.1, 1.6, 1H), 8.48 (s, 1H), 8.24 (dd, J=8.3, 1.6, 1H), 8.14 (d, J=7.5, 1H), 7.76 (d, J=8.1, 1H), 7.62 (t, J=7.8, 1H), 7.47 (dd, J=4.1, 4.1, 1H), 7.38 (d, J=1.4, 1H), 7.34-7.29 (m, 2H), 6.30 (d, J=7.9, 1H), 4.62-4.60 (m, 1H), 3.43 (s, 2H), 3.38 (dd, J=15.0, 5.0, 1H), 2.99-2.93 (m, 2H), 2.74 (dd, J=15.0, 5.0, 1H), 2.15-2.12 (m, 2H).

Example 32

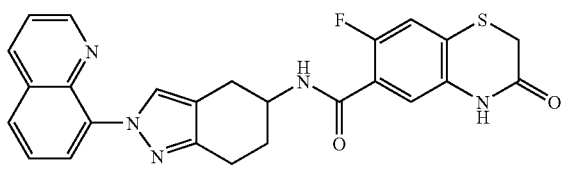

7-Fluoro-3-oxo-3,4-dihydro-2H-benzo[1,4]thiazine-6-carboxylic acid (2-quinolin-8-yl-4,5,6,7-tetrahydro-2H-indazol-5-yl)-amide MS (ESI): exact mass calculated for $C_{25}H_{20}FN_5O_2S$, 473.13; m/z found 474.3 [M+H]$^+$. $^1$H NMR: 8.96 (dd, J=3.6, 1.8, 1H), 8.51 (br s, 1H), 8.48 (br s, 1H), 8.23 (dd, J=8.3, 1.8, 1H), 8.16 (dd, J=7.6, 1.4, 1H), 7.75-7.76 (m, 1H), 7.74 (br s, 1H), 7.62 (t, J=7.9, 1H), 7.47 (q, J=4.2, 1H), 7.08 (d, J=11.3, 1H), 6.89 (dd, J=13.3, 7.7, 1H), 4.67 (br s, 1H), 3.45 (s, 2H), 3.21 (dd, J=15.5, 5.1, 1H), 2.93-3.07 (m, 2H), 2.76 (dd, J=15.4, 7.1, 1H), 2.25-2.19 (m, 1H), 2.13-2.06 (m, 1H).

Example 33

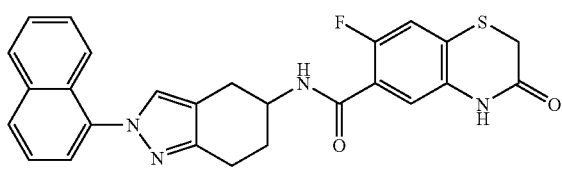

7-Fluoro-3-oxo-3,4-dihydro-2H-benzo[1,4]thiazine-6-carboxylic acid (2-naphthalen-1-yl-4,5,6,7-tetrahydro-2H-indazol-5-yl)-amide To a solution of 7-fluoro-3-oxo-3,4-dihydro-2H-benzo[1,4]thiazine-6-carboxylic acid (17 mg, 0.076 mmol), 2-naphthalen-1-yl-4,5,6,7-tetrahydro-2H-indazol-5-ylamine (18 mg, 0.069 mmol), and HOBT (24.0 mg, 0.103 mmol) in DMF (1 mL) was added EDC (20.0 mg, 0.103 mmol). The reaction mixture was stirred overnight at RT. The reaction was diluted with EtOAc (10 mL) and 1 N NaOH (5 mL). The aqueous layer was extracted with EtOAc (3×10 mL). The combined organic layers were washed with 1 N HCl (10 mL), brine (10 mL), dried (MgSO$_4$), filtered, and concentrated. The crude was purified by acidic reverse phase HPLC. The TFA salt of the title compound was diluted in CH$_3$OH (10 mL) and treated with anionic exchange resin (550 Å, OH). The mixture was stirred at RT for 20 min. The mixture was filtered and the filtrate was concentrated to afford 2.8 mg (8%) of the title compound. MS (ESI): exact mass calculated for $C_{26}H_{21}FN_4O_2S$, 472.14; m/z found, 473.3 [M+H]$^+$. $^1$H NMR (500 MHz, CDCl$_3$): 8.76 (br s, 1H), 7.91-7.84 (m, 4H), 7.54-7.49 (m, 5H), 7.11 (d, J=11.4, 1H), 6.97-6.92 (m, 1H), 4.73-4.71 (m, 1H), 3.46 (s, 2H), 3.20 (dd, J=15.5, 5.0, 1H), 3.08-3.02 (m, 1H), 3.00-2.94 (m, 1H), 2.74 (dd, J=15.5, 7.0, 1H), 2.26-2.22 (m, 1H), 2.17-2.11 (m, 1H).

Example 34

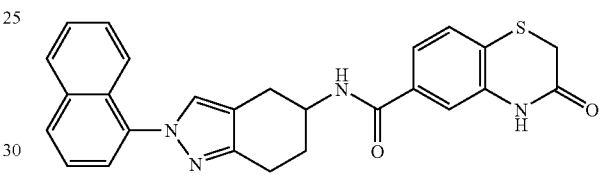

3-Oxo-3,4-dihydro-2H-benzo[1,4]thiazine-6-carboxylic acid (2-naphthalen-1-yl-4,5,6,7-tetrahydro-2H-indazol-5-yl)-amide This compound was prepared according to the methods described for Example 33. MS (ESI): exact mass calculated for $C_{26}H_{22}N_4O_2S$, 454.15; m/z found, 455.3 [M+H]$^+$. $^1$H NMR (500 MHz, CDCl$_3$): 7.94-7.86 (m, 3H), 7.54-7.49 (m, 6H), 7.33-7.27 (m, 2H), 6.35-6.31 (m, 1H), 4.64 (br s, 1H), 3.43 (s, 2H), 3.18 (dd, J=15.7, 4.9, 1H), 3.06-2.94 (m, 2H), 2.70 (dd, J=15.6, 7.1, 1H), 2.25-2.19 (m, 1H), 2.14-2.07 (m, 1H).

Example 35

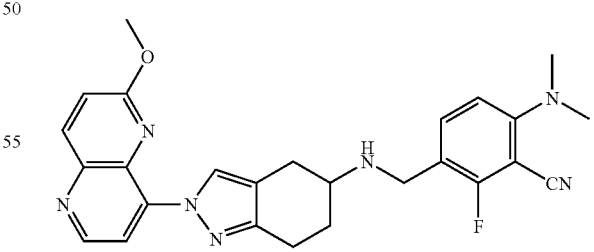

6-Dimethylamino-2-fluoro-3-{[2-(6-methoxy-[1,5]naphthyridin-4-yl)-4,5,6,7-tetrahydro-2H-indazol-5-ylamino]-methyl}-benzonitrile To a solution of 6-dimethylamino-2-fluoro-3-formyl-benzonitrile (69 mg, 0.36 mmol) in CH$_3$OH (7 mL) was added 2-(6-methoxy-[1,5]naphthyridin-4-yl)-4,5,6,7-tetrahydro-2H-indazol-5-ylamine (11 mg, 0.34 mmol). The reaction mixture was stirred overnight at RT. NaBH$_4$ (19 mg, 0.50 mmol) was then added and the suspension was stirred for 30 min at RT. The reaction mixture was diluted with a few drops of H$_2$O, and the solvents were removed under reduced pressure. The crude material was purified by basic reverse phase to provide 70 mg (44%) of the title compound. MS (ESI): exact mass calculated for C$_{26}$H$_{26}$FN$_7$O, 471.22; m/z found, 472.5 [M+H]$^+$. $^1$H NMR (500 MHz, CDCl$_3$): 9.09 (s, 1H), 8.75 (d, J=5.1, 1H), 8.26 (d, J=9.1, 1H), 8.14 (d, J=5.1, 1H), 7.38 (t, J=8.7, 1H), 7.18 (d, J=9.1, 1H), 6.58 (d, J=8.7, 1H), 4.75 (br s, 1H), 4.10 (s, 3H), 3.86 (s, 2H), 3.08 (s, 6H), 3.02-2.97 (m, 3H), 2.84-2.77 (m, 1H), 2.52 (dd, J=16.6, 9.9, 1H), 2.15-2.11 (m, 1H).

The compounds in Examples 36-43 were prepared according to the methods described for Example 35.

Example 36

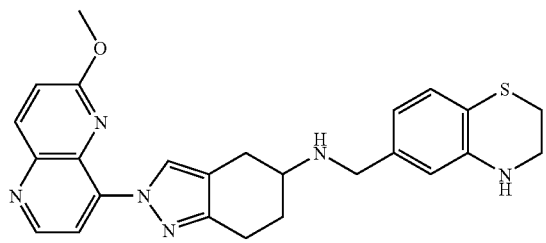

(3,4-Dihydro-2H-benzo[1,4]thiazin-6-ylmethyl)-[2-(6-methoxy-[1,5]naphthyridin-4-yl)-4,5,6,7-tetrahydro-2H-indazol-5-yl]-amine MS (ESI): exact mass calculated for C$_{25}$H$_{26}$N$_6$OS, 458.19; m/z found, 459.5 [M+H]$^+$. $^1$H NMR (500 MHz, CDCl$_3$): 9.08 (s, 1H), 8.75 (d, J=5.1, 1H), 8.25 (d, J=9.1, 1H), 8.14 (d, J=5.1, 1H), 7.18 (d, J=9.1, 1H), 6.94 (d, J=7.9, 1H), 6.60 (dd, J=7.9, 1.7, 1H), 6.50 (s, 1H), 4.10 (s, 3H), 3.99 (br s, 1H), 3.76 (s, 2H), 3.62-3.61 (m, 2H), 3.04-2.96 (m, 5H), 2.83-2.76 (m, 1H), 2.53 (dd, J=15.0, 8.8, 1H), 2.16-2.10 (m, 1H), 1.88-1.80 (m, 1H).

Example 37

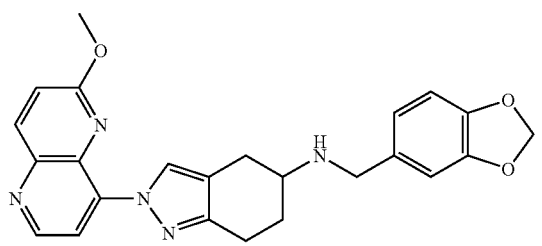

Benzo[1,3]dioxol-5-ylmethyl-[2-(6-methoxy-[1,5]naphthyridin-4-yl)-4,5,6,7-tetrahydro-2H-indazol-5-yl]-amine MS (ESI): exact mass calculated for C$_{24}$H$_{23}$N$_5$O$_3$, 429.18; m/z found, 430.5 [M+H]$^+$. $^1$H NMR (500 MHz, CDCl$_3$): 9.09 (s, 1H), 8.75 (d, J=5.1, 1H), 8.25 (d, J=9.1, 1H), 8.14 (d, J=5.1, 1H), 7.18 (d, J=9.1, 1H), 6.86 (d, J=1.6, 1H), 6.79 (dd, J=7.9, 1.6, 1H), 6.75 (d, J=7.9, 1H), 5.93 (s, 2H), 4.10 (s, 3H), 3.82 (s, 2H), 3.08-2.96 (m, 3H), 2.83-2.77 (m, 1H), 2.51 (dd, J=15.3, 8.3, 1H), 2.16-2.09 (m, 1H), 1.86-1.79 (m, 1H).

Example 38

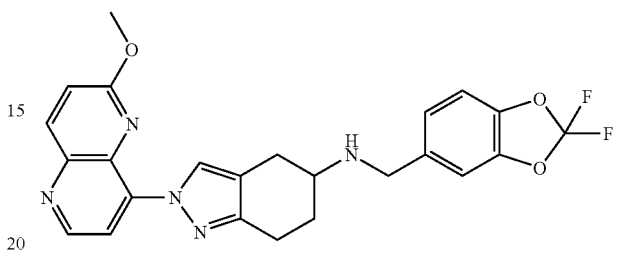

(2,2-Difluoro-benzo[1,3]dioxol-5-ylmethyl)-[2-(6-methoxy-[1,5]naphthyridin-4-yl)-4,5,6,7-tetrahydro-2H-indazol-5-yl]-amine MS (ESI): exact mass calculated for C$_{24}$H$_{21}$F$_2$N$_5$O$_3$, 465.16; m/z found, 466.5 [M+H]$^+$. $^1$H NMR (500 MHz, CDCl$_3$): 9.10 (s, 1H), 8.75 (d, J=5.1, 1H), 8.25 (d, J=9.1, 1H), 8.14 (d, J=5.1, 1H), 7.18 (d, J=9.1, 1H), 7.13 (d, J=1.5, 1H), 7.04 (dd, J=8.1, 1.5, 1H), 6.98 (d, J=8.1, 1H), 4.09 (s, 3H), 3.89 (s, 2H), 3.06-2.96 (m, 3H), 2.84-2.77 (m, 1H), 2.52 (dd, J=15.0, 8.1, 1H), 2.15-2.11 (m, 1H), 1.87-1.80 (m, 1H), 1.34 (br s, 1H).

Example 39

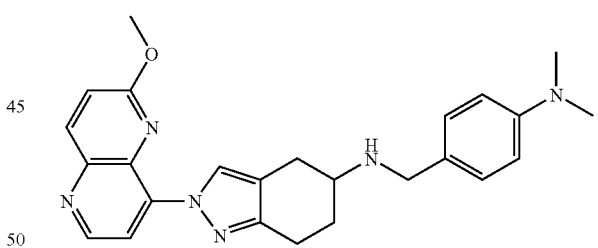

(4-Dimethylamino-benzyl)-[2-(6-methoxy-[1,5]naphthyridin-4-yl)-4,5,6,7-tetrahydro-2H-indazol-5-yl]-amine MS (ESI): exact mass calculated for C$_{25}$H$_{28}$N$_6$O, 428.23; m/z found, 451.8 [M+Na]$^+$. $^1$H NMR (500 MHz, CDCl$_3$): 9.08 (s, 1H), 8.75 (d, J=5.1, 1H), 8.25 (d, J=9.1, 1H), 8.13 (d, J=5.1, 1H), 7.22 (d, J=8.7, 2H), 7.17 (d, J=9.1, 1H), 6.70 (d, J=8.7, 2H), 4.00 (s, 3H), 3.83 (s, 2H), 3.11-3.06 (m, 1H), 3.06-2.96 (m, 2H), 2.91 (s, 6H), 2.82-2.75 (m, 1H), 2.57-2.53 (m, 1H), 2.16-2.13 (m, 2H), 1.87-1.79 (m, 1H).

Example 40

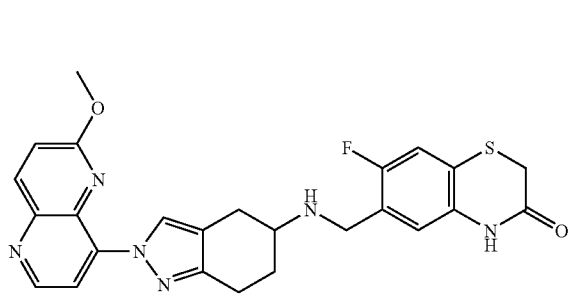

7-Fluoro-6-{[2-(6-methoxy-[1,5]naphthyridin-4-yl)-4,5,6,7-tetrahydro-2H-indazol-5-ylamino]-methyl}-4H-benzo[1,4]thiazin-3-one MS (ESI): exact mass calculated for $C_{25}H_{23}FN_6O_2S$, 490.16; m/z found, 491.7 [M+H]$^+$. $^1$H NMR (500 MHz, CD$_3$OD): 9.07 (s, 1H), 8.70 (d, J=4.8, 1H), 8.23 (d, J=8.6, 1H), 8.07 (d, J=4.8, 1H), 7.26 (d, J=9.2, 1H), 7.05 (d, J=9.2, 1H), 6.99 (d, J=6.4, 1H), 4.10 (s, 3H), 3.88 (s, 2H), 3.38 (s, 2H), 3.06-2.95 (m, 3H), 2.80-2.73 (m, 1H), 2.50 (dd, J=14.6, 8.5, 1H), 2.22-2.17 (m, 1H), 1.82-1.77 (m, 1H).

Example 41

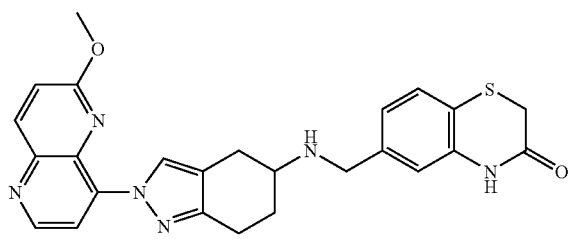

6-{[2-(6-Methoxy-[1,5]naphthyridin-4-yl)-4,5,6,7-tetrahydro-2H-indazol-5-ylamino]-methyl}-4H-benzo[1,4]thiazin-3-one DMF was used in place of CH$_3$OH. HPLC: R$_t$=6.16 min. MS (ESI): exact mass calculated for $C_{25}H_{24}N_6O_2S$, 472.17; m/z found, 473.5 [M+H]$^+$. $^1$H NMR (500 MHz, CDCl$_3$): 9.11 (s, 1H), 8.76 (d, J=5.0, 1H), 8.26 (d, J=9.1, 1H), 8.16 (d, J=5.0, 1H), 7.77 (br s, 1H), 7.27 (d, J=7.9, 1H), 7.19 (d, J=9.1, 1H), 7.02 (dd, J=7.9, 1.4, 1H), 6.86 (d, J=1.4, 1H), 4.11 (s, 3H), 3.87 (s, 2H), 3.41 (s, 2H), 3.01-2.97 (m, 3H), 2.85-2.78 (m, 1H), 2.56-2.51 (m, 1H), 2.17-2.13 (m, 1H), 1.88-1.82 (m, 1H).

Example 42

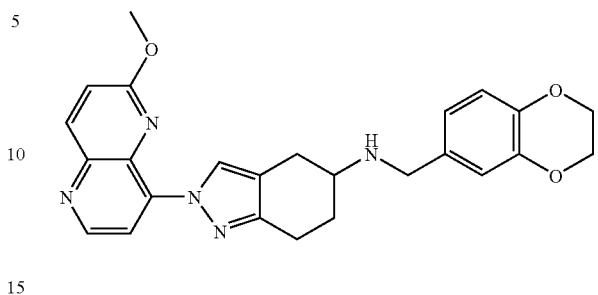

(2,3-Dihydro-benzo[1,4]dioxin-6-ylmethyl)-[2-(6-methoxy-[1,5]naphthyridin-4-yl)-4,5,6,7-tetrahydro-2H-indazol-5-yl]-amine DMF was used in place of CH$_3$OH. HPLC: R$_t$=6.85 min. MS (ESI): exact mass calculated for $C_{25}H_{25}N_5O_3$, 443.2; m/z found, 444.6 [M+H]$^+$. $^1$H NMR (500 MHz, CDCl$_3$): 9.09 (s, 1H), 8.75 (d, J=5.0, 1H), 8.26 (d, J=9.1, 1H), 8.14 (d, J=5.0, 1H), 7.18 (d, J=9.1, 1H), 6.88 (s, 1H), 6.82 (s, 2H), 4.26 (s, 4H), 4.41 (s, 3H), 3.8 (s, 2H), 3.10-3.00 (m, 3H), 2.83-2.77 (m, 1H), 2.56-2.51 (m, 1H), 2.17-2.13 (m, 1H), 1.88-1.80 (m, 1H).

Example 43

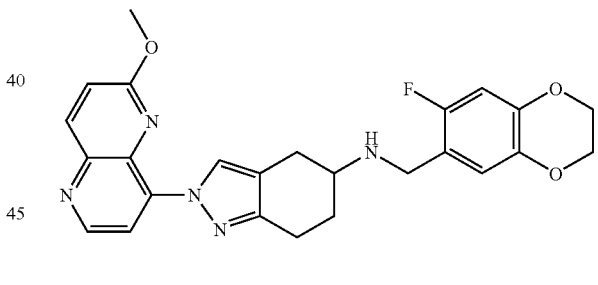

(7-Fluoro-2,3-dihydro-benzo[1,4]dioxin-6-ylmethyl)-[2-(6-methoxy-[1,5]naphthyridin-4-yl)-4,5,6,7-tetrahydro-2H-indazol-5-yl]-amine Once the reaction was complete, the reaction mixture was extracted with EtOAc (3×20 mL), washed with brine (20 mL), dried (MgSO$_4$), and concentrated. The crude material was purified on SiO$_2$ (0-100% EtOAc/hexanes) to provide the title compound. MS (ESI): exact mass calculated for $C_{25}H_{24}FN_5O_3$, 461.19; m/z found, 462.4 [M+H]$^+$. $^1$H NMR (500 MHz, CDCl$_3$): 9.08 (s, 1H), 8.75 (d, J=4.9, 1H), 8.25 (d, J=9.1, 1H), 8.14 (d, J=5.1, 1H), 7.17 (d, J=9.0, 1H), 6.84 (d, J=7.2, 1H), 6.56 (d, J=10.5, 1H), 4.24-4.19 (m, 5H), 4.10 (s, 3H), 3.85 (s, 2H), 3.05-2.96 (m, 3H), 2.83-2.76 (m, 1H), 2.53-2.49 (m, 1H), 2.14-2.11 (m, 1H), 1.86-1.81 (m, 1H).

Example 44

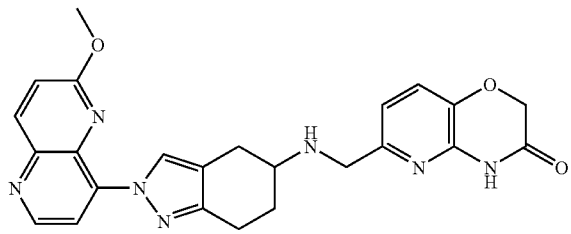

6-{[2-(6-Methoxy-[1,5]naphthyridin-4-yl)-4,5,6,7-tetrahydro-2H-indazol-5-ylamino]-methyl}-4H-pyrido[3,2-b][1,4]oxazin-3-one To a solution of 3-oxo-3,4-dihydro-2H-pyrido[3,2-b][1,4]oxazine-6-carbaldehyde (153 mg, 0.858 mmol) in DMF (1.36 mL) was added 2-(6-methoxy-[1,5]naphthyridin-4-yl)-4,5,6,7-tetrahydro-2H-indazol-5-ylamine (84.4 mg, 0.286 mmol). The reaction mixture was stirred overnight at RT. NaBH$_4$ (37.6 mg, 0.572 mmol) was then added and the suspension was stirred for 1 h at RT. The reaction mixture was diluted with CH$_3$OH and poured into 1 N NaOH. The organic layer was separated, washed with brine (4×), dried (Na$_2$SO$_4$), filtered, and concentrated. The crude material was purified by basic reverse phase HPLC to provide 4.6 mg (3.5%) of the title compound. MS (ESI): exact mass calculated for C$_{24}$H$_{23}$N$_7$O$_3$, 457.19; m/z found, 458.3 [M+H]$^+$. $^1$H NMR (500 MHz, CDCl$_3$): 9.09 (s, 1H), 8.75 (d, J=5.1, 1H), 8.25 (d, J=9.1, 1H), 8.14 (d, J=5.1, 1H), 7.19 (d, J=8.0, 1H), 7.17 (d, J=9.1, 1H), 6.95 (d, J=8.0, 1H), 4.62 (s, 2H), 4.09 (s, 3H), 3.92 (s, 2H), 3.09-2.98 (m, 3H), 2.83-2.77 (m, 1H), 2.56 (dd, J=14.6, 7.9, 1H), 2.17-2.14 (m, 1H), 1.89-1.82 (m, 1H), 1.24 (s, 1H).

Example 45

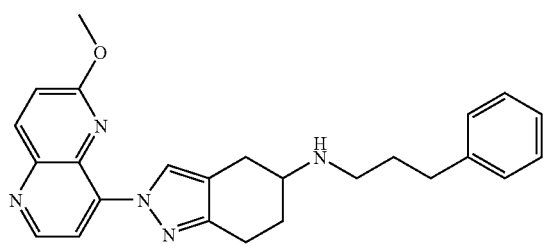

[2-(6-Methoxy-[1,5]naphthyridin-4-yl)-4,5,6,7-tetrahydro-2H-indazol-5-yl]-(3-phenyl-propyl)-amine To a stirring solution of 2-(6-methoxy-[1,5]naphthyridin-4-yl)-4,5,6,7-tetrahydro-2H-indazol-5-ylamine (50 mg, 0.17 mmol) and 3-phenylpropionaldehyde (20 mg, 0.2 mmol) in dichloroethane (2 mL) was added NaB(OAc)$_3$H (37 mg, 0.17 mmol) and acetic acid (2 drops). The reaction mixture was stirred overnight at RT. Water (5 mL) was added, and the aqueous layer was extracted with CH$_2$Cl$_2$ (3×15 mL). The combined organic layers were washed with brine (10 mL), dried (MgSO$_4$), filtered, and concentrated. The crude material was purified on SiO$_2$ (0-5% CH$_3$OH/CH$_2$Cl$_2$) to give 24 mg (36%) of the title compound as a clear oil. MS (ESI): exact mass calculated for C$_{25}$H$_{27}$N$_5$O, 413.22; m/z found, 414.5 [M+H]$^+$. $^1$H NMR (400 MHz, CDCl$_3$): 9.07 (s, 1H), 8.72-8.70 (m, 1H), 8.25-8.23 (m, 1H), 8.08-8.07 (m, 1H), 7.30-7.21 (m, 5H), 7.18-7.16 (m, 1H), 4.09 (s, 3H), 3.06-2.90 (m, 3H), 2.80-2.68 (m, 5H), 2.46-2.40 (m, 1H), 2.19-2.16 (m, 1H), 1.93-1.86 (m, 2H), 1.77-1.67 (m, 1H).

Example 46

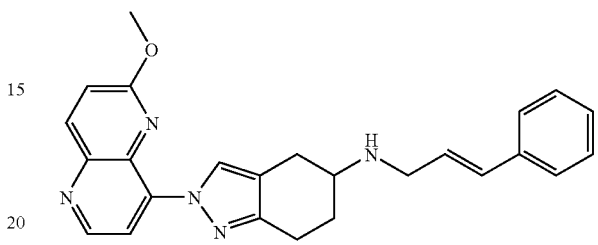

[2-(6-Methoxy-[1,5]naphthyridin-4-yl)-4,5,6,7-tetrahydro-2H-indazol-5-yl]-(3-phenyl-allyl)-amine To a suspension of 2-(6-methoxy-[1,5]naphthyridin-4-yl)-4,5,6,7-tetrahydro-2H-indazol-5-ylamine (50 mg, 0.17 mmol) and trans-cinnamaldehyde (20 mg, 0.15 mmol) in Ti(OiPr)$_4$ (0.074 mL, 0.25 mmol) was added CH$_3$OH (1 mL). The suspension was stirred for 3 h at RT. NaBH$_4$ was added (9.0 mg, 0.24 mmol) and the reaction mixture was stirred for another 10 min, followed by the addition of 3 N NaOH (5 mL). The aqueous layer was extracted with EtOAc (3×20 mL). The combined organic layers were washed with brine (10 mL), dried (MgSO$_4$), filtered, and concentrated. The crude was purified on SiO$_2$ (0-5% CH$_3$OH/CH$_2$Cl$_2$) to give 30 mg (50%) of the title compound as a clear oil. MS (ESI): exact mass calculated for C$_{25}$H$_{25}$N$_5$O, 411.21; m/z found, 412.4 [M+H]$^+$. $^1$H NMR (500 MHz, CDCl$_3$): 9.10 (s, 1H), 8.76 (d, J=5.1, 1H), 8.25 (d, J=9.1, 1H), 8.15 (d, J=5.1, 2H), 7.37 (d, J=7.4, 2H), 7.30 (d, J=7.4, 2H), 7.23-7.20 (m, 1H), 7.18 (d, J=9.1, 1H), 6.57 (d, J=15.9, 1H), 6.34 (dt, J=15.9, 6.4, 1H), 4.10 (s, 3H), 3.55 (d, J=6.4, 2H), 3.15-3.11 (m, 1H), 3.06-3.01 (m, 1H), 2.99 (t, J=5.3, 1H), 2.86-2.80 (m, 1H), 2.53 (q, J=8.5, 1H), 2.17-2.15 (m, 1H), 1.88-1.81 (m, 1H).

Example 47

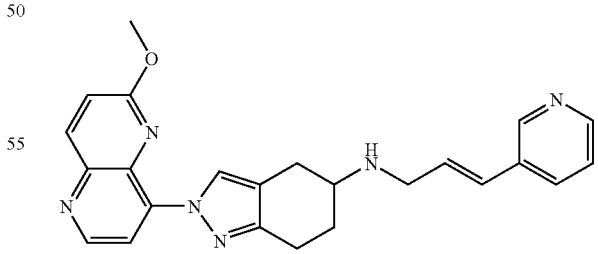

[2-(6-Methoxy-[1,5]naphthyridin-4-yl)-4,5,6,7-tetrahydro-2H-indazol-5-yl]-(3-pyridin-3-yl-allyl)-amine This compound was prepared according to the methods described for Example 35. MS (ESI): exact mass calculated for C₂₄H₂₄N₆O, 412.20; m/z found, 413.4 [M+H]⁺. ¹H NMR (500 MHz, CDCl₃): 9.07 (s, 1H), 8.72 (d, J=5.0, 1H), 8.55 (d, J=2.0, 1H), 8.42-8.41 (m, 1H), 8.22 (d, J=9.0, 1H), 8.11 (d, J=5.0, 1H), 7.66 (d, J=8.0, 1H), 7.25-7.16 (m, 1H), 7.14 (d, J=9.0, 1H), 6.53 (d, J=15.0, 1H), 6.40-6.37 (m, 1H), 4.06 (s, 3H), 3.55 (d, J=5.0, 2H), 3.10-3.08 (m, 1H), 3.03-2.96 (m, 2H), 2.82-2.80 (m, 1H), 2.53-2.48 (m, 1H), 2.13-2.12 (m, 1H), 1.82-1.81 (m, 1H).

Example 48

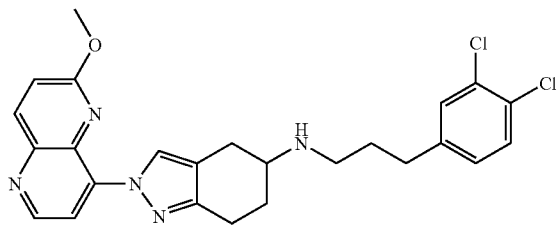

[3-(3,4-Dichloro-phenyl)-propyl]-[2-(6-methoxy-[1,5]naphthyridin-4-yl)-4,5,6,7-tetrahydro-2H-indazol-5-yl]-amine A. 3-(3,4-Dichloro-phenyl)-N-[2-(6-methoxy-[1,5]naphthyridin-4-yl)-4,5,6,7-tetrahydro-2H-indazol-5-yl]-propionamide. To a solution of 3-(3,4-dichloro-phenyl)propionic acid (30 mg, 0.1 mmol) in DMF (1 mL) was added HOBT (28 mg, 0.21 mmol), EDC (40 mg, 0.2 mmol), and a solution of 2-(6-methoxy-[1,5]naphthyridin-4-yl)-4,5,6,7-tetrahydro-2H-indazol-5-ylamine (50 mg, 0.2 mmol) in DMF (1 mL). The reaction mixture was stirred overnight at RT. Water was added (10 mL), and the aqueous layer was extracted with EtOAc (3×30 mL). The combined organic layers were washed with brine (15 mL), dried (MgSO₄), filtered, and concentrated. The crude was purified on SiO₂ (0-5% CH₃OH/CH₂Cl₂), to give a yellow oil. The oil was then washed with 1 N NaOH (3×10 mL), brine (10 mL), dried (MgSO₄), and filtered to provide 50 mg (72%) of a white solid. MS (ESI): exact mass calculated for C₂₅H₂₃Cl₂N₅O₂, 495.12; m/z found, 496.4 [M+H]⁺. ¹H NMR (400 MHz, CDCl₃): 9.13 (s, 1H), 8.78 (d, J=5.1, 1H), 8.27 (d, J=9.1, 1H), 8.16 (d, J=5.1, 1H), 7.34 (d, J=8.2, 1H), 7.31 (d, J=2.0, 1H), 7.20 (d, J=9.1, 1H), 7.05 (dd, J=8.2, 2.0, 1H), 5.43 (d, J=7.5, 1H), 4.40-4.34 (m, 1H), 4.10 (s, 3H), 3.05 (dd, J=15.6, 5.1, 1H), 2.97-2.80 (m, 4H), 2.51-2.41 (m, 3H), 2.07-2.01 (m, 1H), 1.96-1.88 (m, 1H).

B. [3-(3,4-Dichloro-phenyl)-propyl]-[2-(6-methoxy-[1,5]naphthyridin-4-yl)-4,5,6,7-tetrahydro-2H-indazol-5-yl]-amine. A solution of 3-(3,4-dichloro-phenyl)-N-[2-(6-methoxy-[1,5]naphthyridin-4-yl)-4,5,6,7-tetrahydro-2H-indazol-5-yl]-propionamide (20 mg, 0.04 mmol) in CH₂Cl₂ (2 mL) was treated with DIBAL-H (1 M solution in THF, 0.4 mL, 0.4 mmol) at −78° C. for 30 min. The reaction mixture was warmed to 0° C. and stirred for 20 min, then was stirred at RT for 3 h. The solution was re-cooled (−78° C.), and treated with additional DIBAL-H (0.4 mL, 0.4 mmol). The solution was stirred at −78° C. for 30 min, followed by 20 min at 0° C. Satd. potassium sodium tartrate solution (5 mL) was added to the reaction mixture at −30° C. The reaction mixture was warmed to RT and stirred for 2 h. Water (10 mL) was added, and the aqueous layer was extracted with EtOAc (3×30 mL). The combined organic layers were washed with brine (15 mL), dried (MgSO₄), filtered, and concentrated. The crude was purified on SiO₂ (0-5% CH₃OH/CH₂Cl₂) to give 10 mg (50%) of the title compound as a clear oil. MS (ESI): exact mass calculated for C₂₅H₂₅Cl₂N₅O, 481.14; m/z found, 482.4 [M+H]⁺. ¹H NMR (400 MHz, CDCl₃): 9.11 (s, 1H), 8.77 (d, J=5.1, 1H), 8.26 (d, J=9.1, 1H), 8.16 (d, J=5.1, 1H), 7.34 (d, J=8.2, 1H), 7.30 (d, J=2.0, 1H), 7.19 (d, J=9.1, 1H), 7.03 (dd, J=8.2, 2.0, 1H), 4.10 (s, 3H), 3.04-2.95 (m, 3H), 2.85-2.74 (m, 3H), 2.68-2.65 (m, 2H), 2.52-2.48 (m, 1H), 2.14-2.11 (m, 1H), 1.87-1.78 (m, 4H).

Example 49

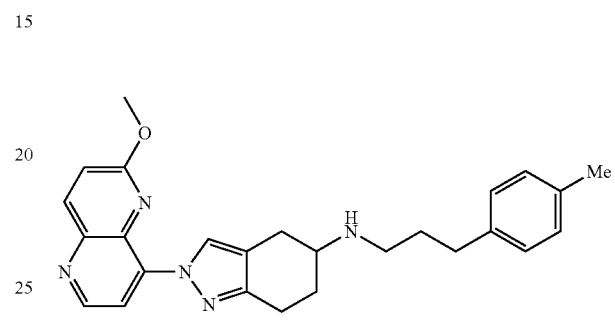

[2-(6-Methoxy-[1,5]naphthyridin-4-yl)-4,5,6,7-tetrahydro-2H-indazol-5-yl]-(3-p-tolyl-propyl)-amine A. N-[2-(6-Methoxy-[1,5]naphthyridin-4-yl)-4,5,6,7-tetrahydro-2H-indazol-5-yl]-3-p-tolyl-propionamide. This compound was prepared according to the methods described in Example 48, step A. MS (ESI): exact mass calculated for C₂₆H₂₇N₅O₂, 441.22; m/z found, 442.5 [M+H]⁺. ¹H NMR (400 MHz, CDCl₃): 9.10 (s, 1H), 8.77 (d, J=5.1, 1H), 8.27 (d, J=9.1, 1H), 8.15 (d, J=5.1, 1H), 7.20 (d, J=9.1, 1H), 7.09 (s, 4H), 5.44 (d, J=7.9, 1H), 4.39-4.31 (m, 1H), 4.09 (s, 3H), 3.04 (dd, J=15.6, 5.1, 1H), 2.96-2.86 (m, 3H), 2.83-2.77 (m, 1H), 2.51-2.45 (m, 3H), 2.32-2.29 (m, 3H), 2.04-2.00 (m, 1H), 1.93-1.86 (m, 1H).

B. [2-(6-Methoxy-[1,5]naphthyridin-4-yl)-4,5,6,7-tetrahydro-2H-indazol-5-yl]-(3-p-tolyl-propyl)-amine. A solution of N-[2-(6-methoxy-[1,5]naphthyridin-4-yl)-4,5,6,7-tetrahydro-2H-indazol-5-yl]-3-p-tolyl-propionamide (0.020 g, 0.045 mmol) in CH₂Cl₂ (2 mL) was treated with DIBAL-H (1 M solution in THF, 0.45 mL, 0.45 mmol) at −78° C. for 30 min. The reaction mixture was warmed to 0° C. and stirred for 20 min, then at RT for 1 h. Satd. potassium sodium tartrate solution (5 mL) was added at −30° C. The solution was warmed to RT and stirred for 1 h. Water (10 mL) was added, and the aqueous layer was extracted with EtOAc (3×30 mL). The combined organic layers were washed with brine (15 mL), dried (MgSO₄), filtered, and concentrated. The crude was purified on SiO₂ (0-5% CH₃OH/CH₂Cl₂) to give 10 mg (53%) of the title compound as a clear oil. MS (ESI): exact mass calculated for C₂₆H₂₉N₅O, 427.24; m/z found, 428.5 [M+H]⁺. ¹H NMR (400 MHz, CDCl₃): 9.10 (s, 1H), 8.77 (d, J=5.1, 1H), 8.26 (d, J=9.1, 1H), 8.15 (d, J=5.1, 1H), 7.19 (d, J=9.1, 1H), 7.09 (s, 4H), 4.10 (s, 3H), 3.03-2.95 (m, 3H), 2.84-2.76 (m, 3H), 2.68-2.64 (m, 2H), 2.54-2.50 (m, 1H), 2.31 (s, 3H), 2.15-2.13 (m, 1H), 1.91-1.80 (m, 4H).

Example 50

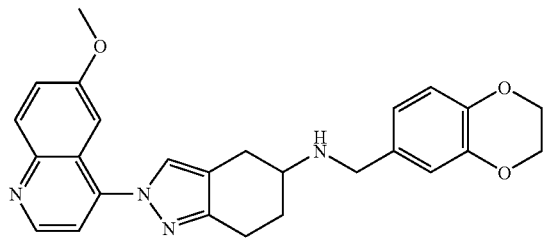

(2,3-Dihydro-benzo[1,4]dioxin-6-ylmethyl)-[2-(6-methoxy-quinolin-4-yl)-4,5,6,7-tetrahydro-2H-indazol-5-yl]-amine This compound was prepared according to the methods described in Example 35, using DMF instead of CH$_3$OH. HPLC: R$_f$=6.45 min. MS (ESI): exact mass calculated for C$_{26}$H$_{26}$N$_4$O$_3$, 442.5; m/z found, 443.4 [M+H]$^+$. $^1$H NMR (500 MHz, CDCl$_3$): 8.78 (d, J=4.7, 1H), 8.06 (d, J=9.2, 1H), 7.69 (d, J=2.8, 1H), 7.63 (s, 1H), 7.40 (dd, J=9.2, 2.8, 1H), 7.32 (d, J=4.7, 1H), 6.88 (s, 1H), 6.83 (s, 1H), 4.27 (s, 4H), 3.92, (s, 3H), 3.79 (s, 2H), 3.11-2.78 (m, 3H), 2.85-2.78 (m, 1H), 2.54-2.49 (m, 1H), 2.17-2.13 (m, 1H), 1.88-1.83 (m, 2H).

Example 51

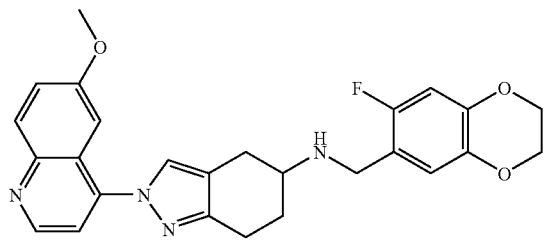

(7-Fluoro-2,3-dihydro-benzo[1,4]dioxin-6-ylmethyl)-[2-(6-methoxy-quinolin-4-yl)-4,5,6,7-tetrahydro-2H-indazol-5-yl]-amine This compound was prepared according to the methods described for Example 43. MS (ESI): exact mass calculated for C$_{26}$H$_{25}$FN$_4$O$_3$, 460.19; m/z found, 461.4 [M+H]$^+$. $^1$H NMR (500 MHz, CDCl$_3$): 8.77 (d, J=4.7, 1H), 8.05 (d, J=9.2, 1H), 7.69 (d, J=2.8, 1H), 7.63 (s, 1H), 7.41 (dd, J=7.0, 2.8, 1H), 7.32 (d, J=4.7, 1H), 6.84 (d, J=7.2, 1H), 6.60 (d, J=10.4, 1H), 4.24-4.20 (m, 4H), 3.90 (s, 3H), 3.86 (s, 2H), 3.07-2.97 (m, 3H), 2.84-2.78 (m, 1H), 2.52 (dd, J=15.1, 8.2, 1H), 2.15-2.12 (m, 1H), 1.86-1.81 (m, 1H).

Example 52

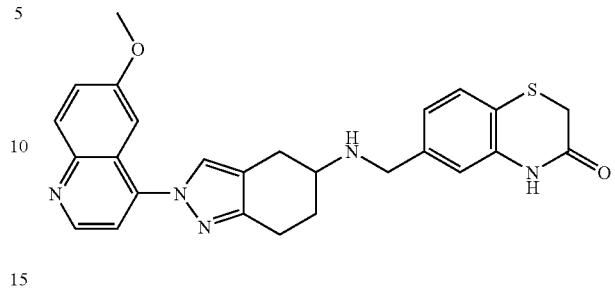

6-{[2-(6-Methoxy-quinolin-4-yl)-4,5,6,7-tetrahydro-2H-indazol-5-ylamino]-methyl}-4H-benzo[1,4]thiazin-3-one This compound was prepared according to the methods described in Example 35, using DMF instead of CH$_3$OH. HPLC: R$_f$=5.86 min. MS (ESI): exact mass calculated for C$_{26}$H$_{25}$N$_5$O$_2$S, 471.17; m/z found, 472.4 [M+H]$^+$. $^1$H NMR (500 MHz, CDCl$_3$): 9.78 (d, J=4.7, 1H), 8.06 (d, J=9.2, 1H), 7.80 (br s, 1H), 7.69 (d, J=2.7, 1H), 7.64 (s, 1H), 7.42 (dd, J=9.2, 2.7, 1H), 7.32 (d, J=4.7, 1H), 7.27 (d, J=7.9, 1H), 7.02 (dd, J=7.9, 1.5, 1H), 6.88 (d, J=1.4, 1H), 3.92-3.81 (m, 5H), 3.42 (s, 2H), 3.11-2.98 (m, 3H), 2.86-2.80 (m, 1H), 2.55-2.50 (m, 1H), 2.18-2.15 (m, 1H), 1.89-1.81 (m, 1H).

Example 53

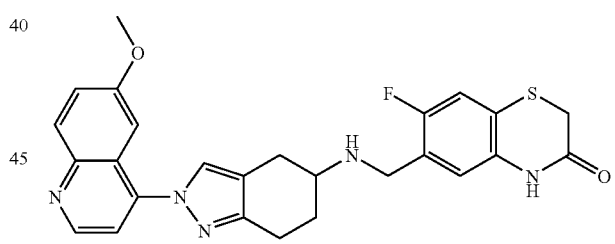

7-Fluoro-6-{[2-(6-methoxy-quinolin-4-yl)-4,5,6,7-tetrahydro-2H-indazol-5-ylamino]-methyl}-4H-benzo[1,4]thiazin-3-one This compound was prepared according to the methods described in Example 35, using DMF instead of CH$_3$OH. MS (ESI): exact mass calculated for C$_{26}$H$_{24}$FN$_5$O$_2$S, 489.16; m/z found, 490.8 [M+H]$^+$. $^1$H NMR (400 MHz, CDCl$_3$): 8.78 (d, J=4.7, 1H), 8.09-8.06 (m, 2H), 7.69 (d, J=2.8, 1H), 7.65 (s, 1H), 7.42 (dd, J=9.2, 2.8, 1H), 7.33 (d, J=4.7, 1H), 7.05 (d, J=9.3, 1H), 6.92 (d, J=6.3, 1H), 3.93 (s, 2H), 3.91 (s, 3H), 3.42 (s, 2H), 3.05-3.00 (m, 3H), 2.88-2.80 (m, 1H), 2.54 (dd, J=14.4, 7.6, 1H), 2.19-2.16 (m, 1H), 1.91-1.82 (m, 1H).

Example 54

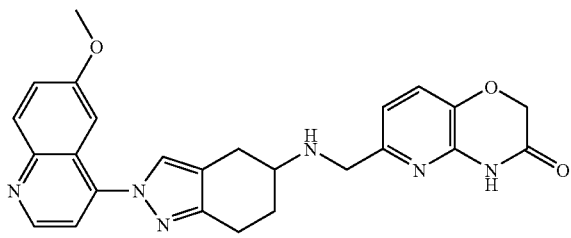

6-{[2-(6-Methoxy-quinolin-4-yl)-4,5,6,7-tetrahydro-2H-indazol-5-ylamino]-methyl}-4H-pyrido[3,2-b][1,4]oxazin-3-one This compound was prepared according to the methods described for Example 44. MS (ESI): exact mass calculated for $C_{25}H_{24}N_6O_3$, 456.19; m/z found, 457.4 [M+H]+. 1H NMR (500 MHz, CDCl$_3$): 8.77 (d, J=4.7, 1H), 8.06 (d, J=9.2, 1H), 7.69 (d, J=2.8, 1H), 7.63 (s, 1H), 7.41 (dd, J=9.2, 2.8, 1H), 7.31 (d, J=4.7, 1H), 7.21 (d, J=8.0, 1H), 6.96 (d, J=8.1, 1H), 4.63 (s, 2H), 3.93 (s, 2H), 3.89 (s, 3H), 3.05-3.00 (m, 3H), 2.85-2.80 (m, 1H), 2.56 (dd, J=15.0, 8.3, 1H), 2.58-2.54 (m, 1H), 1.89-1.83 (m, 1H), 1.66 (br s, 1H).

Example 55

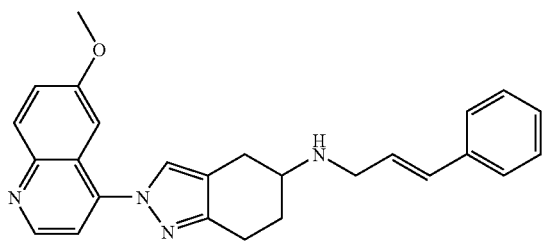

[2-(6-Methoxy-quinolin-4-yl)-4,5,6,7-tetrahydro-2H-indazol-5-yl]-(3-phenyl-allyl)-amine To a solution of trans-cinnamaldehyde (0.0275 mL, 0.218 mmol) in DMF (0.74 mL) was added 2-(6-methoxy-quinolin-4-yl)-4,5,6,7-tetrahydro-2H-indazol-5-ylamine (45.7 mg, 0.155 mmol). The reaction mixture was stirred overnight at RT. NaBH$_4$ (11.7 mg, 0.31 mmol) was then added and the suspension was stirred for 30 min at RT. The reaction mixture was diluted with CH$_3$OH and purified directly by acidic reverse phase HPLC to provide 23.8 mg of the TFA salt of the title compound. To this salt in CH$_3$OH was added anionic exchange resin (550 Å, OH). The mixture was stirred at RT for 20 min. The mixture was filtered and the filtrate was concentrated to afford 13.6 mg (21%) of the title compound. MS (ESI): exact mass calculated for $C_{26}H_{26}N_4O$, 410.21; m/z found, 411.8 [M+H]+. 1H NMR (400 MHz, CDCl$_3$): 8.78 (d, J=4.7, 1H), 8.06 (d, J=9.2, 1H), 7.70 (d, J=2.8, 1H), 7.65 (s, 1H), 7.43-7.20 (m, 8H), 6.58 (d, J=15.9, 1H), 6.36 (dt, J=15.9, 6.4, 1H), 3.90 (s, 3H), 3.57 (d, J=6.1, 2H), 3.19-3.12 (m, 1H), 3.07-2.99 (m, 2H), 2.89-2.81 (m, 1H), 2.53 (dd, J=15.3, 8.5, 1H), 2.20-2.17 (m, 1H), 1.90-1.81 (m, 1H).

Example 56

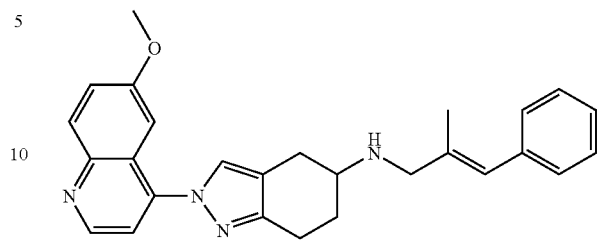

[2-(6-Methoxy-quinolin-4-yl)-4,5,6,7-tetrahydro-2H-indazol-5-yl]-(2-methyl-3-phenyl-allyl)-amine This compound was prepared according to the methods described in Example 35. MS (ESI): exact mass calculated for $C_{27}H_{28}N_4O$, 424.23; m/z found, 425.4 [M+H]+. 1H NMR (400 MHz, CDCl$_3$): 8.78 (d, J=4.7, 1H), 8.06 (d, J=9.2, 1H), 7.71 (d, J=2.7, 1H), 7.65 (s, 1H), 7.42 (dd, J=9.2, 2.8, 1H), 7.36-7.26 (m, 5H), 7.23-7.20 (m, 1H), 6.51 (s, 1H), 3.90 (s, 3H), 3.48 (s, 2H), 3.13-2.99 (m, 3H), 2.89-2.85 (m, 1H), 2.54 (dd, J=15.0, 8.3, 1H), 2.20-2.17 (m, 1H), 1.95 (s, 3H), 1.88-1.84 (m, 1H), 1.28-1.25 (m, 1H).

Example 57

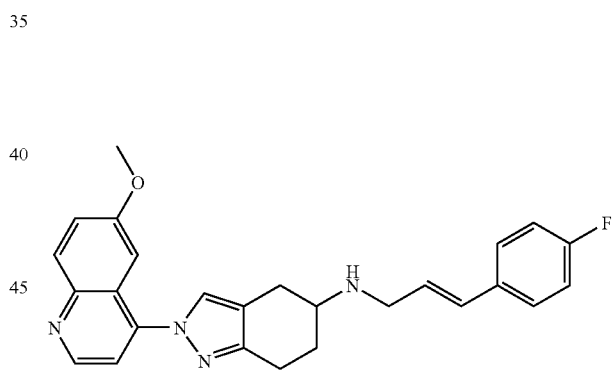

[3-(4-Fluoro-phenyl)-allyl]-[2-(6-methoxy-quinolin-4-yl)-4,5,6,7-tetrahydro-2H-indazol-5-yl]-amine This compound was prepared according methods described for Example 35. MS (ESI): exact mass calculated for $C_{26}H_{25}FN_4O$, 428.20; m/z found, 429.4 [M+H]+. 1H NMR (500 MHz, CDCl$_3$): 8.76 (d, J=4.7, 1H), 8.05 (d, J=9.2, 1H), 7.68 (d, J=2.8, 1H), 7.64 (s, 1H), 7.40 (dd, J=9.2, 2.8, 1H), 7.35-7.30 (m, 3H), 7.04-6.96 (m, 2H), 6.53 (d, J=15.9, 1H), 6.28-6.23 (m, 1H), 3.89 (s, 3H), 3.54 (d, J=6.4, 2H), 3.46 (s, 1H), 3.14-3.11 (m, 1H), 3.05-2.97 (m, 2H), 2.87-2.82 (m, 1H), 2.52 (dd, J=15.3, 8.5, 1H), 2.18-2.15 (m, 1H), 1.86-1.81 (m, 1H).

Example 58

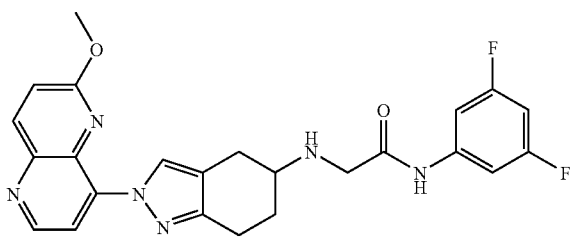

N-(3,5-Difluoro-phenyl)-2-[2-(6-methoxy-[1,5]naphthyridin-4-yl)-4,5,6,7-tetrahydro-2H-indazol-5-ylamino]-acetamide

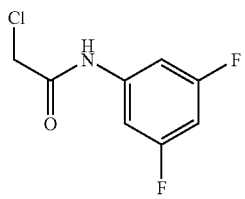

A. 2-Chloro-N-(3,5-difluoro-phenyl)-acetamide. To a solution of 3,5-difluoroaniline (390 mg, 3.0 mmol) in $CH_2Cl_2$ (30 mL) at 0° C., was added diisopropylethylamine (0.63 mL, 3.6 mmol) followed by chloroacetyl chloride (0.263 mL, 3.3 mmol), and the mixture was allowed to warm up to RT over 3 h. The mixture was quenched with satd. aq. $NaHCO_3$ (10 mL), and the aqueous layer was extracted with $CH_2Cl_2$ (3×25 mL), washed with brine (25 mL), dried ($MgSO_4$), and concentrated. The resulting residue was purified on $SiO_2$ (20-60% EtOAc/hexanes) to provide 600 mg (97%) of the title compound as a pale yellow solid. $^1$H NMR (500 MHz, $CDCl_3$): 8.27 (br s, 1H), 7.20-7.15 (m, 2H), 6.64-6.59 (m, 1H), 4.18 (s, 2H).

B. To a solution of 2-(6-methoxy-[1,5]naphthyridin-4-yl)-4,5,6,7-tetrahydro-2H-indazol-5-ylamine (30 mg, 0.1 mmol) in DMF (1 mL) were added $K_2CO_3$ (40 mg, 0.3 mmol) and 2-chloro-N-(3,5-difluoro-phenyl)-acetamide (20 mg, 0.1 mmol), and the mixture was stirred for 15 h. A catalytic amount of NaI was added and the mixture heated at 50° C. for 15 h. The mixture was diluted with EtOAc (25 mL), washed with brine (4×10 mL), dried ($MgSO_4$) and concentrated. The resulting residue was purified on $SiO_2$ (0-5% $CH_3OH/CH_2Cl_2$) to provide 30 mg (64%) of the title compound as a pale yellow solid. MS (ESI): exact mass calculated for $C_{24}H_{22}F_2N_6O_2$, 464.18; m/z found, 465.3 [M+H]$^+$. $^1$H NMR (500 MHz, $CDCl_3$): 9.30 (br s, 1H), 9.08 (s, 1H), 8.76 (d, J=9.2, 1H), 8.24 (d, J=5.9, 1H), 8.19 (d, J=5.1, 1H), 7.15 (d, J=9.1, 1H), 6.93-6.87 (m, 2H), 6.26 (tt, J=8.9, 2.3, 1H), 3.89 (s, 3H), 3.59 (d, J=17.7, 1H), 3.36 (d, J=17.7, 1H), 3.26-3.23 (m, 1H), 3.08-3.02 (m, 1H), 2.93-2.85 (m, 2H), 2.62 (dd, J=15.7, 5.7, 1H), 2.12-2.08 (m, 1H), 2.00-1.96 (m, 1H).

The compounds in Examples 59-62 were prepared according to the methods described in Example 58.

Example 59

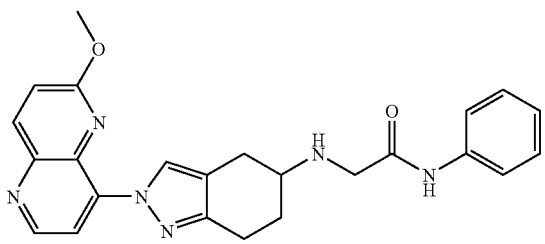

2-[2-(6-Methoxy-[1,5]naphthyridin-4-yl)-4,5,6,7-tetrahydro-2H-indazol-5-ylamino]-N-phenyl-acetamide MS (ESI): exact mass calculated for $C_{24}H_{24}N_6O_2$, 428.20; m/z found, 429.4 [M+H]$^+$. $^1$H NMR (500 MHz, $CDCl_3$): 9.19 (br s, 1H), 9.06 (s, 1H), 8.78 (d, J=5.1, 1H), 8.25 (d, J=9.1, 1H), 8.19 (d, J=5.1, 1H), 7.35 (d, J=5.6, 2H), 7.14 (d, J=9.1, 1H), 7.05 (t, J=5.6, 2H), 6.86 (t, J=8.5, 1H), 3.91 (s, 3H), 3.59 (d, J=17.5, 1H), 3.36 (d, J=17.5, 1H), 3.22-3.20 (m, 1H), 3.08-3.04 (m, 1H), 2.93-2.86 (m, 2H), 2.62 (dd, J=15.6, 6.3, 1H), 2.14-2.08 (m, 1H), 1.99-1.93 (m, 1H).

Example 60

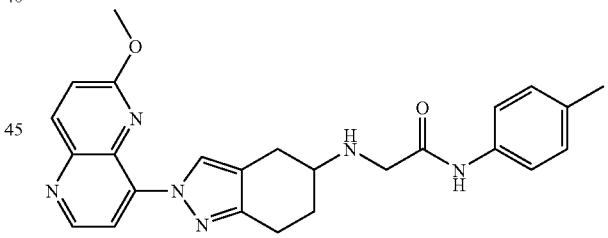

2-[2-(6-Methoxy-[1,5]naphthyridin-4-yl)-4,5,6,7-tetrahydro-2H-indazol-5-ylamino]-N-p-tolyl-acetamide MS (ESI): exact mass calculated for $C_{25}H_{26}N_6O_2$, 442.21; m/z found, 443.4 [M+H]$^+$. $^1$H NMR (500 MHz, $CDCl_3$): 9.10 (s, 1H), 9.06 (s, 1H), 8.78 (d, J=5.1, 1H), 8.25 (d, J=9.1, 1H), 8.19 (d, J=5.1, 1H), 7.22 (d, J=8.4, 2H), 7.14 (d, J=9.1, 1H), 6.81 (d, J=8.3, 2H), 3.89 (s, 3H), 3.58 (d, J=17.4, 1H), 3.36 (d, J=17.4, 1H), 3.24-3.20 (m, 1H), 3.09-3.03 (m, 1H), 2.92-2.86 (m, 2H), 2.62 (dd, J=15.7, 6.2, 1H), 2.15-2.10 (m, 4H), 2.00-1.93 (m, 1H).

Example 61

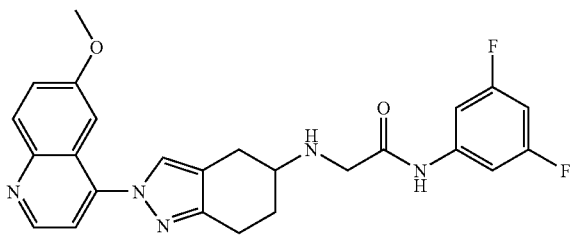

N-(3,5-Difluoro-phenyl)-2-[2-(6-methoxy-quinolin-4-yl)-4,5,6,7-tetrahydro-2H-indazol-5-ylamino]-acetamide The crude material was purified by basic reverse phase HPLC to provide 30 mg (31%) of the title compound as a white solid. MS (ESI): exact mass calculated for $C_{25}H_{23}F_2N_5O_2$, 463.18; m/z found, 464.8 [M+H]$^+$. $^1$H NMR (400 MHz, CDCl$_3$): 9.44 (br s, 1H), 8.78 (d, J=4.8, 1H), 8.08 (d, J=9.2, 1H), 7.66 (d, J=2.7, 1H), 7.64 (s, 1H), 7.43 (dd, J=9.2, 2.8, 1H), 7.27 (s, 1H), 7.10-7.07 (m, 2H), 6.51 (tt, J=8.9, 2.3, 1H), 3.89 (s, 3H), 3.59 (d, J=17.6, 1H), 3.46 (d, J=17.6, 1H), 3.21-2.92 (m, 4H), 2.61 (dd, J=15.6, 7.0, 1H), 2.17-2.15 (m, 1H), 1.95-1.86 (m, 1H).

Example 62

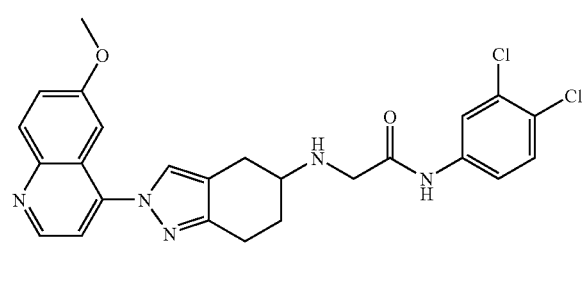

N-(3,4-Dichloro-phenyl)-2-[2-(6-methoxy-quinolin-4-yl)-4,5,6,7-tetrahydro-2H-indazol-5-ylamino]-acetamide MS (ESI): exact mass calculated for $C_{25}H_{23}Cl_2N_5O_2$, 495.12; m/z found, 496.3 [M+H]$^+$. $^1$H NMR (500 MHz, CDCl$_3$): 8.77 (d, J=4.7, 1H), 8.08 (d, J=9.2, 1H), 7.74 (t, J=2.6, 1H), 7.67 (d, J=2.8, 1H), 7.62 (s, 1H), 7.43 (dd, J=9.2, 2.8, 1H), 7.24 (s, 2H), 7.20 (d, J=4.7, 1H), 3.89 (s, 3H), 3.59 (d, J=17.5, 1H), 3.45 (d, J=17.5, 1H), 3.22-3.21 (m, 1H), 3.08-3.04 (m, 1H), 2.97-2.90 (m, 2H), 2.62 (dd, J=15.6, 6.84, 1H), 2.17-2.15 (m, 1H), 1.97-1.95 (m, 1H).

Example 63

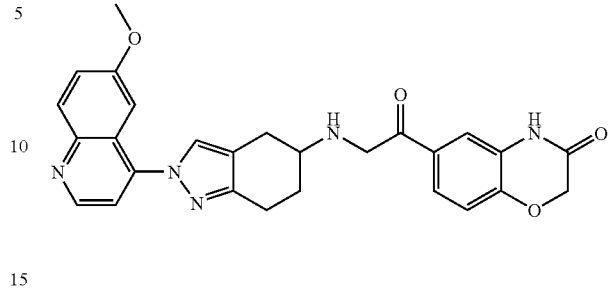

6-{2-[2-(6-Methoxy-quinolin-4-yl)-4,5,6,7-tetrahydro-2H-indazol-5-ylamino]-acetyl}-4H-benzo[1,4]oxazin-3-one To a solution of 2-(6-methoxy-quinolin-4-yl)-4,5,6,7-tetrahydro-2H-indazol-5-ylamine (50 mg, 0.2 mmol) in DMF (0.5 mL) was added 6-(2-chloro-acetyl)-4H-benzo[1,4]oxazin-3-one (0.05 g, 0.22 mmol) and Et$_3$N (0.033 mL, 0.22 mmol). The reaction was heated to 50° C. and stirred for 12 h. The crude was purified directly by basic reverse phase HPLC to afford 0.8 mg (10%) of the title compound. HPLC: R$_t$=5.50 min. MS (ESI): exact mass calculated for $C_{27}H_{25}N_5O_4$, 483.19; m/z found, 484.5 [M+H]$^+$. $^1$H NMR (500 MHz, CDCl$_3$): 8.78 (d, J=4.7, 1H), 8.06 (d, J=9.1, 1H), 7.69-7.61 (m, 3H), 7.42 (d, J=2.6, 1H), 7.40 (dd, J=9.1, 2.6, 1H), 7.32 (d, J=4.7, 1H), 7.04 (d, J=8.9, 1H), 4.70 (s, 2H), 4.21 (s, 1H), 3.89 (s, 3H), 3.11-2.80 (m, 5H), 2.62-2.58 (m, 1H), 2.26-2.17 (m, 1H), 1.93-1.86 (m, 1H).

Example 64

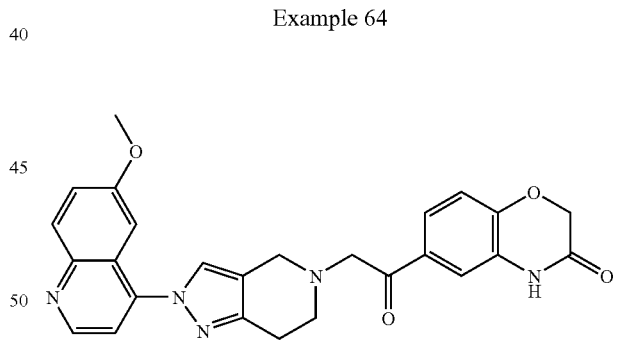

6-{2-[2-(6-Methoxy-quinolin-4-yl)-2,4,6,7-tetrahydro-pyrazolo[4,3-c]pyridin-5-yl]-acetyl}-4H-benzo[1,4]oxazin-3-one This compound was prepared according to the methods described for Example 63. HPLC: R$_t$=5.49 min. MS (ESI): exact mass calculated for $C_{26}H_{23}N_5O_4$, 469.18; m/z found, 470.5 [M+H]$^+$. $^1$H NMR (500 MHz, CDCl$_3$): 8.93-8.89 (m, 1H), 8.21-8.19 (m, 1H), 7.95 (s, 1H), 7.59-7.32 (m, 5H), 7.03-7.01 (m, 1H), 4.90 (s, 1H), 4.66-4.63 (m, 4H), 3.94 (s, 2H), 3.93-3.79 (m, 2H), 3.72-3.68 (m, 2H), 3.37-3.34 (m, 2H).

Example 65

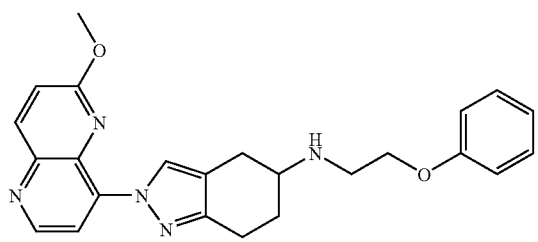

[2-(6-Methoxy-[1,5]naphthyridin-4-yl)-4,5,6,7-tetrahydro-2H-indazol-5-yl]-(2-phenoxy-ethyl)-amine A. [2-(6-Methoxy-[1,5]naphthyridin-4-yl)-4,5,6,7-tetrahydro-2H-indazol-5-yl]-(2-phenoxy-ethyl)-carbamic acid tert-butyl ester. To a solution of [2-(6-methoxy-[1,5]naphthyridin-4-yl)-4,5,6,7-tetrahydro-2H-indazol-5-yl]carbamic acid tert-butyl ester (104 mg, 0.260 mmol) in DMF (2.6 mL) was added NaH (60% in mineral oil, 27 mg, 0.66 mmol) at 0° C. The reaction mixture was warmed to RT and stirred for 30 min. Upon cooling the reaction mixture to 0° C., β-bromophenetole (78 mg, 0.39 mmol) was added. The mixture was warmed to RT, and treated with additional NaH (31 mg, 1.3 mmol) and β-bromophenetole (261 mg, 1.30 mmol). After 30 h, H$_2$O (30 mL) and EtOAc (40 mL) were added to the reaction mixture. The organic layer was separated, washed with brine (20 mL), dried (MgSO$_4$), filtered, and concentrated. The crude was purified on SiO$_2$ (0-100% EtOAc/hexanes) to give 65 mg (48%) of the title compound as a white solid. MS (ESI): exact mass calculated for C$_{29}$H$_{33}$N$_5$O$_4$, 515.25; m/z found, 516.4 [M+H]$^+$. $^1$H NMR (500 MHz, CDCl$_3$): 9.09 (br s, 1H), 8.77 (d, J=5.0, 1H), 8.26 (d, J=9.1, 1H), 8.15 (d, J=5.0, 1H), 7.30-7.27 (m, 2H), 7.18 (d, J=9.1, 1H), 6.97-6.92 (m, 1H), 6.90 (d, J=7.8, 2H), 4.16-4.04 (m, 6H), 3.65-3.59 (m, 2H), 3.09-3.05 (m, 1H), 2.92 (br s, 3H), 2.11 (br s, 2H), 1.49 (s, 9H).

B. [2-(6-Methoxy-[1,5]naphthyridin-4-yl)-4,5,6,7-tetrahydro-2H-indazol-5-yl]-(2-phenoxy-ethyl)-amine. To a solution of [2-(6-methoxy-[1,5]naphthyridin-4-yl)-4,5,6,7-tetrahydro-2H-indazol-5-yl]-(2-phenoxy-ethyl)-carbamic acid tert-butyl ester (60 mg, 0.1 mmol) in CH$_2$Cl$_2$ (4 mL) was added TFA (1 mL). After stirring at RT for 1 h, the reaction mixture was concentrated. To the residue was added CH$_3$OH (5 mL) and anionic exchange resin (550 Å OH, 50 mg). The mixture was stirred at RT for 2 h. The mixture was filtered and the filtrate was concentrated to afford 46 mg (96%) of the title compound as a tan solid. MS (ESI): exact mass calculated for C$_{24}$H$_{25}$N$_5$O$_2$, 415.20; m/z found, 416.4 [M+H]$^+$. $^1$H NMR (500 MHz, CDCl$_3$): 9.11 (s, 1H), 8.76 (d, J=5.1, 1H), 8.26 (d, J=9.1, 1H), 8.15 (d, J=5.1, 1H), 7.30-7.26 (m, 2H), 7.18 (d, J=9.1, 1H), 6.96-6.91 (m, 3H), 4.16-4.10 (m, 5H), 3.74-3.69 (m, 1H), 3.16-3.06 (m, 3H), 3.05-2.98 (m, 2H), 2.86-2.79 (m, 1H), 2.51 (d, J=8.5, 1H), 2.17-2.15 (m, 1H), 1.87-1.79 (m, 1H).

Example 66

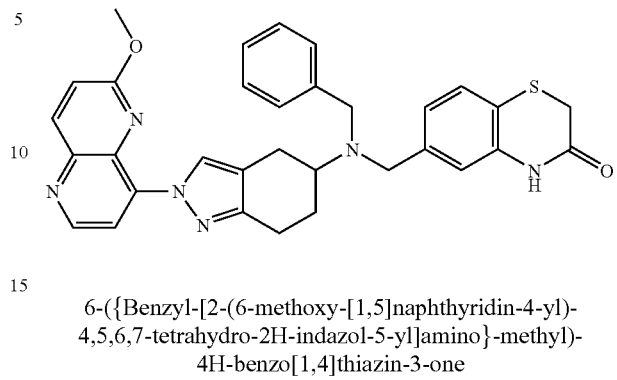

6-({Benzyl-[2-(6-methoxy-[1,5]naphthyridin-4-yl)-4,5,6,7-tetrahydro-2H-indazol-5-yl]amino}-methyl)-4H-benzo[1,4]thiazin-3-one To a mixture of 6-{[2-(6-methoxy-[1,5]naphthyridin-4-yl)-4,5,6,7-tetrahydro-2H-indazol-5-ylamino]-methyl}-4H-benzo[1,4]thiazin-3-one (30 mg, 0.06 mmol) and 4 Å molecular sieves (30 mg) was added dichloroethane (0.4 mL) and benzaldehyde (13 µL, 0.13 mmol). The solution was stirred for 1 h, after which NaB(OAc)$_3$H (27 mg, 0.13 mmol) was added. After stirring overnight at RT, the reaction mixture was heated at 60° C. for 7 h. DMF (0.5 mL), NaBH$_4$ (30 mg, 0.8 mmol) and CH$_2$Cl$_2$ (0.2 mL) were then added, and the reaction mixture was heated at 60° C. overnight. The mixture was diluted with satd. aq. NaHCO$_3$ (10 mL) and extracted with EtOAc (3×10 mL). The combined organic layers were dried (Na$_2$SO$_4$), filtered, and concentrated. The crude was purified directly by basic reverse phase HPLC to afford 2 mg (5%) of the title compound. MS (ESI): exact mass calculated for C$_{32}$H$_{30}$N$_6$O$_2$S, 562.22; m/z found, 563.5 [M+H]$^+$.

Example 67

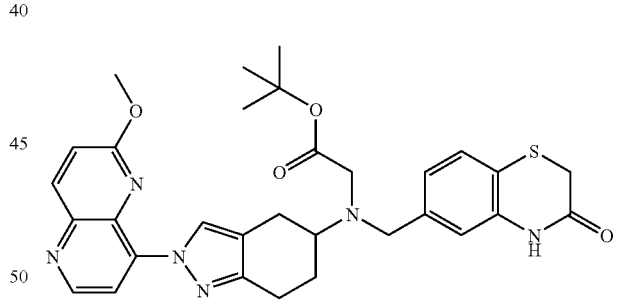

[[2-(6-Methoxy-[1,5]naphthyridin-4-yl)-4,5,6,7-tetrahydro-2H-indazol-5-yl]-(3-oxo-3,4-dihydro-2H-benzo[1,4]thiazin-6-ylmethyl)-amino]-acetic acid tert-butyl ester To a solution of 6-{[2-(6-methoxy-[1,5]naphthyridin-4-yl)-4,5,6,7-tetrahydro-2H-indazol-5-ylamino]-methyl}-4H-benzo[1,4]thiazin-3-one (50 mg, 0.1 mmol) in DMF (600 µL) was added Et$_3$N (19 µL, 0.13 mmol) and tert-butyl bromoacetate (19 µL, 0.13 mmol). The reaction mixture was heated at 50° C. overnight. The crude was purified directly by basic reverse phase HPLC to afford 15 mg (24%) of the title compound. MS (ESI): exact mass calculated for C$_{31}$H$_{34}$N$_6$O$_4$S, 586.24; m/z found, 587.23 [M+H]$^+$.

Example 68

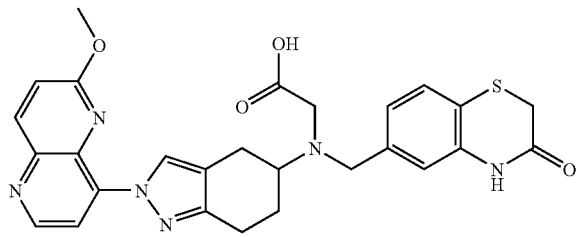

[[2-(6-Methoxy-[1,5]naphthyridin-4-yl)-4,5,6,7-tetrahydro-2H-indazol-5-yl]-(3-oxo-3,4-dihydro-2H-benzo[1,4]thiazin-6-ylmethyl)-amino]-acetic acid A solution of [[2-(6-methoxy-[1,5]naphthyridin-4-yl)-4,5,6,7-tetrahydro-2H-indazol-5-yl]-(3-oxo-3,4-dihydro-2H-benzo[1,4]thiazin-6-ylmethyl)-amino]-acetic acid tert-butyl ester (5 mg, 0.009 mmol) in 4 M HCl in $Et_2O$ (1 mL) was stirred at RT for 3 h. The reaction mixture was concentrated to provide 4.5 mg (100%) of the title compound. MS (ESI): exact mass calculated for $C_{27}H_{26}N_6O_4S$, 530.17; m/z found, 531.08 $[M+H]^+$.

Examples 69-97 were prepared as described in the preceding examples.

Example 69

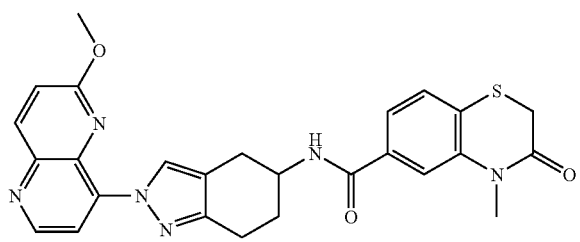

4-Methyl-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide MS (ESI): exact mass calculated for $C_{26}H_{24}N_6O_3S$, 500.16; m/z found, 501.3 $[M+H]^+$.

Example 70

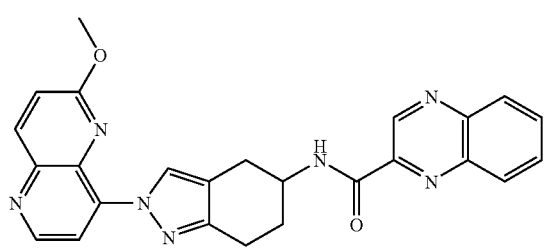

Quinoxaline-2-carboxylic acid [2-(6-methoxy-[1,5]naphthyridin-4-yl)-4,5,6,7-tetrahydro-2H-indazol-5-yl]-amide MS (ESI): exact mass calculated for $C_{25}H_{21}N_7O_2$, 451.18; m/z found, 452.5 $[M+H]^+$.

Example 71

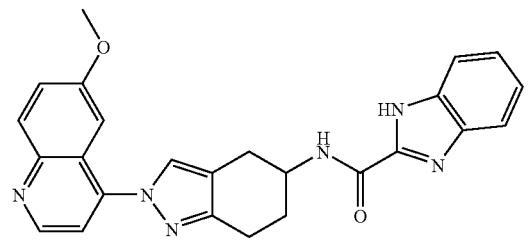

1H-Benzoimidazole-2-carboxylic acid [2-(6-methoxy-quinolin-4-yl)-4,5,6,7-tetrahydro-2H-indazol-5-yl]-amide MS (ESI): exact mass calculated for $C_{25}H_{22}N_6O_2$, 438.18; m/z found, 439.4 $[M+H]^+$.

Example 72

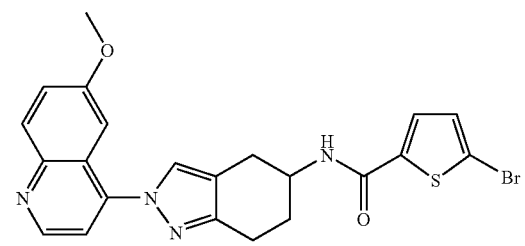

5-Bromo-thiophene-2-carboxylic acid [2-(6-methoxy-quinolin-4-yl)-4,5,6,7-tetrahydro-2H-indazol-5-yl]-amide MS (ESI): exact mass calculated for $C_{22}H_{19}BrN_4O_2S$, 482.04; m/z found, 483.2 $[M+H]^+$.

Example 73

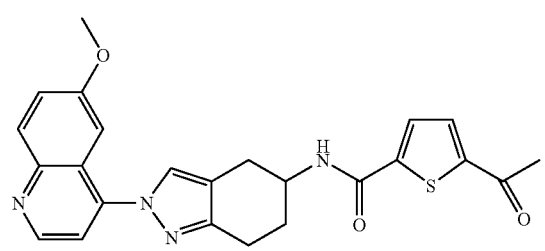

5-Acetyl-thiophene-2-carboxylic acid [2-(6-methoxy-quinolin-4-yl)-4,5,6,7-tetrahydro-2H-indazol-5-yl]-amide MS (ESI): exact mass calculated for $C_{24}H_{22}N_4O_3S$, 446.14; m/z found, 447.3 $[M+H]^+$.

Example 74

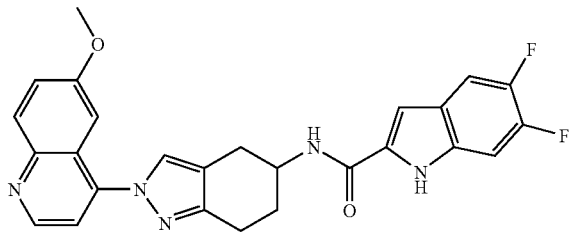

5,6-Difluoro-1H-indole-2-carboxylic acid [2-(6-methoxy-quinolin-4-yl)-4,5,6,7-tetrahydro-2H-indazol-5-yl]-amide MS (ESI): exact mass calculated for $C_{26}H_{21}F_2N_5O_2$, 473.17; m/z found, 474.3 $[M+H]^+$.

Example 75

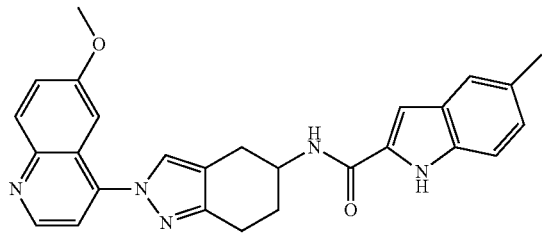

5-Methyl-1H-indole-2-carboxylic acid [2-(6-methoxy-quinolin-4-yl)-4,5,6,7-tetrahydro-2H-indazol-5-yl]-amide MS (ESI): exact mass calculated for $C_{27}H_{25}N_5O_2$, 451.20; m/z found, 452.4 $[M+H]^+$.

Example 76

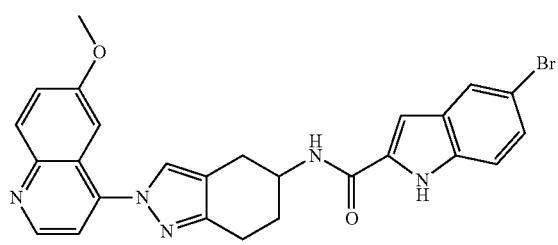

5-Bromo-1H-indole-2-carboxylic acid [2-(6-methoxy-quinolin-4-yl)-4,5,6,7-tetrahydro-2H-indazol-5-yl]-amide MS (ESI): exact mass calculated for $C_{26}H_{22}BrN_5O_2$, 515.10; m/z found, 518.2 $[M+H]^+$.

Example 77

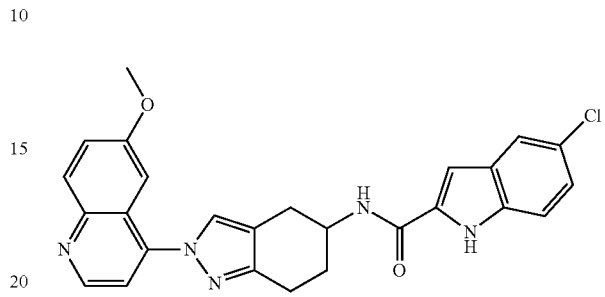

5-Chloro-1H-indole-2-carboxylic acid [2-(6-methoxy-quinolin-4-yl)-4,5,6,7-tetrahydro-2H-indazol-5-yl]-amide MS (ESI): exact mass calculated for $C_{26}H_{22}ClN_5O_2$, 471.15; m/z found, 472.3 $[M+H]^+$.

Example 78

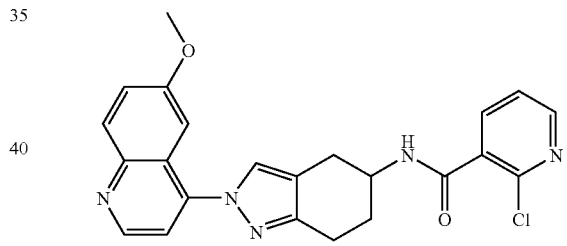

2-Chloro-N-[2-(6-methoxy-quinolin-4-yl)-4,5,6,7-tetrahydro-2H-indazol-5-yl]-nicotinamide MS (ESI): exact mass calculated for $C_{23}H_{20}ClN_5O_2$, 433.13; m/z found, 434.3 $[M+H]^+$.

Example 79

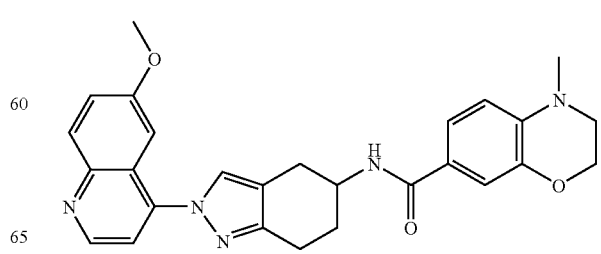

4-Methyl-3,4-dihydro-2H-benzo[1,4]oxazine-7-carboxylic acid [2-(6-methoxy-quinolin-4-yl)-4,5,6,7-tetrahydro-2H-indazol-5-yl]-amide MS (ESI): exact mass calculated for $C_{27}H_{27}N_5O_3$, 469.21; m/z found, 470.4 $[M+H]^+$.

Example 80

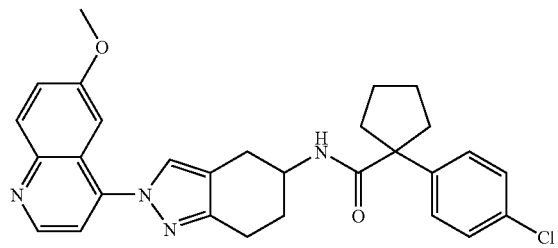

1-(4-Chloro-phenyl)-cyclopentanecarboxylic acid [2-(6-methoxy-quinolin-4-yl)-4,5,6,7-tetrahydro-2H-indazol-5-yl]-amide MS (ESI): exact mass calculated for $C_{29}H_{29}ClN_4O_2$, 500.20; m/z found, 501.4 $[M+H]^+$.

Example 81

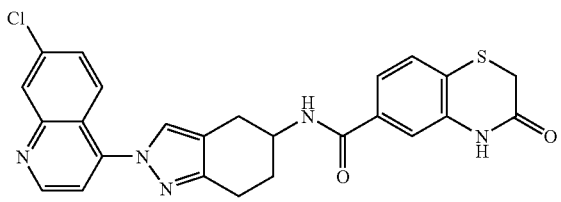

3-Oxo-3,4-dihydro-2H-benzo[1,4]thiazine-6-carboxylic acid [2-(7-chloro-quinolin-4-yl)-4,5,6,7-tetrahydro-2H-indazol-5-yl]-amide MS (ESI): exact mass calculated for $C_{25}H_{20}ClN_5O_2S$, 489.10; m/z found, 490.30 $[M+H]^+$.

Example 82

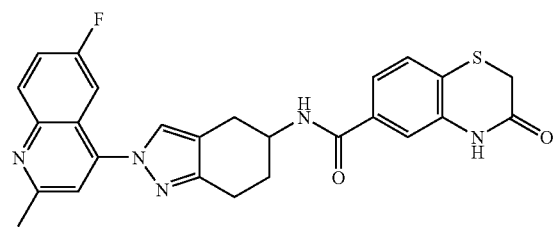

3-Oxo-3,4-dihydro-2H-benzo[1,4]thiazine-6-carboxylic acid [2-(6-fluoro-2-methyl-quinolin-4-yl)-4,5,6,7-tetrahydro-2H-indazol-5-yl]-amide MS (ESI): exact mass calculated for $C_{26}H_{22}FN_5O_2S$, 487.15; m/z found, 488.3 $[M+H]^+$.

Example 83

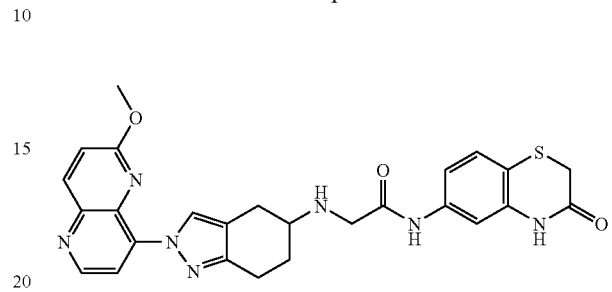

2-[2-(6-Methoxy-[1,5]naphthyridin-4-yl)-4,5,6,7-tetrahydro-2H-indazol-5-ylamino]-N-(3-oxo-3,4-dihydro-2H-benzo[1,4]thiazin-6-yl)-acetamide MS (ESI): exact mass calculated for $C_{26}H_{25}N_7O_3S$, 515.17; m/z found, 516.3 $[M+H]^+$.

Example 84

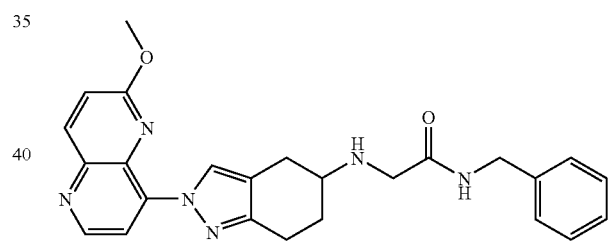

N-Benzyl-2-[2-(6-methoxy-[1,5]naphthyridin-4-yl)-4,5,6,7-tetrahydro-2H-indazol-5-ylamino]-acetamide MS (ESI): exact mass calculated for $C_{25}H_{26}N_6O_2$, 442.21; m/z found, 443.4 $[M+H]^+$.

Example 85

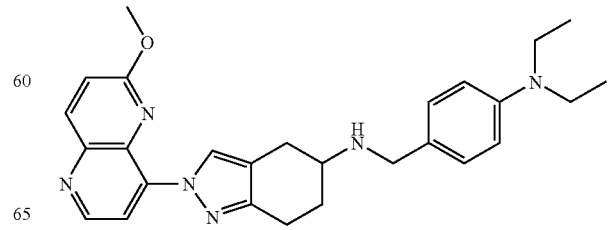

(4-Diethylamino-benzyl)-[2-(6-methoxy-[1,5]naph-thyridin-4-yl)-4,5,6,7-tetrahydro-2H-indazol-5-yl]-amine MS (ESI): exact mass calculated for $C_{27}H_{32}N_6O$, 456.26; m/z found, 455.4 $[M-2+H]^+$.

Example 86

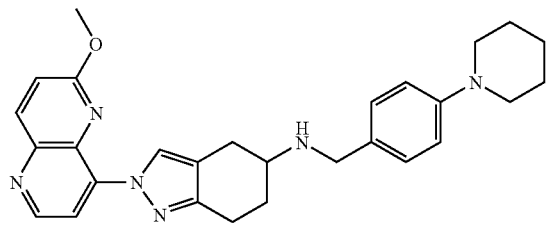

[2-(6-Methoxy-[1,5]naphthyridin-4-yl)-4,5,6,7-tet-rahydro-2H-indazol-5-yl]-(4-piperidin-1-yl-benzyl)-amine MS (ESI): exact mass calculated for $C_{28}H_{32}N_6O$, 468.26; m/z found, 467.4 $[M-2+H]^+$.

Example 87

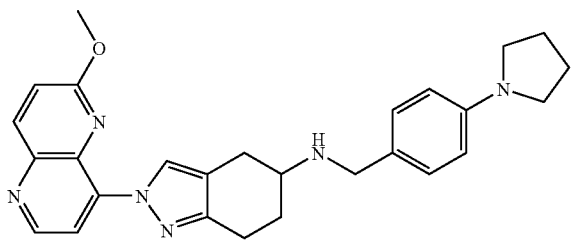

[2-(6-Methoxy-[1,5]naphthyridin-4-yl)-4,5,6,7-tet-rahydro-2H-indazol-5-yl]-(4-pyrrolidin-1-yl-benzyl)-amine MS (ESI): exact mass calculated for $C_{27}H_{30}N_6O$, 454.25; m/z found, 453.4 $[M-2+H]^+$.

Example 88

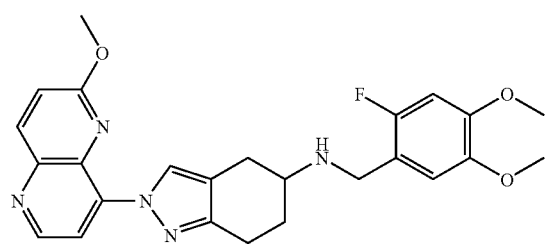

(2-Fluoro-4,5-dimethoxy-benzyl)-[2-(6-methoxy-[1,5]naphthyridin-4-yl)-4,5,6,7-tetrahydro-2H-indazol-5-yl]-amine MS (ESI): exact mass calculated for $C_{25}H_{26}FN_5O_3$, 463.20; m/z found, 464.4 $[M+H]^+$.

Example 89

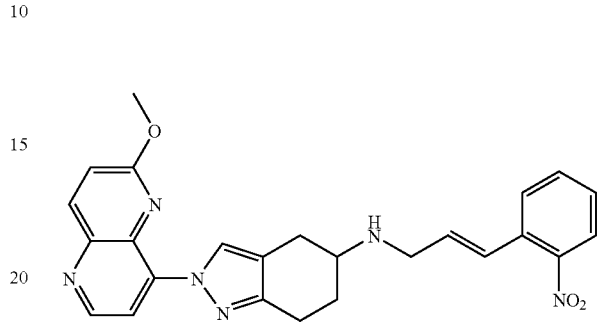

[2-(6-Methoxy-[1,5]naphthyridin-4-yl)-4,5,6,7-tet-rahydro-2H-indazol-5-yl]-[3-(2-nitro-phenyl)-allyl]-amine MS (ESI): exact mass calculated for $C_{25}H_{24}N_6O_3$, 456.19; m/z found, 457.4 $[M+H]^+$.

Example 90

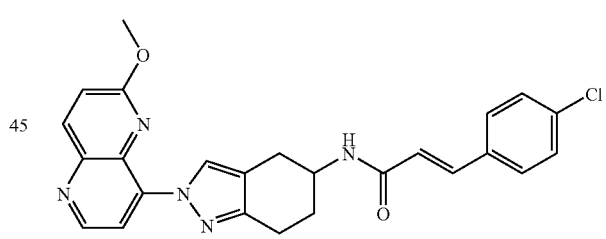

3-(4-Chloro-phenyl)-N-[2-(6-methoxy-[1,5]naphthy-ridin-4-yl)-4,5,6,7-tetrahydro-2H-indazol-5-yl]-acry-lamide MS (ESI): exact mass calculated for $C_{25}H_{22}ClN_5O_2$, 459.15; m/z found, 460.3 $[M+H]^+$. $^1$H NMR (400 MHz, CDCl$_3$/CD$_3$OD): 9.11 (s, 1H), 8.74 (d, J=5.1, 1H), 8.26 (d, J=9.1, 1H), 8.12 (d, J=5.1, 1H), 7.56 (d, J=15.6, 1H), 7.51-7.46 (m, 2H), 7.39-7.34 (m, 2H), 7.26 (d, J=9.1, 1H), 6.55 (d, J=15.5, 1H), 4.40-4.38 (m, 1H), 4.11 (s, 3H), 3.16 (dd, J=15.3, 5.1, 1H), 3.04-2.96 (m, 2H), 2.66 (dd, J=15.4, 8.6, 1H), 2.22-2.20 (m, 1H), 2.02-1.99 (m, 1H).

Example 91

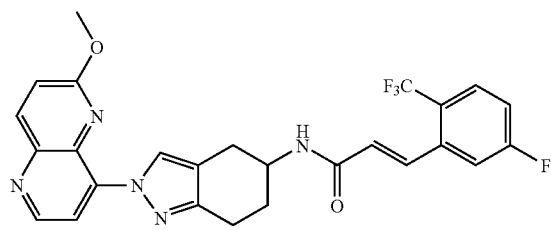

3-(5-Fluoro-2-trifluoromethyl-phenyl)-N-[2-(6-methoxy-[1,5]naphthyridin-4-yl)-4,5,6,7-tetrahydro-2H-indazol-5-yl]-acrylamide MS (ESI): exact mass calculated for $C_{26}H_{21}F_4N_5O_2$, 511.16; m/z found, 512.3 $[M+H]^+$.

Example 92

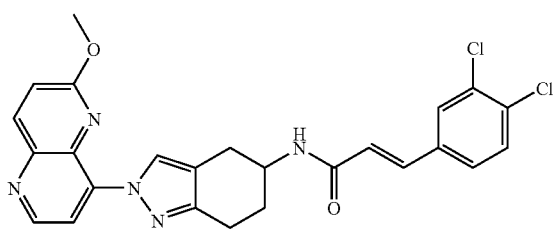

3-(3,4-Dichloro-phenyl)-N-[2-(6-methoxy-[1,5]naphthyridin-4-yl)-4,5,6,7-tetrahydro-2H-indazol-5-yl]-acrylamide MS (ESI): exact mass calculated for $C_{25}H_{21}O_2N_5O_2$, 493.11; m/z found, 494.3 $[M+H]^+$.

Example 93

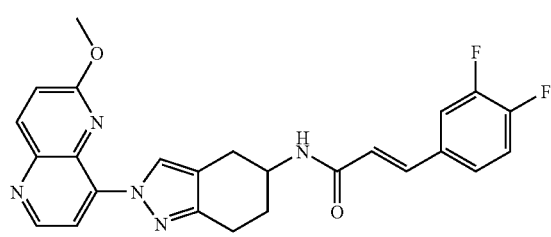

3-(3,4-Difluoro-phenyl)-N-[2-(6-methoxy-[1,5]naphthyridin-4-yl)-4,5,6,7-tetrahydro-2H-indazol-5-yl]-acrylamide MS (ESI): exact mass calculated for $C_{25}H_{21}F_2N_5O_2$, 461.17; m/z found, 462.3 $[M+H]^+$.

Example 94

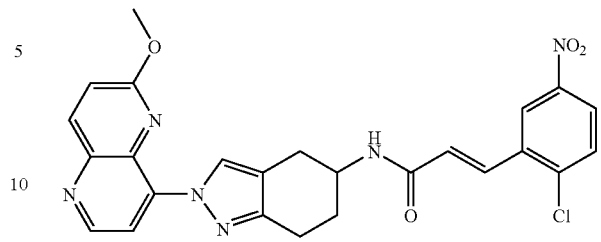

3-(2-Chloro-5-nitro-phenyl)-N-[2-(6-methoxy-[1,5]naphthyridin-4-yl)-4,5,6,7-tetrahydro-2H-indazol-5-yl]-acrylamide MS (ESI): exact mass calculated for $C_{25}H_{21}ClN_6O_4$, 504.13; m/z found, 505.3 $[M+H]^+$.

Example 95

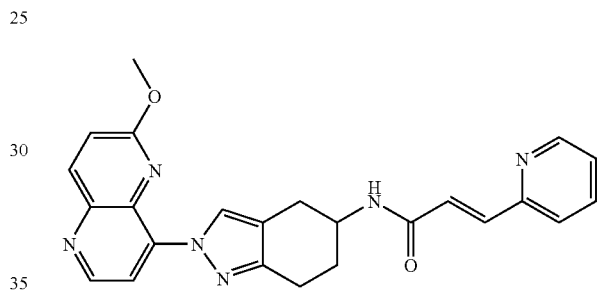

N-[2-(6-Methoxy-[1,5]naphthyridin-4-yl)-4,5,6,7-tetrahydro-2H-indazol-5-yl]-3-pyridin-2-yl-acrylamide MS (ESI): exact mass calculated for $C_{24}H_{22}N_6O_2$, 426.18; m/z found, 427.3 $[M+H]^+$.

Example 96

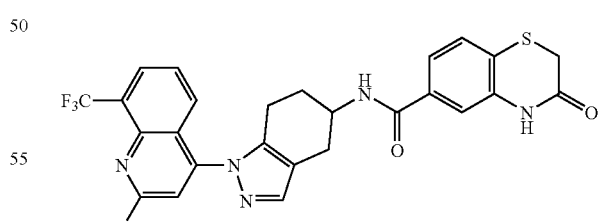

3-Oxo-3,4-dihydro-2H-benzo[1,4]thiazine-6-carboxylic acid [1-(2,8-bis-trifluoromethyl-quinolin-4-yl)-4,5,6,7-tetrahydro-1H-indazol-5-yl]-amide MS (ESI): exact mass calculated for $C_{27}H_{19}F_6N_5O_2S$, 591.12; m/z found, 592.3 $[M+H]^+$.

Example 97

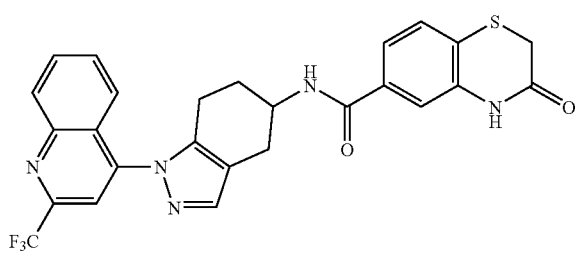

3-Oxo-3,4-dihydro-2H-benzo[1,4]thiazine-6-carboxylic acid [1-(2-trifluoromethyl-quinolin-4-yl)-4,5,6,7-tetrahydro-1H-indazol-5-yl]-amide MS (ESI): exact mass calculated for $C_{26}H_{20}F_3N_5O_2S$, 523.13; m/z found, 524.80 [M+H]$^+$.

Example 98

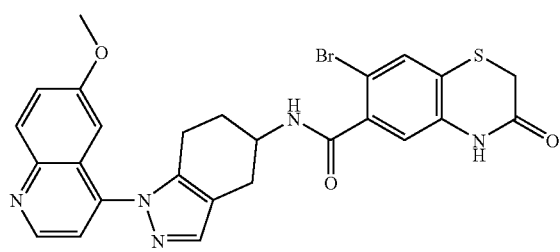

7-Bromo-3-oxo-3,4-dihydro-2H-benzo[1,4]thiazine-6-carboxylic acid [1-(6-methoxy-quinolin-4-yl)-4,5,6,7-tetrahydro-1H-indazol-5-yl]-amide This compound was prepared according to methods described for Example 1. Once the reaction was complete, the reaction mixture was diluted with EtOAc (20 mL) and washed with satd. NaHCO$_3$ (10 mL), H$_2$O (4×20 mL), and brine (10 mL), dried (Na$_2$SO$_4$), and concentrated. The crude residue was diluted with CH$_3$OH and purified by basic reverse phase HPLC. MS (ESI): exact mass calculated for $C_{26}H_{22}BrN_5O_3S$, 563.06; m/z found, 564.0 [M+H]$^+$. $^1$H NMR (600 MHz, CDCl$_3$): 8.85 (d, J=4.6, 1H), 8.71 (s, 1H), 8.09 (d, J=9.2, 1H), 7.67 (s, 1H), 7.53 (s, 1H), 7.43 (dd, J=9.2, 2.7, 1H), 7.37 (s, 1H), 7.29 (d, J=4.6, 1H), 7.06 (d, J=2.7, 1H), 6.47 (d, J=7.9, 1H), 4.67-4.62 (m, 1H), 3.84 (s, 3H), 3.43 (s, 2H), 3.16 (dd, J=15.4, 5.0, 1H), 2.80-2.71 (m, 2H), 2.68-2.62 (m, 1H), 2.19-2.13 (m, 1H), 2.12-2.06 (m, 1H).

Example 99

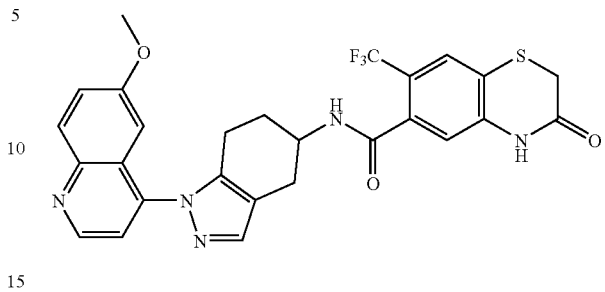

3-Oxo-7-trifluoromethyl-3,4-dihydro-2H-benzo[1,4]thiazine-6-carboxylic acid [1-(6-methoxy-quinolin-4-yl)-4,5,6,7-tetrahydro-1H-indazol-5-yl]-amide This compound was prepared according to methods described for Example 1. MS (ESI): exact mass calculated for $C_{27}H_{22}F_3N_5O_3S$, 553.14; m/z found, 554.1 [M+H]$^+$. $^1$H NMR (600 MHz, CDCl$_3$): 8.85 (d, J=4.6, 1H), 8.38 (s, 1H), 8.09 (d, J=9.2, 1H), 7.65 (s, 2H), 7.43 (dd, J=9.2, 2.8, 1H), 7.09 (s, 1H), 7.04 (d, J=2.8, 1H), 5.93 (d, J=8.1, 1H), 4.59-4.54 (m, 1H), 3.83 (s, 3H), 3.47 (s, 2H), 3.15 (dd, J=15.2, 5.1, 1H), 2.77-2.72 (m, 1H), 2.67-2.60 (m, 2H), 2.18-2.14 (m, 1H), 1.99-1.94 (m, 1H).

The compounds in Examples 100-107 were prepared according to the methods described for Example 35.

Example 100

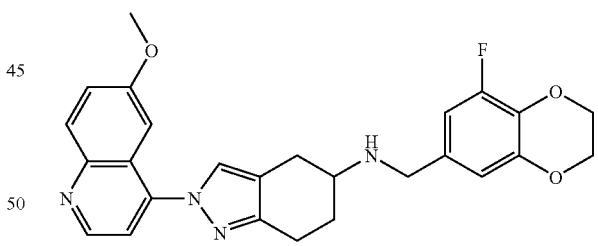

(8-Fluoro-2,3-dihydro-benzo[1,4]dioxin-6-ylmethyl)-[2-(6-methoxy-quinolin-4-yl)-4,5,6,7-tetrahydro-2H-indazol-5-yl]-amine MS (ESI): exact mass calculated for $C_{26}H_{25}FN_4O_3$, 460.51; m/z found, 461.1 [M+H]$^+$. $^1$H NMR (500 MHz, CDCl$_3$): 8.78 (d, J=4.7, 1H), 8.06 (d, J=9.2, 1H), 7.69 (d, J=2.8, 1H), 7.63 (br s, 1H), 7.41 (dd, J=9.2, 2.8, 1H), 7.33 (d, J=4.7, 1H), 6.72 (dd, J=11.1, 2.0, 1H), 6.68 (br s, 1H), 4.31-4.27 (m, 4H), 3.90 (s, 3H), 3.81 (s, 2H), 3.08-2.97 (m, 3H), 2.85-2.79 (m, 1H), 2.51 (dd, J=15.2, 8.4, 1H), 2.16-2.13 (m, 1H), 1.85-1.82 (m, 1H).

Example 101

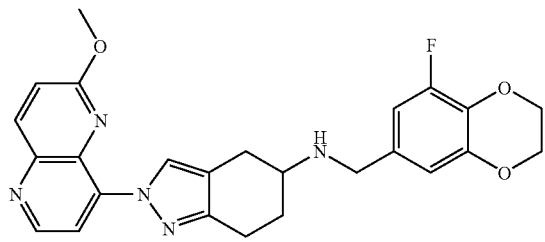

(8-Fluoro-2,3-dihydro-benzo[1,4]dioxin-6-ylmethyl)-[2-(6-methoxy-[1,5]naphthyridin-4-yl)-4,5,6,7-tetrahydro-2H-indazol-5-yl]-amine MS (ESI): exact mass calculated for $C_{25}H_{24}FN_5O_3$, 461.50; m/z found, 462.1 [M+H]$^+$, 484.1 [M+Na]$^+$. $^1$H NMR (500 MHz, CDCl$_3$): 9.09 (br s, 1H), 8.76 (d, J=5.1, 1H), 8.25 (d, J=9.1, 1H), 8.15 (d, J=5.1, 1H), 7.18 (d, J=9.1, 1H), 6.71 (dd, J=11.1, 1.9, 1H), 6.67 (br s, 1H), 4.30-4.26 (m, 4H), 4.11 (s, 3H), 3.79 (s, 2H), 3.07-2.96 (m, 3H), 2.83-2.77 (m, 1H), 2.51 (dd, J=14.9, 8.1, 1H), 2.15-2.11 (m, 1H), 1.86-1.78 (m, 1H).

Example 102

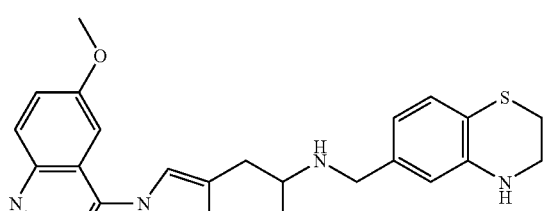

3,4-Dihydro-2H-benzo[1,4]thiazin-6-ylmethyl)-[2-(6-methoxy-quinolin-4-yl)-4,5,6,7-tetrahydro-2H-indazol-5-yl]-amine MS (ESI): exact mass calculated for $C_{26}H_{27}N_5OS$, 457.59; m/z found, 458.1 [M+H]$^+$. $^1$H NMR (500 MHz, CD$_3$OD): 8.74 (d, J=4.8, 1H), 8.01 (d, J=9.2, 1H), 7.93 (s, 1H), 7.69 (d, J=2.7, 1H), 7.50-7.48 (m, 2H), 6.85 (d, J=7.8, 1H), 6.58 (dd, J=7.8, 1.7, 1H), 6.54 (d, J=1.7, 1H), 3.89 (s, 3H), 3.73 (s, 2H), 3.56-3.54 (m, 2H), 3.08-2.94 (m, 5H), 2.78 (ddd, J=16.7, 11.0, 5.7, 1H), 2.50 (dd, J=14.4, 8.5, 1H), 2.23-2.20 (m, 1H), 1.83-1.75 (m, 1H).

Example 103

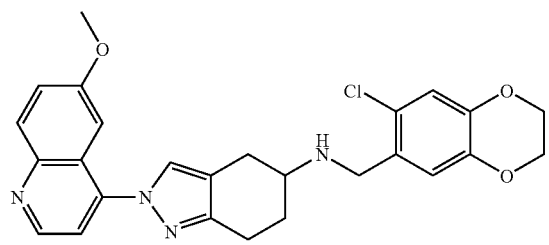

(7-Chloro-2,3-dihydro-benzo[1,4]dioxin-6-ylmethyl)-[2-(6-methoxy-quinolin-4-yl)-4,5,6,7-tetrahydro-2H-indazol-5-yl]-amine MS (ESI): exact mass calculated for $C_{26}H_{25}ClN_4O_3$, 476.97; m/z found, 477.1 [M+H]$^+$. $^1$H NMR (500 MHz, CDCl$_3$): 8.77 (d, J=4.7, 1H), 8.05 (d, J=9.2, 1H), 7.69 (d, J=2.8, 1H), 7.63 (s, 1H), 7.40 (dd, J=9.2, 2.8, 1H), 7.32 (d, J=4.7, 1H), 6.93 (s, 1H), 6.90 (s, 1H), 4.23 (s, 4H), 3.91-3.89 (m, 5H), 3.08-2.98 (m, 3H), 2.85-2.78 (m, 1H), 2.54 (dd, J=15.0, 8.2, 1H), 2.17-2.13 (m, 1H), 1.88-1.83 (m, 1H).

Example 104

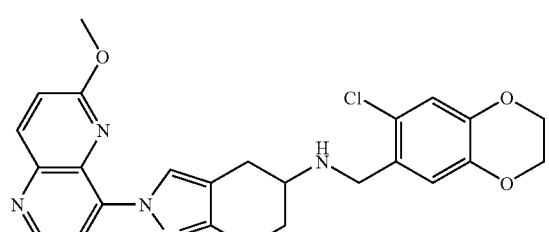

(7-Chloro-2,3-dihydro-benzo[1,4]dioxin-6-ylmethyl)-[2-(6-methoxy-[1,5]naphthyridin-4-yl)-4,5,6,7-tetrahydro-2H-indazol-5-yl]-amine MS (ESI): exact mass calculated for $C_{25}H_{24}ClN_5O_3$, 477.95; m/z found, 478.1 [M+H]$^+$, 500.1 [M+Na]$^+$. $^1$H NMR (500 MHz, CDCl$_3$): 9.09 (s, 1H), 8.76 (d, J=5.1, 1H), 8.26 (d, J=9.1, 1H), 7.18 (d, J=9.1, 1H), 6.92 (s, 1H), 6.92 (s, 1H), 6.89 (s, 1H), 4.23 (s, 4H), 4.11 (s, 3H), 3.89 (s, 2H), 3.06-2.98 (m, 3H), 2.84-2.77 (m, 1H), 2.54 (dd, J=15.3, 8.6, 1H), 2.17-2.12 (m, 1H), 1.85-1.80 (m, 1H).

Example 105

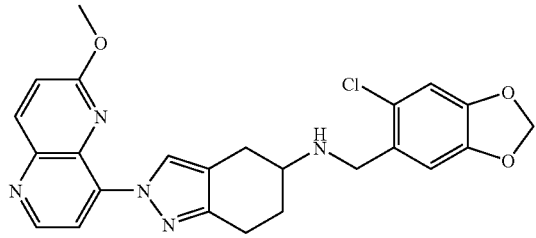

N-((6-chlorobenzo[d][1,3]dioxol-5-yl)methyl)-2-(6-methoxy-1,5-naphthyridin-4-yl)-4,5,6,7-tetrahydro-2H-indazol-5-amine MS (ESI): exact mass calculated for $C_{24}H_{22}ClN_5O_3$, 463.93; m/z found, 464.2 [M+H]$^+$, 500.1 [M+Na]$^+$. $^1$H NMR (500 MHz, CDCl$_3$): 9.10 (s, 1H), 8.76 (d, J=5.1, 1H), 8.26 (d, J=9.1, 1H), 8.15 (d, J=5.1, 1H), 7.18 (d, J=9.1, 1H), 6.92 (s, 1H), 6.84 (s, 1H), 5.96 (s, 2H), 4.11 (s, 2H), 3.90 (s, 3H), 3.07-2.98 (m, 3H), 2.85-2.78 (m, 1H), 2.54 (dd, J=15.3, 8.5, 1H), 2.17-2.14 (m, 1H), 1.88-1.81 (m, 1H).

Example 106

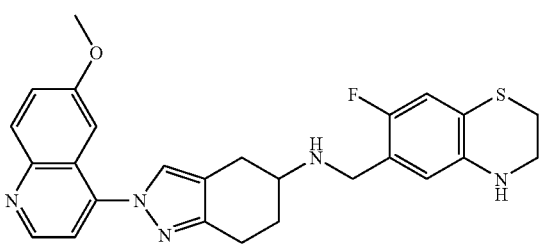

(7-Fluoro-3,4-dihydro-2H-benzo[1,4]thiazin-6-ylmethyl)-[2-(6-methoxy-quinolin-yl)-4,5,6,7-tetrahydro-2H-indazol-5-yl]-amine MS (ESI): exact mass calculated for $C_{26}H_{26}FN_5OS$, 475.58; m/z found, 476.1 [M+H]$^+$. $^1$H NMR (500 MHz, CD$_3$OD): 8.74 (d, J=4.8, 1H), 8.01 (d, J=9.3, 1H), 7.94 (s, 1H), 7.70 (d, J=2.8, 1H), 7.50-7.48 (m, 2H), 6.66 (d, J=10.2, 1H), 6.56 (d, J=6.7, 1H), 3.89 (s, 3H), 3.80 (s, 2H), 3.52-3.50 (m, 2H), 3.09-2.94 (m, 5H), 2.79 (ddd, J=16.6, 10.8, 5.8, 1H), 2.51 (dd, J=14.9, 8.8, 1H), 2.23-2.20 (m, 1H), 1.84-1.76 (m, 1H).

Example 107

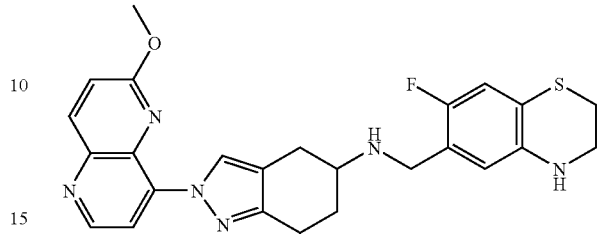

(7-Fluoro-3,4-dihydro-2H-benzo[1,4]thiazin-6-ylmethyl)-[2-(6-methoxy-[1,5]naphthyridin-4-yl)-4,5,6,7-tetrahydro-2H-indazol-5-yl]-amine MS (ESI): exact mass calculated for $C_{25}H_{25}FN_6OS$, 476.57; m/z found, 477.2 [M+H]$^+$. $^1$H NMR (500 MHz, CD$_3$OD): 9.31 (s, 1H), 8.81 (d, J=5.4, 1H), 8.33 (d, J=9.2, 1H), 8.27 (d, J=5.4, 1H), 7.41 (d, J=9.2, 1H), 6.84 (d, J=10.1, 1H), 6.63 (d, J=6.6, 1H), 4.27 (d, J=5.1, 2H), 4.15 (s, 3H), 3.70-3.64 (m, 1H), 3.55-3.53 (m, 2H), 3.42 (dd, J=15.1, 5.0, 1H), 3.10 (ddd, J=17.1, 5.4, 3.5, 1H), 3.05-3.04 (m, 2H), 2.94 (ddd, J=17.2, 11.4, 5.8, 1H), 2.85 (dd, J=15.1, 10.3, 1H), 2.51-2.48 (m, 1H), 2.09-2.01 (m, 1H).

The compounds in Examples 108-120 were prepared according to the methods described for Example 1.

Example 108

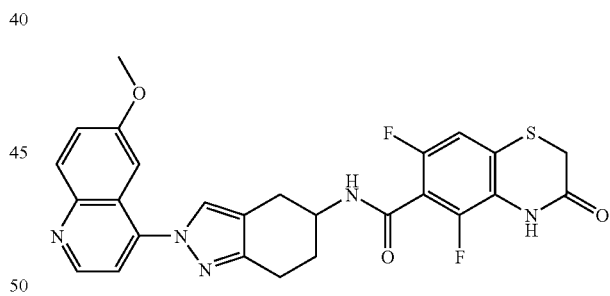

5,7-Difluoro-3-oxo-3,4-dihydro-2H-benzo[1,4]thiazine-6-carboxylic acid [2-(6-methoxy-quinolin-4-yl)-4,5,6,7-tetrahydro-2H-indazol-5-yl]-amide MS (ESI): exact mass calculated for $C_{26}H_{21}F_2N_5O_3S$, 521.1; m/z found, 522 [M+H]$^+$. $^1$H NMR (400 MHz, CDCl$_3$): 8.80 (d, J=4.7, 1H), 8.80 (d, J=9.2, 1H), 7.69 (br s, 2H), 7.63 (d, J=2.7, 1H), 7.44 (dd, J=9.2, 2.8, 1H), 7.34 (d, J=4.7, 1H), 6.96 (dd, J=9.0, 1.8, 1H), 6.05 (d, J=7.9, 1H), 4.67-4.56 (m, 1H), 3.91 (s, 3H), 3.48 (s, 2H), 3.23 (dd, J=15.7, 5.0, 1H), 3.08-2.95 (m, 2H), 2.72 (dd, J=15.8, 7.7, 1H), 2.29-2.20 (m, 1H), 2.20-2.10 (m, 1H). HPLC (reverse phase, Waters Xterra RP18 5µ column, 4.6×100 mm, 1% to 99% acetonitrile in water with 20 mM NH$_4$OH gradient elution, 1.5 mL/min): R$_T$=4.50 min.

Example 109

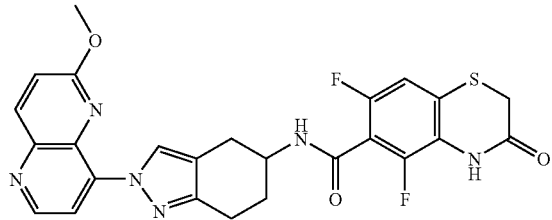

5,7-Difluoro-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide MS (ESI): exact mass calculated for $C_{25}H_{20}F_2N_6O_3S$, 522.1; m/z found, 523 [M+H]+. $^1$H NMR (400 MHz, CDCl$_3$): 9.17 (s, 1H), 8.78 (d, J=5.0, 1H), 8.27 (d, J=9.1, 1H), 8.17 (d, J=5.0, 1H), 7.75-7.68 (m, 1H), 7.20 (d, J=9.1, 1H), 6.94 (dd, J=8.9, 1.7, 1H), 6.07 (d, J=7.4, 1H), 4.66-4.57 (m, 1H), 4.10 (s, 3H), 3.46 (s, 2H), 3.22 (dd, J=15.8, 5.0, 1H), 3.09-2.92 (m, 2H), 2.72 (dd, J=15.8, 7.1, 1H), 2.30-2.08 (m, 2H). HPLC (reverse phase, Waters Xterra RP18 5µ column, 4.6×100 mm, 1% to 99% acetonitrile in water with 20 mM NH$_4$OH gradient elution, 1.5 mL/min): R$_T$=4.64 min.

Example 110

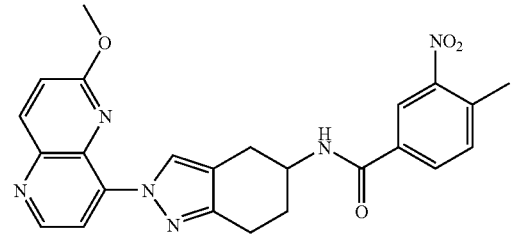

N-[2-(6-Methoxy-[1,5]naphthyridin-4-yl)-4,5,6,7-tetrahydro-2H-indazol-5-yl]-4-methyl-3-nitro-benzamide MS (ESI): exact mass calculated for $C_{24}H_{22}N_6O_4$, 458.17; m/z found, 459.1 [M+H]+. $^1$H NMR (600 MHz, CDCl$_3$): 9.20 (s, 1H), 8.79 (d, J=5.1, 1H), 8.33 (d, J=1.6, 1H), 8.28 (d, J=9.1, 1H), 8.19 (d, J=5.0, 1H), 7.95 (d, J=9.6, 1H), 7.45 (d, J=8.1, 1H), 7.21 (d, J=9.1, 1H), 6.22 (d, J=7.2, 1H), 4.62-4.56 (m, 1H), 4.11 (s, 3H), 3.26 (dd, J=15.3, 4.9, 1H), 3.03 (dd, J=7.8, 7.8, 2H), 2.73 (dd, J=15.3, 7.6, 1H), 2.66 (s, 3H), 2.28-2.23 (m, 1H), 2.16-2.10 (m, 1H).

Example 111

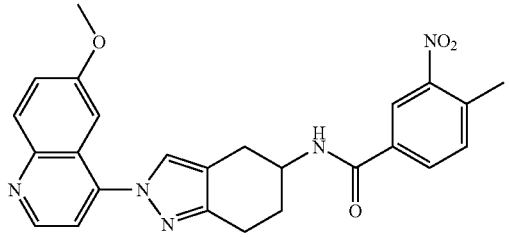

N-[2-(6-Methoxy-quinolin-4-yl)-4,5,6,7-tetrahydro-2H-indazol-5-yl]-4-methyl-3-nitro-benzamide MS (ESI): exact mass calculated for $C_{25}H_{23}N_5O_4$, 457.18; m/z found, 458.1 [M+H]+. $^1$H NMR (600 MHz, CDCl$_3$): 8.80 (d, J=4.7, 1H), 8.35 (d, J=1.6, 1H), 8.08 (d, J=9.2, 1H), 7.98 (d, J=9.6, 1H), 7.70 (s, 1H), 7.65 (d, J=2.7, 1H), 7.46 (d, J=8.0, 1H), 7.44 (dd, J=9.2, 2.8, 1H), 7.36 (d, J=4.7, 1H), 6.29 (d, J=7.8, 1H), 4.61-4.56 (m, 1H), 3.92 (s, 3H), 3.26 (dd, J=15.4, 5.0, 1H), 3.04 (dd, J=6.9, 6.9, 2H), 2.72 (dd, J=15.4, 8.3, 1H), 2.67 (s, 3H), 2.31-2.26 (m, 1H), 2.14-2.08 (m, 1H).

Example 112

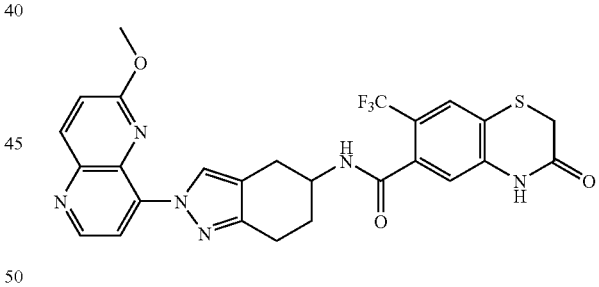

3-Oxo-7-trifluoromethyl-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide MS (ESI): exact mass calculated for $C_{26}H_{21}F_3N_6O_3S$, 554.13; m/z found, 555.1 [M+H]+. $^1$H NMR (600 MHz, DMF-d$_7$): 9.30 (s, 1H), 8.86 (d, J=5.0, 1H), 8.58 (d, J=7.7, 1H), 8.38 (d, J=9.1, 1H), 8.22 (d, J=5.0, 1H), 7.77 (s, 1H), 7.39 (d, J=9.1, 1H), 7.25 (s, 1H), 4.35-4.29 (m, 1H), 4.17 (s, 3H), 3.74-3.69 (m, 1H), 3.68 (s, 2H), 3.16 (dd, J=15.3, 5.3, 1H), 3.06-2.98 (m, 1H), 2.96-2.88 (m, 2H), 2.25-2.17 (m, 1H), 2.06-1.97 (m, 1H).

Example 113

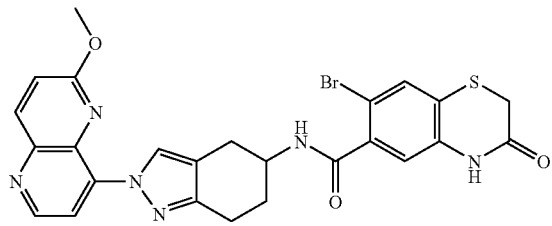

7-Bromo-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide MS (ESI): exact mass calculated for $C_{25}H_{21}BrN_6O_3S$, 565.44; m/z found, 566.4 $[M+H]^+$. $^1H$ NMR (600 MHz, CDCl$_3$): 9.16 (s, 1H), 8.78 (d, J=5.0, 1H), 8.27 (d, J=9.0, 1H), 8.16 (d, J=5.0, 1H), 7.82 (s, 1H), 7.52 (s, 1H), 7.19 (d, J=9.0, 1H), 7.16 (s, 1H), 6.31 (d, J=8.5, 1H), 4.62-4.56 (m, 1H), 4.09 (s, 3H), 3.42 (s, 2H), 3.20 (dd, J=15.5, 5.1, 1H), 3.01 (dd, J=6.6, 6.6, 2H), 2.76 (dd, J=15.0, 6.7, 1H), 2.27-2.18 (m, 1H), 2.17-2.10 (m, 1H).

Example 114

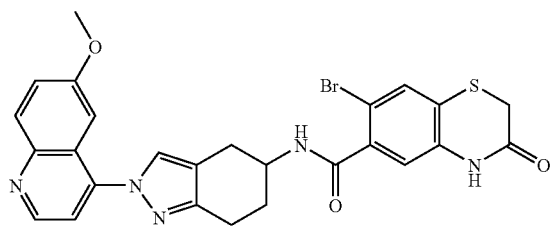

7-Bromo-3-oxo-3,4-dihydro-2H-benzo[1,4]thiazine-6-carboxylic acid [2-(6-methoxy-quinolin-4-yl)-4,5,6,7-tetrahydro-2H-indazol-5-yl]-amide MS (ESI): exact mass calculated for $C_{26}H_{22}BrN_5O_3S$, 564.45; m/z found, 565.4 $[M+H]^+$. $^1H$ NMR (600 MHz, DMSO-d$_6$): 10.75 (s, 1H), 8.79 (d, J=4.7, 1H), 8.63 (d, J=7.6, 1H), 8.20 (s, 1H), 8.03 (d, J=9.2, 1H), 7.87 (d, J=2.8, 1H), 7.64 (s, 1H), 7.54 (d, J=4.8, 1H), 7.51 (dd, J=9.2, 2.8, 1H), 6.96 (s, 1H), 4.22-4.16 (m, 1H), 3.87 (s, 3H), 3.51 (s, 2H), 3.03 (dd, J=15.4, 5.2, 1H), 2.98-2.93 (m, 1H), 2.87-2.82 (m, 1H), 2.62 (dd, J=15.7, 9.1, 1H), 2.13-2.10 (m, 1H), 1.93-1.87 (m, 1H).

Example 115

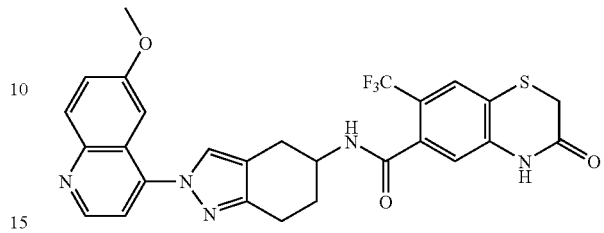

3-Oxo-7-trifluoromethyl-3,4-dihydro-2H-benzo[1,4]thiazine-6-carboxylic acid [2-(6-methoxy-quinolin-4-yl)-4,5,6,7-tetrahydro-2H-indazol-5-yl]-amide MS (ESI): exact mass calculated for $C_{27}H_{22}F_3N_5O_3S$, 553.14; m/z found, 554.1 $[M+H]^+$. $^1H$ NMR (600 MHz, CDCl$_3$): 8.80 (d, J=4.7, 1H), 8.30 (br s, 1H), 8.08 (d, J=9.2, 1H), 7.69 (s, 1H), 7.65 (s, 1H), 7.61 (d, J=2.8, 1H), 7.43 (dd, J=9.2, 2.8, 1H), 7.34 (d, J=4.7, 1H), 7.08 (s, 1H), 5.95 (d, J=8.2, 1H), 4.61-4.56 (m, 1H), 3.90 (s, 3H), 3.47 (s, 2H), 3.20 (dd, J=15.7, 4.9, 1H), 3.07-2.95 (m, 2H), 2.71 (dd, J=15.5, 7.7, 1H), 2.27-2.22 (m, 1H), 2.13-2.05 (m, 1H).

Example 116

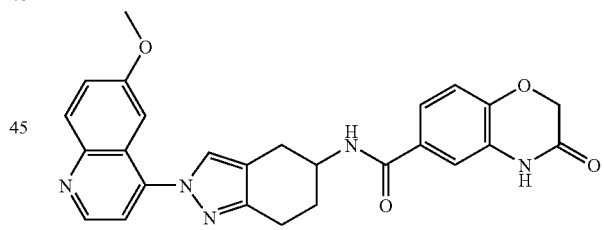

3-Oxo-3,4-dihydro-2H-benzo[1,4]oxazine-6-carboxylic acid [2-(6-methoxy-quinolin-4-yl)-4,5,6,7-tetrahydro-2H-indazol-5-yl]-amide MS (ESI): exact mass calculated for $C_{26}H_{23}N_5O_4$, 469.18; m/z found, 470.2 $[M+H]^+$. $^1H$ NMR (600 MHz, CDCl$_3$): 8.80 (d, J=4.7, 1H), 8.61 (br s, 1H), 8.08 (d, J=9.2, 1H), 7.70 (s, 1H), 7.66 (d, J=2.7, 1H), 7.58 (d, J=1.3, 1H), 7.44 (dd, J=9.2, 2.1, 1H), 7.36 (d, J=4.7, 1H), 7.29 (dd, J=8.4, 2.0, 1H), 6.99 (d, J=8.3, 1H), 6.21 (d, J=7.8, 1H), 4.67 (s, 2H), 4.65-4.58 (m, 1H), 3.92 (s, 3H), 3.25 (dd, J=15.5, 5.0, 1H), 3.09-2.99 (m, 2H), 2.71 (dd, J=15.5, 7.8, 1H), 2.29-2.23 (m, 1H), 2.14-2.07 (m, 1H).

Example 117

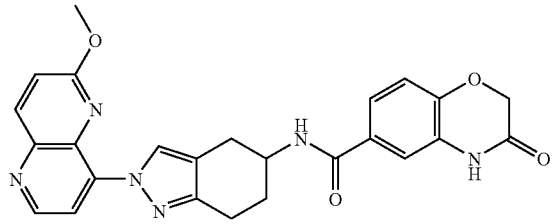

3-Oxo-3,4-dihydro-2H-benzo[1,4]oxazine-6-carboxylic acid [2-(6-methoxy-[1,5]naphthyridin-4-yl)-4,5,6,7-tetrahydro-2H-indazol-5-yl]-amide MS (ESI): exact mass calculated for $C_{25}H_{22}N_6O_4$, 470.17; m/z found, 471.1 [M+H]$^+$. $^1$H NMR (600 MHz, CDCl$_3$): 9.20 (s, 1H), 8.79 (d, J=5.1, 1H), 8.28 (d, J=9.9, 1H), 8.19 (d, J=5.0, 1H), 7.95 (br s, 1H), 7.44-7.43 (m, 1H), 7.30-7.27 (m, 1H), 7.21 (d, J=9.8, 1H), 6.99 (d, J=8.3, 1H), 6.14 (d, J=8.0, 1H), 4.67 (s, 2H), 4.62-4.56 (m, 1H), 4.10 (s, 3H), 3.24 (dd, J=15.1, 5.2, 1H), 3.06-2.95 (m, 2H), 2.72 (dd, J=15.5, 7.5, 1H), 2.26-2.19 (m, 1H), 2.16-2.08 (m, 1H).

Example 118

2-Fluoro-N-[2-(6-methoxy-quinolin-4-yl)-4,5,6,7-tetrahydro-2H-indazol-5-yl]-4-nitro-benzamide MS (ESI): exact mass calculated for $C_{24}H_{20}FN_5O_4$, 461.15; m/z found, 462.1 [M+H]$^+$. $^1$H NMR (600 MHz, CDCl$_3$): 8.81 (d, J=4.7, 1H), 8.33 (dd, J=8.12, 8.12, 1H), 8.19 (dd, J=8.6, 2.1, 1H), 8.09 (d, J=9.2, 1H), 8.02 (dd, J=11.1, 2.1, 1H), 7.70 (s, 1H), 7.64 (d, J=2.8, 1H), 7.44 (dd, J=9.2, 2.8, 1H), 7.36 (d, J=4.7, 1H), 6.83-6.80 (m, 1H), 4.66-4.60 (m, 1H), 3.92 (s, 3H), 3.26 (dd, J=15.6, 5.1, 1H), 3.06-3.03 (m, 2H), 2.75 (dd, J=15.5, 7.9, 1H), 2.32-2.27 (m, 1H), 2.16-2.10 (m, 1H).

Example 119

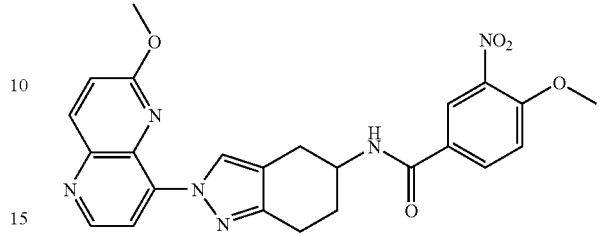

4-Methoxy-N-[2-(6-methoxy-[1,5]naphthyridin-4-yl)-4,5,6,7-tetrahydro-2H-indazol-5-yl]-3-nitro-benzamide MS (ESI): exact mass calculated for $C_{24}H_{22}N_6O_5$, 474.17; m/z found, 475.1 [M+H]$^+$. $^1$H NMR (600 MHz, CDCl$_3$): 9.17 (s, 1H), 8.78 (d, J=5.0, 1H), 8.27 (d, J=9.1, 1H), 8.24 (d, J=2.3, 1H), 8.17 (d, J=5.0, 1H), 8.06 (dd, J=8.8, 2.3, 1H), 7.19 (d, J=9.1, 1H), 7.14 (d, J=8.8, 1H), 6.27 (d, J=7.6, 1H), 4.59-4.54 (m, 1H), 4.09 (s, 3H), 4.01 (s, 3H), 3.24 (dd, J=15.4, 5.1, 1H), 3.01 (dd, J=6.6, 6.6, 2H), 2.72 (dd, J=15.4, 7.7, 1H), 2.26-2.21 (m, 1H), 2.13-2.09 (m, 1H).

Example 120

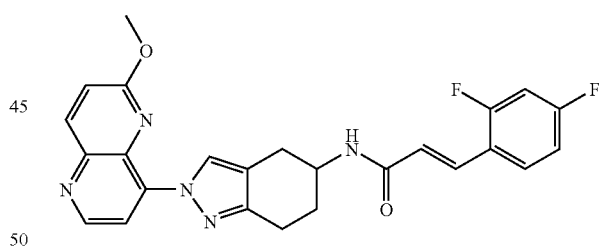

3-(2,4-Difluoro-phenyl)-N-[2-(6-methoxy-[1,5]naphthyridin-4-yl)-4,5,6,7-tetrahydro-2H-indazol-5-yl]-acrylamide MS (ESI): exact mass calculated for $C_{26}H_{22}F_2N_4O_2$, 461.17; m/z found 462.3, [M+H]$^+$. $^1$H NMR (400 MHz, CDCl$_3$): 9.09 (s, 1H), 8.72 (d, J=5.1, 1H), 8.23 (d, J=9.1, 1H), 8.11 (d, J=5.1, 1H), 7.62 (d, J=15.8, 1H), 7.45-7.41 (m, 1H), 7.17 (d, J=9.1, 1H), 6.87-6.78 (m, 2H), 6.49 (d, J=15.8, 1H), 6.26 (d, J=7.0, 1H), 4.51-4.48 (m, 1H), 4.05 (s, 3H), 3.12 (dd, J=15.5, 5.0, 1H), 2.95-2.85 (m, 2H), 2.62 (dd, J=15.6, 7.2, 1H), 2.16-2.03 (m, 2H).

Example 121

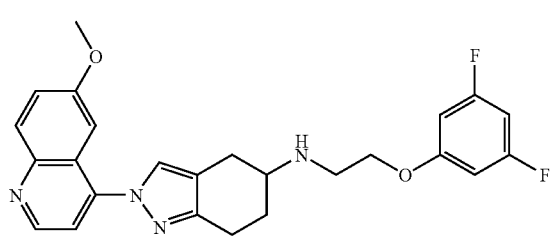

[2-(3,5-Difluoro-phenoxy)-ethyl]-{2-[1-(6-methoxy-quinolin-4-yl)-1H-pyrazol-4-yl]-1-methyl-ethyl}-amine To a solution of 2-(6-methoxy-[1,5]naphthyridin-4-yl)-4,5,6,7-tetrahydro-2H-indazol-5-ylamine (160 mg, 0.54 mmol) in DMF (3 mL) was added 1-(2-bromo-ethoxy)-3,5-difluoro-benzene (154 mg, 0.65 mmol), $Cs_2CO_3$ (267 mg, 0.82 mmol) and catalytic NaI (25 mg, 0.002 mmol). After 48 h at 50° C., the mixture was concentrated, and the residue was dissolved in EtOAc, washed with $H_2O$, dried ($MgSO_4$), and concentrated. The resulting residue was purified by basic reverse phase HPLC to provide 53.8 mg (29%) of the title compound as a brown gum. MS (ESI): exact mass calculated for $C_{25}H_{24}F_2N_4O_2$, 450.48; m/z found, 451.2 [M+H]$^+$. $^1$H NMR (500 MHz, $CD_3OD$): 8.74 (d, J=4.9, 1H), 8.01 (d, J=9.2, 1H), 7.95 (s, 1H), 7.71 (d, J=2.7 1H), 7.50-7.48 (m, 2H), 6.61 (dd, J=9.2, 2.1, 2H), 6.52 (tt, J=9.2, 2.2, 1H), 4.14 (t, J=5.3, 2H), 3.90 (s, 3H), 3.13-3.09 (m, 4H), 3.00-2.96 (m, 1H), 2.83 (ddd, J=16.6, 10.7, 5.8, 1H), 2.54-2.51 (m, 1H), 2.26-2.23 (m, 1H), 1.85-1.77 (m, 1H).

The compounds in Examples 122-123 were prepared according to the methods described in Example 58.

Example 122

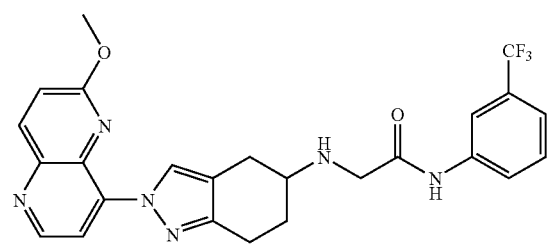

2-[2-(6-Methoxy-[1,5]naphthyridin-4-yl)-4,5,6,7-tetrahydro-2H-indazol-5-ylamino]-N-(3-trifluoromethyl-phenyl)-acetamide MS (ESI): exact mass calculated for $C_{25}H_{23}F_3N_6O_2$, 496.18; m/z found, 497.3 [M+H]$^+$. $^1$H NMR (500 MHz, $CDCl_3$): 9.37 (s, 1H), 9.09 (s, 1H), 8.79 (d, J=5.0, 1H), 8.24 (d, J=7.8, 1H), 8.2 (d, J=5.0, 1H), 7.82 (br s, 1H), 7.38 (d, J=8.0, 1H), 7.15 (d, J=9.0, 1H), 7.11-7.02 (m, 2H), 3.88 (s, 3H), 3.62 (d, J=17.8, 1H), 3.43 (d, J=17.8, 1H), 3.29-3.20 (m, 1H), 3.11-3.04 (m, 1H), 2.96-2.89 (m, 2H), 2.64 (dd, J=15.7, 9.0, 1H), 2.17-2.13 (m, 1H), 2.03-1.97 (m, 1H).

Example 123

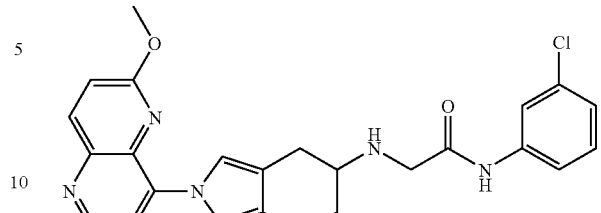

N-(3-Chloro-phenyl)-2-[2-(6-methoxy-[1,5]naphthyridin-4-yl)-4,5,6,7-tetrahydro-2H-indazol-5-ylamino]-acetamide MS (ESI): exact mass calculated for $C_{24}H_{23}ClN_6O_2$, 462.16; m/z found, 463.3 [M+H]$^+$. $^1$H NMR (500 MHz, $CDCl_3$): 9.22 (s, 1H), 9.09 (s, 1H), 8.78 (d, J=5.0, 1H), 8.25 (d, J=9.1, 1H), 8.21 (d, J=5.0, 1H), 7.37 (t, J=1.8, 1H), 7.20-7.18 (m, 1H), 7.16 (d, J=9.0, 1H), 6.89 (t, J=8.0, 1H), 6.80-6.78 (m, 1H), 3.88 (s, 3H), 3.62 (d, J=17.5, 1H), 3.37 (d, J=17.5, 1H), 3.27-3.25 (m, 1H), 3.10-3.05 (m, 1H), 2.94-2.86 (m, 2H), 2.65 (dd, J=15.8, 5.6, 1H), 2.14-2.11 (m, 1H), 2.02-1.99 (m, 1H).

The compounds in Examples 124-134 were prepared according to the methods described in the preceding examples.

Example 124

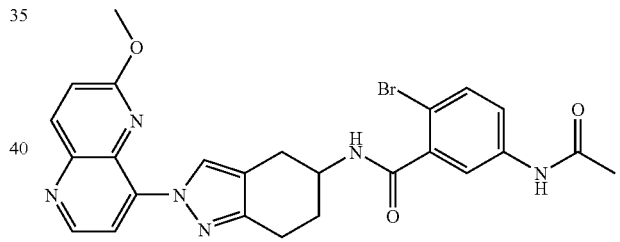

5-Acetylamino-2-bromo-N-[2-(6-methoxy-[1,5] naphthyridin-4-yl)-4,5,6,7-tetrahydro-2H-indazol-5-yl]-benzamide MS (ESI): exact mass calculated for $C_{25}H_{23}BrN_6O_3$, 534.10; m/z found, 535.1 [M+H]$^+$.

Example 125

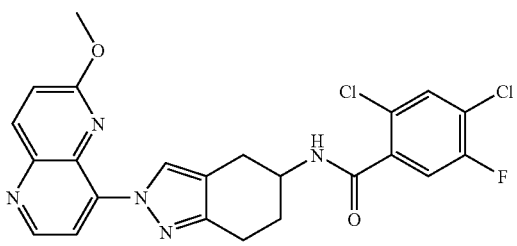

111

2,4-Dichloro-5-fluoro-N-[2-(6-methoxy-[1,5]naph-thyridin-4-yl)-4,5,6,7-tetrahydro-2H-indazol-5-yl]-benzamide MS (ESI): exact mass calculated for $C_{23}H_{18}Cl_2FN_5O_2$, 485.08; m/z found, 486.1 [M+H]$^+$.

Example 126

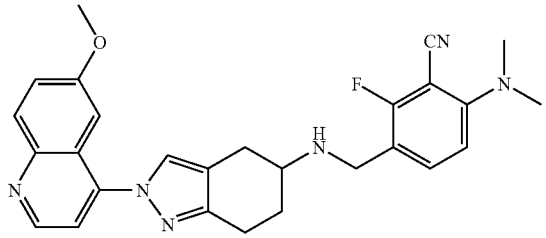

6-Dimethylamino-2-fluoro-3-{[2-(6-methoxy-quinolin-4-yl)-4,5,6,7-tetrahydro-2H-indazol-5-ylamino]-methyl}-benzonitrile MS (ESI): exact mass calculated for $C_{27}H_{27}FN_6O$, 470.22; m/z found, 471.2 [M+H]$^+$.

Example 127

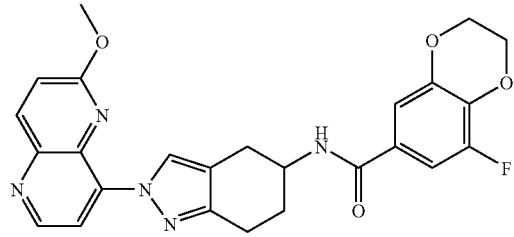

8-Fluoro-2,3-dihydro-benzo[1,4]dioxine-6-carboxylic acid [2-(6-methoxy-[1,5]naphthyridin-4-yl)-4,5,6,7-tetrahydro-2H-indazol-5-yl]-amide MS (ESI): exact mass calculated for $C_{25}H_{22}FN_5O_4$, 475.17; m/z found, 476.2 [M+H]$^+$.

Example 128

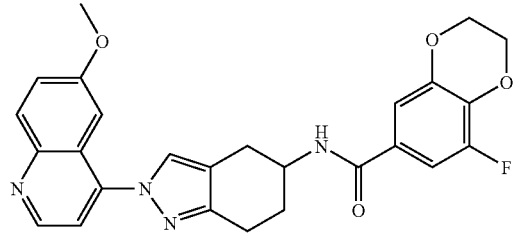

112

8-Fluoro-2,3-dihydro-benzo[1,4]dioxine-6-carboxylic acid [2-(6-methoxy-quinolin-4-yl)-4,5,6,7-tetrahydro-2H-indazol-5-yl]-amide MS (ESI): exact mass calculated for $C_{26}H_{23}FN_4O_4$, 474.17; m/z found, 475.2 [M+H]$^+$.

Example 129

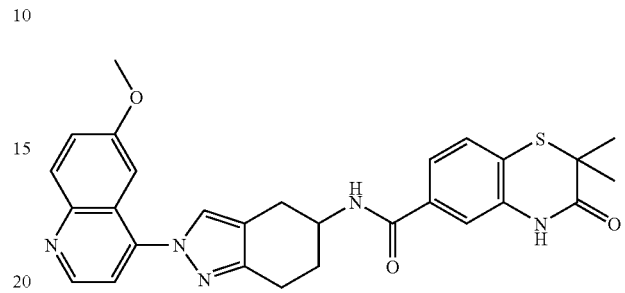

2,2-Dimethyl-3-oxo-3,4-dihydro-2H-benzo[1,4]thiazine-6-carboxylic acid [2-(6-methoxy-quinolin-4-yl)-4,5,6,7-tetrahydro-2H-indazol-5-yl]-amide MS (ESI): exact mass calculated for $C_{28}H_{27}N_5O_3S$, 513.18; m/z found, 514.2 [M+H]$^+$.

Example 130

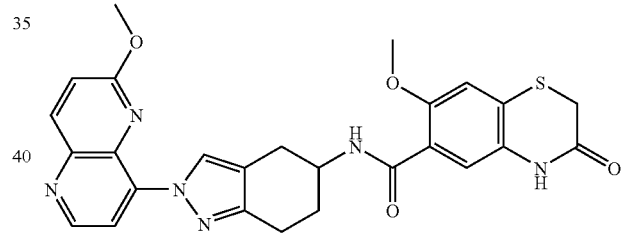

7-Methoxy-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide MS (ESI): exact mass calculated for $C_{26}H_{24}N_6O_4S$, 516.16; m/z found, 517.2 [M+H]$^+$.

Example 131

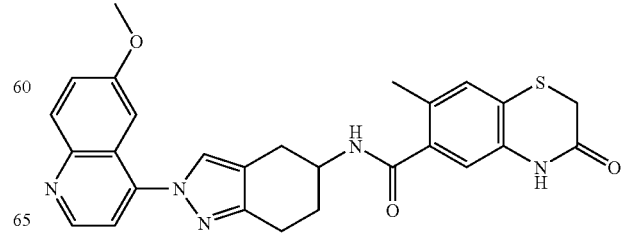

7-Methyl-3-oxo-3,4-dihydro-2H-benzo[1,4]thiazine-
6-carboxylic acid [2-(6-methoxy-quinolin-4-yl)-4,5,
6,7-tetrahydro-2H-indazol-5-yl]-amide MS (ESI): exact mass calculated for $C_{27}H_{25}N_5O_3S$, 499.17; m/z found, 500.2 [M+H]$^+$.

Example 132

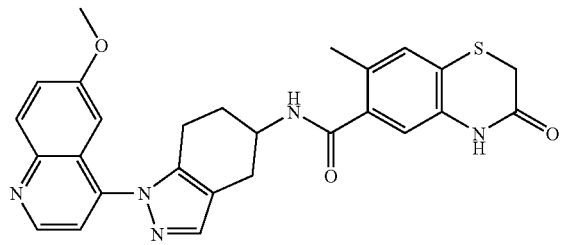

7-Methyl-3-oxo-3,4-dihydro-2H-benzo[1,4]thiazine-
6-carboxylic acid [1-(6-methoxy-quinolin-4-yl)-4,5,
6,7-tetrahydro-1H-indazol-5-yl]-amide MS (ESI): exact mass calculated for $C_{27}H_{25}N_5O_3S$, 499.17; m/z found, 500.2 [M+H]$^+$.

Example 133

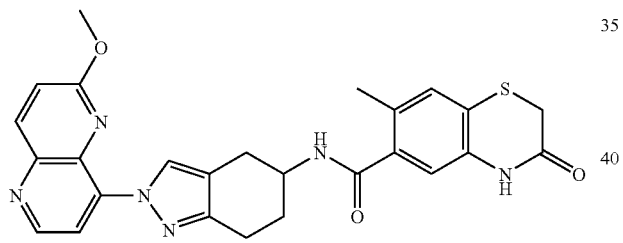

7-Methyl-3-oxo-3,4-dihydro-2H-benzo[1,4]thiazine-
6-carboxylic acid [2-(6-methoxy-[1,5]naphthyridin-
4-yl)-4,5,6,7-tetrahydro-2H-indazol-5-yl]-amide MS (ESI): exact mass calculated for $C_{26}H_{24}N_6O_3S$, 500.16; m/z found, 501.2 [M+H]$^+$.

Example 134

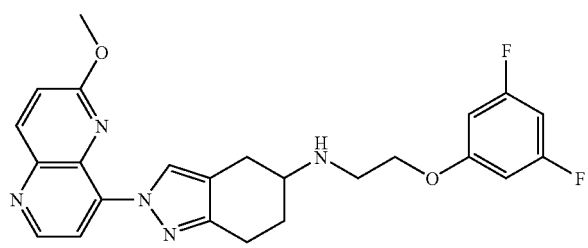

[2-(3,5-Difluoro-phenoxy)-ethyl]-[2-(6-methoxy-[1,
5]naphthyridin-4-yl)-4,5,6,7-tetrahydro-2H-indazol-
5-yl]-amine MS (ESI): exact mass calculated for $C_{24}H_{23}F_2N_5O_2$, 451.18; m/z found, 452.2 [M+H]$^+$.

Example 135

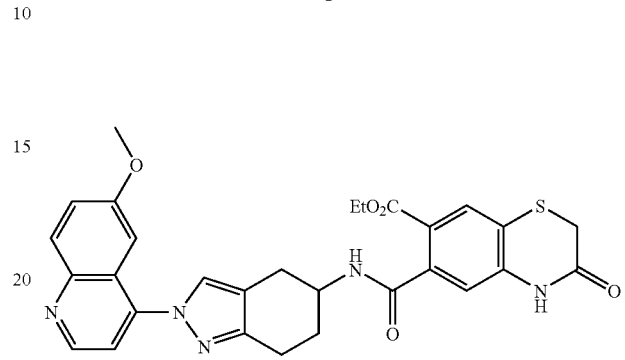

6-[2-(6-Methoxy-quinolin-4-yl)-4,5,6,7-tetrahydro-
2H-indazol-5-ylcarbamoyl]-3-oxo-3,4-dihydro-2H-
benzo[1,4]thiazine-7-carboxylic acid ethyl ester

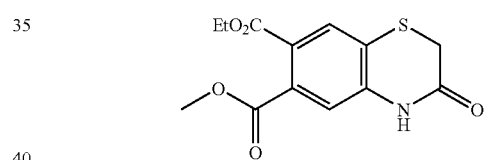

A. 3-Oxo-3,4-dihydro-2H-benzo[1,4]thiazine-6,7-dicarboxylic acid 7-ethyl ester 6-methyl ester. The title compound was prepared as described in Example H.

MS (ESI): exact mass calculated for $C_{13}H_{13}NO_5S$, 295.05; m/z found, 296.1 [M+H]$^+$.

B. 3-Oxo-3,4-dihydro-2H-benzo[1,4]thiazine-6,7-dicarboxylic acid 7-ethyl ester. To a slurry of potassium trimethyl silanolate (16 mg, 0.125 mmol) in dry $CH_2Cl_2$ (0.78 mL) was added 3-oxo-3,4-dihydro-2H-benzo[1,4]thiazine-6,7-dicarboxylic acid 7-ethyl ester 6-methyl ester (37 mg, 0.125 mmol), and the mixture was stirred at rt under a nitrogen atmosphere for 3 h. The mixture was diluted with 1 N HCl (20 mL), and extracted with EtOAc (1×20 mL). The organic layer was washed with $H_2O$ (2×20 mL) and satd. aq. NaCl (1×20 mL), then dried ($Na_2SO_4$), filtered, and concentrated to afford the title compound, which was used without further purification. MS (ESI): exact mass calculated for $C_{12}H_{11}NO_5S$, 281.04; m/z found, 282.0 [M+H]$^+$.

C. The title compound was prepared as described in the preceding examples.

MS (ESI): exact mass calculated for $C_{29}H_{27}N_5O_5S$, 557.17; m/z found, 558.2 [M+H]$^+$.

Example 136

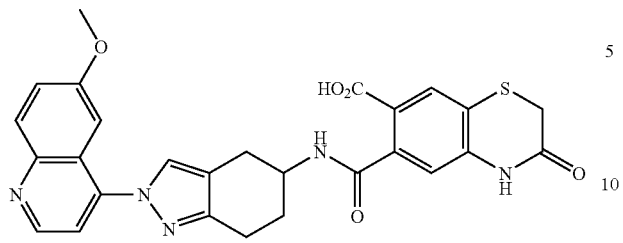

6-[2-(6-Methoxy-quinolin-4-yl)-4,5,6,7-tetrahydro-2H-indazol-5-ylcarbamoyl]-3-oxo-3,4-dihydro-2H-benzo[1,4]thiazine-7-carboxylic acid, potassium salt To a solution of 6-[2-(6-methoxy-[1,5]naphthyridin-4-yl)-4,5,6,7-tetrahydro-2H-indazol-5-ylcarbamoyl]-3-oxo-3,4-dihydro-2H-benzo[1,4]thiazine-7-carboxylic acid ethyl ester (5.9 mg, 0.011 mmol) in isopropanol (0.5 mL) was added KOH (0.21 M in H$_2$O; 50 µL, 1 eq. KOH). After stirring at rt for 3 h the mixture was concentrated, redissolved in warm acetonitrile, and cooled to −78° C. The resulting frozen sample was dried on a lyophilizer to afford 5.8 mg (100%) of the title compound as the potassium carboxylate salt. MS (ESI): exact mass calculated for C$_{27}$H$_{23}$N$_5$O$_5$S, 529.14; m/z found, 530.1 [M+H]$^+$.

Example 137

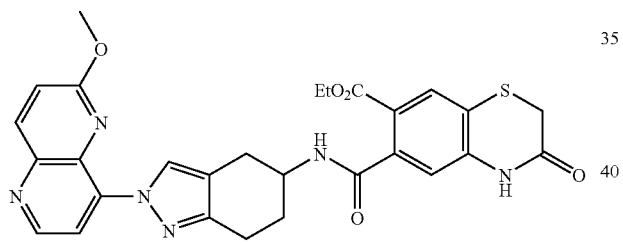

6-[2-(6-Methoxy-[1,5]naphthyridin-4-yl)-4,5,6,7-tetrahydro-2H-indazol-5-ylcarbamoyl]-3-oxo-3,4-dihydro-2H-benzo[1,4]thiazine-7-carboxylic acid ethyl ester The title compound was prepared as described in Example 135. MS (ESI): exact mass calculated for C$_{29}$H$_{26}$N$_6$O$_5$S, 558.17; m/z found, 559.2 [M+H]$^+$.

Example 138

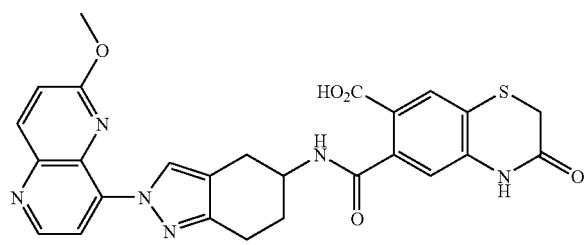

6-[2-(6-Methoxy-[1,5]naphthyridin-4-yl)-4,5,6,7-tetrahydro-2H-indazol-5-ylcarbamoyl]-3-oxo-3,4-dihydro-2H-benzo[1,4]thiazine-7-carboxylic acid The title compound was prepared as described in Example 136. MS (ESI): exact mass calculated for C$_{26}$H$_{22}$N$_6$O$_5$S, 530.14; m/z found, 531.1 [M+H]$^+$.

Example 139

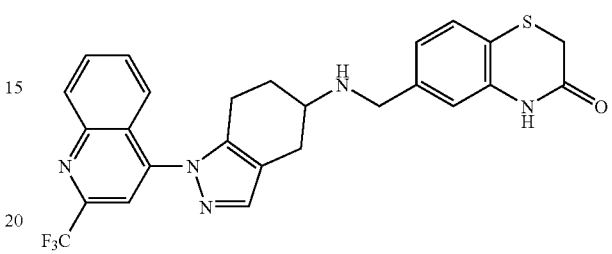

6-{[1-(2-Trifluoromethyl-quinolin-4-yl)-4,5,6,7-tetrahydro-1H-indazol-5-ylamino]-methyl}-4H-benzo[1,4]thiazin-3-one MS (ESI): exact mass calculated for C$_{26}$H$_{22}$F$_3$N$_5$OS, 509.15; m/z found, 510.8 [M+H]$^+$.

Embodiments of compounds according to the present invention comprise structural elements with the framework (FM)

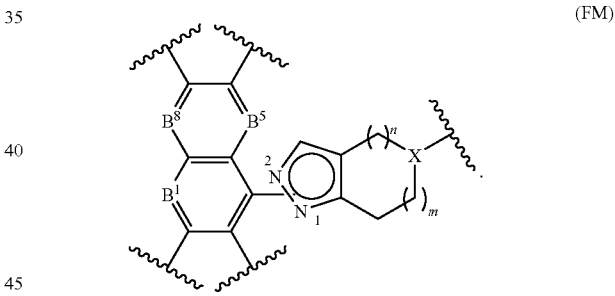

(FM)

Additional illustrative embodiments of this invention are provided by combinations of substituents in (FM) and in combinations of assignments for B$^1$, B$^5$, B$^8$, n, m, and X, as well as for the N1 or N2 bonding, that are not explicitly listed herein, but that one of ordinary skill in the art would be able to prepare in light of the teachings provided herein.

Further examples of embodiments of this invention are provided by salt, ester and amide forms of compounds exemplified herein and equivalents thereof. By way of illustration, the carboxylic group in compounds such as Example 68 can form salts, preferably pharmaceutically acceptable salts; the basic nitrogen member in compounds such as Examples 1-99 can form salts, preferably pharmaceutically acceptable salts; and the carboxylic acid group in compounds such as Example 68 can form amides, wherein such salts, esters and amides are formed by methods known in the art.

Assay Methods

Assay results provided herein are illustrative results of the assays that were performed for compounds of this invention.

Biological Example 1

In Vitro Antibacterial Activity (MIC Assay)

Minimal inhibitory concentration (MIC) has been an indicator of in vitro antibacterial activity widely used in the art. The in vitro antibacterial activity of the compounds was determined by the broth microdilution method described by the National Committee for Clinical Laboratory Standards (NCCLS) in the NCCLS Document M7-A5, Vol. 20, No. 2, "Methods for Dilution Antimicrobial Susceptibility Test for Bacteria that Grow Aerobically—Fifth Edition", which is incorporated herein by reference.

In this method, an aliquot of test compound from an 11-point series of 2-fold serial dilutions of compounds in 100% DMSO was added to wells in microdilution plates. The test organisms were prepared by adjusting the turbidity of actively growing broth cultures so that the final concentration of test organism after addition to wells with or without compounds was approximately $5 \times 10^5$ CFU/mL.

Following inoculation of the microdilution plates, the plates were incubated at 35° C. for 16-24 h and then scored for bacterial growth. The MIC is defined as the lowest concentration of test compound that completely inhibits the visible growth of the test organism. The amount of growth in the wells containing the test compound was compared with the amount of growth in the growth-control wells (no test compound used) in each plate, and with the amount of growth in the wells containing control compounds (such as ciprofloxacin). Compounds of the present invention were tested against several bacterial strains. The MIC values (in µg/mL) are presented in Table 1 for Gram-negative (*E. coli* KL-16 (GSC strain 4245); data marked as (*) was obtained with *E. coli* ATCC25922) and Gram-positive bacteria (*S. aureus* ATCC13709; *S. pneumoniae* ATCC49619).

Biological Example 2

DNA Gyrase Inhibition Assay

Inhibition of the supercoiling activity of *E. coli* DNA gyrase was determined using enzymes, buffers and substrates received from John Innes Enterprises Ltd. (John Innes Centre, UK). The reactions were performed according to the manufacturer's directions, with the following modifications.

DNA supercoiling reactions were carried out in a total reaction volume of 20 µL containing 250 ng of relaxed pBR322, 35 mM Tris-HCl (pH 7.5), 24 mM KCl, 4 mM $MgCl_2$, 2 mM dithiothreitol, 1.8 mM spermidine, 1 mM ATP, 6.5% glycerol and 100 µg/mL albumin. Compounds diluted in 10% DMSO were added to the reaction mixture to reach a final concentration of 0.5% DMSO. Enzyme was diluted to 0.08 unit/4 in a solution of 50 mM Tris-HCl (pH 7.5), 100 mM KCl, 2 mM dithiothreitol, 1 mM EDTA, and 50% glycerol. Diluted enzyme (0.2 unit) was added to each reaction.

The reactions were incubated at 37° C. for 30 min. The reactions were then cooled to 0° C., followed by addition of 3 µL of 40% glycerol, 100 mM Tris-HCl (pH 7.5), 50 mM EDTA, 0.5% SDS and 0.1% bromophenol blue. Samples were separated on 1.0% agarose gels. Gels were stained with Ethidium bromide and photographed with a Stratagene Eagle Eye II. $IC_{50}$ values (in µg/mL) were determined by visual inspection of the photographs, and are listed in Table 1.

TABLE 1

| Ex. | *E. coli* KL-16 MIC (µg/mL) | *S. aureus* ATCC13709 MIC (µg/mL) | *S. pneumoniae* ATCC49619 MIC (µg/mL) | DNA Gyrase $IC_{50}$ |
|---|---|---|---|---|
| 1 | >128 | 0.5 | 8 | >32 |
| 2 | >128 | 0.5 | 8 | 16 |
| 3 | >128 | 1 | 4 | 4 |
| 4 | >128 | 0.06 | 4 | 0.25 |
| 5 | 128 | 0.25 | 2 | 0.12 |
| 6 | 2 | <0.125 | 4 | 0.12 |
| 7 | >128 | 0.25 | >128 | 2 |
| 8 | >128 | 0.25 | 4 | >16 |
| 9 | >128 | 0.25 | 4 | >16 |
| 10 | >128 | 0.25 | 2 | 8 |
| 11 | >128 | <0.125 | 16 | 2 |
| 12 | >128 | 0.25 | 8 | 2 |
| 13 | >128 | 0.5 | 8 | >16 |
| 14 | >128 | 1 | 16 | 1 |
| 15 | >128 | 1 | 16 | >32 |
| 16 | >128 | 2 | 8 | 4 |
| 17 | 4 | 0.25 | 2 | 0.12 |
| 18 | 4 | 0.03 | 1 | 8 |
| 19 | >128 | 0.5 | 8 | >32 |
| 20 | 2 | <0.125 | 2 | 0.5 |
| 21 | >128 | 1 | 8 | >16 |
| 22 | >128 | 0.5 | 8 | 0.5 |
| 23 | >128 | <0.125 | 2 | 4 |
| 24 | >128 | <0.125 | 4 | 16 |
| 25 | >128 | 1 | 8 | >16 |
| 26 | >128 | 0.25 | 2 | >16 |
| 27 | 4 | 0.125 | 4 | 4 |
| 28 | 16 | 0.25 | 4 | 2 |
| 29 | >128 | 1 | 4 | 16 |
| 30 | >128 | 1 | 8 | 16 |
| 31 | 16 | 0.25 | 4 | 2 |
| 32 | 16 | 0.25 | 4 | 16 |
| 33 | >128 | 1 | 8 | 2 |
| 34 | >128 | 0.5 | 8 | 2 |
| 35 | >128 | <0.125 | 1 | 2 |
| 36 | 8 | <0.125 | 0.25 | 0.5 |
| 37 | 32 | 0.5 | 2 | 0.25 |
| 38 | >128 | 0.25 | 4 | 2 |
| 39 | >128 | 0.5 | 1 | 4 |
| 40 | 4 | 0.25 | 4 | 2 |
| 41 | 2 | 0.25 | 2 | 0.06 |
| 42 | 32 | 0.03 | 0.5 | 1 |
| 43 | 16 | >0.125 | 1 | 0.5 |
| 44 | 2 | 0.5 | 2 | <0.125 |
| 45 | 128 | 0.25 | <0.125 | 0.8 |
| 46 | 16 | 0.06 | <0.125 | 0.12 |
| 47 | 128 | 1 | 4 | 2 |
| 48 | 32 | 0.25 | 1 | >32 |
| 49 | 128 | <0.125 | 0.5 | 3 |
| 50 | 128 | 0.5 | 1 | 2 |
| 51 | >128 | 1 | 1 | 4 |
| 52 | 2 | 0.25 | 1 | 0.125 |
| 53 | 4 | 0.25 | 2 | 0.5 |
| 54 | 2 | 1 | 2 | 0.06 |
| 55 | 64 | 0.5 | 1 | 4 |
| 56 | 128 | 1 | 2 | 4 |
| 57 | 64 | 1 | 2 | 2 |
| 58 | 16 | 0.25 | 4 | 1 |
| 59 | 128 | 1 | 8 | 16 |
| 60 | >128 | 1 | 8 | >16 |
| 61 | 16 | 0.5 | 8 | 2 |
| 62 | >128 | 1 | 16 | 4 |
| 63 | 6 | 0.1 | 0.8 | 4 |
| 64 | 64 | 4 | 128 | >4 |
| 65 | >128 | 0.5 | 1 | 1 |
| 66 | >128 | 8 | >128 | 2 |
| 67 | >128 | 4 | 64 | >8 |
| 68 | >128 | 8 | 8 | 1 |
| 69 | >128 | 4 | 64 | >4 |
| 70 | >128 | 2 | 32 | >32 |
| 71 | >128 | 2 | 8 | 16 |
| 72 | >128 | 2 | >128 | >16 |
| 73 | >128 | 4 | 64 | >16 |
| 74 | >128 | 1 | 8 | 2 |
| 75 | >128 | 4 | 16 | >16 |
| 76 | >128 | 2 | >128 | 16 |

TABLE 1-continued

| Ex. | E. coli KL-16 MIC (μg/mL) | S. aureus ATCC13709 MIC (μg/mL) | S. pneumoniae ATCC49619 MIC (μg/mL) | DNA Gyrase $IC_{50}$ |
|---|---|---|---|---|
| 77 | >128 | 2 | 16 | >16 |
| 78 | >128 | 16 | >128 | >16 |
| 79 | >128 | 4 | 8 | >16 |
| 80 | >128 | 8 | 128 | >16 |
| 81 | >128 | 2 | >128 | 16 |
| 82 | >128 | 8 | >128 | 4 |
| 83 | >128 | 2 | 32 | <0.25 |
| 84 | >128 | 2 | 16 | 8 |
| 85 | 64 | 8 | 8 | 2 |
| 86 | >128 | 4 | 4 | 2 |
| 87 | 64 | 2 | 8 | 2 |
| 88 | >128 | 4 | 8 | NT |
| 89 | 16 | 2 | 2 | 0.125 |
| 90 | >128 | 0.5 | >128 | >16 |
| 91 | >128 | 4 | >128 | >16 |
| 92 | >128 | 0.5 | >128 | >16 |
| 93 | >128 | 0.25 | 16 | >16 |
| 94 | >128 | 2 | >128 | 4 |
| 95 | >128 | 2 | 8 | >16 |
| 96 | 64 | 8 | 32 | >4 |
| 97 | >128 | >128 | >128 | >16 |
| 98 | >128 | 16 | 64 | NT |
| 99 | >128 | 2 | >128 | 8 |
| 100 | 16 | 0.25 | 0.5 | 0.5 |
| 101 | 4 | 0.125 | 1 | 0.25 |
| 102 | 8 | 0.5 | 0.5 | 0.5 |
| 103 | 32 | 0.5 | 4 | 2 |
| 104 | 8 | 0.125 | 1 | 0.5 |
| 105 | >128 | 0.5 | 4 | 2 |
| 106 | 8 | 0.5 | 1 | 2 |
| 107 | 8* | 0.25 | 2 | NT |
| 108 | 8 | 0.125 | 1 | 1 |
| 109 | >128 | 0.125 | 4 | 1 |
| 110 | >128 | 0.25 | 8 | NT |
| 111 | >128 | 0.25 | 4 | >16 |
| 112 | 4 | 0.125 | 8 | 0.25 |
| 113 | 2 | 0.125 | 2 | 0.25 |
| 114 | 2 | 0.125 | 2 | 0.5 |
| 115 | 8 | 0.125 | 8 | 1 |
| 116 | 2 | 0.125 | 4 | 0.25 |
| 117 | 4 | 0.125 | 8 | 1 |
| 118 | >128 | 4 | >128 | >16 |
| 119 | >128 | 4 | 8 | NT |
| 120 | >128 | 0.125 | 4 | 2 |
| 121 | 8 | 1 | 2 | 0.5 |
| 122 | >128 | 2 | 32 | 4 |
| 123 | >128 | 1 | >128 | 4 |
| 124 | >128 | 4 | >128 | NT |
| 125 | >128 | 0.25 | 8 | NT |
| 126 | >128 | 1 | 2 | NT |
| 127 | >128 | 0.5 | 8 | NT |
| 128 | >128 | 2 | 8 | NT |
| 129 | >16* | 1 | 4 | NT |
| 130 | >16* | 2 | 16 | NT |
| 131 | 8 | 0.5 | 16 | NT |
| 132 | >16* | 2 | >16 | NT |
| 133 | >16* | 0.25 | >16 | NT |
| 134 | >16* | 1 | 4 | NT |
| 135 | >16* | 2 | >16 | NT |
| 136 | >16* | 1 | >16 | NT |
| 137 | >16* | 0.5 | >16 | NT |
| 138 | >16* | 0.5 | 16 | NT |
| 139 | >128 | 8 | 32 | >16 |

NT = not tested

Biological Example 3

Topoisomerase IV Inhibition Assay

Inhibition of the relaxation activity of *E. coli* topoisomerase IV was determined using enzyme, buffers and substrates received from John Innes Enterprises Ltd. (John Innes Centre, UK). The reactions were performed according to the manufacturer's directions, with the following modifications.

DNA relaxation reactions were carried out in a total reaction volume of 20 μL, containing 300 ng of supercoiled pBR322, 40 mM HEPES-KOH (pH 7.6), 100 mM potassium glutamate, 10 mM Mg(OAc)$_2$, 10 mM DTT, 4 μg/mL tRNA, 2 mM ATP, and 50 μg/mL BSA. Compounds, diluted in 10% DMSO, were added to the reaction mixture to reach a final concentration of 0.5% DMSO. Enzyme was diluted to 0.45 unit/μL in a solution of 40 mM HEPES-KOH (pH 7.6), 150 mM potassium glutamate, 1 mM DTT, 1 mM EDTA, and 40% glycerol. Diluted enzyme (0.9 unit) was added to each reaction.

The reactions were incubated at 37° C. for 45 min. The reactions were then cooled to 0° C. followed by addition of 3 μL of 40% glycerol, 100 mM Tris-HCl (pH 7.5), 50 mM EDTA, 0.5% SDS and 0.1% bromophenol blue. Samples were separated on 1.0% agarose gels. Gels were stained with Ethidium bromide and photographed with a Stratagene Eagle Eye II. $IC_{50}$ values (in μg/mL) were determined by visual inspection of the photographs, and are listed in Table 2.

TABLE 2

| Ex. | Topoisomerase IV $IC_{50}$ |
|---|---|
| 1 | >1 |
| 3 | 1 |
| 4 | 0.25 |
| 5 | 0.125 |
| 17 | 0.125 |
| 18 | 0.25 |
| 21 | 1 |
| 23 | >1 |
| 25 | 1 |
| 27 | 0.5 |
| 28 | 0.5 |
| 29 | 0.5 |
| 31 | 0.125 |
| 32 | 0.125 |
| 33 | 1 |
| 34 | 0.125 |
| 36 | 0.03 |
| 37 | 0.25 |
| 38 | 0.25 |
| 39 | 0.5 |
| 40 | 0.06 |
| 41 | 0.016 |
| 42 | 0.25 |
| 44 | 0.016 |
| 46 | <0.015 |
| 50 | 0.06 |
| 52 | 0.03 |
| 53 | 0.016 |
| 54 | 0.016 |
| 58 | 0.016 |
| 64 | 0.25 |
| 68 | 0.5 |
| 69 | 0.5 |
| 70 | >1 |
| 80 | >1 |
| 81 | >0.5 |
| 82 | 0.5 |
| 83 | 0.25 |
| 86 | 1 |
| 87 | 0.5 |
| 89 | 0.015 |
| 102 | 0.0625 |
| 103 | 0.25 |
| 113 | 0.25 |
| 114 | 0.125 |
| 115 | 0.25 |
| 116 | 0.5 |
| 117 | 0.25 |
| 121 | 0.125 |

Biological Example 4

Resistant Strains Assays

Compounds of the present invention were tested for activity against susceptible and resistant bacterial strains in vitro, and activity was compared to known anti-bacterial agents. Testing protocols followed NCCLS methodology for broth microdilution assays. MIC values in μg/mL are presented in Table 3 for the following strains: Column A: MSSA ATCC13709 (Smith); Column B: MSSA ATCC 29213; Column C: MRSA OC3726 (COL); Column D: MRSA OC2878.

TABLE 3

| Ex. or Name | A | B | C | D |
|---|---|---|---|---|
| Ciprofloxacin | 0.25-0.5 | 0.25-0.5 | 0.5-1 | 0.5 |
| Norfloxacin | 1 | 2 | 2 | 1 |
| Sparfloxacin | 0.062 | 0.062 | 0.125 | 0.062 |
| 4 | 0.06 | 1 | 0.062 | 0.031 |
| 5 | 0.25 | 0.031 | 0.062 | 0.031 |
| 17 | 0.25 | 0.062 | 0.125 | 0.125 |
| 18 | 0.031 | 0.25 | 0.062 | 0.062 |
| 31 | 0.25 | 16 | 0.5 | 0.25 |
| 41 | 0.25 | 0.25 | 1 | 0.5 |
| 46 | 0.062 | 8 | 0.25 | 0.125 |
| 50 | 0.5 | 16 | 1 | 0.5 |
| 52 | 0.25 | 1 | 0.5 | 0.5 |
| 55 | 0.5 | 2 | 1 | 0.5 |

MIC values in μg/mL are presented in Table 4 for the following strains: Column E: CipR MRSA OC3946; Column F: CipR MRSA OC4159; Column G: CipR MRSA OC4222; Column H: CipR MRSA OC5273.

TABLE 4

| Ex. or Name | E | F | G | H |
|---|---|---|---|---|
| Ciprofloxacin | 16 | 128 | 64 | 128 |
| Norfloxacin | 128 | >128 | >128 | >128 |
| Sparfloxacin | 4 | 16 | 8 | 16 |
| 4 | 0.007 | 0.5 | 0.5 | 0.062 |
| 5 | 0.007 | 0.007 | 0.015 | 0.031 |
| 17 | 0.015 | 0.031 | 0.062 | 0.25 |
| 18 | 0.015 | 0.031 | 0.031 | 0.062 |
| 31 | 0.125 | 4 | 4 | 0.5 |
| 41 | 0.25 | 0.25 | 0.25 | 0.5 |
| 46 | 0.062 | 0.062 | 0.062 | 0.125 |
| 50 | 0.5 | 16 | 16 | 1 |
| 52 | 0.125 | 0.25 | 0.125 | 0.5 |
| 55 | 0.5 | 0.5 | 0.25 | 1 |

Additional data obtained for CipR MRSA OC4222 is shown in Table 4A.

TABLE 4A

| Ex. or Name | G |
|---|---|
| 107 | 0.5 |
| 108 | 0.06 |
| 109 | 0.03 |
| 129 | 1 |
| 130 | 2 |
| 131 | 0.5 |
| 132 | 2 |
| 133 | 0.25 |
| 134 | 0.5 |
| 135 | 2 |
| 136 | 2 |
| 137 | 0.5 |
| 138 | 0.5 |

References cited in the specification are incorporated herein by reference. Having described the invention in specific detail and exemplified the manner in which it may be carried into practice, it will be apparent to those skilled in the art that innumerable variations, applications, modifications, and extensions of the basic principles involved may be made without departing from its spirit or scope. It is to be understood that the foregoing is merely exemplary and the present invention is not to be limited to the specific form or arrangements of parts herein described and shown.

What is claimed is:

1. A compound of formula (I):

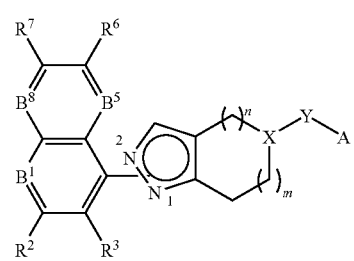

where said formula (I) has a B-containing bicyclic ring system

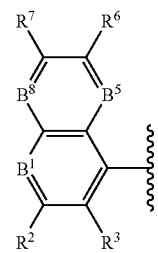

and a fused pyrazole moiety

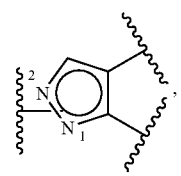

wherein
$B^8$ is $CR^a$, and $B^1$ and $B^5$ are N;
each of $R^a$, $R^2$, $R^3$, $R^6$ and $R^7$ is independently selected from the group consisting of —H, —$C_{1-4}$alkyl, —$C_{2-4}$alkenyl, —$C_{2-4}$alkynyl, —$C_{3-6}$cycloalkyl, —$OR^b$, —$NR^cR^d$, —O(CH$_2$)$_{2-3}$NR$^c$R$^d$, —$SR^b$, —S(O)$R^b$, —$SO_2R^b$, cyano, —$CF_3$, halo, —$NO_2$, —$OCF_3$, —C(O)$R^b$, —OC(O)$R^b$, —C(O)NR$^c$R$^d$, and —$CO_2R^b$; wherein each of $R^b$, $R^c$ and $R^d$ is independently selected from the group consisting of —H, —$C_{1-4}$alkyl, —$C_{3-6}$cycloalkyl, and —$C_{1-2}$alkyl($C_{3-6}$cycloalkyl)-; and wherein each alkyl or cycloalkyl moiety in any of $R^a$, $R^2$, $R^3$, $R^6$, $R^7$, $R^b$, $R^c$, and $R^d$ is optionally and independently substituted with one, two or three substituents selected from —$C_{1-3}$alkyl, halo, hydroxy, amino, and —$C_{1-3}$alkoxy;

the B-containing bicyclic ring system is attached at the 1- or 2-position of the fused pyrazole moiety;

m is 0 or 1;

n is 1 or 2, wherein m+n is 2 or 3;

X is CH or N;

provided that when X is N, then Y is —C(O)—, —CH$_2$C(O)—, or —(CH$_2$)$_{2-3}$O— optionally substituted with —C$_{1-3}$alkyl;

and when X is CH, then Y is —N(R$^e$)Z—;

Z is selected from the group consisting of: C$_{1-3}$alkylene optionally substituted with —C$_{1-3}$alkyl; C$_3$alkenylene optionally substituted with —C$_{1-3}$alkyl; —C(O)C$_2$alkenyl- optionally substituted with —C$_{1-3}$alkyl; —(CH$_2$)$_{0-1}$C(O)—; —CH$_2$C(O)N(R$^f$)(CH$_2$)$_{0-1}$—; —(CH$_2$)$_{2-3}$O—; and —C(O)C(R$^{g1}$)(R$^{g2}$)—;

where R$^e$ is —H, —C$_{1-4}$alkyl, benzyl, —C(O)C$_{1-6}$alkyl, —C(O)phenyl, —C(O)benzyl, —C$_{1-6}$alkylCO$_2$C$_{1-6}$alkyl, or —C$_{1-6}$alkylCO$_2$H;

R$^f$ is —H or —C$_{1-4}$alkyl; and each of R$^{g1}$ and R$^{g2}$ is independently —H or methyl, or R$^{g1}$ and R$^{g2}$ are taken together with their carbon of attachment to form a C$_{3-7}$cycloalkyl, or the group C(R$^{g1}$)(R$^{g2}$) is the group C=O;

A is an aryl or heteroaryl ring selected from the group consisting of:
  a) unsubstituted phenyl, unsubstituted pyridyl, substituted phenyl, and substituted pyridyl, wherein said substituted phenyl is moiety (M1) or moiety (M2)

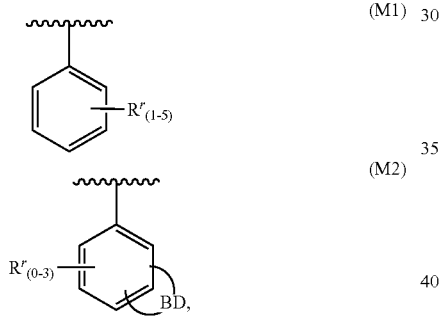

and said substituted pyridyl is moiety (M3) or moiety (M4)

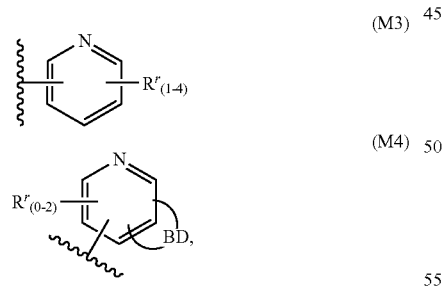

wherein R$^r_{(p-q)}$ stands for a number of R$^r$ substituents that is at least p and does not exceed q, and

is a disubstituent at two adjacent carbon members, said disubstituent being selected from the group consisting of —O—C14AL-O—, —N(R$^h$)(CH$_2$)$_{2-3}$S—, —N(R$^h$)C(O)(CH$_2$)$_{1-2}$S—, —N(R$^h$)C(O)C(CH$_3$)$_2$S—, —N(R$^h$)(CH$_2$)$_{2-3}$O—, —N(R$^h$)C(O)(CH$_2$)$_{1-2}$O—, —N(R$^h$)(CH$_2$)$_{2-3}$NH—, and —N(R$^h$)C(O)(CH$_2$)$_{1-2}$NH—, wherein said C14AL is a C$_{1-4}$alkylene optionally mono- or di-substituted with F, where each —R$^r$ is independently selected from the group consisting of —OH, —C$_{1-6}$alkyl, —OC$_{1-6}$alkyl, —C$_{2-6}$alkenyl, —OC$_{3-6}$alkenyl, —C$_{2-6}$alkynyl, —OC$_{3-6}$alkynyl, —CN, —NO$_2$, —N(R$^y$)R$^z$, —C(O)N(R$^y$)R$^z$, —N(R$^t$)C(O)R$^t$, —N(R$^t$)SO$_2$C$_{1-6}$alkyl, —C(O)C$_{1-6}$alkyl, —SC$_{1-6}$alkyl, —SO$_2$C$_{1-6}$alkyl, —SO$_2$N(R$^y$)R$^z$, halo, —CF$_3$, —OCF$_3$, —CO$_2$H and —CO$_2$C$_{1-6}$alkyl;

wherein R$^t$ is —H or —C$_{1-6}$alkyl;

R$^y$ and R$^z$ are independently selected from —H and —C$_{1-6}$alkyl, or R$^y$ and R$^z$ are taken together with their nitrogen of attachment to form pyrrolidinyl or piperidinyl; and R$^h$ is selected from the group consisting of —H, —C$_{1-6}$alkyl, —C$_{1-6}$alkylCO$_2$H, —C$_{1-6}$alkylCO$_2$C$_{1-6}$alkyl, and benzyl;

b) a five-membered monocyclic heteroaromatic group having a carbon member which is the point of attachment, having one hetero-member that is >O, >S, >NH or >N(C$_{1-4}$alkyl), having up to one additional hetero-member that is —N=, said five-membered monocyclic heteroaromatic group being optionally mono- or di-substituted with R$^r$ and optionally benzofused or pyridofused, where the benzofused or pyridofused moiety is optionally mono-, di-, or tri-substituted with R$^r$; and c) a six-membered monocyclic heteroaromatic group having a carbon member which is the point of attachment, having two hetero-members each being —N=, said six-membered monocyclic heteroaromatic group being optionally mono- or di-substituted with R$^r$ and optionally benzofused or pyridofused, where the benzofused or pyridofused moiety is optionally mono- or di-substituted with R$^r$;

a stereoisomer, racemate, tautomer, pharmaceutically acceptable salt, ester, or amide thereof.

2. A compound of formula (I):

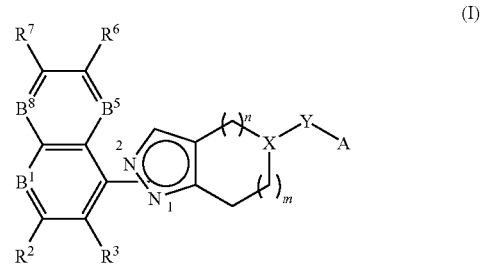

where said formula (I) has a B-containing bicyclic ring system

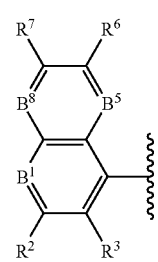

and a fused pyrazole moiety

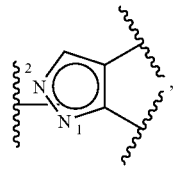

wherein
$B^8$ is $CR^a$, and $B^1$ and $B^5$ are N;
each of $R^a$, $R^2$, $R^3$, $R^6$ and $R^7$ is independently selected from the group consisting of —H, —$C_{1-4}$alkyl, —$C_{2-4}$alkenyl, —$C_{2-4}$alkynyl, —$C_{3-6}$cycloalkyl, —$OR^b$, —$NR^cR^d$, —$O(CH_2)_{2-3}NR^cR^d$, —$SR^b$, —$S(O)R^b$, —$SO_2R^b$, cyano, —$CF_3$, halo, —$NO_2$, —$OCF_3$, —$C(O)R^b$, —$OC(O)R^b$, —$C(O)NR^cR^d$, and —$CO_2R^b$; wherein each of $R^b$, $R^c$ and $R^d$ is independently selected from the group consisting of —H, —$C_{1-4}$alkyl, —$C_{3-6}$cycloalkyl, and —$C_{1-2}$alkyl($C_{3-6}$cycloalkyl)—; and wherein each alkyl or cycloalkyl moiety in any of $R^a$, $R^2$, $R^3$, $R^6$, $R^7$, $R^b$, $R^c$, and $R^d$ is optionally and independently substituted with one, two or three substituents selected from —$C_{1-3}$alkyl, halo, hydroxy, amino, and —$C_{1-3}$alkoxy;
the B-containing bicyclic ring system is attached at the 1- or 2-position of the fused pyrazole moiety;
m is 0 or 1;
n is 1 or 2, wherein m+n is 2 or 3;
X is CH or N;
provided that when X is N, then Y is —C(O)—, —$CH_2C(O)$—, or —$(CH_2)_{2-3}O$— optionally substituted with —$C_{1-3}$alkyl;
and when X is CH, then Y is —$N(R^e)Z$—;
Z is selected from the group consisting of: $C_{1-3}$alkylene optionally substituted with —$C_{1-3}$alkyl; $C_3$alkenylene optionally substituted with —$C_{1-3}$alkyl; —C(O)$C_2$alkenyl- optionally substituted with —$C_{1-3}$alkyl; —$(CH_2)_{0-1}C(O)$—; —$CH_2C(O)N(R^f)(CH_2)_{0-1}$—; —$(CH_2)_{2-3}O$—; and —$C(O)C(R^{g1})(R^{g2})$—;
where $R^e$ is —H, —$C_{1-4}$alkyl, benzyl, —$C(O)C_{1-6}$alkyl, —C(O)phenyl, —C(O)benzyl, —$C_{1-6}$alkyl$CO_2C_{1-6}$alkyl, or —$C_{1-6}$alkyl$CO_2H$;
$R^f$ is —H or —$C_{1-4}$alkyl; and
each of $R^{g1}$ and $R^{g2}$ is independently —H or methyl, or $R^{g1}$ and $R^{g2}$ are taken together with their carbon of attachment to form a $C_{3-7}$cycloalkyl, or the group $C(R^{g1})(R^{g2})$ is the group C=O;
A is an aryl or heteroaryl ring selected from the group consisting of:
a) unsubstituted phenyl, unsubstituted pyridyl, substituted phenyl, and substituted pyridyl, wherein said substituted phenyl is moiety (M1) or moiety (M2)

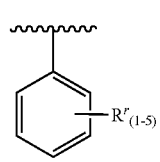
(M1)

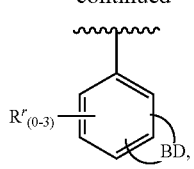
(M2)

and said substituted pyridyl is moiety (M3) or moiety (M4)

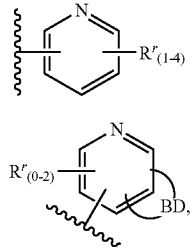
(M3)

(M4)

wherein $R^r_{(p-q)}$ stands for a number of $R^r$ substituents that is at least p and does not exceed q, and

is a disubstituent at two adjacent carbon members, said disubstituent being selected from the group consisting of —O—C14AL-O—, —$N(R^h)(CH_2)_{2-3}S$—, —$N(R^h)C(O)(CH_2)_{1-2}S$—, —$N(R^h)(CH_2)_{2-3}O$—, —$N(R^h)C(O)(CH_2)_{1-2}O$—, —$N(R^h)(CH_2)_{2-3}NH$—, and —$N(R^h)C(O)(CH_2)_{1-2}NH$—, wherein said C14AL is a $C_{1-4}$alkylene optionally mono- or di-substituted with F,
where each —$R^r$ is independently selected from the group consisting of —OH, —$C_{1-6}$alkyl, —$OC_{1-6}$alkyl, —$C_{2-6}$alkenyl, —$OC_{3-6}$alkenyl, —$C_{2-6}$alkynyl, —$OC_{3-6}$alkynyl, —CN, —$NO_2$, —$N(R^y)R^z$, —$C(O)N(R^y)R^z$, —$N(R^y)C(O)R^t$, —$N(R^t)SO_2C_{1-6}$alkyl, —$C(O)C_{1-6}$alkyl, —$SC_{1-6}$alkyl, —$SO_2C_{1-6}$alkyl, —$SO_2N(R^y)R^z$, halo, —$CF_3$, —$OCF_3$, —$CO_2H$ and —$CO_2C_{1-6}$alkyl;
wherein $R^t$ is —H or —$C_{1-6}$alkyl;
$R^y$ and $R^z$ are independently selected from —H and —$C_{1-6}$alkyl, or $R^y$ and $R^z$ are taken together with their nitrogen of attachment to form pyrrolidinyl or piperidinyl; and
$R^h$ is selected from the group consisting of —H, —$C_{1-6}$alkyl, —$C_{1-6}$alkyl$CO_2H$, —$C_{1-6}$alkyl$CO_2C_{1-6}$alkyl, and benzyl;
b) a five-membered monocyclic heteroaromatic group having a carbon member which is the point of attachment, having one hetero-member that is >O, >S, >NH or >N($C_{1-4}$alkyl), having up to one additional hetero-member that is —N=, said five-membered monocyclic heteroaromatic group being optionally mono- or di-substituted with $R^r$ and optionally benzofused or pyridofused, where the benzofused or pyridofused moiety is optionally mono-, di-, or tri-substituted with $R^r$; and c) a six-membered monocyclic heteroaromatic group having a carbon member which is the point of attachment, having two hetero-members each being —N=, said six-membered monocyclic heteroaromatic group being optionally mono- or di-substituted with $R^r$ and optionally benzofused or pyridofused, where the benzofused or pyridofused moiety is optionally mono- or di-substituted with $R^r$;

a stereoisomer, racemate, tautomer pharmaceutically acceptable salt, ester, or amide thereof.

3. The compound of claim 2, wherein $B^1$ is N, $B^5$ is N, and $B^8$ is CH.

4. The compound of claim 2, wherein $R^a$, $R^2$, $R^3$, $R^6$, and $R^7$ are each independently selected from —H, —$C_{1-3}$alkyl, —$OC_{1-3}$alkyl, halo, or —$CF_3$.

5. The compound of claim 2, wherein $R^a$ is —H or —$CF_3$.

6. The compound of claim 2, wherein $R^2$ is —H, —$CH_3$, or —$CF_3$.

7. The compound of claim 2, wherein $R^6$ is —H, —$OC_{1-3}$alkyl, or halo.

8. The compound of claim 2, wherein $R^6$ is —$OC_{1-3}$alkyl.

9. The compound of claim 2, wherein $R^6$ is —H, —$OCH_3$, or —F.

10. The compound of claim 2, wherein $R^6$ is —$OCH_3$.

11. The compound of claim 2, wherein $R^7$ is —H or —Cl.

12. The compound of claim 2, wherein the B-containing bicyclic ring system is attached at the 2-position of the fused pyrazole moiety.

13. The compound of claim 2, wherein m=n=1.

14. The compound of claim 2, wherein n is 2 and m is 1.

15. The compound of claim 2, wherein X is N.

16. The compound of claim 2, wherein X is CH.

17. The compound of claim 16, wherein Y is —N(benzyl)$CH_2$—, —N($CH_2CO_2tBu$)$CH_2$—, —N($CH_2CO_2H$)$CH_2$—, —NHCH$_2$—, —NH($CH_2$)$_3$—, —NHCH$_2$CHCH—, —NHCH$_2$C(Me)CH—, —NHC(O)—, —NHC(O)CHCH—, —NHCH$_2$C(O)NH—, —NHCH$_2$C(O)NHCH$_2$—, —NHCH$_2$C(O)—, —NHC(O)C(O)—, —NH(CH$_2$)$_2$O—, or —NHC(O)C($R^{g1}$)($R^{g2}$)—.

18. The compound of claim 2, wherein X is CH, and Z is one of $C_{1-3}$alkylene, $C_3$alkenylene, —C(O)$C_2$alkenyl-, —(CH$_2$)$_{0-1}$C(O)—, —CH$_2$C(O)N($R^f$)(CH$_2$)$_{0-1}$—, —(CH$_2$)$_{2-3}$O—, and —C(O)C($R^{g1}$)($R^{g2}$)—.

19. The compound of claim 2, wherein X is CH, $R^e$ is —H, and Z is C=O.

20. The compound of claim 2, wherein $R^6$ is —$OC_{1-3}$alkyl, X is CH, $B^8$ is CH, $B^1$ is N, and $B^5$ is N, m=n=1, the B-containing bicyclic ring system is attached at the 2-position of the fused pyrazole moiety, and A is an aryl or heteroaryl ring selected from the group consisting of a), b) and c) as defined for compound of formula (I).

21. The compound of claim 2, wherein A is phenyl, 4-methylphenyl, 3-chlorophenyl, 4-chlorophenyl, 3,4-dichlorophenyl, 4-fluorophenyl, 3,4-difluorophenyl, 3,5-difluorophenyl, 2-nitrophenyl, 5-fluoro-2-trifluoromethylphenyl, 4-dimethylaminophenyl, 4-diethylaminophenyl, 4-piperidin-1-ylphenyl, 4-pyrrolidin-1-ylphenyl, 2-fluoro-4,5-dimethoxyphenyl, 2-chloro-5-nitrophenyl, 2-fluoro-3-cyano-4-dimethylaminophenyl, pyridin-3-yl, 2-chloro-pyridin-3-yl, or pyridin-2-yl.

22. The compound of claim 2, wherein A is 4-methyl-3-nitrophenyl, 2-fluoro-4-nitrophenyl, 2,4-difluorophenyl, 3-trifluoromethylphenyl, 5-acetylamino-2-bromophenyl, or 2,4-dichloro-5-fluorophenyl.

23. The compound of claim 2, wherein A is 2,3-dihydro-benzo[1,4]dioxin-6-yl, 7-fluoro-2,3-dihydro-benzo[1,4]dioxin-6-yl, 3,4-dihydro-2H-benzo[b][1,4]dioxepin-6-yl, 3-oxo-3,4-dihydro-2H-benzo[1,4]thiazin-6-yl, 7-fluoro-3-oxo-3,4-dihydro-2H-benzo[1,4]thiazin-6-yl, 7-chloro-3-oxo-3,4-dihydro-2H-benzo[1,4]thiazin-6-yl, 3,4-dihydro-2H-benzo[1,4]thiazin-6-yl, benzo[1,3]dioxol-5-yl, 2,2-difluoro-benzo[1,3]dioxol-5-yl, 3-oxo-4H-pyrido[3,2-b][1,4]oxazin-6-yl, 3-oxo-4H-benzo[1,4]oxazin-6-yl, 4-methyl-3-oxo-3,4-dihydro-2H-benzo[1,4]thiazin-6-yl, or 4-methyl-3,4-dihydro-2H-benzo[1,4]oxazin-7-yl.

24. The compound of claim 2, wherein A is 8-fluoro-2,3-dihydro-benzo[1,4]dioxin-6-yl, 7-chloro-2,3-dihydro-benzo[1,4]dioxin-6-yl, 6-chloro-benzo[1,3]dioxol-5-yl, 7-fluoro-3,4-dihydro-2H-benzo[1,4]thiazin-6-yl, 5,7-difluoro-3-oxo-3,4-dihydro-2H-benzo[1,4]thiazin-6-yl, 3-oxo-7-trifluoromethyl-3,4-dihydro-2H-benzo[1,4]thiazin-6-yl, 7-bromo-3-oxo-3,4-dihydro-2H-benzo[1,4]thiazin-6-yl, 3-oxo-3,4-dihydro-2H-benzo[1,4]oxazin-6-yl, 2,2-dimethyl-3-oxo-3,4-dihydro-2H-benzo[1,4]thiazin-6-yl, 7-methoxy-3-oxo-3,4-dihydro-2H-benzo[1,4]thiazin-6-yl, 7-methyl-3-oxo-3,4-dihydro-2H-benzo[1,4]thiazin-6-yl, 7-ethoxycarbonyl-3-oxo-3,4-dihydro-2H-benzo[1,4]thiazin-6-yl, or 7-carboxy-3-oxo-3,4-dihydro-2H-benzo[1,4]thiazin-6-yl.

25. The compound of claim 2, wherein A is 4,6-difluoro-1H-indol-2-yl, 1H-benzimidazol-2-yl, 1H-indol-2-yl, benzo[b]thiophen-2-yl, 4-fluoro-benzo[b]thiophen-2-yl, benzofuran-2-yl, thiophen-2-yl, quinoxalin-2-yl, 5-bromo-thiophen-2-yl, 5-acetyl-thiophen-2-yl, 5,6-difluoro-1H-indol-2-yl, 5-methyl-1H-indol-2-yl, 5-bromo-1H-indol-2-yl, or 5-chloro-1H-indol-2-yl.

26. A compound selected from:
2,3-Dihydro-benzo[1,4]dioxine-6-carboxylic acid [2-(6-methoxy-[1,5]naphthyridin-4-yl)-4,5,6,7-tetrahydro-2H-indazol-5-yl]-amide;
7-Fluoro-2,3-dihydro-benzo[1,4]dioxine-6-carboxylic acid [2-(6-methoxy-[1,5]naphthyridin-4-yl)-4,5,6,7-tetrahydro-2H-indazol-5-yl]-amide;
3,4-Dihydro-2H-benzo[b][1,4]dioxepine-7-carboxylic acid [2-(6-methoxy-[1,5]naphthyridin-4-yl)-4,5,6,7-tetrahydro-2H-indazol-5-yl]-amide;
3-Oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide;
7-Fluoro-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide;
7-Chloro-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide;
4,6-Difluoro-1H-indole-2-carboxylic acid [2-(6-methoxy-[1,5]naphthyridin-4-yl)-4,5,6,7-tetrahydro-2H-indazol-5-yl]-amide;
1H-Benzoimidazole-2-carboxylic acid [2-(6-methoxy-[1,5]naphthyridin-4-yl)-4,5,6,7-tetrahydro-2H-indazol-5-yl]-amide;
2-(1H-Indol-2-yl)-N-[2-(6-methoxy-[1,5]naphthyridin-4-yl)-4,5,6,7-tetrahydro-2H-indazol-5-yl]-2-oxo-acetamide;
N-[2-(6-Methoxy-[1,5]naphthyridin-4-yl)-4,5,6,7-tetrahydro-2H-indazol-5-yl]-3-phenyl-acrylamide;
3-(3,5-Difluoro-phenyl)-N-[2-(6-methoxy-[1,5]naphthyridin-4-yl)-4,5,6,7-tetrahydro-2H-indazol-5-yl]-acrylamide;
3-(3-Chloro-phenyl)-N-[2-(6-methoxy-[1,5]naphthyridin-4-yl)-4,5,6,7-tetrahydro-2H-indazol-5-yl]-acrylamide;
3-(4-Fluoro-phenyl)-N-[2-(6-methoxy-[1,5]naphthyridin-4-yl)-4,5,6,7-tetrahydro-2H-indazol-5-yl]-acrylamide;

N-[2-(6-Methoxy-[1,5]naphthyridin-4-yl)-4,5,6,7-tetrahydro-2H-indazol-5-yl]-3-(3-nitro-phenyl)-acrylamide;
6-[2-(6-Methoxy-[1,5]naphthyridin-4-yl)-4,5,7,8-tetrahydro-2H-1,2,6-triaza-azulene-6-carbonyl]-4H-benzo[1,4]thiazin-3-one;
6-Dimethylamino-2-fluoro-3-{[2-(6-methoxy-[1,5]naphthyridin-4-yl)-4,5,6,7-tetrahydro-2H-indazol-5-ylamino]-methyl}-benzonitrile;
(3,4-Dihydro-2H-benzo[1,4]thiazin-6-ylmethyl)-[2-(6-methoxy-[1,5]naphthyridin-4-yl)-4,5,6,7-tetrahydro-2H-indazol-5-yl]-amine;
Benzo[1,3]dioxol-5-ylmethyl-[2-(6-methoxy-[1,5]naphthyridin-4-yl)-4,5,6,7-tetrahydro-2H-indazol-5-yl]-amine;
(2,2-Difluoro-benzo[1,3]dioxol-5-ylmethyl)-[2-(6-methoxy-[1,5]naphthyridin-4-yl)-4,5,6,7-tetrahydro-2H-indazol-5-yl]-amine;
(4-Dimethylamino-benzyl)-[2-(6-methoxy-[1,5]naphthyridin-4-yl)-4,5,6,7-tetrahydro-2H-indazol-5-yl]-amine;
7-Fluoro-6-{[2-(6-methoxy-[1,5]naphthyridin-4-yl)-4,5,6,7-tetrahydro-2H-indazol-5-ylamino]-methyl}-4H-benzo[1,4]thiazin-3-one;
6-{[2-(6-Methoxy-[1,5]naphthyridin-4-yl)-4,5,6,7-tetrahydro-2H-indazol-5-ylamino]-methyl}-4H-benzo[1,4]thiazin-3-one;
(2,3-Dihydro-benzo[1,4]dioxin-6-ylmethyl)-[2-(6-methoxy-[1,5]naphthyridin-4-yl)-4,5,6,7-tetrahydro-2H-indazol-5-yl]-amine;
(7-Fluoro-2,3-dihydro-benzo[1,4]dioxin-6-ylmethyl)-[2-(6-methoxy-[1,5]naphthyridin-4-yl)-4,5,6,7-tetrahydro-2H-indazol-5-yl]-amine;
6-{[2-(6-Methoxy-[1,5]naphthyridin-4-yl)-4,5,6,7-tetrahydro-2H-indazol-5-ylamino]-methyl}-4H-pyrido[3,2-b][1,4]oxazin-3-one;
[2-(6-Methoxy-[1,5]naphthyridin-4-yl)-4,5,6,7-tetrahydro-2H-indazol-5-yl]-(3-phenyl-propyl)-amine;
[2-(6-Methoxy-[1,5]naphthyridin-4-yl)-4,5,6,7-tetrahydro-2H-indazol-5-yl]-(3-phenyl-allyl)-amine;
[2-(6-Methoxy-[1,5]naphthyridin-4-yl)-4,5,6,7-tetrahydro-2H-indazol-5-yl]-(3-pyridin-3-yl-allyl)-amine;
[3-(3,4-Dichloro-phenyl)-propyl]-[2-(6-methoxy-[1,5]naphthyridin-4-yl)-4,5,6,7-tetrahydro-2H-indazol-5-yl]-amine;
[2-(6-Methoxy-[1,5]naphthyridin-4-yl)-4,5,6,7-tetrahydro-2H-indazol-5-yl]-(3-p-tolyl-propyl)-amine;
N-(3,5-Difluoro-phenyl)-2-[2-(6-methoxy-[1,5]naphthyridin-4-yl)-4,5,6,7-tetrahydro-2H-indazol-5-ylamino]-acetamide;
2-[2-(6-Methoxy-[1,5]naphthyridin-4-yl)-4,5,6,7-tetrahydro-2H-indazol-5-ylamino]-N-phenyl-acetamide;
2-[2-(6-Methoxy-[1,5]naphthyridin-4-yl)-4,5,6,7-tetrahydro-2H-indazol-5-ylamino]-N-p-tolyl-acetamide;
[2-(6-Methoxy-[1,5]naphthyridin-4-yl)-4,5,6,7-tetrahydro-2H-indazol-5-yl]-(2-phenoxy-ethyl)-amine;
6-({Benzyl-[2-(6-methoxy-[1,5]naphthyridin-4-yl)-4,5,6,7-tetrahydro-2H-indazol-5-yl]-amino}-methyl)-4H-benzo[1,4]thiazin-3-one;
[[2-(6-Methoxy-[1,5]naphthyridin-4-yl)-4,5,6,7-tetrahydro-2H-indazol-5-yl]-(3-oxo-3,4-dihydro-2H-benzo[1,4]thiazin-6-ylmethyl)-amino]-acetic acid tert-butyl ester;
[[2-(6-Methoxy-[1,5]naphthyridin-4-yl)-4,5,6,7-tetrahydro-2H-indazol-5-yl]-(3-oxo-3,4-dihydro-2H-benzo[1,4]thiazin-6-ylmethyl)-amino]-acetic acid;
4-Methyl-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide;
Quinoxaline-2-carboxylic acid [2-(6-methoxy-[1,5]naphthyridin-4-yl)-4,5,6,7-tetrahydro-2H-indazol-5-yl]-amide;
2-[2-(6-Methoxy-[1,5]naphthyridin-4-yl)-4,5,6,7-tetrahydro-2H-indazol-5-ylamino]-N-(3-oxo-3,4-dihydro-2H-benzo[1,4]thiazin-6-yl)-acetamide;
N-Benzyl-2-[2-(6-methoxy-[1,5]naphthyridin-4-yl)-4,5,6,7-tetrahydro-2H-indazol-5-ylamino]-acetamide;
(4-Diethylamino-benzyl)-[2-(6-methoxy-[1,5]naphthyridin-4-yl)-4,5,6,7-tetrahydro-2H-indazol-5-yl]-amine;
[2-(6-Methoxy-[1,5]naphthyridin-4-yl)-4,5,6,7-tetrahydro-2H-indazol-5-yl]-(4-piperidin-1-yl-benzyl)-amine;
[2-(6-Methoxy-[1,5]naphthyridin-4-yl)-4,5,6,7-tetrahydro-2H-indazol-5-yl]-(4-pyrrolidin-1-yl-benzyl)-amine;
(2-Fluoro-4,5-dimethoxy-benzyl)-[2-(6-methoxy-[1,5]naphthyridin-4-yl)-4,5,6,7-tetrahydro-2H-indazol-5-yl]-amine;
[2-(6-Methoxy-[1,5]naphthyridin-4-yl)-4,5,6,7-tetrahydro-2H-indazol-5-yl]-[3-(2-nitro-phenyl)-allyl]-amine;
3-(4-Chloro-phenyl)-N-[2-(6-methoxy-[1,5]naphthyridin-4-yl)-4,5,6,7-tetrahydro-2H-indazol-5-yl]-acrylamide;
[3-(5-Fluoro-2-trifluoromethyl-phenyl)-allyl]-[2-(6-methoxy-[1,5]naphthyridin-4-yl)-4,5,6,7-tetrahydro-2H-indazol-5-yl]-amine;
3-(3,4-Dichloro-phenyl)-N-[2-(6-methoxy-[1,5]naphthyridin-4-yl)-4,5,6,7-tetrahydro-2H-indazol-5-yl]-acrylamide;
3-(3,4-Difluoro-phenyl)-N-[2-(6-methoxy-[1,5]naphthyridin-4-yl)-4,5,6,7-tetrahydro-2H-indazol-5-yl]-acrylamide;
3-(2-Chloro-5-nitro-phenyl)-N-[2-(6-methoxy-[1,5]naphthyridin-4-yl)-4,5,6,7-tetrahydro-2H-indazol-5-yl]-acrylamide;
N-[2-(6-Methoxy-[1,5]naphthyridin-4-yl)-4,5,6,7-tetrahydro-2H-indazol-5-yl]-3-pyridin-2-yl-acrylamide;
and pharmaceutically acceptable salts thereof.

27. A compound selected from:
(8-Fluoro-2,3-dihydro-benzo[1,4]dioxin-6-ylmethyl)-[2-(6-methoxy-[1,5]naphthyridin-4-yl)-4,5,6,7-tetrahydro-2H-indazol-5-yl]-amine;
(7-Chloro-2,3-dihydro-benzo[1,4]dioxin-6-ylmethyl)-[2-(6-methoxy-[1,5]naphthyridin-4-yl)-4,5,6,7-tetrahydro-2H-indazol-5-yl]-amine;
N-((6-chlorobenzo[d][1,3]dioxol-5-yl)methyl)-2-(6-methoxy-1,5-naphthyridin-4-yl)-4,5,6,7-tetrahydro-2H-indazol-5-amine
(7-Fluoro-3,4-dihydro-2H-benzo[1,4]thiazin-6-ylmethyl)-[2-(6-methoxy-[1,5]naphthyridin-4-yl)-4,5,6,7-tetrahydro-2H-indazol-5-yl]-amine;
5,7-Difluoro-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide;
N-[2-(6-Methoxy-[1,5]naphthyridin-4-yl)-4,5,6,7-tetrahydro-2H-indazol-5-yl]-4-methyl-3-nitro-benzamide;
3-Oxo-7-trifluoromethyl-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide;
7-Bromo-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide;

3-Oxo-3,4-dihydro-2H-benzo[1,4]oxazine-6-carboxylic acid [2-(6-methoxy-[1,5]naphthyridin-4-yl)-4,5,6,7-tetrahydro-2H-indazol-5-yl]-amide;

4-Methoxy-N-[2-(6-methoxy-[1,5]naphthyridin-4-yl)-4,5,6,7-tetrahydro-2H-indazol-5-yl]-3-nitro-benzamide;

3-(2,4-Difluoro-phenyl)-N-[2-(6-methoxy-[1,5]naphthyridin-4-yl)-4,5,6,7-tetrahydro-2H-indazol-5-yl]-acrylamide;

2-[2-(6-Methoxy-[1,5]naphthyridin-4-yl)-4,5,6,7-tetrahydro-2H-indazol-5-ylamino]-N-(3-trifluoromethyl-phenyl)-acetamide;

N-(3-Chloro-phenyl)-2-[2-(6-methoxy-[1,5]naphthyridin-4-yl)-4,5,6,7-tetrahydro-2H-indazol-5-ylamino]-acetamide;

5-Acetylamino-2-bromo-N-[2-(6-methoxy-[1,5]naphthyridin-4-yl)-4,5,6,7-tetrahydro-2H-indazol-5-yl]-benzamide;

2,4-Dichloro-5-fluoro-N-[2-(6-methoxy-[1,5]naphthyridin-4-yl)-4,5,6,7-tetrahydro-2H-indazol-5-yl]-benzamide;

8-Fluoro-2,3-dihydro-benzo[1,4]dioxine-6-carboxylic acid [2-(6-methoxy-[1,5]naphthyridin-4-yl)-4,5,6,7-tetrahydro-2H-indazol-5-yl]-amide;

7-Methoxy-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide;

7-Methyl-3-oxo-3,4-dihydro-2H-benzo[1,4]thiazine-6-carboxylic acid [2-(6-methoxy-[1,5]naphthyridin-4-yl)-4,5,6,7-tetrahydro-2H-indazol-5-yl]-amide;

[2-(3,5-Difluoro-phenoxy)-ethyl]-[2-(6-methoxy-[1,5]naphthyridin-4-yl)-4,5,6,7-tetrahydro-2H-indazol-5-yl]-amine;

6-[2-(6-Methoxy-[1,5]naphthyridin-4-yl)-4,5,6,7-tetrahydro-2H-indazol-5-ylcarbamoyl]-3-oxo-3,4-dihydro-2H-benzo[1,4]thiazine-7-carboxylic acid ethyl ester;

6-[2-(6-Methoxy-[1,5]naphthyridin-4-yl)-4,5,6,7-tetrahydro-2H-indazol-5-ylcarbamoyl]-3-oxo-3,4-dihydro-2H-benzo[1,4]thiazine-7-carboxylic acid;

6-{[1-(2-Trifluoromethyl-quinolin-4-yl)-4,5,6,7-tetrahydro-1H-indazol-5-ylamino]-methyl}-4H-benzo[1,4]thiazin-3-one; and pharmaceutically acceptable salts thereof.

28. A pharmaceutical composition comprising at least one compound of claim 1.

* * * * *